(12) United States Patent
Shirahase et al.

(10) Patent No.: US 10,059,663 B2
(45) Date of Patent: Aug. 28, 2018

(54) AROMATIC COMPOUND AND USE THEREOF

(71) Applicant: Kyoto Pharmaceutical Industries, Ltd., Kyoto (JP)

(72) Inventors: Hiroaki Shirahase, Kyoto (JP); Kenji Takahashi, Kyoto (JP); Yoshimichi Shoji, Kyoto (JP); Shigemitsu Takeda, Kyoto (JP)

(73) Assignee: KYOTO PHARMACEUTICAL INDUSTRIES, LTD., Kyoto (JP)

( * ) Notice: Subject to any disclaimer, the term of this patent is extended or adjusted under 35 U.S.C. 154(b) by 0 days.

(21) Appl. No.: 14/914,941

(22) PCT Filed: Aug. 29, 2014

(86) PCT No.: PCT/JP2014/072773
§ 371 (c)(1),
(2) Date: Feb. 26, 2016

(87) PCT Pub. No.: WO2015/030189
PCT Pub. Date: Mar. 5, 2015

(65) Prior Publication Data
US 2016/0207883 A1 Jul. 21, 2016

(30) Foreign Application Priority Data
Aug. 29, 2013 (JP) .................. 2013-178712

(51) Int. Cl.
C07D 205/04 (2006.01)
C07D 401/14 (2006.01)
C07D 405/14 (2006.01)
C07D 309/12 (2006.01)
C07D 319/12 (2006.01)
C07D 335/02 (2006.01)
(Continued)

(52) U.S. Cl.
CPC .......... *C07D 205/04* (2013.01); *C07C 235/84* (2013.01); *C07C 237/40* (2013.01); *C07D 211/46* (2013.01); *C07D 295/14* (2013.01); *C07D 295/15* (2013.01); *C07D 295/155* (2013.01); *C07D 307/20* (2013.01); *C07D 307/33* (2013.01); *C07D 309/12* (2013.01); *C07D 319/12* (2013.01); *C07D 335/02* (2013.01); *C07D 401/12* (2013.01); *C07D 401/14* (2013.01); *C07D 405/12* (2013.01); *C07D 405/14* (2013.01)

(58) Field of Classification Search
CPC .. C07D 401/12; C07D 401/14; C07D 405/14; C07D 205/04; C07D 205/14; C07D 211/46; C07D 295/14; C07D 95/14; C07D 295/155; C07D 307/20; C07D 307/33; C07D 309/12; C07D 319/12; C07D 335/02; C07C 325/84; C07C 237/40
See application file for complete search history.

(56) References Cited

U.S. PATENT DOCUMENTS 4,118,572 A * 10/1978 Gerecke ............... C07D 313/14
544/369
4,822,787 A 4/1989 Murata et al.
(Continued)

FOREIGN PATENT DOCUMENTS

CS 190653 B1 * 6/1979
CZ 193 369 1/1979
(Continued)

OTHER PUBLICATIONS

Wrobel et al. "Simple Synthesis of N-Aryl-2-nitrosoanilines in the Reaction of Nitroarenes with aniline Anion Derivatives", Synthesis, 2010, No. 22, pp. 3865-3872.*
(Continued)

*Primary Examiner* — Kendra D Carter
(74) *Attorney, Agent, or Firm* — Wenderoth, Lind & Ponack, L.L.P.

(57) ABSTRACT

Provided is a compound showing a bone formation promoting action (and/or bone resorption suppressive action). A compound of the formula (I) or a pharmacologically acceptable salt:

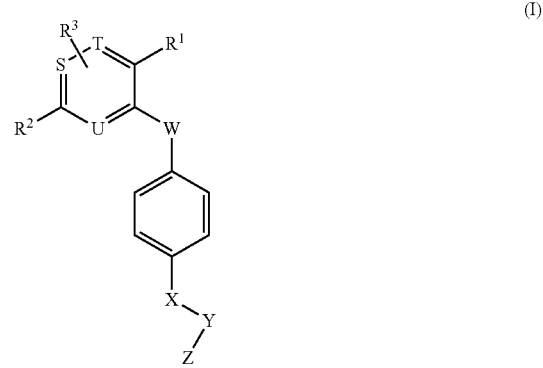

(I)

[wherein each substituent is as defined in the DESCRIPTION], has low toxicity, shows good pharmacokinetics, has an action to promote bone formation, and is useful for the prophylaxis or treatment of metabolic bone diseases (osteoporosis, fibrous osteitis (hyperparathyroidism), osteomalacia, Paget's disease that influences the systemic bone metabolism parameter etc.) associated with a decrease in the bone formation ability as compared to the bone resorption capacity.

24 Claims, No Drawings

(51) Int. Cl.
*C07D 401/12* (2006.01)
*C07D 405/12* (2006.01)
*C07C 235/84* (2006.01)
*C07D 295/14* (2006.01)
*C07D 307/33* (2006.01)
*C07D 307/20* (2006.01)
*C07C 237/40* (2006.01)
*C07D 211/46* (2006.01)
*C07D 295/15* (2006.01)
*C07D 295/155* (2006.01)

(56) References Cited

U.S. PATENT DOCUMENTS

| | | |
|---|---|---|
| 4,866,091 A | 9/1989 | Matsuo et al. |
| 4,963,543 A | 10/1990 | Murata et al. |
| 5,034,417 A | 7/1991 | Matsuo et al. |
| 5,424,280 A | 6/1995 | Condon et al. |
| 5,990,146 A | 11/1999 | Boschelli et al. |
| 6,025,379 A | 2/2000 | Iyengar et al. |
| 6,218,388 B1 | 4/2001 | Boschelli et al. |
| 6,346,521 B1 | 2/2002 | Sohda et al. |
| 6,576,643 B2 * | 6/2003 | Bondinell ............ C07D 213/73 514/275 |
| 6,632,807 B1 | 10/2003 | Sohda et al. |
| 6,710,054 B2 * | 3/2004 | Nakao .................. A61K 31/00 514/303 |
| 7,173,033 B2 | 2/2007 | Igarshi et al. |
| 7,906,521 B2 * | 3/2011 | Trotter ................ C07D 239/88 514/266.31 |
| 8,163,906 B2 | 4/2012 | Abbot et al. |
| 8,481,568 B2 | 7/2013 | Muller et al. |
| 8,501,770 B2 | 8/2013 | Ashwell et al. |
| 8,653,089 B2 * | 2/2014 | Heald ................. C07D 401/12 514/263.21 |
| 2002/0077329 A1 | 6/2002 | Audoly et al. |
| 2002/0147334 A1 | 10/2002 | Miller et al. |
| 2007/0049618 A1 | 3/2007 | Muller et al. |
| 2008/0287458 A1 | 11/2008 | Abbot et al. |
| 2008/0287460 A1 | 11/2008 | Burrows et al. |
| 2009/0233943 A9 | 9/2009 | Burrows et al. |
| 2011/0144158 A1 | 6/2011 | Muller et al. |
| 2011/0172203 A1 | 7/2011 | Ashwell et al. |
| 2012/0202785 A1 | 8/2012 | Heald et al. |
| 2013/0029964 A1 | 1/2013 | Aoki et al. |

FOREIGN PATENT DOCUMENTS

| | | |
|---|---|---|
| EP | 0 137 524 | 4/1985 |
| JP | 60-87211 | 5/1985 |
| JP | 63-313765 | 12/1988 |
| JP | 2-282359 | 11/1990 |
| JP | 7-165659 | 6/1995 |
| JP | 9-188665 | 7/1997 |
| JP | 2000-506529 | 5/2000 |
| JP | 2002-506033 | 2/2002 |
| JP | 2003-306433 | 10/2003 |
| JP | 2004-511518 | 4/2004 |
| JP | 2007-131617 | 5/2007 |
| JP | 2009-506117 | 2/2009 |
| JP | 2013-516419 | 5/2013 |
| WO | 2009/015917 | 2/2009 |
| WO | 2011/136264 | 11/2011 |
| WO | 2012/107465 | 8/2012 |
| WO | 2012/146667 | 11/2012 |

OTHER PUBLICATIONS

English translation of CS 190653 , provided May 16, 2018 (Year: 2018).*
International Search Report dated Nov. 25, 2014 in International (PCT) Application No. PCT/JP2014/072773.
Protiva et al., "Potential metabolites of Tricyclic Neuroleptics: 2,8-Dihydroxy and 3,8-Dihydroxy Derivatives of 10-(4-Methylpiperazino)-10,11-dihydrodibenzo[b,f] thiepin", Collection Czechoslov. Chem. Commun, vol. 44, 1979, pp. 2987-2996.
Mathur et al., "Studies in Potential Antimycobacterial Agents: XVII—Synthesis of Some Cyclic Analogues of Thiocarbanilides", Indian Journal of Chemistry, vol. 3, No. 9, 1965, pp. 397-401.
Gerasimova et al., "Synthesis of some 1, 2, 3, 4-Tetrafluoro-9-methylacridines", Izvestiya Sibirskogo Otdeleniya Akademii Nauk SSSR, Seriya Khimicheskikh Nauk, vol. 2, 1973, pp. 96-100 (English abstract).
Brieux et al., "αρ Relationships in the Ultraviolet Spectra of 4-R-, 5-R-, and 6-R-2-Nitro-diphenyl Sulphides in Methanol and in Cyclohexane", Journal of the Chemical Society [Section] B: Physical Organic, No. 7, 1971, pp. 1360-1366.
Belton et al., "Antitubercular substances—XXI. Synthesis of 2-Nitrodiphenylamines", Proceedings of the Royal Irish Academy, Section B: Biological, Geological and Chemical Science, vol. 69, No. 2, 1970, pp. 21-29.
Masuya et al., "Small molecules for bone diseases", Expert Opinion on Therapeutic Patents, 20(4):563-582 (2010).

* cited by examiner

AROMATIC COMPOUND AND USE THEREOF

TECHNICAL FIELD

The present invention relates to a compound or a pharmacologically acceptable salt thereof, which is useful for the prophylaxis or treatment of a disease associated with bone metabolism, for example, osteoporosis, fibrous osteitis (hyperparathyroidism), osteomalacia, Paget's disease, chronic articular rheumatism, arthritis deformans and the like.

BACKGROUND ART

Bone plays an important role of not only a supporting organ or motility organ of the living body, but also a reservoir organ of $Ca^{2+}$. To perform such functions, bone formation by osteoblast and bone resorption by osteoclast are repeated in bone tissues, whereby old bone is constantly substituted by a new bone and the strength of the whole bone is maintained.

It is considered that when bone formation and bone resorption are imbalanced, a decrease in the bone mass and degradation of the bone tissues occur, which in turn leads to the affection with bone diseases such as osteoporosis, fibrous osteitis(hyperparathyroidism), osteomalacia, Paget's disease, chronic articularrheumatism, arthritis deformans and the like. Particularly, osteoporosis is often found in elderly people and women, and 11 million patients are assumed to be present in Japan and not less than 30 million patients in the United States. The symptoms include bone fracture and pain such as lumbago and the like, which may produce bedridden patients, body deformation, and bone fracture such as hip fracture and the like, which could be fatal depending on the fracture site.

Therapeutic drugs for osteoporosis include bone resorption inhibitors that suppress osteoclast activity and bone formation promoters that activate osteoblast. As the bone resorption inhibitor, calcitonin, bisphosphonate, estrogen receptor modulator and the like are used. However, these therapeutic drugs prevent a further decrease in the bone mass but cannot reconstruct lost bones. On the other hand human PTH (1-34) is used as the bone formation promoter, which can be utilized for increasing the bone mass and bone density and reconstructing a bone structure. However, the use period is limited to one and a half years to two years, and subcutaneous injection is required for a long term, which is difficult for the patients to comply.

Thus, the development of an orally administrable bone formation promoter having a high clinical effect has been desired.

Recently, benzothiepin derivatives having an alkaline phosphatase-inducing activity (patent document 1, 2), N-quinolylanthranilic acid derivative (patent document 3), triazolopyridazine derivative (patent document 4), thienopyridine derivative (patent document 5) and [5,6]heterocyclic compound (patent document 6) have been reported to be useful for the treatment of diseases associated with promoted bone formation and bone metabolism. However, its clinical usefulness is unknown.

DOCUMENT LIST

Patent Documents patent document 1: U.S. Pat. No. 6,346,521
patent document 2: U.S. Pat. No. 6,632,807
patent document 3: JP-A-H09-188665
patent document 4: U.S. Pat. No. 7,173,033
patent document 5: JP-A-2007-131617
patent document 6: WO 2011/136264

SUMMARY OF THE INVENTION

Problems to be Solved by the Invention

To decrease the risk of pain and bone fracture in a disease associated with bone metabolism such as osteoporosis and the like, it is necessary to increase bone mass and bone strength. As a means to increase the bone mass and bone strength, it is considered to be important to promote bone formation by osteoblast. Therefore, it is the problem of the present invention to provide an orally administrable novel low-molecular-weight compound showing a bone formation promoting action (and/or bone resorption suppressive action) and high safety.

Means of Solving the Problems

The present inventors have conducted intensive studies in an attempt to develop a therapeutic drug having a bone formation promoting action and found the superior compound of the present invention, which shows a potent bone formation promoting action (and/or bone resorption inhibitory action) and can be a prophylactic or therapeutic drug for a disease associated with bone metabolism, which resulted in the completion of the present invention.

Accordingly, the present invention is as follows.

[1] A compound of the formula (I) or a pharmacologically acceptable salt (hereinafter sometimes to be abbreviated as compound (I)):

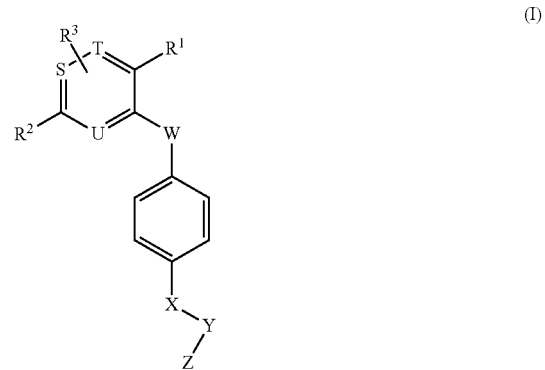

[wherein each substituent is as defined below $R^1$:
cyano group, C1-6 alkylcarbonyl group, C1-6 alkylcarbonylamino group, nitro group, halogeno C1-6 alkyl group, C2-6 alkenyl group, halogeno C2-6 alkenyl group, carbamoyl group, or hydroxy C1-6 alkyl group
$R^2$:
C1-6 alkoxy group, carbamoyl group, C1-6 alkylaminocarbonyl group, or C1-6 alkylcarbonyl group
$R^3$:
hydrogen atom, or halogen atom
S, T and U:
when any one of S, T and U is =N—, others are =CH— (=C— when $R^3$ is substituted); or
all of S, T and U are =CH— (=C— when $R^3$ is substituted)

W:

—NH—, —O—, or —S—

X:

single bond, -saturated heterocycle-, —CH$_2$—(CH$_2$)$_n$—, —O—(CH$_2$)$_n$—, —(CH$_2$)$_n$—O—, or —CH═CH—(CH$_2$)$_n$— n:

any one integer selected from 1-4

Y:

single bond, —O—, or —CO—

Z:

hydrogen atom, saturated heterocyclic group optionally substituted by any group selected from substituent group α, or C1-6 alkyl group optionally substituted by any group selected from substituent group α substituent group α:

saturated heterocyclic group, hydroxy C1-6 alkyl group, aminosulfonylamino group, carboxy group, hydroxy group, C1-6 alkoxy group, C1-6 alkyl group].

[1A] A compound of the formula (I) or a pharmacologically acceptable salt (hereinafter sometimes to be abbreviated as compound (I)):

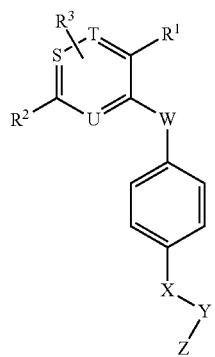

(I)

wherein each substituent is as defined below

R$^1$:

cyano group, C1-6 alkylcarbonyl group, C1-6 alkylcarbonylamino group, nitro group, halogeno C1-6 alkyl group, halogeno C2-6 alkenyl group, carbamoyl group, or hydroxy C1-6 alkyl group

R$^2$:

C1-6 alkoxy group, carbamoyl group, C1-6 alkylaminocarbonyl group, or C1-6 alkylcarbonyl group

R$^3$:

hydrogen atom, or halogen atom

S, T and U:

when any one of S, T and U is ═N—, and others are ═CH— (═C— when R$^3$ is substituted); or all of S, T and U are ═CH— (═C— when R$^3$ is substituted)

W:

—NH—, —O—, or —S—

X:

-saturated heterocycle-, —CH$_2$—(CH$_2$)$_n$—, —O—(CH$_2$)$_n$—, —(CH$_2$)$_n$—O—, or —CH═CH—(CH$_2$)$_n$— n:

any one integer selected from 1-4

Y:

single bond, —O—, or —CO—

Z:

hydrogen atom, saturated heterocyclic group optionally substituted by any group selected from substituent group α, or C1-6 alkyl group optionally substituted by any group selected from substituent group α substituent group α:

hydroxy C1-6 alkyl group, aminosulfonylamino group, carboxy group, hydroxy group, C1-6 alkoxy group, C1-6 alkyl group.

A preferable embodiment of the present invention is, for example, the following invention.

[2] The compound of [1] or [1A], wherein

R$^1$ is cyano group, acetyl group, acetylamino group, nitro group, trifluoromethyl group, 1,1-difluoroethyl group, 1-fluoroethyl group, difluoromethyl group, carbamoyl group, or 1-hydroxyethyl group, or a pharmacologically acceptable salt thereof.

[3] The compound of [1], [1A] or [2], wherein

R$^2$ is methoxy group, carbamoyl group, methylaminocarbonyl group, or acetyl group, or a pharmacologically acceptable salt thereof.

[4] The compound of any one item selected from [1]-[3] and [1A], wherein all of S, T and U are ═CH—, or a pharmacologically acceptable salt thereof.

[5] The compound of any one item selected from [1]-[4] and [1A], wherein

X is -saturated heterocycle-, or —O—(CH$_2$)$_n$—, and n is 2, or a pharmacologically acceptable salt thereof.

[6] The compound of any one item selected from [1]-[5] and [1A], wherein

Y is a single bond, or —O—, or a pharmacologically acceptable salt thereof.

[7] The compound of any one item selected from [1]-[6] and [1A], wherein

Z is C1-6 alkyl group substituted by a hydroxy group, tetrahydrofuranyl group, tetrahydropyranyl group, piperazinyl group, or morpholinyl group, or a pharmacologically acceptable salt thereof.

[8] Any compound selected from the compounds described below, or a pharmacologically acceptable salt thereof:

(1) N-(4-{4-[3-(2-hydroxyethoxy)azetidin-1-yl]phenylamino}-6-methoxypyridin-3-yl)acetamide

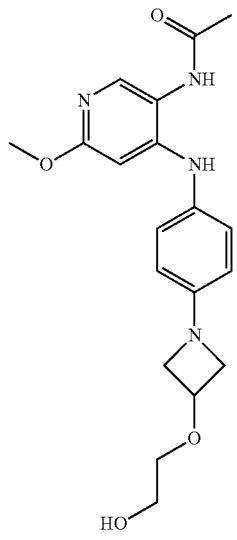

(2) 3-{4-[3-(2-hydroxyethoxy)azetidin-1-yl]phenylamino}-4-nitrobenzamide

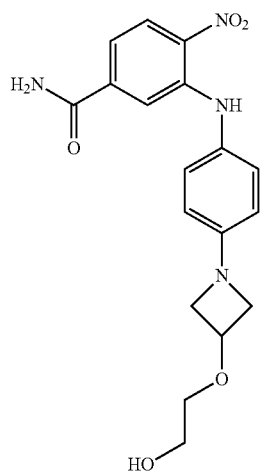
(3) 3-{4-[4-(4-fluoro-5-methoxy-2-nitrophenylamino)phenyl]piperazin-1-yl}-2,2-dimethylpropionic acid
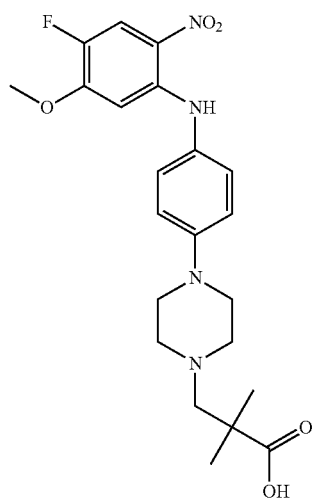 [SMILES: COc1cc(Nc2ccc(N3CCN(CC(C)(C)C(=O)O)CC3)cc2)c([N+](=O)[O-])cc1F]
(4) 4-acetyl-3-{4-[2-(1,1-dioxohexahydro-1λ⁶-thiopyran-4-yloxy)ethoxy]phenylamino}benzamide
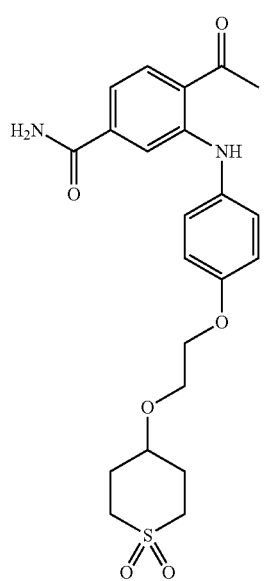 [SMILES: CC(=O)c1ccc(C(N)=O)cc1Nc1ccc(OCCOC2CCS(=O)(=O)CC2)cc1]
(5) 4-acetyl-3-{4-[4-(2-hydroxyethoxy)piperidin-1-yl]phenoxy}benzamide
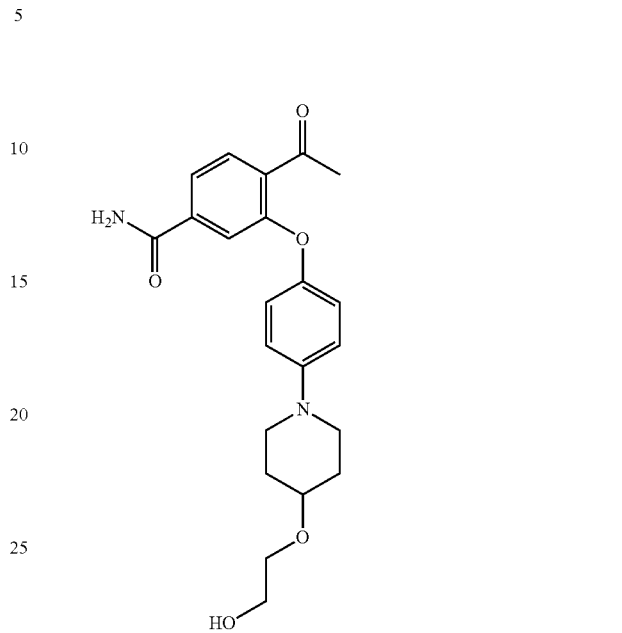
(6) 4-acetyl-3-{4-[2-(tetrahydropyran-4-yloxy)ethoxy]phenoxy}benzamide
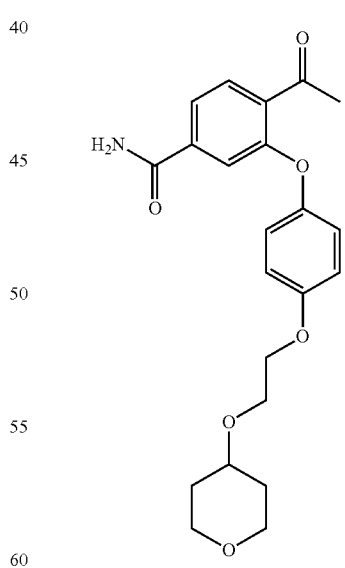
(7) 4-acetyl-3-{4-[2-(2-isopropoxyethoxy)ethoxy]phenoxy}benzamide

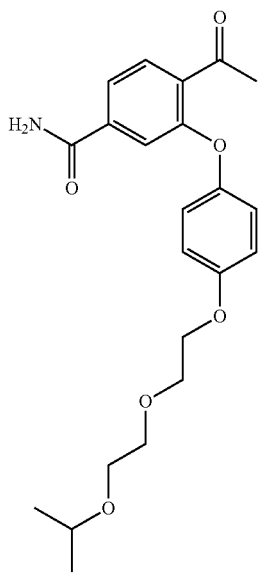 [SMILES: CC(=O)c1ccc(C(N)=O)cc1Oc1ccc(OCCOCCOC(C)C)cc1]
(8) 4-difluoromethyl-3-{4-[2-(tetrahydropyran-4-yloxy)ethoxy]phenoxy}benzamide
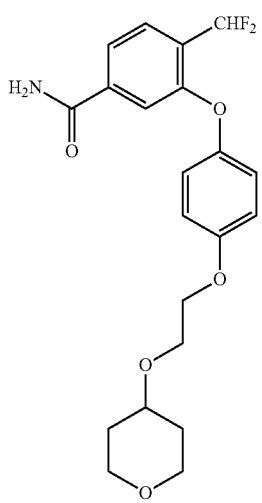 [SMILES: NC(=O)c1ccc(C(F)F)c(Oc2ccc(OCCOC3CCOCC3)cc2)c1]
(9) 4-(1-hydroxyethyl)-3-{4-[2-(tetrahydropyran-4-yloxy)ethoxy]phenoxy}benzamide
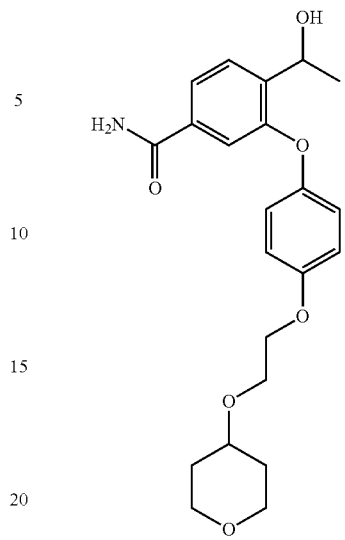
(10) (R)-4-(1-hydroxyethyl)-3-{4-[2-(tetrahydropyran-4-yloxy)ethoxy]phenoxy}benzamide
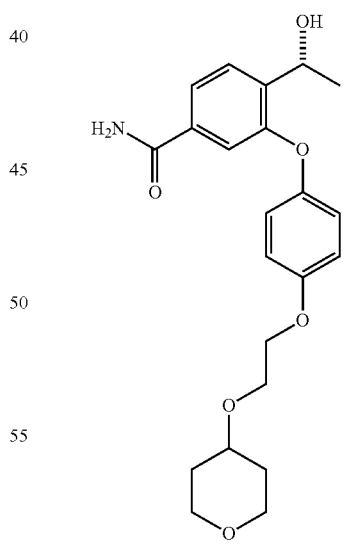
(11) 4-nitro-3-{4-[2-(tetrahydropyran-4-yloxy)ethoxy]phenylamino}benzamide

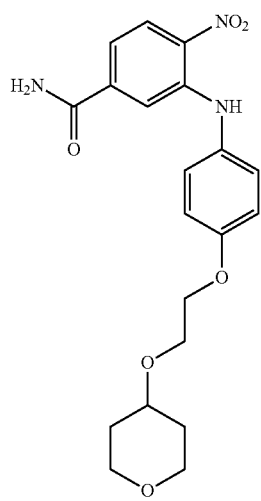 [SMILES: NC(=O)c1ccc([N+](=O)[O-])c(Nc2ccc(OCCOC3CCOCC3)cc2)c1]
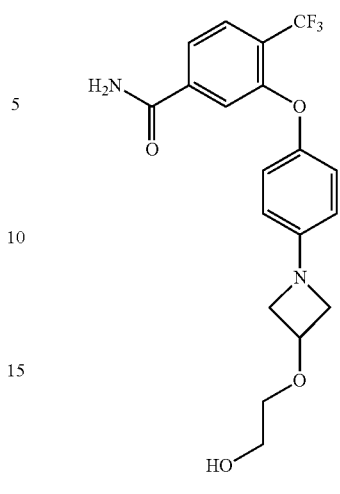
(12) 4-acetyl-2-{4-[2-(1,1-dioxohexahydro-1λ⁶-thiopyran-4-yloxy)ethoxy]phenylamino}benzamide
(14) 4-acetyl-3-{4-[2-(tetrahydrofuran-3-yloxy)ethoxy]phenoxy}benzamide
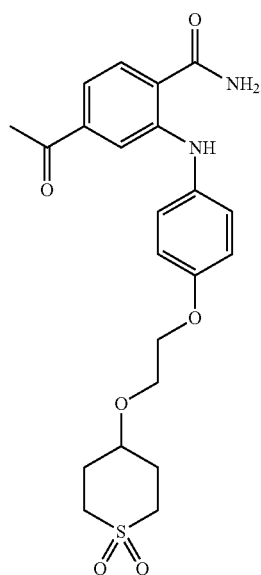 [SMILES: CC(=O)c1ccc(C(N)=O)c(Nc2ccc(OCCOC3CCS(=O)(=O)CC3)cc2)c1]
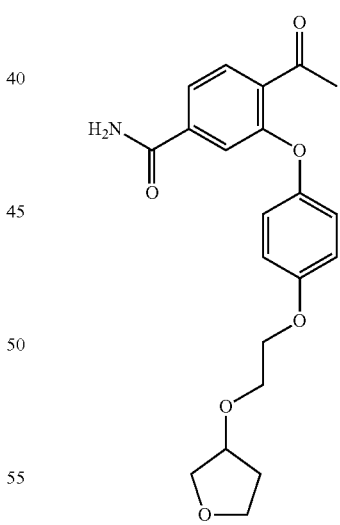
(13) 3-{4-[3-(2-hydroxyethoxy)azetidin-1-yl]phenoxy}-4-trifluoromethylbenzamide
(15) (S)-4-acetyl-3-{4-[2-(tetrahydrofuran-3-yloxy)ethoxy]phenoxy}benzamide

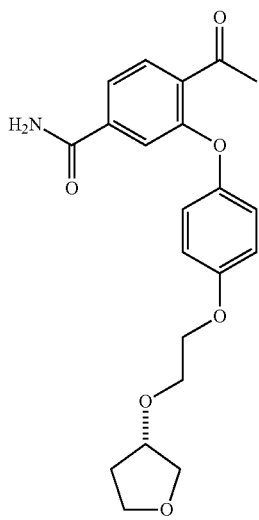

(16) (R)-4-acetyl-3-{4-[2-(tetrahydrofuran-3-yloxy)ethoxy]phenoxy}benzamide

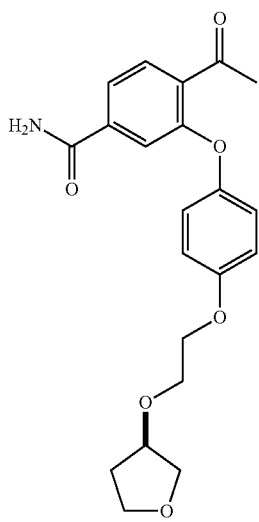

(17) 4-[(R)-1-hydroxyethyl]-3-(4-{2-[(S)-tetrahydrofuran-3-yloxy]ethoxy}phenoxy)benzamide

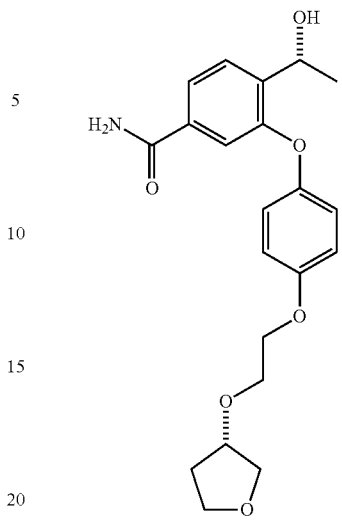

[9] A pharmaceutical composition comprising the compound of any one item selected from [1]-[8] and [1A], or a pharmacologically acceptable salt thereof, as an active ingredient.

[10] The pharmaceutical composition of [9], which is used for promoting bone formation.

[11] The pharmaceutical composition of [9], which is used for improving bone metabolism.

[12] The pharmaceutical composition of [9], which is used for the prophylaxis or treatment of a disease associated with bone metabolism.

[13] The pharmaceutical composition of [12], wherein the disease associated with bone metabolism is osteoporosis.

[14] A method of improving bone metabolism, comprising administering an effective amount of the pharmaceutical composition of [9] to a mammal.

[15] A method of preventing or treating a disease associated with bone metabolism, comprising administering an effective amount of the pharmaceutical composition of [9] to a mammal.

[16] A method of preventing or treating osteoporosis, comprising administering an effective amount of the pharmaceutical composition of [9] to a mammal.

Effect of the Invention

The compound of the present invention has low toxicity, shows good in vivo kinetics, has a bone formation promoting action, and is useful for the prophylaxis or treatment of a metabolic bone disease associated with a decrease in the bone formation ability as compared to the bone resorption capacity. Examples of such metabolic bone disease include osteoporosis, fibrous osteitis (hyperparathyroidism), osteomalacia, and further, Paget's disease that influences the systemic bone metabolism parameter. Particularly, it is useful for senile osteoporosis with reduced bone formation ability. In addition, the pharmaceutical composition of the present invention containing the compound as an active ingredient is also expected to be applicable as a bone formation promoter to the acceleration of healing of bone diseases in the orthopedics field such as bone fracture, bone defect, osteoarthritis and the like, and the treatment of periodontal diseases, stabilization of artificial tooth root and the like in the dental field.

DESCRIPTION OF EMBODIMENTS

The present invention is explained in detail in the following.

The meanings of the terms used for the indication of the compound such as substituent and the like in the present specification are as described below.

halogen atom:
fluorine atom, chlorine atom, bromine atom or iodine atom

C1-C6 alkyl group:
straight chain or branched chain alkyl group having 1 to 6 carbon atoms, preferably methyl group, ethyl group, propyl group, isopropyl group, isobutyl group or tert-butyl group C1-C6 alkylcarbonyl group:
group wherein the above-mentioned C1-C6 alkyl group is bonded to carbonyl group, preferably acetyl group, ethylcarbonyl group, propylcarbonyl group, isopropylcarbonyl group or butylcarbonyl group C1-C6 alkoxy group:
group wherein the above-mentioned C1-C6 alkyl group is bonded to oxygen atom, preferably methoxy group, ethoxy group, propoxy group, isopropoxy group or t-butoxy group C1-C6 alkylcarbonylamino group:
group wherein the above-mentioned C1-C6 alkyl group is bonded to carbonylamino group, preferably acetylamino group, ethylcarbonylamino group, propylcarbonylamino group, isopropylcarbonylamino group or butylcarbonylamino group Halogeno C1-C6 alkyl group:
group wherein the above-mentioned C1-C6 alkyl group is substituted by 1-9 (preferably 1-6, more preferably 1-3) halogen atoms, for example, fluoromethyl group, difluoromethyl group, trifluoromethyl group, fluoroethyl group, difluoroethyl group, trifluoroethyl group, fluoropropyl group, difluoropropyl group, trifluoropropyl group, fluorobutyl group, difluorobutyl group, trifluorobutyl group, fluoropentyl group, difluoropentyl group, trifluoropentyl group, fluorohexyl group, difluorohexyl group, trifluorohexyl group, pentafluoroethyl group, hexafluoropropyl group, nonafluorobutyl group, chloromethyl group, dichloromethyl group, trichloromethyl group, chloroethyl group, dichloroethyl group, trichloroethyl group, chloropropyl group, dichloropropyl group or trichloropropyl group hydroxy C1-C6 alkyl group:
group wherein one hydroxy group is bonded to the above-mentioned C1-C6 alkyl group, preferably 1-hydroxymethyl group, 1-hydroxyethyl group, 1-hydroxypropyl group, 2-hydroxyethyl group or 3-hydroxypropyl group C1-C6 alkylaminocarbonyl group:
group wherein the above-mentioned C1-C6 alkyl group is bonded to aminocarbonyl group, preferably methylaminocarbonyl group or ethylaminocarbonyl group C2-6 alkenyl group:
straight chain or branched chain alkenyl group having 2 to 6 carbon atoms, for example, vinyl group, 1-propenyl (allyl) group, 2-propenyl group, isopropenyl group, 2-methyl-1-propenyl group, 1-butenyl group, 2-butenyl group, 3-butenyl group, 2-buten-2-yl group, 3-methyl-2-butenyl group, 3-methyl-2-buten-2-yl group, 1-pentenyl group, 2-pentenyl group, 3-pentenyl group, 4-pentenyl group, 5-pentenyl group, 2-penten-2-yl group, 2-penten-3-yl group, 4-methyl-1-pentenyl group, 1-hexenyl group, 2-hexenyl group, 3-hexenyl group halogeno C2-C6 alkenyl group:
group wherein straight chain or branched chain alkenyl group having 2 to 6 carbon atoms is substituted by 1-5 (preferably 1-3, more preferably 1 or 2) halogen atoms, for example, 1-fluorovinyl group, 1-chlorovinyl group, 1-bromovinyl group, trifluorovinyl group, trichlorovinyl group or tribromovinyl group saturated heterocyclic group:
saturated 5-7 membered heterocyclic group containing 1 to 3 sulfur atoms, oxygen atoms and/or nitrogen atoms, for example, tetrahydropyranyl group, tetrahydrofuranyl group, oxotetrahydrofuranyl group, morpholinyl group, thiomorpholinyl group, 1-oxothiomorpholinyl group, 1,1-dioxothiomorpholinyl group, pyrrolidinyl group, pyrrolinyl group, imidazolidinyl group, pyrazolidinyl group, piperidinyl group, piperazinyl group, oxazolidinyl group, isoxazolidinyl group, thiazolidinyl group, 1,4-dioxanyl group or 1,1-dioxohexahydrothiopyranyl group.

The "-saturated heterocycle-" shows a divalent group derived from a saturated hetero ring, and examples of the saturated hetero ring include azetidine ring, tetrahydropyran ring, tetrahydrofuran ring, a morpholine ring, thiomorpholine ring, 1-oxothiomorpholine ring, 1,1-dioxothiomorpholine ring, pyrrolidine ring, pyrroline ring, imidazolidine ring, pyrazolidine ring, piperidine ring, piperazine ring, oxazolidine ring, isoxazolidine ring, and thiazolidine ring.

The "optionally substituted" means unsubstituted or any of 1 to 3 substitutions. When di- or tri-substituted, the respective substituents may be the same or different.

The definition of each symbol in the formula (I) is described in detail below.

$R^1$ is cyano group, C1-6 alkylcarbonyl group, C1-6 alkylcarbonylamino group, nitro group, halogeno C1-6 alkyl group, C2-6 alkenyl group, halogeno C2-6 alkenyl group, carbamoyl group, or hydroxy C1-6 alkyl group.

In another embodiment of the present invention, $R^1$ is cyano group, C1-6 alkylcarbonyl group, C1-6 alkylcarbonylamino group, nitro group, halogeno C1-6 alkyl group, halogeno C2-6 alkenyl group, carbamoyl group, or hydroxy C1-6 alkyl group.

As "C1-6 alkylcarbonyl group" for $R^1$, methylcarbonyl group (acetyl group) is preferable.

As "C1-6 alkylcarbonylamino group" for $R^1$, methylcarbonylamino group (acetylamino group), ethylcarbonylamino group, or propylcarbonylamino group is preferable.

As "halogeno C1-6 alkyl group" for $R^1$, fluoromethyl group, difluoromethyl group, trifluoromethyl group, 1-fluoroethyl group, or 1,1-difluoroethyl group is preferable.

As "C2-6 alkenyl group" for $R^1$, vinyl group is preferable.

As "halogeno C2-6 alkenyl group" for $R^1$, 1-fluorovinyl group is preferable.

As "hydroxy C1-6 alkyl group" for $R^1$, hydroxymethyl group, or 1-hydroxyethyl group is preferable.

$R^1$ is preferably cyano group, acetyl group, acetylamino group, ethylcarbonylamino group, propylcarbonylamino group, nitro group, fluoromethyl group, trifluoromethyl group, 1,1-difluoroethyl group, 1-fluoroethyl group, difluoromethyl group, vinyl group, 1-fluorovinyl group, carbamoyl group, hydroxymethyl group, or 1-hydroxyethyl group, more preferably, cyano group, acetyl group, acetylamino group, nitro group, trifluoromethyl group, 1,1-difluoroethyl group, 1-fluoroethyl group, difluoromethyl group, carbamoyl group, or 1-hydroxyethyl group.

In another embodiment of the present invention, $R^1$ is preferably cyano group, acetyl group, acetylamino group, ethylcarbonylamino group, propylcarbonylamino group, nitro group, fluoromethyl group, trifluoromethyl group, 1,1- difluoroethyl group, 1-fluoroethyl group, difluoromethyl group, 1-fluorovinyl group, carbamoyl group, hydroxymethyl group, or 1-hydroxyethyl group, more preferably, cyano group, acetyl group, acetylamino group, nitro group, trifluoromethyl group, 1,1-difluoroethyl group, 1-fluoroethyl group, difluoromethyl group, carbamoyl group, or 1-hydroxyethyl group.

$R^2$ is C1-6 alkoxy group, carbamoyl group, C1-6 alkylaminocarbonyl group, or 01-6 alkylcarbonyl group.

As "C1-6 alkoxy group" for $R^2$, methoxy group is preferable.

As "C1-6 alkylaminocarbonyl group" for $R^2$, methylaminocarbonyl group, ethylaminocarbonyl group is preferable.

As "C1-6 alkylcarbonyl group" for $R^2$, methylcarbonyl group (acetyl group) is preferable.

$R^2$ is preferably methoxy group, carbamoyl group, methylaminocarbonyl group, ethylaminocarbonyl group, or methylcarbonyl group (acetyl group), more preferably, methoxy group, carbamoyl group, methylaminocarbonyl-'group, or acetyl group.

$R^3$ is a hydrogen atom, or a halogen atom.

As "halogen atom" for $R^3$, fluorine atom is preferable.

$R^3$ is preferably a hydrogen atom, or a fluorine atom.

As for S, T and U, when any one of S, T and U is =N—, the others are =CH— (=C— when $R^3$ is substituted); or all of S, T and U are =CH— (=C— when $R^3$ is substituted).

As for S, T and U, S is preferably =N—, and T and U are =CH—, or all of S, T and U are =CH—, more preferably all of S, T and U are =CH—.

W is —NH—, —O—, or —S—.

W is preferably —NH—, or —O—.

X is a single bond, -saturated heterocycle-, —CH$_2$—(CH$_2$)$_n$—, —O—(CH$_2$)$_n$—, —(CH$_2$)$_n$—O—, or —CH=CH—(CH$_2$)$_n$— [n is any one integer selected from 1-4].

In another embodiment of the present invention, X is -saturated heterocycle-, —CH$_2$—(CH$_2$)$_n$—, —O—(CH$_2$)$_n$—, —(CH$_2$)$_n$—O—, or —CH=CH—(CH$_2$)$_n$— [n is any one integer selected from 1-4].

As "-saturated heterocycle-" for X, azetidinediyl, piperidinediyl, or piperazinediyl is preferable.

When X is —CH$_2$—(CH$_2$)$_n$—, n is preferably 1 or 2, i.e., X is preferably —CH$_2$—CH$_2$— or —CH$_2$—CH$_2$—CH$_2$—.

When X is —O—(CH$_2$)$_n$—, n is preferably 1 or 2, i.e., X is preferably —O—CH$_2$— or —O—CH$_2$—CH$_2$—.

When X is —(CH$_2$)$_n$—O—, n is preferably 1, i.e., X is preferably —CH$_2$—O—.

When X is —CH=CH—(CH$_2$)$_n$—, n is preferably 1, i.e., X is preferably —CH=CH—CH$_2$—.

X is preferably a single bond, -saturated heterocycle- (e.g., azetidinediyl, piperidinediyl, piperazinediyl), —CH$_2$—CH$_2$—, —CH$_2$—CH$_2$—CH$_2$—, —O—CH$_2$—, —O—CH$_2$—CH$_2$—, —CH$_2$—O—, or —CH=CH—CH$_2$—, more preferably, -saturated heterocycle- (e.g., azetidinediyl, piperidinediyl, piperazinediyl), or —O—CH$_2$—CH$_2$—[—O—(CH$_2$)$_n$—, n is 2].

In another embodiment of the present invention, X is preferably -saturated heterocycle- (e.g., azetidinediyl, piperidinediyl, piperazinediyl), —CH$_2$—CH$_2$—, —CH$_2$—CH$_2$—CH$_2$—, —O—CH$_2$—, —O—CH$_2$—CH$_2$—, —CH$_2$—O—, or —CH=CH—CH$_2$—, more preferably -saturated heterocycle- (e.g., azetidinediyl, piperidinediyl, piperazinediyl), or —O—CH$_2$—CH$_2$— [—O—(CH$_2$)$_n$—, n is 2].

Y is a single bond, —O—, or —CO—.

Y is preferably a single bond, or —O—.

Z is a hydrogen atom, saturated heterocyclic group optionally substituted by any group selected from substituent group α, or C1-6 alkyl group optionally substituted by any group selected from substituent group α, and the substituent group α includes saturated heterocyclic group, hydroxy C1-6 alkyl group, aminosulfonylamino group, carboxy group, hydroxy group, C1-6 alkoxy group, and C1-6 alkyl group.

In another embodiment of the present invention, Z is a hydrogen atom, saturated heterocyclic group optionally substituted by any group selected from substituent group α, or C1-6 alkyl group optionally substituted by any group selected from substituent group α, the substituent group α includes hydroxy C1-6 alkyl group, aminosulfonylamino group, carboxy group, hydroxy group, C1-6 alkoxy group, and C1-6 alkyl group.

As the "saturated heterocyclic group" of the "saturated heterocyclic group optionally substituted by any group selected from substituent group α" for Z, tetrahydrofuranyl group, oxotetrahydrofuranyl group, tetrahydropyranyl group, morpholinyl group, piperidinyl group, piperazinyl group, 1,4-dioxanyl group, or 1,1-dioxohexahydrothiopyranyl group is preferable.

As the group selected from the substituent group α, hydroxy C1-6 alkyl group (e.g., hydroxymethyl group), or C1-6 alkyl group (e.g., methyl group) is preferable.

As the "C1-6 alkyl group" of the "C1-6 alkyl group optionally substituted by any group selected from substituent group α" for Z, methyl group, ethyl group, propyl group, isopropyl group, or isobutyl group is preferable.

As the group selected from the substituent group α, saturated heterocyclic group (e.g., tetrahydrofuranyl group, morpholinyl group), aminosulfonylamino group, carboxy group, hydroxy group, or C1-6 alkoxy group (e.g., isopropoxy group) is preferable.

In another embodiment of the present invention, as the group selected from the substituent group α, aminosulfonylamino group, carboxy group, hydroxy group, or C1-6 alkoxy group (e.g., isopropoxy group) is preferable.

Z is preferably saturated heterocyclic group (e.g., tetrahydrofuranyl group, oxotetrahydrofuranyl group, tetrahydropyranyl group, morpholinyl group, piperidinyl group, piperazinyl group, 1,4-dioxanyl group, 1,1-dioxohexahydrothiopyranyl group) optionally substituted by any group selected from a hydrogen atom, hydroxy C1-6 alkyl group (e.g., hydroxymethyl group), and C1-6 alkyl group (e.g., methyl group), or C1-6 alkyl group (e.g., methyl group, ethyl group, propyl group, isopropyl group, isobutyl group) optionally substituted by any group selected from saturated heterocyclic group (e.g., tetrahydrofuranyl group, morpholinyl group), aminosulfonylamino group, carboxy group, hydroxy group, and C1-6 alkoxy group (e.g., isopropoxy group), more preferably C1-6 alkyl group substituted by a hydroxy group (e.g., methyl group, ethyl group, propyl group, isopropyl group, isobutyl group), tetrahydrofuranyl group, tetrahydropyranyl group, piperazinyl group, or morpholinyl group.

In another embodiment of the present invention, Z is preferably a saturated heterocyclic group (e.g., tetrahydrofuranyl group, oxotetrahydrofuranyl group, tetrahydropyranyl group, morpholinyl group, piperidinyl group, piperazinyl group, 1,4-dioxanyl group, 1,1-dioxohexahydrothiopyranyl group) optionally substituted by any group selected from hydrogen atom, hydroxy C1-6 alkyl group (e.g., hydroxymethyl group), and C1-6 alkyl group (e.g., methyl group), or C1-6 alkyl group (e.g., methyl group, ethyl group, propyl group, isopropyl group, isobutyl group) optionally substituted by any group selected from aminosulfonylamino group, carboxy group, hydroxy group, and C1-6 alkoxy group (e.g., isopropoxy group), more preferably, C1-6 alkyl group substituted by a hydroxy group (e.g., methyl group, ethyl group, propyl group, isopropyl group, isobutyl group), tetrahydrofuranyl group, tetrahydropyranyl group, piperazinyl group, or morpholinyl group.

As preferable compound (I), the following compounds can be mentioned.

[Compound I-1-1]

Compound (I) wherein $R^1$ is cyano group, acetyl group, acetylamino group, ethylcarbonylamino group, propylcarbonylamino group, nitro group, fluoromethyl group, trifluoromethyl group, 1,1-difluoroethyl group, 1-fluoroethyl group, difluoromethyl group, vinyl group, 1-fluorovinyl group, carbamoyl group, hydroxymethyl group, or 1-hydroxyethyl group;

$R^2$ is methoxy group, carbamoyl group, methylaminocarbonyl group, ethylaminocarbonyl group, or methylcarbonyl group (acetyl group);

$R^3$ is a hydrogen atom or a fluorine atom;

S is =N—, and T and U are =CH—, or all of S, T and U are =CH—;

W is —NH—, —O—, or —S—;

X is a single bond, -saturated heterocycle- (e.g., azetidinediyl, piperidinediyl, piperazinediyl), —CH$_2$—CH$_2$—, —CH$_2$—CH$_2$—CH$_2$—, —O—CH$_2$—, —O—CH$_2$—CH$_2$—, —CH$_2$—O—, or —CH=CH—CH$_2$—;

Y is a single bond, —O—, or —CO—; and

Z is saturated heterocyclic group (e.g., tetrahydrofuranyl group, oxotetrahydrofuranyl group, tetrahydropyranyl group, morpholinyl group, piperidinyl group, piperazinyl group, 1,4-dioxanyl group, 1,1-dioxohexahydrothiopyranyl group) optionally substituted by any group selected from a hydrogen atom, hydroxy C1-6 alkyl group (e.g., hydroxymethyl group), and C1-6 alkyl group (e.g., methyl group), or C1-6 alkyl group (e.g., methyl group, ethyl group, propyl group, isopropyl group, isobutyl group) optionally substituted by any group selected from saturated heterocyclic group (e.g., tetrahydrofuranyl group, morpholinyl group), aminosulfonylamino group, carboxy group, hydroxy group, and C1-6 alkoxy group (e.g., isopropoxy group).

[Compound I-1-2]

Compound (I) wherein $R^1$ is cyano group, acetyl group, acetylamino group, ethylcarbonylamino group, propylcarbonylamino group, nitro group, fluoromethyl group, trifluoromethyl group, 1,1-difluoroethyl group, 1-fluoroethyl group, difluoromethyl group, 1-fluorovinyl group, carbamoyl group, hydroxymethyl group, or 1-hydroxyethyl group;

$R^2$ is methoxy group, carbamoyl group, methylaminocarbonyl group, ethylaminocarbonyl group, or methylcarbonyl group (acetyl group);

$R^3$ is a hydrogen atom or a fluorine atom;

S is =N—, and T and U are =CH—, or all of S, T and U are =CH—;

W is —NH—, —O—, or —S—;

X is -saturated heterocycle- (e.g., azetidinediyl, piperidinediyl, piperazinediyl), —CH$_2$—CH$_2$—, —CH$_2$—CH$_2$—CH$_2$—, —O—CH$_2$—, —O—CH$_2$—CH$_2$—, —CH$_2$—O—, or —CH=CH—CH$_2$—;

Y is a single bond, —O—, or —CO—; and

Z is saturated heterocyclic group (e.g., tetrahydrofuranyl group, oxotetrahydrofuranyl group, tetrahydropyranyl group, morpholinyl group, piperidinyl group, piperazinyl group, 1,4-dioxanyl group, 1,1-dioxohexahydrothiopyranyl group) optionally substituted by any group selected from a hydrogen atom, hydroxy C1-6 alkyl group (e.g., hydroxymethyl group), and C1-6 alkyl group (e.g., methyl group), or C1-6 alkyl group (e.g., methyl group, ethyl group, propyl group, isopropyl group, isobutyl group) optionally substituted by any group selected from aminosulfonylamino group, carboxy group, hydroxy group, and C1-6 alkoxy group (e.g., isopropoxy group).

[Compound I-2]

Compound (I) wherein $R^1$ is cyano group, acetyl group, acetylamino group, nitro group, trifluoromethyl group, 1,1-difluoroethyl group, 1-fluoroethyl group, difluoromethyl group, carbamoyl group, or 1-hydroxyethyl group;

$R^2$ is methoxy group, carbamoyl group, methylaminocarbonyl group, or acetyl group;

$R^3$ is a hydrogen atom or a fluorine atom;

all of S, T and U are =CH—;

W is —NH—, or —O—;

X is -saturated heterocycle- (e.g., azetidinediyl, piperidinediyl, piperazinediyl), or —O—CH$_2$—CH$_2$—;

Y is a single bond, or —O—; and

Z is C1-6 alkyl group (e.g., methyl group, ethyl group, propyl group, isopropyl group, isobutyl group) substituted by a hydroxy group, tetrahydrofuranyl group, tetrahydropyranyl group, piperazinyl group, or morpholinyl group.

[Compound I-3]

Compound (I) wherein $R^1$ is acetyl group, acetylamino group, nitro group, trifluoromethyl group, difluoromethyl group, carbamoyl group, or 1-hydroxyethyl group;

$R^2$ is methoxy group, carbamoyl group, or acetyl group;

$R^3$ is a hydrogen atom or a fluorine atom;

S is =N—, and T and U are =CH—, or all of S, T and U are =CH—;

W is —NH—, or —O—;

X is -saturated heterocycle- (e.g., azetidinediyl, piperidinediyl, piperazinediyl), or —O—CH$_2$—CH$_2$—;

Y is a single bond, or —O—; and

Z is C1-6 alkyl group (e.g., ethyl group, isobutyl group) substituted by any group selected from carboxy group, hydroxy group, and C1-6 alkoxy group (e.g., isopropoxy group), tetrahydrofuranyl group, tetrahydropyranyl group, or 1,1-dioxohexahydrothiopyranyl group.

Specific examples of compound (I) include the compounds of Examples 1-99, among others, (1) N-(4-{4-[3-(2-hydroxyethoxy)azetidin-1-yl]phenylamino}-6-methoxypyridin-3-yl)acetamide, (2) 3-{4-[3-(2-hydroxyethoxy)azetidin-1-yl]phenylamino}-4-nitrobenzamide, (3) 3-{4-[4-(4-fluoro-5-methoxy-2-nitrophenylamino)phenyl]piperazin-1-yl}-2,2-dimethylpropionic acid, (4) 4-acetyl-3-{4-[2-(1,1-dioxohexahydro-1$\lambda^6$-thiopyran-4-yloxy)ethoxy]phenylamino}benzamide, (5) 4-acetyl-3-{4-[4-(2-hydroxyethoxy)piperidin-1-yl]phenoxy}benzamide, (6) 4-acetyl-3-{4-[2-(tetrahydropyran-4-yloxy)ethoxy]phenoxy}benzamide, (7) 4-acetyl-3-{4-[2-(2-isopropoxyethoxy)ethoxy]phenoxy}benzamide, (8) 4-difluoromethyl-3-{4-[2-(tetrahydropyran-4-yloxy)ethoxy]phenoxy}benzamide, (9) 4-(1-hydroxyethyl)-3-{4-[2-(tetrahydropyran-4-yloxy)ethoxy]phenoxy}benzamide,

(10) (R)-4-(1-hydroxyethyl)-3-{4-[2-(tetrahydropyran-4-yloxy)ethoxy]phenoxy}benzamide,

(11) 4-nitro-3-{4-[2-(tetrahydropyran-4-yloxy)ethoxy]phenylamino}benzamide,

(12) 4-acetyl-2-{4-[2-(1,1-dioxohexahydro-1λ$^6$-thiopyran-4-yloxy)ethoxy]phenylamino}benzamide,
(13) 3-{4-[3-(2-hydroxyethoxy)azetidin-1-yl]phenoxy}-4-trifluoromethylbenzamide,
(14) 4-acetyl-3-{4-[2-(tetrahydrofuran-3-yloxy)ethoxy]phenoxy}benzamide,
(15) (S)-4-acetyl-3-{4-[2-(tetrahydrofuran-3-yloxy)ethoxy]phenoxy}benzamide,
(16) (R)-4-acetyl-3-{4-[2-(tetrahydrofuran-3-yloxy)ethoxy]phenoxy}benzamide, or
(17) 4-[(R)-1-hydroxyethyl]-3-(4-{2-[(S)-tetrahydrofuran-3-yloxy]ethoxy}phenoxy)benzamide is preferable.

To "treat" means curing a disease or symptom.

A "pharmacologically acceptable salt thereof" shows a salt that can be used as a medicament. When the compound of the present invention has an acidic group or basic group, since it can be converted to a basic salt or acidic salt by reacting with a base or acid, a salt thereof is used.

A pharmacologically acceptable "basic salt" of the compound of the present invention is preferably an alkali metal salt such as sodium salt, potassium salt, and lithium salt; alkaline earth metal salt such as magnesium salt, and calcium salt; a salt with organic base such as N-methylmorpholine salt, triethylamine salt, tributylamine salt, diisopropylethylamine salt, dicyclohexylamine salt, N-methylpiperidine salt, pyridine salt, 4-pyrrolidinopyridine salt, and picoline salt or an amino acid salt such as glycine salt, lysine salt, arginine salt, ornithine salt, glutamate, and aspartate, preferably an alkali metal salt.

A pharmacologically acceptable "acidic salt" of the compound of the present invention is preferably inorganic acid salt such as hydrohalide (e.g., hydrofluoride, hydrochloride, hydrobromide, hydroiodide), nitrate, perchlorate, sulfate, phosphate and the like; organic acid salt such as lower alkanesulfonate (e.g., methanesulfonate, trifluoromethanesulfonate, ethanesulfonate), arylsulfonate (e.g., benzenesulfonate, p-toluenesulfonate), acetate, malate, fumarate, succinate, citrate, ascorbate, tartrate, oxalate, maleate and the like; or amino acid salt such as glycine salt, lysine salt, arginine salt, ornithine salt, glutamate, aspartate, most preferably hydrohalide (particularly, hydrochloride).

The compound of the present invention or a pharmacologically acceptable salt thereof sometimes absorbs moisture, is attached with adsorbed water, or becomes hydrate by being left in the air or recrystallized, and the present invention also encompasses such various hydrates, solvates and compounds with crystal polymorphism.

The compound of the present invention, a pharmacologically acceptable salt thereof or a solvate thereof may contain, depending on the kind and combination of substituents, various isomers such as geometric isomer (e.g., cis form, trans form and the like), tautomer, optical isomer (e.g., d form, l form and the like), and the like. Unless particularly limited, the compound of the present invention also encompasses all those isomers, stereoisomers and mixtures of these isomers and stereoisomers at any ratio. The mixtures of these isomers and stereoisomers can be isolated by a known separation means. The above-mentioned isomer can also be produced by asymmetric synthesis.

The compound of the present invention also includes labeled compounds, that is, the compound of the present invention wherein one or more atoms are substituted by an isotope (e.g., $^2$H, $^3$H, $^{13}$C, $^{14}$C $^{35}$S etc.)

The present invention also encompasses a pharmacologically acceptable prodrug of the compound of the present invention. The pharmacologically acceptable prodrug is a compound having a group convertible to amino group, hydroxy group, carboxy group and the like of the compound of the present invention by hydrolysis or under physiological conditions. A group that forms such prodrug includes, for example, the groups described in Prog. Med., vol. 5, pages 2157-2161, 1985, and "Development of Pharmaceutical Product" (Hirokawa-Shoten Ltd., 1990) vol. 7, molecule design, pages 163-198. More specific examples of the prodrug include, when the compound of the present invention has an amino group, the compound wherein the amino group thereof is acylated, alkylated, phosphorylated (e.g., compounds wherein the amino group thereof is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, or tert-butylated) and the like, when the compound of the present invention has a hydroxy group, the compound wherein a hydroxy group thereof is acylated, alkylated, phosphorylated, or borated (e.g., compounds wherein the hydroxy group thereof is acetylated, palmitoylated, propanoylated, pivaloylated, succinylated, fumarylated, alanylated, or dimethylaminomethylcarbonylated, etc.), and the like. When the compound of the present invention contains a carboxy group, the compound wherein a carboxy group thereof is esterified or amidated (e.g., compounds wherein the carboxy group thereof is ethyl esterified, phenyl esterified, carboxymethyl esterified, dimethylaminomethyl esterified, pivaloyloxymethyl esterified, 1-ethoxycarbonyloxyethyl esterified, 1-cyclohexyloxycarbonyloxyethyl esterified, amidated or methylamidated etc.) and the like can be mentioned.

(Production Method)

The compound of the present invention can be produced utilizing the characteristics based on the kind of the basic skeleton or substituent, and applying various known production methods. Examples of the known method include the methods described in "ORGANIC FUNCTIONAL GROUP PREPARATIONS", 2nd edition, ACADEMIC PRESS, INC., 1989, "Comprehensive Organic Transformations", VCH Publishers Inc., 1989, and the like.

In this case, depending on the kind of the functional group, it is sometimes effective for the production techniques to protect the functional group with a suitable protecting group in the stage of a starting material or intermediate, or replace same with a group easily convertible to the functional group.

Examples of such functional group include amino group, hydroxy group, carboxy group and the like and examples of the protecting group thereof include the protecting groups described in T.W. Greene and P.G. Wuts, "Protective Groups in Organic Synthesis (3rd ed., 1999)", from which an appropriate one can be selected and used according to the reaction conditions thereof. According to such method, a desired compound can be obtained by introducing the substituent, performing the reaction, and removing the protecting group as necessary, or converting to a desired group.

A prodrug of the compound of the present invention can be produced by, similar to the above-mentioned protecting groups, introducing a particular group in the stage of a starting material or intermediate, or by a reaction using the obtained compound of the present invention. The reaction can be performed by applying a method known to those of ordinary skill in the art such as general esterification, amidation, dehydration, hydrogenation and the like.

The production method of the compound of the present invention is described below. However, the production method is not at all limited by the following methods.

As the starting compound of each reaction, unless specific production method is described, a commercially available one can be readily obtained and used, or can also be produced according to a method known per se, or a method analogous thereto.

(Method A)

In Method A, compound (a-1) and compound (a-2) are coupled to produce the compound (a-3) of the present invention.

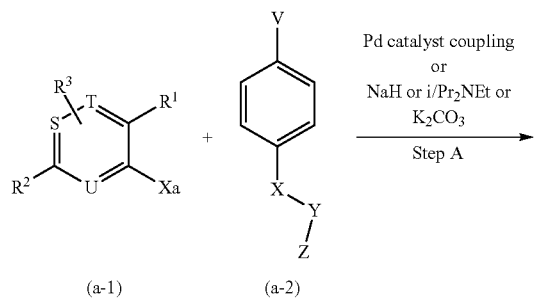

(a-1)  (a-2)

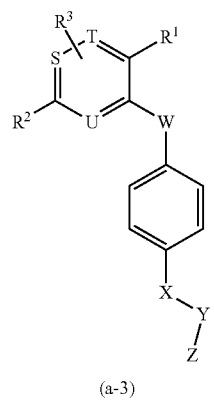

(a-3)

In the above-mentioned scheme, $R^1$, $R^2$, $R^3$, S, T, U, W, X, Y and Z are as defined above, Xa is a leaving group such as a halogen atom, a trifluoromethanesulfonyloxy group and the like, and V is —$NH_2$, —OH or —SH.

Step A: This step includes a reaction using a palladium catalyst and a nucleophilic substitution reaction using a metal hydride such as NaH and the like, an organic base such as i-$Pr_2$NEt, or an inorganic base such as $K_2CO_3$ and the like, by which the compound (a-3) of the present invention is produced from compound (a-1) and compound (a-2) in an inert solvent.

The amount of compound (a-2) to be used is generally 1-3 equivalents, preferably 1-1.5 equivalents, relative to compound (a-1).

The amount of the palladium catalyst to be used is generally 0.01-0.2 equivalent, preferably 0.01-0.1 equivalent, relative to compound (a-1).

The amount of metal hydride to be used is generally 1-3 equivalents, preferably 1-1.5 equivalents, relative to compound (a-1).

The amount of the organic base to be used is generally 1-5 equivalents, preferably 1-3 equivalents, relative to compound (a-1).

The amount of the inorganic base to be used is generally 1-5 equivalents, preferably 1-3 equivalents, relative to compound (a-1).

The inert solvent to be used includes, for example, alcohols such as methanol, ethanol, propanol, 2-propanol and butanol; aromatic hydrocarbons such as benzene, toluene, and xylene; ethers such as diethyl ether, diisopropyl ether, tetrahydrofuran, dioxane and 1,2-dimethoxyethane; amides such as N,N-dimethylformamide, N,N-dimethylacetamide, N-methyl-2-pyrrolidone, N-methylpyrrolidinone and hexamethylphosphorotriamide; halogenated hydrocarbons such as methylene chloride, chloroform, carbon tetrachloride, dichloroethane, chlorobenzene, o-dichlorobenzene, m-dichlorobenzene, fluorobenzene, trichloromethylbenzene and trifluoromethylbenzene, and a mixture of these.

While the reaction temperature varies depending on the starting compound and the solvent to be used, it is generally 0° C. to the refluxing temperature of the reaction mixture, preferably room temperature to the refluxing temperature of the reaction mixture.

While the reaction time varies depending on the starting compound, the solvent to be used and the reaction temperature, it is generally 30 min to 96 hr, preferably 30 min to 24 hr.

(Method B)

In Method B, similar to Method A, compound (b-1) and compound (b-2) are coupled to produce the compound (a-3) of the present invention.

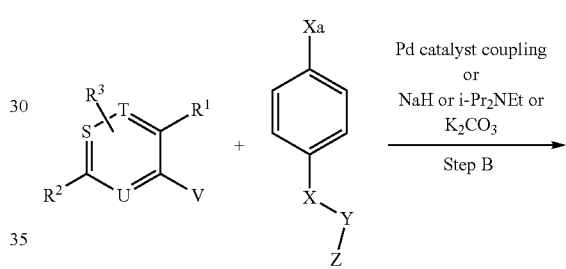

(b-1)  (b-2)

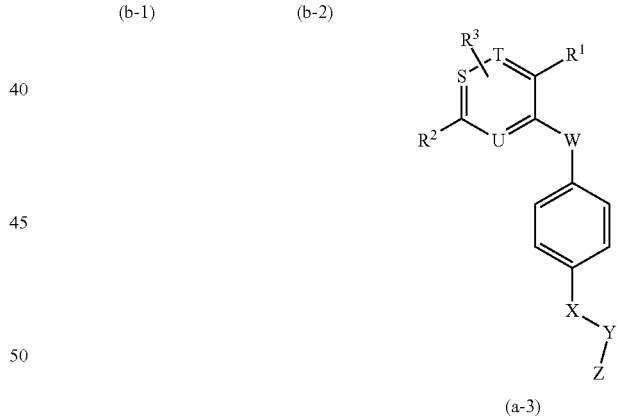

(a-3)

In the above-mentioned scheme, $R^1$, $R^2$, $R^3$, S, T, U, V, X, Y, Z and Xa are as defined above.

Step B: This step includes a reaction using a palladium catalyst and a nucleophilic substitution reaction using a metal hydride such as NaH and the like, an organic base such as i-$Pr_2$NEt, or an inorganic base such as $K_2CO_3$ and the like, by which the compound (a-3) is produced from compound (b-1) and compound (b-2).

(Method C)

In Method C, the compound (c-4) of the present invention wherein $R^2$ in the formula (I) is a carbamoyl group or C1-6 alkylaminocarbonyl group is produced.

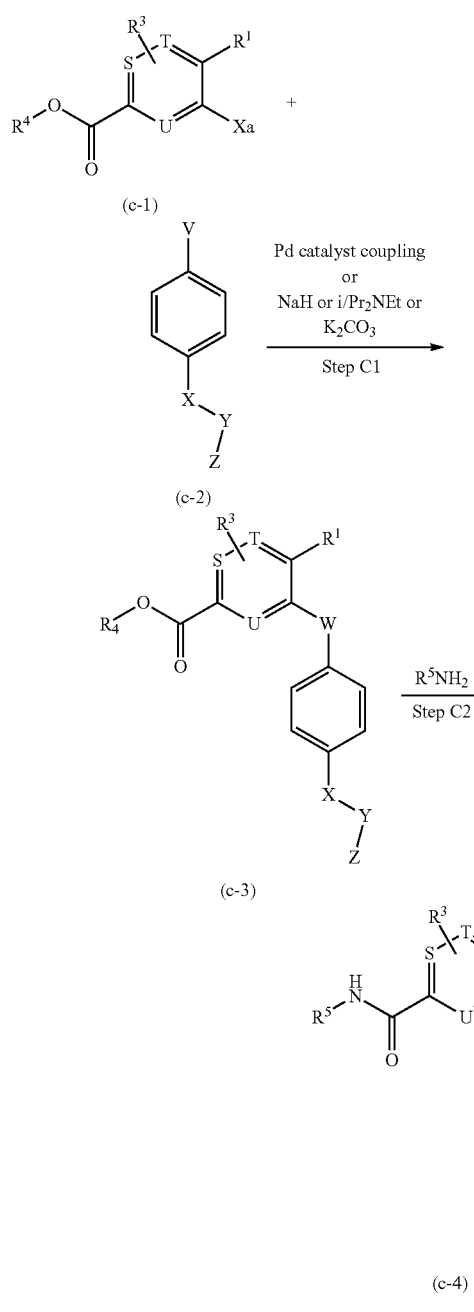

(c-1)

(c-2)

(c-3)

(c-4)

performing a condensation reaction with amine. The amidation reaction to directly convert an ester group to an amide group can be performed according to the methods described in Chem. Rev., 1948, 45, 203, J. Am. Chem. Soc., 1950, 72, 1888, Org. Biol. Chem., 1962, 84, 4457, J. Am. Chem. Soc., 1973, 95, 875, J. Am. Chem. Soc., 1981, 103, 7090 and the like.

(Method D)

In Method D, the compound (d-2) of the formula (I) wherein $R^1$ is a C1-6 alkylcarbonyl group and $R^2$ is a carbamoyl group or a C1-6 alkylaminocarbonyl group of the present invention is produced.

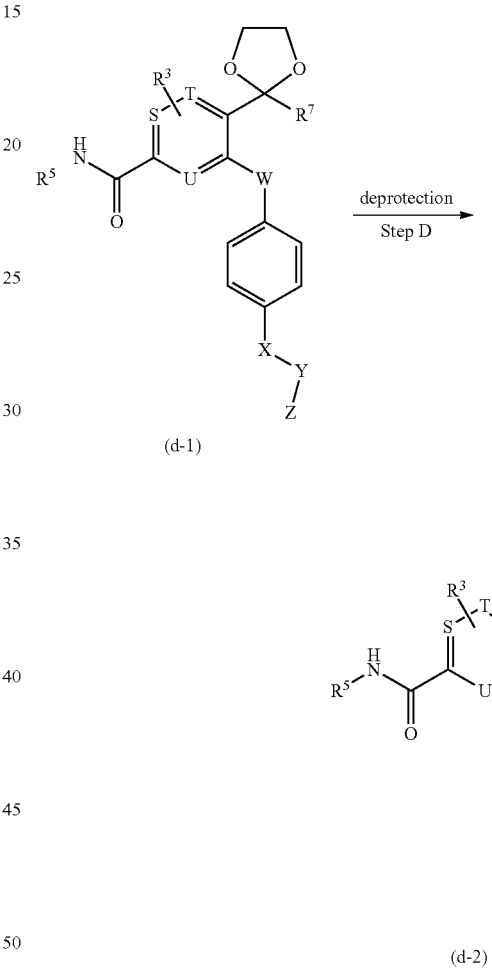

(d-1)

(d-2)

In the above-mentioned scheme, $R^1$, $R^3$, S, T, U, V, X, Y, Z and Xa are as defined above, $R^4$ is a carboxyl-protecting group such as C1-6 alkyl group and the like, and $R^5$ is hydrogen or a C1-6 alkyl group.

Step C1: This step is a coupling reaction using a palladium catalyst or a nucleophilic substitution reaction using a metal hydride such as NaH and the like, an organic base such as i-Pr$_2$NEt, an inorganic base such as K$_2$CO$_3$ and the like, and compound (c-3) is produced from compound (c-1) and compound (c-2). This step can be performed under conditions similar to those in Method A.

Step C2: In this step, compound (c-3) is converted to compound (c-4) by an amidation reaction. This amidation step includes a method of directly converting an ester group to an amide group, and an amidation method including hydrolyzing an ester group into a carboxyl group, and In the above-mentioned scheme, $R^3$, $R^5$, S, T, U, X, Y and Z are as defined above, and $R^7$ is a C1-6 alkyl group.

Step D: In compound (d-1), the carbonyl group is protected by acetal. This step is a step for deprotecting the protecting group. The deprotection method of acetal can be performed according to the method described in, for example, T.W. Greene and P.G. Wuts, "Protective Groups in Organic Synthesis (3rd ed., 1999)".

(Method E)

In Method E, the compound (e-3) of the formula (I) wherein $R^1$ and $R^2$ are each independently a C1-6 alkylcarbonyl group or a carbamoyl group of the present invention is produced.

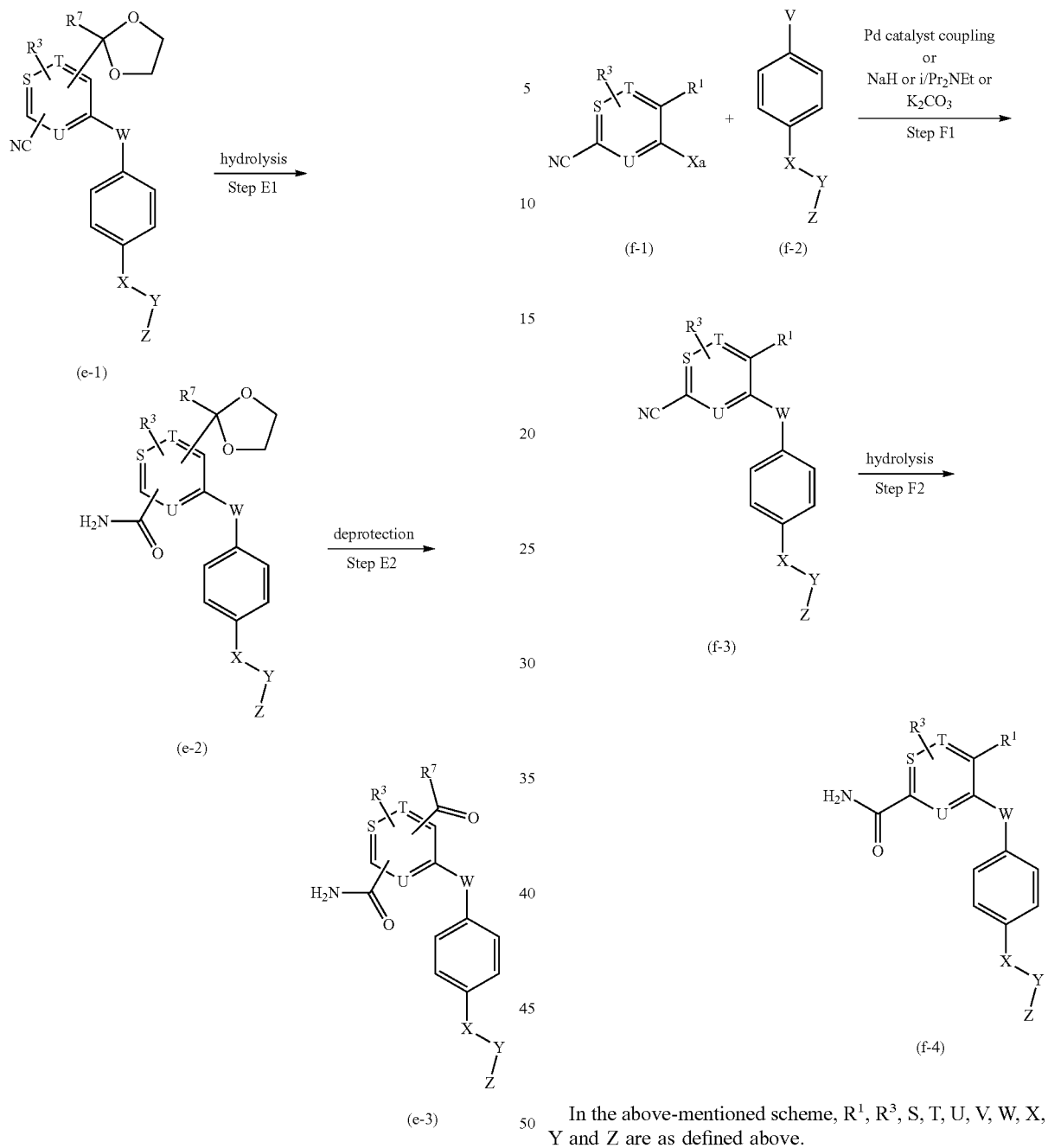

In the above-mentioned scheme, $R^3$, $R^7$, S, T, U, X, Y and Z are as defined above.

Step E1: In this step, compound (e-2) is produced by subjecting the cyano group of compound (e-1) to hydrolysis for conversion to a carbamoyl group. Hydrolysis of the cyano group can be performed according to a known method.

Step E2: In this step, compound (e-3) is produced by deprotecting acetal in compound (e-2). This step can be performed under conditions similar to those in Method D.

(Method F)

In Method F, the compound (f-4) of the formula (I) wherein $R^2$ is a carbamoyl group of the present invention is produced.

In the above-mentioned scheme, $R^1$, $R^3$, S, T, U, V, W, X, Y and Z are as defined above.

Step F1: This step includes a reaction using a palladium catalyst and a nucleophilic substitution reaction using a metal hydride such as NaH and the like, an organic base such as i-Pr$_2$NEt, or an inorganic base such as K$_2$CO$_3$ and the like, by which the compound (f-3) is produced from compound (f-1) and compound (f-2). This step can be performed under conditions similar to those in Method A.

Step F2: This step includes hydrolysis of a cyano group, wherein compound (f-4) is produced from compound (f-3). This step can be performed under conditions similar to those in Method E, Step E1.

(Method G)

In Method G, the compound (g-2) of the formula (I) wherein $R^1$ is a C1-6 alkylcarbonylamino group of the present invention is produced.

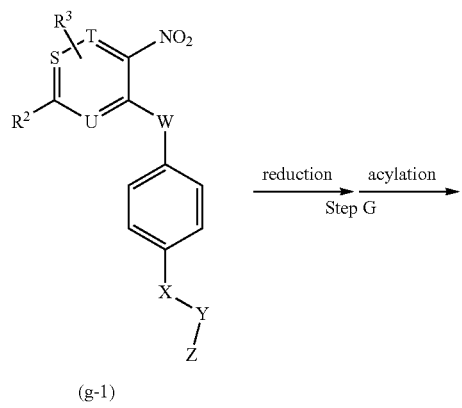

(g-1)

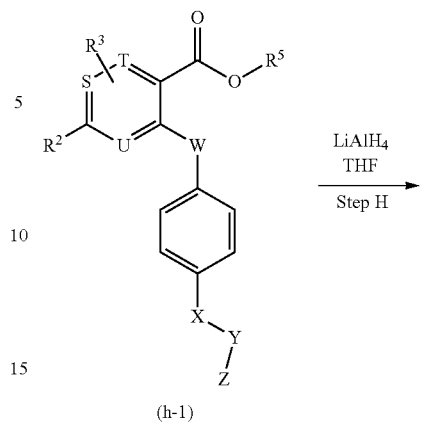

(h-1)

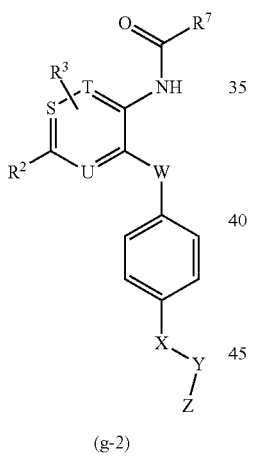

(g-2)

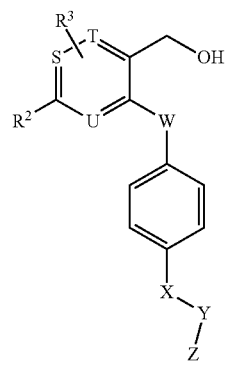

(h-2)

In the above-mentioned scheme, $R^2$, $R^3$, S, T, U, W, X, Y, Z and $R^7$ are as defined above.

Step G: In this step, compound (g-2) is produced by converting a nitro group to an amino group by catalytic hydrogenation using palladium carbon and the like or reduction reaction including reacting in the presence of calcium chloride and zinc in an aqueous ethanol solution under reflux and the like, followed by acylation.

The reduction reaction can be performed according to a known method.

Acylation can be performed according to a known method and using the corresponding carboxylic acid ($R^7$—COOH) or a derivative thereof.

(Method H)

In Method H, the compound (h-2) of the formula (I) wherein $R^1$ is a hydroxymethyl group of the present invention is produced.

In the above-mentioned scheme, $R^2$, $R^3$, $R^5$, S, T, U, W, X, Y and Z are as defined above.

Step H: This step is a reduction reaction, wherein compound (h-2) is produced from compound (h-1). This step can be performed by reacting compound (h-1) in the presence of lithium aluminum hydride in tetrahydrofuran under ice-cooling to room temperature.

The amount of lithium aluminum hydride to be used is generally 1-3 equivalents relative to compound (h-1).

While the reaction time varies depending on the starting compound, it is generally 30 min to 3 hr, preferably 30 min to 1 hr.

(Method I)

In Method I, the compound (i-3) of the formula (I) wherein $R^1$ is a halogeno C1-6 alkyl group, and $R^2$ is a carbamoyl group of the present invention is produced.

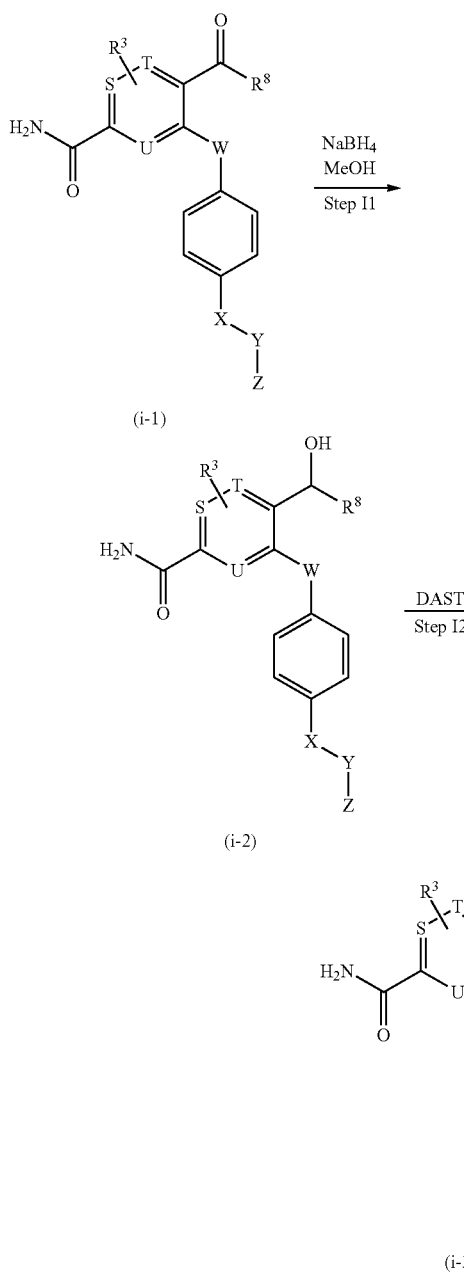

(i-1)

(i-2)

(i-3)

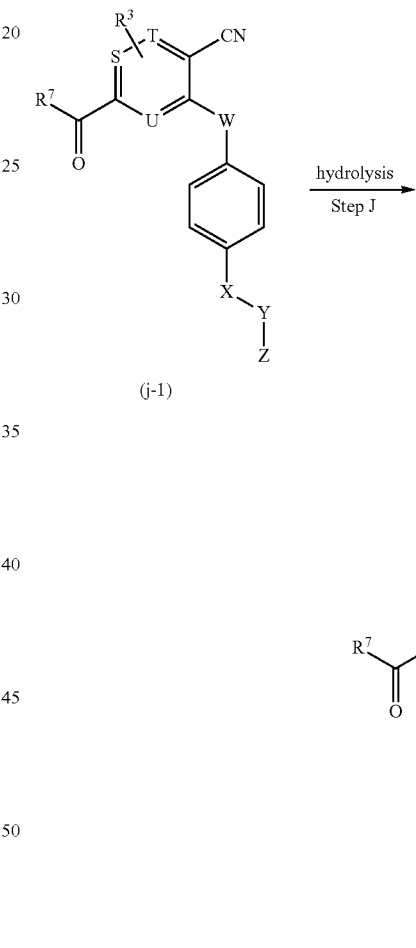

(j-1)

(j-2)

In the above-mentioned scheme, $R^3$, S, T, U, W, X, Y and Z are as defined above, and $R^8$ is a hydrogen atom or a C1-5 alkyl group.

Step I1: This step is a reduction reaction, wherein compound (i-2) is produced from compound (i-1). This step can be performed by reacting compound (i-1) in the presence of sodium borohydride in methanol under ice-cooling to room temperature.

The amount of sodium borohydride to be used is generally 1-3 equivalents, preferably 1-2 equivalents, relative to compound (i-1).

While the reaction time varies depending on the starting compound, it is generally 30 min to 3 hr, preferably 30 min to 1 hr.

Step I2: This step includes halogenation (fluorination reaction is described as an example in the above-mentioned scheme) wherein compound (i-3) is produced from compound (i-2). This step can be performed by reacting compound (i-2) in the presence of N,N-diethylaminosulfur trifluoride (DAST) as a halogenating agent (fluorinating agent) in chloroform under ice-cooling to room temperature.

The amount of N,N-diethylaminosulfur trifluoride to be used is generally 1-5 equivalents, preferably 1-3 equivalents, relative to compound (i-2).

While the reaction time varies depending on the starting compound, it is generally 30 min to 3 hr, preferably 30 min to 1 hr.

(Method J)

In Method J, the compound (j-2) of the formula (I) wherein $R^1$ is a carbamoyl group and $R^2$ is a C1-6 alkylcarbonyl group of the present invention is produced.

In the above-mentioned scheme, $R^3$, $R^7$, S, T, U, W, X, Y and Z are as defined above.

Step J: This step includes hydrolysis of a cyano group, wherein compound (j-2) is produced from compound (j-1). This step can be performed under conditions similar to those in Method E, Step E1.

(Method K)

In Method K, the compound (k-3) of the formula (I) wherein $R^1$ is a halogeno C1-6 alkyl group and $R^2$ is a carbamoyl group of the present invention is produced.

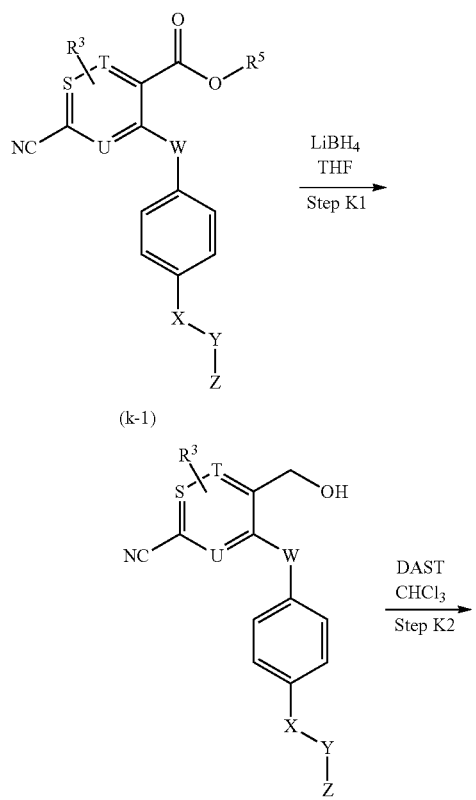

(k-1)

(k-2)

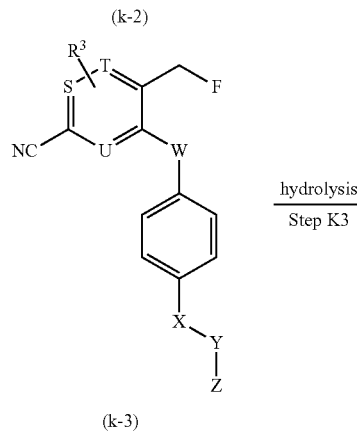

(k-3)

(k-4)

Step K1: This step is a reduction reaction wherein compound (k-2) is produced from compound (k-1). This step can be performed by heating compound (k-1) in the presence of lithium borohydride in tetrahydrofuran.

The amount of lithium borohydride to be used is generally 1 - 5 equivalents, preferably 1 - 3 equivalents, relative to compound (k-1).

While the reaction time varies depending on the starting compound, it is generally 1 to 5 hr, preferably 1 to 3 hr.

Step K2: This step includes halogenation (fluorination reaction is described as an example in the above-mentioned scheme) wherein compound (k-3) is produced from compound (k-2). This step can be performed by reacting compound (k-2) in the presence of N,N-diethylaminosulfur trifluoride as a halogenating agent (fluorinating agent) in chloroform under ice-cooling ro room temperature.

The amount of N,N-diethylaminosulfur trifluoride to be used is generally 1 - 5 equivalents, preferably 1 - 3 equivalents, relative to compound (k-2).

While the reaction time varies depending on the starting compound, generally 30 min to 3 hr, preferably 30 min to 1 hr.

Step K3: This step is a hydrolysis reaction of a cyano group wherein compound (k-4) is produced from compound (k-3). This step can be performed under conditions similar to those in Method E, Step E1.

(Method L)

In Method L, the compound (1-2) of the formula (I) wherein $R^1$ is a halogeno C1-6 alkyl group of the present invention is produced.

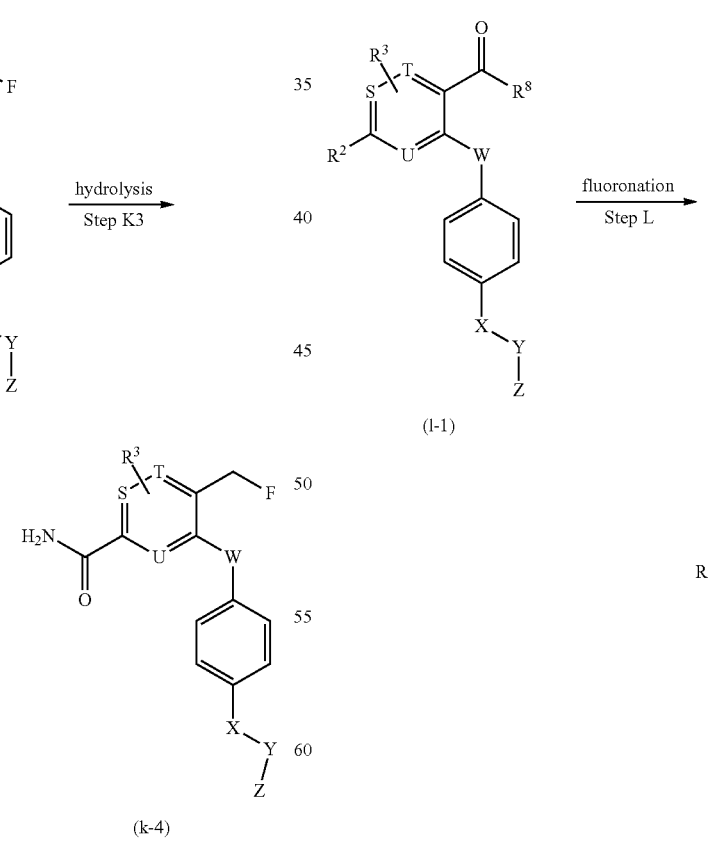

(l-1)

(l-2)

In the above-mentioned scheme, $R^3$, $R^5$, S, T, U, W, X, Y and Z are as defined above.

In the above-mentioned scheme, $R^2$, $R^3$, $R^8$, S, T, U, W, X, Y and Z are as defined above.

Step L: This step includes halogenation (fluorination reaction is described as an example in the above-mentioned scheme) wherein compound (l-2) is produced from compound (l-1). This step can be performed by heating compound (l-1) in the presence of a fluorinating agent such as bis(2-methoxyethyl)aminosulfur trifluoride and the like in chloroform.

The amount of the fluorinating agent to be used is generally 1-5 equivalents, preferably 1-3 equivalents, relative to compound (l-1).

While the reaction time varies depending on the starting compound, it is generally 1 to 120 hr, preferably 1 to 72 hr.

(Method M)

In Method M, the compound (m-2) of the formula (I) wherein $R^1$ is a hydroxy C1-6 alkyl group of the present invention is produced.

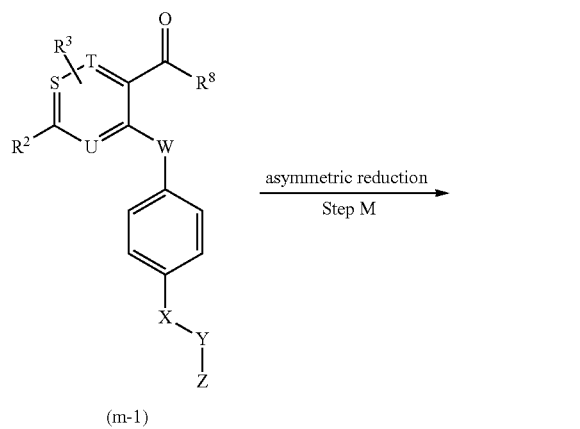

(m-1)

asymmetric reduction
Step M (m-2)

In the above-mentioned scheme, $R^2$, $R^3$, $R^8$, S, T, U, W, X, Y and Z are as defined above.

Step M: This step is an asymmetric reduction reaction, wherein compound (m-2) is produced from compound (m-1). This step can be performed according to the methods described in, for example, J. Org. Chem., 1988, 53, 2861, Tetrahedron Asymmetry, 1992, 3, 1583, Tetrahedron Letters, 1994, 35, 2141 and the like.

(Method N)

In Method N, the compound (a-3) of the present invention is produced by removing the protecting group of compound (n-1) which can be produced according to Method A to Method M.

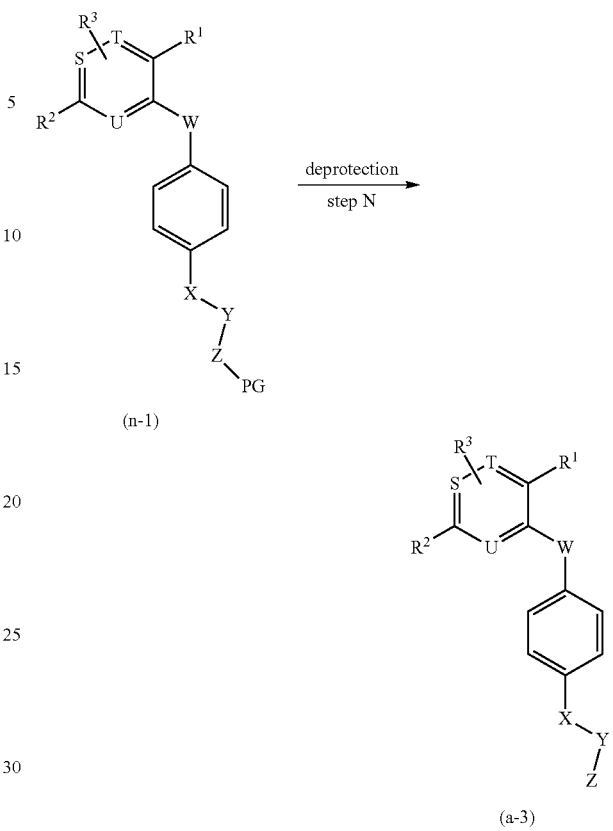

(n-1)

deprotection
step N (a-3)

In the above-mentioned scheme, $R^1$, $R^2$, $R^3$, S, T, U, X, Y and Z are as defined above, and PG is a protecting group of Z.

Step N: In compound (n-1), Z is protected by a protecting group. This step is a step for deprotecting the protecting group. The deprotection method of each protecting group can be performed according to the method described in, for example, T.W. Greene and P.G. Wuts, "Protective Groups in Organic Synthesis (3rd ed., 1999)".

The compound of the present invention produced above can be isolated and purified by a known method, for example, extraction, precipitation, distillation, chromatography, fractional recrystallization, recrystallization and the like.

When the compound of the formula (I) of the present invention or a production intermediate has an asymmetric carbon, optical isomers are present. These optical isomers can be each isolated and purified by a conventional method such as fractional recrystallization (salt resolution) for recrystallization with an appropriate salt, column chromatography and the like. The above-mentioned isomers can also be produced by asymmetric synthesis. As a reference document of a method of resolving an optical isomer of the above-mentioned isomer from a racemate, J. Jacques et al, "Enantiomers, Racemates and Resolution, John Wiley And Sons, Inc." can be mentioned.

Since the compound of the present invention is useful since it has high safety, shows good pharmacokinetics, and has a superior bone formation promoting action, and can be used for the prophylaxis or treatment (particularly treatment) of diseases associated with bone metabolism such as osteoporosis, Paget's disease of bone, osteoarthritis and the like.

When the compound of the present invention or a pharmacologically acceptable salt thereof is administered to a mammal (particularly human), it can be administered systemically or topically, and orally or parenterally.

The pharmaceutical composition of the present invention can be produced by selecting a suitable form according to the administration method and according to a preparation method generally used for various preparations.

The form of a pharmaceutical composition for oral use includes tablet, pill, powder, granule, capsule, solution, suspension, emulsion, syrup, elixir and the like. Medicaments in these forms can be prepared according to a conventional method and using those appropriately selected as necessary from excipient, binder, disintegrant, lubricant, swelling agent, swelling aid, coating agent, plasticizer, stabilizer, preservative, antioxidant, colorant, solubilizing agents, suspending agent, emulsifier, sweetening agent, preservative, buffering agent, diluent, wetting agent and the like, which are generally used as additives.

Examples of the form of the parenteral pharmaceutical composition include injection, ointment, gel, cream, fomentation, patch, spray, inhalant, spray, eye drop, nasal drop, suppository, inhalant and the like. The medicaments in these forms can be prepared according to a conventional method and using those appropriately selected as necessary from stabilizer, preservative, solubilizing agents, moisturizer, preservative, antioxidant, flavoring agent, gellant, neutralizing agent, solubilizing agents, buffering agent, isotonic agent, surfactant, colorant, buffering agent, thickener, wetting agent, filler, absorption promoter, suspending agent, binder and the like, which are generally used as additives.

While the dose of the compound of the formula (I) or a pharmacologically acceptable salt thereof varies depending on the symptom, age, body weight, the kind of medicament to be administered in combination and the like, a single dose thereof is generally within the range of 0.001-1000 mg based on the compound of the formula (I), for one adult (body weight about 60 kg), which is preferably administered systemically or topically once to several times per month, once to several times per week, once to several times per day, orally or parenterally, or continuously administered intravenously for 1-24 hr per day.

EXAMPLES

The present invention is explained in detail in the following by referring to Examples, which are not to be construed as limitative.

Reference Example 1

4-{3-[2-(tetrahydropyran-2-yloxy)ethoxy]azetidin-1-yl}phenylamine (1a) 1-benzhydryl-3-[2-(tetrahydropyran-2-yloxy)ethoxy]azetidine

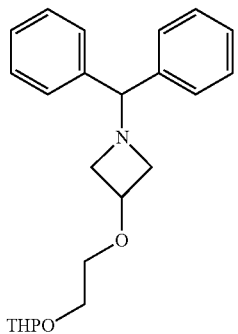

1-Benzhydrylazetidin-3-ol (20.0 g, 83.6 mmol) was dissolved in dimethylformamide (150 mL), sodium hydride (P=60%) (5.02 g, 125 mmol) was separately added under ice-cooling, and the mixture was stirred at the same temperature. 2-(2-Bromoethoxy)tetrahydropyran (18.9 mL, 125 mmol) was added dropwise at 60° C. and the mixture was stirred for 30 min. Sodium hydride (P=60%) (2.00 g, 50 mmol) was added and the mixture was stirred for 12 hr and allowed to cool to room temperature. Water was added to the reaction mixture and the mixture was extracted twice with ethyl acetate. The organic layer was washed with water and saturated brine, and dried over anhydrous sodium sulfate. The solvent was evaporated under reduced pressure, and the obtained residue was purified by silica gel column chromatography (hexane:ethyl acetate, 6:1→43:1, V/V). The solvent of the object fraction was evaporated under reduced pressure to give the title object compound as a pale-brown oil (23.8 g, yield 77%).

$^1$H-NMR (CDCl$_3$, 400 MHz) δ: 1.40-1.85 (6H, m), 2.88-2.95 (2H, m), 3.45-3.58 (6H, m), 3.75-3.85 (2H, m), 4.15-4.22 (1H, m), 4.36 (1H, s), 4.55-4.62 (1H, m), 7.12-7.19 (2H, m), 7.20-7.28 (4H, m), 7.35-7.40 (4H, m).

(1b) 1-(4-nitrophenyl)-3-[2-(tetrahydropyran-2-yloxy)ethoxy]azetidine

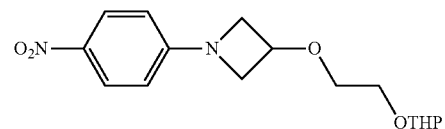

20% Palladium hydroxide-carbon (3.0 g) was suspended in methanol (250 mL), 1-benzhydryl-3-[2-(tetrahydropyran-2-yloxy)ethoxy]azetidine (23.8 g, 64.8 mmol) produced in Reference Example 1 (1a) was added, and catalytic hydrogenation was performed at 25° C., 0.40 MPa for 3 hr. The insoluble material was filtered off, and the solvent was evaporated under reduced pressure to give 1-(4-amino)-3-[2-(tetrahydropyran-2-yloxy)ethoxy]azetidine as a brown oil (23.3 g, yield 98%).

The obtained oil (3.00 g, 8.16 mmol) was dissolved in dimethylformamide (30 mL), 4-nitrofluorobenzene (1.04 mL, 9.79 mmol) and diisopropylethylamine (2.13 mL, 12.2 mmol) were added and the mixture was stirred under a nitrogen atmosphere at 60° C. for 15 hr. The reaction mixture was allowed to cool to room temperature, water was added and the mixture was extracted twice with ethyl acetate. The organic layer was washed with water and saturated brine, and dried over anhydrous sodium sulfate. The solvent was evaporated under reduced pressure, and the obtained residue was purified by silica gel column chromatography (hexane:ethyl acetate, 4:1→1:1, V/V). The solvent of the object fraction was evaporated under reduced pressure to give the title object compound as a yellow oil (2.08 g, yield 79%).

$^1$H-NMR (CDCl$_3$, 400 MHz) δ: 1.50-1.88 (6H, m), 3.48-3.64 (2H, m), 3.65-3.69 (2H, m), 3.84-3.98 (4H, m), 4.20-4.26 (2H, m), 4.53-4.57 (1H, m), 4.61-4.63 (1H, m), 6.30-6.32 (2H, m), 8.08-8.11 (2H, m).

(1c) 4-{3-[2-(tetrahydropyran-2-yloxy)ethoxy]azetidin-1-yl}phenylamine

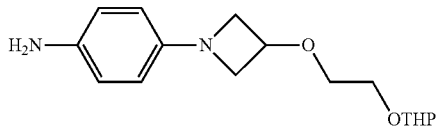

5% palladium carbon (500 mg) was suspended in methanol (30 mL), 1-(4-nitrophenyl)-3-[2-(tetrahydropyran-2-yloxy)ethoxy]azetidine (2.07 g, 6.42 mmol) produced in Reference Example 1 (1b) was added, and catalytic hydrogenation was performed at 25° C., 0.40 MPa for 1 hr. The insoluble material was filtered off, and the solvent was evaporated under reduced pressure to give the title object compound as a brown oil (1.9 g, yield 100%).

$^1$H-NMR (CDCl$_3$, 400 MHz) δ: 1.46-1.88 (6H, m), 3.25-3.40 (2H, br), 3.45-3.55 (1H, m), 3.56-3.65 (5H, m), 3.83-3.90 (2H, m), 4.02-4.06 (2H, m), 4.44-4.47 (1H, m), 4.61-4.63 (1H, m), 6.35-6.37 (2H, m), 6.61-6.63 (2H, m).

Reference Example 2

1-(4-iodophenyl)-3-[2-(tetrahydropyran-2-yloxy)ethoxy]azetidine

(2a) 1-phenyl-3-[2-(tetrahydropyran-2-yloxy)ethoxy]azetidine

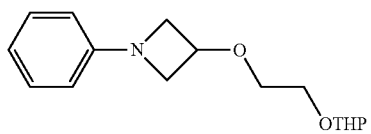

20% Palladium hydroxide-carbon (0.90 g) was suspended in methanol (200 mL), 1-benzhydryl-3-[2-(tetrahydropyran-2-yloxy)ethoxy]azetidine (17.7 g, 48.2 mmol) produced in Reference Example 1 (1a) was added, and catalytic hydrogenation was performed at room temperature, 0.3 MPa for 46 hr. The insoluble material was filtered off, and the solvent was evaporated under reduced pressure.

To the obtained residue were added iodobenzene (7.0 mL, 63 mmol), copper(I) iodide (918 mg, 4.82 mmol), L-proline (1.11 g, 9.64 mmol), potassium carbonate (13.3 g, 96.2 mmol) and dimethyl sulfoxide (24 mL), nitrogen was bubbled for 1 minute, and the mixture was stirred under a nitrogen atmosphere at 70° C. for 19 hr. The mixture was allowed to cool, poured into water (120 mL) and the mixture was extracted twice with ethyl acetate (100 mL). The organic layers were combined, washed successively with water and saturated brine, dried over anhydrous sodium sulfate and the solvent was evaporated under reduced pressure. The residue was purified by silica gel column chromatography (hexane:ethyl acetate, 5:1→2:1, V/V), and the solvent of the object fraction was evaporated under reduced pressure to give the title object compound as a yellow oil (7.8 g, yield 55%).

$^1$H-NMR (CDCl$_3$, 400 MHz) δ: 1.40-1.90 (6H, m), 3.47-3.67 (4H, m), 3.69-3.78 (2H, m), 3.82-3.92 (2H, m), 4.08-4.16 (2H, m), 4.47-4.55 (1H, m), 4.62-4.68 (1H, m), 6.44-6.52 (2H, m), 6.70-6.78 (1H, m), 7.16-7.26 (2H, m).

(2b) 1-(4-iodophenyl)-3-[2-(tetrahydropyran-2-yloxy)ethoxy]azetidine

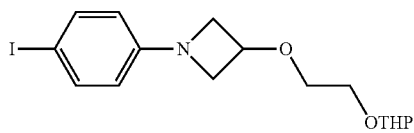

1-Phenyl-3-[2-(tetrahydropyran-2-yloxy)ethoxy]azetidine (7.8 g, 28 mmol) produced in Reference Example 2 (2a) was dissolved in methylene chloride (40 mL), sodium bicarbonate (3.5 g, 42 mmol) and water (40 mL) were added, iodine (7.46 g, 29.4 mmol) was separately added at room temperature over 1 hr, and the mixture was further stirred for 1.5 hr. 5% Sodium thiosulfate water (40 mL) was added and the mixture was stirred for 30 min and the solvent was evaporated under reduced pressure. The residue was extracted with ethyl acetate (200 mL), and the organic layer was washed successively with 5% sodium thiosulfate water and saturated brine, and dried over anhydrous sodium sulfate. The solvent was evaporated under reduced pressure, and the residue was purified by silica gel column chromatography (hexane:ethyl acetate, 4:1→2:1, V/V), and the solvent of the object fraction was evaporated under reduced pressure to give the title object compound as a yellow oil (10.34 g, yield 92%).

$^1$H-NMR (CDCl$_3$, 400 MHz) δ: 1.40-1.90 (6H, m), 3.47-3.65 (4H, m), 3.68-3.75 (2H, m), 3.83-3.91 (2H, m), 4.07 (2H, t, J=7.1 Hz), 4.44-4.52 (1H, m), 4.60-4.65 (1H, m), 6.20-6.25 (2H, m), 7.43-7.47 (2H, m).

Reference Example 3

2-(tetrahydrofuran-3-yloxy)ethanol

(3a) 2-[2-(tetrahydrofuran-3-yloxy)ethoxy]tetrahydropyran

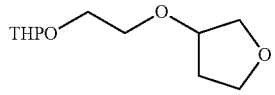

Tetrahydrofuran-3-ol (10.0 g, 114 mmol) was dissolved in dimethylformamide (200 mL), sodium hydride (P=60%) (5.9 g, 0.15 mol) was added under ice-cooling, and the mixture was stirred at room temperature for 30 min. 2-(2-Bromoethoxy)tetrahydropyran (30.9 g, 148 mmol) was added, and the mixture was stirred at 90° C. for 1 hr. To the reaction mixture was added ethyl acetate, and the mixture was washed successively with water and then with saturated brine, and dried over anhydrous sodium sulfate, and the solvent was evaporated under reduced pressure. The obtained residue was purified by silica gel column chromatography (hexane:ethyl acetate, 8:1→4:1, V/V), and the solvent of the object fraction was evaporated under reduced pressure to give the title object compound as a pale-yellow oil (8.88 g, yield 36%).

$^1$H-NMR (CDCl$_3$, 400 MHz) δ: 1.47-1.64 (4H, m), 1.67-1.89 (2H, m), 1.94-2.03 (2H, m), 3.45-3.54 (1H, m), 3.54-3.66 (3H, m), 3.75-3.93 (6H, m), 4.14-4.22 (1H, m), 4.58-4.66 (1H, m).

(3b) 2-(tetrahydrofuran-3-yloxy)ethanol

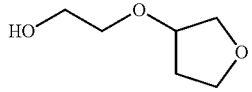

2-[2-(Tetrahydrofuran-3-yloxy)ethoxy]tetrahydropyran (8.88 g, 41.1 mmol) produced in Reference Example 3 (3a) was dissolved in methanol (90 mL), 8.6 M hydrogen chloride/isopropanol (14.3 mL, 0.12 mol) was added, and the mixture was stirred at room temperature for 15 min. The solvent was evaporated under reduced pressure to give the title object compound as a yellow oil (4.29 g, yield 79%).

$^1$H-NMR (CDCl$_3$, 400 MHz) δ: 1.95-2.04 (2H, m), 2.10-2.20 (1H, br), 3.50-3.60 (2H, m), 3.70-3.95 (6H, m), 4.14-4.20 (1H, m).

Reference Example 4

2-(tetrahydropyran-4-yloxy)ethanol (4a) 1-(tetrahydropyran-4-yloxy)-2-(tetrahydropyran-2-yloxy)ethane

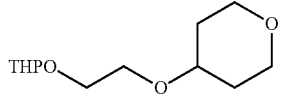

Tetrahydropyran-4-ol (375 mg, 3.67 mmol) was dissolved in dimethylformamide (2.5 mL), sodium hydride (P=60%) (190 mg, 4.75 mmol) was added under ice-cooling, and the mixture was stirred at room temperature for 15 min. 2-(2-Bromoethoxy)tetrahydropyran (1.0 g, 4.8 mmol) was added, and the mixture was stirred at 60° C. for 3 hr, and then at room temperature for 2 days. Ethyl acetate was added, and the mixture was washed successively with water and then with saturated brine, and dried over anhydrous sodium sulfate, and the solvent was evaporated under reduced pressure. The obtained residue was purified by silica gel column chromatography (hexane:ethyl acetate, 10:1→2:1, V/V), and the solvent of the object fraction was evaporated under reduced pressure to give the title object compound as a colorless oil (190 mg, yield 22%).

$^1$H-NMR (CDCl$_3$, 400 MHz) δ: 1.47-1.87 (8H, m), 1.87-1.96 (2H, m), 3.39-3.47 (2H, m), 3.47-3.70 (5H, m), 3.80-3.90 (2H, m), 3.90-3.99 (2H, m), 4.61-4.69 (1H, m).

(4b) 2-(tetrahydropyran-4-yloxy)ethanol

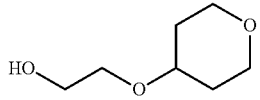

1-(Tetrahydropyran-4-yloxy)-2-(tetrahydropyran-2-yloxy)ethane (180 mg, 0.782 mmol) produced in Reference Example 4 (4a) was dissolved in methanol (2.0 mL), 8.6 M hydrogen chloride/isopropanol solution (0.27 mL, 2.3 mmol) was added, and the mixture was stirred at room temperature for 15 min. The solvent was evaporated under reduced pressure to give the title object compound as a colorless oil (110 mg, yield 96%).

$^1$H-NMR (CDCl$_3$, 400 MHz) δ: 1.54-1.66 (2H, m), 1.84 (1H, s), 1.86-1.97 (2H, m), 3.39-3.49 (2H, m), 3.49-3.57 (1H, m), 3.59 (2H, t, J=4.9 Hz), 3.74 (2H, t, J=4.9 Hz), 3.91-3.99 (2H, m).

Reference Example 5

4-[3-[2-(tetrahydropyran-2-yloxy)ethoxy]azetidin-1-yl]phenol (5a) 1-[4-(tert-butyldimethylsilanyloxy)phenyl]-3-[2-(tetrahydropyran-2-yloxy)ethoxy]azetidine

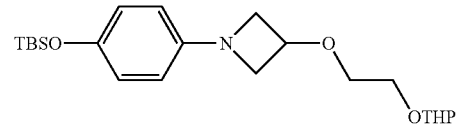

Palladium(II) acetate (56 mg, 0.25 mmol) and 2,2'-bis(diphenylphosphino)-1,1'-binaphthyl (234 mg, 0.375 mmol) were suspended in toluene (5 mL), and the mixture was stirred at 100° C. for 10 min. tert-Butyl-(4-iodophenoxy)dimethylsilane (2.00 g, 6.00 mmol), 3-[2-(tetrahydropyran-2-yloxy)ethoxy]azetidine (1.0 g, 5.0 mmol) produced in Reference Example 1 (1b), sodium tert-butoxide (721 mg, 7.50 mmol), and toluene (15 mL) were added and the mixture was stirred at the same temperature for 3 hr. To the reaction mixture was added water (100 mL), and the mixture was extracted twice with ethyl acetate. The organic layer was washed with saturated brine, and dried over anhydrous sodium sulfate. The solvent was evaporated under reduced pressure. The obtained residue was purified by silica gel column chromatography (hexane:ethyl acetate, 5:1, V/V), and the solvent of the object fraction was evaporated under reduced pressure, and the obtained residue was purified once again by basic silica gel column chromatography (hexane:ethyl acetate, 4:1, V/V), and the solvent of the object fraction was evaporated under reduced pressure to give the title object compound as a yellow oil (1.32 g, yield 65%).

$^1$H-NMR (CDCl$_3$, 400 MHz) δ: 0.15 (6H, s), 0.96 (9H, s), 1.51-1.87 (6H, m), 3.48-3.52 (1H, m), 3.57-3.67 (5H, m), 3.84-3.89 (2H, m), 4.05-4.08 (2H, m), 4.44-4.49 (1H, m), 4.62-4.63 (1H, m), 6.35-6.37 (2H, m), 6.69-6.72 (2H, m).

(5b) 4-{3-[2-(tetrahydropyran-2-yloxy)ethoxy]azetidin-1-yl}phenol

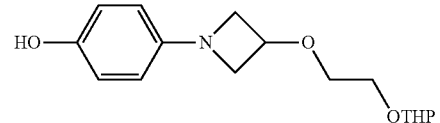

1-[4-(tert-butyldimethylsilanyloxy)phenyl]-3-[2-(tetrahydropyran-2-yloxy)ethoxy]azetidine (1.31 g, 3.21 mmol) produced in Reference Example 5 (5a) was dissolved in tetrahydrofuran (5 mL), 1.0 M tetrabutylammonium fluoride/tetrahydrofuran solution (4.8 mL, 4.8 mmol) was added under ice-cooling and the mixture was stirred at the same temperature for 2 hr. 1.0 M Tetrabutylammonium fluoride/tetrahydrofuran solution (1.9 mL, 1.9 mmol) was added again and the mixture was stirred at the same temperature for 30 min, and at room temperature for 1.5 hr. To the reaction mixture was added water (100 mL), and the mixture was extracted twice with ethyl acetate. The organic layer was washed with saturated brine, and dried over anhydrous sodium sulfate. The solvent was evaporated under reduced pressure. The obtained residue was purified by silica gel column chromatography (hexane:ethyl acetate, 4:1→2:1→1:1, V/V), and the solvent of the object fraction was evaporated under reduced pressure to give the title object compound as a yellow oil (975 mg, yield 100%).

$^{1}$H-NMR (CDCl$_{3}$, 400 MHz) δ: 1.50-1.88 (6H, m), 3.47-3.53 (1H, m), 3.58-3.65 (5H, m), 3.85-3.91 (2H, m), 4.04-4.07 (2H, m), 4.43-4.49 (1H, m), 4.62-4.64 (1H, m), 4.68 (1H, s), 6.36-6.39 (2H, m), 6.70-6.72 (2H, m).

Example 1

N-(4-{4-[3-(2-hydroxyethoxy)azetidin-1-yl]phenylamino}-6-methoxypyridin-3-yl)acetamide (1a)
N-(6-methoxypyridin-3-yl)-2,2-dimethylpropionamide

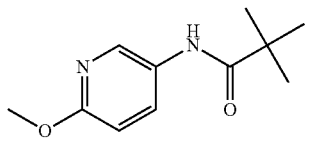

6-Methoxypyridin-3-ylamine (13.2 g, 10.6 mmol) was dissolved in methylene chloride (130 mL), triethylamine (17.7 mL, 12.7 mmol) and pivaloyl chloride (13.6 mL, 11.1 mmol) were added under ice-cooling, and the mixture was stirred at the same temperature for 30 min. The reaction mixture was washed successively with water and saturated brine, and dried over anhydrous sodium sulfate. The solvent was evaporated under reduced pressure to give the title object compound as a pale-red powder (22.0 g, yield 100%).

$^{1}$H-NMR (CDCl$_{3}$, 400 MHz) δ: 1.32 (9H, s), 3.91 (3H, s), 6.71 (1H, d, J=8.8 Hz), 7.91 (1H, dd, J=8.8, 2.7 Hz), 7.33-7.40 (1H, br), 8.11 (1H, d, J=2.7 Hz).

(1b) N-(4-iodo-6-methoxypyridin-3-yl)-2,2-dimethylpropanamide

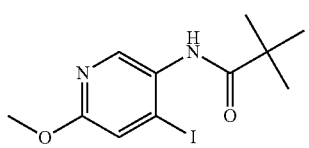 [SMILES: COc1cc(I)c(NC(=O)C(C)(C)C)cn1]

N-(6-Methoxypyridin-3-yl)-2,2-dimethylpropionamide (25.2 g, 0.120 mol) produced in Example 1 (1a) was dissolved in tetrahydrofuran (200 mL), and 1.7 M tert-butyllithium/pentane solution (200 mL, 0.34 mol) was added dropwise over 1 hr at −78° C. After stirring at the same temperature for 30 min, a solution (200 mL) of iodine (55.2 g, 0.220 mol) in tetrahydrofuran was added dropwise over 1 hr, and the mixture was stirred at room temperature for 2 hr. Water was added to the reaction mixture, and the mixture was extracted twice with ethyl acetate. The organic layer was washed successively with water and saturated brine, and dried over anhydrous sodium sulfate. The solvent was evaporated under reduced pressure, and the obtained residue was purified by silica gel column chromatography (hexane:ethyl acetate, 40:1→8:1→6:1, V/V). The solvent of the object fraction was evaporated under reduced pressure to give the title object compound as a pale-brown powder (15.0 g, yield 37%).

$^{1}$H-NMR (CDCl$_{3}$, 400 MHz) δ: 1.36 (9H, s), 3.90 (3H, s), 7.23 (1H, s), 7.33-7.40 (1H, br), 8.69 (1H, s).

(1c) 4-iodo-6-methoxypyridin-3-ylamine

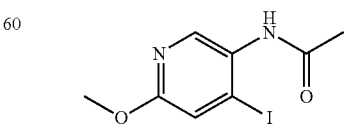

To N-(4-iodo-6-methoxypyridin-3-yl)-2,2-dimethylpropanamide (15.0 g, 44.9 mmol) produced in Example 1 (1b) was added 10% sulfuric acid (165 mL), and the mixture was heated under reflux for 8 hr. The reaction mixture was neutralized with sodium bicarbonate, extracted twice with ethyl acetate, and dried over anhydrous sodium sulfate. The solvent was evaporated under reduced pressure, and the obtained residue was purified by silica gel column chromatography (hexane:ethyl acetate, 1:3, V/V). The solvent of the object fraction was evaporated under reduced pressure to give the title object compound as a pale-brown powder (6.0 g, yield 54%).

$^{1}$H-NMR (CDCl$_{3}$, 400 MHz) δ: 3.63-3.80 (2H, br), 3.84 (3H, s), 7.14 (1H, s), 7.64 (1H, s).

(1d) N-(4-iodo-6-methoxypyridin-3-yl)acetamide

4-Iodo-6-methoxypyridin-3-ylamine (5.10 g, 20.4 mmol) produced in Example 1 (1c) was dissolved in methylene chloride (50 mL), triethylamine (4.27 mL, 30.6 mmol) and acetyl chloride (1.74 mL, 24.5 mmol) were added under ice-cooling and the mixture was stirred at room temperature for 1 hr. The reaction mixture was washed successively with water and saturated brine, and dried over anhydrous sodium sulfate. The solvent was evaporated under reduced pressure, and the precipitated powder was washed with isopropyl ether and collected by filtration to give the title object compound as a white powder (4.60 g, yield 77%).

$^1$H-NMR (CDCl$_3$, 400 MHz) δ: 2.24 (3H, s), 3.91 (3H, s), 6.96-7.10 (1H, br), 7.24 (1H, s), 8.59 (1H, s).

(1e) N-[6-methoxy-4-(4-{3-[2-(tetrahydropyran-2-yloxy)ethoxy]azetidin-1-yl}phenylamino)pyridin-3-yl]acetamide

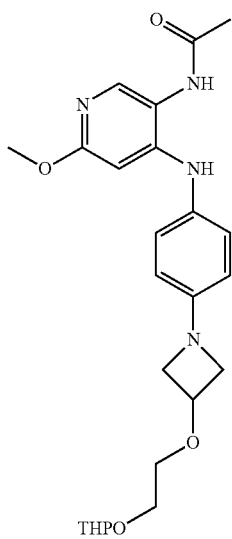

N-(4-Iodo-6-methoxypyridin-3-yl)acetamide (3.46 g, 11.8 mmol) produced in Example 1 (1d) was dissolved in tert-butanol (35 mL), 4-{3-[2-(tetrahydropyran-2-yloxy)ethoxy]azetidin-1-yl}phenylamine (3.46 g, 11.8 mmol) produced in Reference Example 1 (1c), tris(dibenzylideneacetone)dipalladium (540 mg, 0.590 mmol), 2-(dicyclohexylphosphino)-2',4',6'-triisopropylbiphenyl (562 mg, 1.18 mmol), and potassium phosphate (5.00 g, 23.6 mmol) were added under a nitrogen atmosphere, and the mixture was heated under reflux for 2 hr. Water was added to the reaction mixture, and the mixture was extracted twice with ethyl acetate, washed successively with water and saturated brine, and dried over anhydrous sodium sulfate. The solvent was evaporated under reduced pressure, and the obtained residue was purified by silica gel column chromatography (hexane:ethyl acetate, 1:1→chloroform:methanol, 50:1→20:1, V/V). The solvent of the object fraction was evaporated under reduced pressure to give the title object compound as a pale-brown oil (4.50 g, yield 83%).

$^1$H-NMR (CDCl$_3$, 400 MHz) δ: 1.50-1.80 (6H, m), 1.96 (1H, s), 2.24 (2H, s), 3.46-3.92 (11H, m), 4.05-4.20 (2H, m), 4.45-4.55 (1H, m), 4.60-4.70 (1H, m), 6.07-6.30 (2H, m), 6.40-6.54 (2H, m), 6.95-7.10 (2H, m), 7.76-7.84 (1H, s).

(1f) N-(4-{4-[3-(2-hydroxyethoxy)azetidin-1-yl]phenylamino}-6-methoxypyridin-3-yl)acetamide

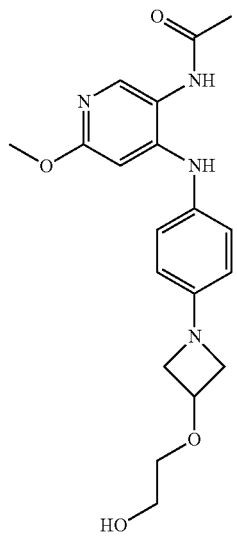 [SMILES: COc1cc(Nc2ccc(N3CC(OCCO)C3)cc2)c(NC(C)=O)cn1]

N-[6-Methoxy-4-(4-{3-[2-(tetrahydropyran-2-yloxy)ethoxy]azetidin-1-yl}phenylamino)pyridin-3-yl]acetamide (320 mg, 0.68 mmol) produced in Example 1 (1e) was dissolved in methanol (3 mL), 8.6 M hydrogen chloride/isopropanol solution (0.24 mL, 2.0 mmol) was added under ice-cooling, and the mixture was stirred at the same temperature for 30 min. The reaction mixture was neutralized with saturated aqueous sodium hydrogen carbonate, extracted twice with ethyl acetate, washed with water and saturated brine, and dried over anhydrous sodium sulfate. The solvent was evaporated under reduced pressure, and the obtained powder was washed with isopropyl ether to give the title object compound as a white powder (150 mg, yield 59%).

$^1$H-NMR (CDCl$_3$, 400 MHz) δ: 1.96 (1H, s), 2.24 (2H, s), 3.52-3.62 (2H, m), 3.70-3.90 (7H, m), 4.09-4.18 (2H, m), 4.42-4.53 (1H, m), 6.09-6.14 (1H, m), 6.40-6.54 (3H, m), 6.97-7.10 (3H, m), 7.78-7.79 (1H, s).

MS (ESI) m/z: 373 (M+H)$^+$.

Example 2

2-{1-[4-(4-fluoro-5-methoxy-2-nitrophenylamino)phenyl]azetidin-3-yloxy}ethanol (2a) 1,4-difluoro-2-methoxy-5-nitrobenzene

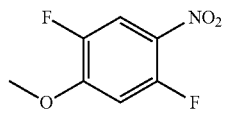

1,2,4-Trifluoro-5-nitrobenzene (2.00 g, 11.3 mmol) was dissolved in methanol (10 mL), 28% sodium methoxide/methanol solution (2.4 mL, 12 mmol) was added dropwise under ice-cooling, and the mixture was stirred at room temperature for 45 min. Water was added to the reaction mixture and the precipitated powder was collected by filtration and washed with water. The obtained powder was dissolved in ethyl acetate, and dried over anhydrous sodium sulfate, and the solvent was evaporated under reduced pressure to give the title object compound as a white powder (2.0 g, yield 94%).

$^1$H-NMR (CDCl$_3$, 400 MHz) δ: 4.00 (3H, s), 6.75-6.88 (1H, m), 7.85-7.95 (1H, m).

(2b) (4-fluoro-5-methoxy-2-nitrophenyl)-(4-{3-[2-(tetrahydropyran-2-yloxy)ethoxy]azetidin-1-yl}phenyl)amine

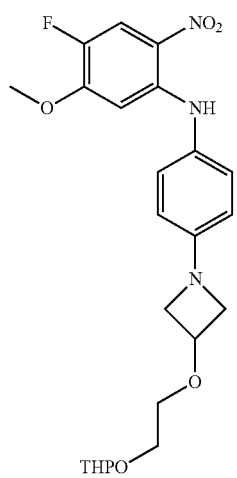

1,4-difluoro-2-methoxy-5-nitrobenzene (192 mg, 1.02 mmol) produced in Example 2 (2a) was dissolved in dimethylformamide (3 mL), 4-{3-[2-(tetrahydropyran-2-yloxy)ethoxy]azetidin-1-yl}phenylamine (297 mg, 1.02 mmol) produced in Reference Example 1 (1c) and diisopropylethylamine (0.27 mL, 1.5 mmol were added and the mixture was stirred at 80° C. for 15 hr. Water was added to the reaction mixture, and the mixture was extracted twice with ethyl acetate, washed successively with water and saturated brine, and dried over anhydrous sodium sulfate. The solvent was evaporated under reduced pressure, and the obtained residue was purified by silica gel column chromatography (hexane:ethyl acetate, 1:4, V/V). The solvent of the object fraction was evaporated under reduced pressure to give the title object compound as a red oil (410 mg, yield 87%).

$^1$H-NMR (CDCl$_3$, 400 MHz) δ: 1.50-1.90 (6H, m), 3.45-3.58 (1H, m), 3.59-3.70 (3H, m), 3.73 (3H, s), 3.76-3.84 (2H, m), 3.85-3.92 (2H, m), 4.10-4.18 (2H, m), 4.50-4.58 (1H, m), 4.60-4.65 (1H, m), 6.34 (1H, d, J=7.3 Hz), 6.49-6.51 (2H, m), 7.09-7.11 (2H, m), 7.91 (1H, d, J=11.7 Hz), 9.63 (1H, s).

(2c) 2-{1-[4-(4-fluoro-5-methoxy-2-nitrophenylamino)phenyl]azetidin-3-yloxy}ethanol

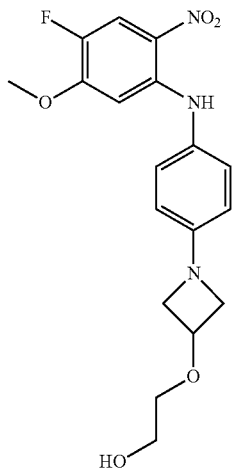 [SMILES: COc1cc(Nc2ccc(N3CC(OCCO)C3)cc2)c([N+](=O)[O-])cc1F]

(4-fluoro-5-methoxy-2-nitrophenyl)-(4-{3-[2-(tetrahydropyran-2-yloxy)ethoxy]azetidin-1-yl}phenyl)amine (150 mg, 0.33 mmol) produced in Example 2 (2b) was dissolved in methylene chloride-methanol (1:2) (3 mL) and, under ice-cooling, 8.6 M hydrogen chloride/isopropanol solution (0.11 mL, 0.99 mmol) was added and the mixture was stirred at the same temperature for 15 min. The reaction mixture was neutralized with saturated aqueous sodium hydrogen carbonate, extracted twice with ethyl acetate, and dried over anhydrous sodium sulfate. The solvent was evaporated under reduced pressure, and the precipitated powder was collected by filtration with isopropyl ether to give the title object compound as a red powder (95 mg, yield 77%).

$^1$H-NMR (CDCl$_3$, 400 MHz) δ: 1.85-2.00 (1H, br), 3.55-3.64 (2H, m), 3.73 (3H, s), 3.77-3.88 (4H, m), 4.14-4.28 (2H, m), 4.47-4.58 (1H, m), 6.35 (1H, d, J=7.6 Hz), 6.50-6.52 (2H, m), 7.10-7.12 (2H, m), 7.92 (1H, d, J=11.7 Hz), 9.60-9.70 (1H, br).

MS (ESI) m/z: 373 (M+H)$^+$.

Example 3

N-(5-fluoro-2-{4-[3-(2-hydroxyethoxy)azetidin-1-yl]phenylamino}-4-methoxyphenyl)acetamide

(3a) 4-fluoro-5-methoxy-N$^1$-(4-{3-[2-(tetrahydropyran-2-yloxy)ethoxy]azetidin-1-yl}phenyl)benzene-1,2-diamine

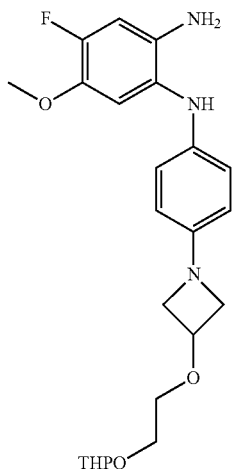

5% Palladium-carbon (80 mg) was suspended in methanol-tetrahydrofuran (3:1) (12 mL), (4-fluoro-5-methoxy-2-nitrophenyl)-(4-{3-[2-(tetrahydropyran-2-yloxy)ethoxy]azetidin-1-yl}phenyl)amine (410 mg, 0.888 mmol) produced in Example 2 (2b) was added, and catalytic hydrogenation was performed at 25° C., 0.30 MPa for 1.5 hr. The insoluble material was filtered off, and the solvent was evaporated under reduced pressure to give the title object compound as a purple oil (340 mg, yield 89%).

$^1$H-NMR (CDCl$_3$, 400 MHz) δ: 1.50-1.90 (6H, m), 3.45-3.68 (6H, m), 3.74 (3H, s), 3.82-3.95 (2H, m), 4.04-4.12 (2H, m), 4.44-4.52 (1H, m), 4.60-4.65 (1H, m), 4.75-4.85 (2H, br), 6.41-6.43 (2H, m), 6.55 (1H, d, J=12.2 Hz), 6.66-6.70 (3H, m).

(3b) N-[5-fluoro-4-methoxy-2-(4-{3-[2-(tetrahydropyran-2-yloxy)ethoxy]azetidin-1-yl}phenylamino)phenyl]acetamide

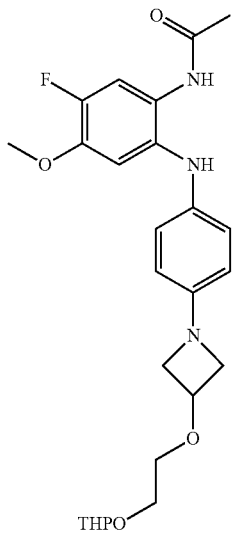

4-Fluoro-5-methoxy-N$^1$-(4-{3-[2-(tetrahydropyran-2-yloxy)ethoxy]azetidin-1-yl}phenyl)benzene-1,2-diamine (230 mg, 0.530 mmol) produced in Example 3 (3a) was dissolved in pyridine (2 mL) and, under ice-cooling, acetic anhydride (0.060 mL, 0.64 mmol) was added, and the mixture was stirred at the same temperature for 1 hr. Water was added to the reaction mixture, and the mixture was extracted twice with ethyl acetate, washed successively with water and saturated brine, and dried over anhydrous sodium sulfate. The solvent was evaporated under reduced pressure, and the obtained residue was purified by silica gel column chromatography (hexane:ethyl acetate, 1:1→0:1, V/V). The solvent of the object fraction was evaporated under reduced pressure to give the title object compound as a blue oil (240 mg, yield 96%).

$^1$H-NMR (CDCl$_3$, 400 MHz) δ: 1.40-1.80 (6H, m), 2.01 (3H, s), 3.45-3.60 (6H, m), 3.66 (3H, s), 3.69-3.80 (2H, m), 3.97-4.08 (2H, m), 4.37-4.48 (1H, m), 4.55-4.62 (1H, m), 6.39-6.41 (2H, m), 6.66 (1H, d, J=8.8 Hz), 6.80-6.90 (3H, m), 7.26 (1H, d, J=13.0 Hz), 9.16 (1H, s).

(3c) N-(5-fluoro-2-{4-[3-(2-hydroxyethoxy)azetidin-1-yl]phenylamino}-4-methoxyphenyl)acetamide

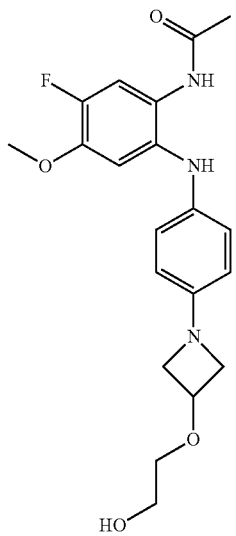 [SMILES: COc1cc(Nc2ccc(N3CC(OCCO)C3)cc2)c(NC(C)=O)cc1F]

N-[5-fluoro-4-methoxy-2-(4-{3-[2-(tetrahydropyran-2-yloxy)ethoxy]azetidin-1-yl}phenylamino)phenyl]acetamide (62 mg, 0.13 mmol) produced in Example 3 (3b) was dissolved in methanol (1 mL) and, under ice-cooling, 8.6 M hydrogen chloride/isopropanol solution (0.045 mL, 0.39 mmol) was added and the mixture was stirred at the same temperature for 20 min. The reaction mixture was neutralized with saturated aqueous sodium hydrogen carbonate, extracted twice with ethyl acetate, and dried over anhydrous sodium sulfate. The solvent was evaporated under reduced pressure, and the precipitated powder was washed with was isopropyl ether, and collected by filtration to give the title object compound as a pale-purple powder (37 mg, yield 73%).

$^1$H-NMR (CD$_3$CN, 400 MHz) δ: 2.07 (3H, m), 2.75-2.85 (2H, m), 3.49-3.55 (2H, m), 3.60-3.68 (4H, m), 3.72 (3H, s), 4.35-4.55 (1H, m), 7.30-7.63 (5H, m), 8.50-8.80 (1H, m).

MS (ESI) m/z: 390 (M+H)$^+$.

Example 4

2-{1-[4-(2-methoxy-5-nitropyridin-4-ylamino)phenyl]azetidin-3-yloxy}ethanol (4a) 4-chloro-3-nitropyridine

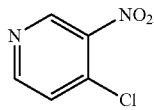

To phosphorus pentachloride (16.3 g, 78.6 mmol) was added phosphorus oxychloride (16.2 mL, 173 mmol), 3-nitropyridin-4-ol (10.0 g, 71.4 mmol) was separately added at 60° C. over 15 min, and the mixture was stirred at 140° C. for 3.5 hr. The solvent was evaporated under reduced pressure, and the residue was poured into ice water, and neutralized with potassium carbonate. The mixture was extracted twice with chloroform, and dried over anhydrous sodium sulfate. The solvent was evaporated under reduced pressure, and the obtained residue was purified by silica gel column chromatography (hexane:ethyl acetate, 1:1, V/V). The solvent of the object fraction was evaporated under reduced pressure to give the title object compound as a pale-yellow powder (10.1 g, yield 89%).

$^1$H-NMR (CDCl$_3$, 400 MHz) δ: 7.54 (1H, d, J=5.4 Hz), 8.69 (1H, d, J=5.4 Hz), 9.12 (1H, s).

(4b) 4-chloro-5-nitropyridin-2-ol

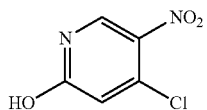

Ammonia gas was bubbled against tetrahydrofuran (60 mL) at −78° C. for 1.5 hr, potassium tert-butoxide (8.88 g, 78.8 mmol) was added, and the mixture was heated to −35° C. 4-Chloro-3-nitropyridine (5.00 g, 31.5 mmol) produced in Example 4 (4a) was dissolved in tetrahydrofuran (25 mL) and, under ice-cooling, 5.5 M tert-butylhydrogen peroxide/decane solution (31.0 mL, 171 mmol) was added. This solution was added dropwise to the ammonia solution prepared earlier over 1 hr, and the mixture was stirred at the same temperature for 1.5 hr. To the reaction mixture was added saturated ammonium chloride water to separate the mixture into two layers. The organic layer was evaporated under reduced pressure, saturated aqueous ammonium chloride was added and the precipitate was collected by filtration and washed with water to give the title object compound as a pale-brown powder (670 mg). The filtrate was extracted twice with ethyl acetate, and dried over anhydrous sodium sulfate. The solvent was evaporated under reduced pressure, and the precipitated powder was collected by filtration with hexane to give the title object compound as a pale-brown powder (1.18 g, total yield 34%).

$^1$H-NMR (CDCl$_3$, 400 MHz) δ: 6.69 (1H, s), 8.71 (1H, s), 12.80-13.05 (1H, br).

(4c) 4-chloro-2-methoxy-5-nitropyridine

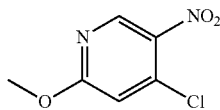

4-Chloro-5-nitropyridin-2-ol (1.18 g, 6.76 mmol) produced in Example 4 (4b) was suspended in tetrahydrofuran (15 mL) and, silver carbonate (2.80 g, 10.1 mmol) and methyl iodide (2.10 ml, 33.8 mmol) were added at room temperature, and the mixture was stirred at the same temperature for 13 hr. The insoluble material was filtered off with celite, and the filtrate was evaporated under reduced pressure. The obtained residue was purified by silica gel column chromatography (chloroform). The solvent of the object fraction was evaporated under reduced pressure to give the title object compound as a pale-yellow powder (730 mg, yield 57%).

$^1$H-NMR (CDCl$_3$, 400 MHz) δ: 4.03 (3H, s), 6.90 (1H, s), 8.88 (1H, s)

(4d) (2-methoxy-5-nitropyridin-4-yl)-(4-{3-[2-(tetrahydropyran-2-yloxy)ethoxy]azetidin-1-yl}phenyl) amine

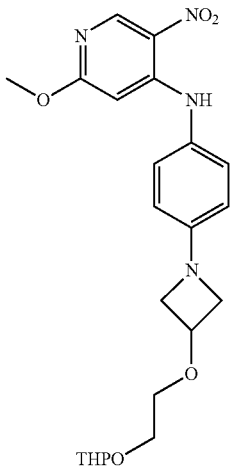

4-{3-[2-(Tetrahydropyran-2-yloxy) ethoxy]azetidin-1-yl}phenylamine (2.02 g, 6.89 mmol) produced in Reference Example 1 (1c) was dissolved in dimethylformamide (25 mL), 4-chloro-2-methoxy-5-nitropyridine (1.30 g, 6.89 mmol) produced in Example 4 (4c) and potassium carbonate (1.43 g, 10.3 mmol) were added and the mixture was stirred at 80° C. for 12 hr. Water was added to the reaction mixture, and the mixture was extracted twice with ethyl acetate, washed successively with water and saturated brine, and dried over anhydrous sodium sulfate. The solvent was evaporated under reduced pressure, and the obtained residue was purified by silica gel column chromatography (hexane:ethyl acetate, 3:1→2:1, V/V). The solvent of the object fraction was evaporated under reduced pressure to give the title object compound as a red oil (2.72 g, yield 89%).

$^1$H-NMR (CDCl$_3$, 400 MHz) δ: 1.50-1.90 (6H, m), 3.46-3.58 (1H, m), 3.58-3.68 (3H, m), 3.78-3.83 (2H, m), 3.84-3.96 (5H, m), 4.09-4.20 (2H, m), 4.48-4.58 (1H, m), 4.60-4.70 (1H, m), 6.02 (1H, s), 6.47-6.50 (2H, m), 7.06-7.08 (2H, m), 9.02 (1H, s), 9.27 (1H, s).

(4e) 2-{1-[4-(2-methoxy-5-nitropyridin-4-ylamino) phenyl]azetidin-3-yloxy}ethanol

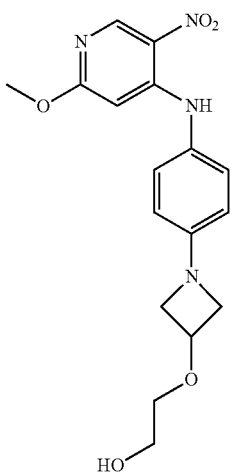 [SMILES: COc1cc(Nc2ccc(N3CC(OCCO)C3)cc2)c([N+](=O)[O-])cn1]

(2-Methoxy-5-nitropyridin-4-yl)-(4-{3-[2-(tetrahydropyran-2-yloxy)ethoxy]azetidin-1-yl}phenyl)amine (192 mg, 0.432 mmol) produced in Example 4 (4d) was dissolved in methanol (3 mL) and, under ice-cooling, 8.6 M hydrogen chloride/isopropanol solution (0.15 mL, 1.3 mmol) was added and the mixture was stirred at the same temperature for 30 min. The reaction mixture was neutralized with saturated aqueous sodium hydrogen carbonate, extracted twice with ethyl acetate, and dried over anhydrous sodium sulfate. The solvent was evaporated under reduced pressure, and the precipitated powder was washed with was isopropyl ether, collected by filtration to give the title object compound as a reddish brown powder (110 mg, yield 71%).

$^{1}$H-NMR (DMSO-$d_6$, 400 MHz) δ: 1.93 (1H, t, J=6.1 Hz), 3.54-3.62 (2H, m), 3.72-3.84 (4H, m), 3.90 (3H, s), 4.12-4.20 (2H, m), 4.45-4.58 (1H, m), 6.02 (1H, s), 6.48-6.50 (2H, m), 7.07-7.09 (2H, m), 9.02 (1H, s), 9.26 (1H, br).

MS (ESI) m/z: 361 (M+H)$^{+}$.

Example 5

3-{4-[3-(2-hydroxyethoxy)azetidin-1-yl]phenylamino}-4-nitrobenzamide (5a) 3-fluoro-4-nitrobenzamide

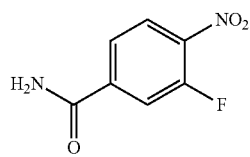 [SMILES: NC(=O)c1ccc([N+](=O)[O-])c(F)c1]

3-Fluoro-4-nitrobenzoic acid (1.57 g, 8.48 mmol) was dissolved in tetrahydrofuran (20 mL) and, under ice-cooling, N-methylmorpholine (1.12 mL, 10.2 mmol) and isobutyl chloroformate (1.21 mL, 9.33 mmol) were added, and the mixture was stirred at room temperature for 1 hr. Under ice-cooling, 14.8 M aqueous ammonia (2.87 mL, 42.4 mmol) was added dropwise, and the mixture was stirred at room temperature for 0.5 hr. The reaction mixture was diluted with ethyl acetate, washed successively with water and saturated brine, and dried over anhydrous sodium sulfate. The solvent was evaporated under reduced pressure. The obtained residue collected by filtration with isopropyl ether to give the title object compound as a pale-yellow powder (1.28 g, yield 82%).

$^{1}$H-NMR (CDCl$_3$, 400 MHz) δ: 7.80-7.92 (2H, m), 7.95-8.01 (1H, m), 8.21-8.37 (2H, m).

(5b) 4-nitro-3-(4-{3-[2-(tetrahydropyran-2-yloxy)ethoxy]azetidin-1-yl}phenylamino)benzamide

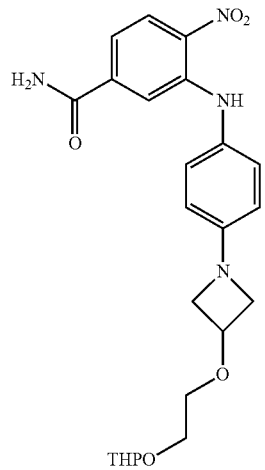

3-Fluoro-4-nitrobenzamide (1.79 g, 9.76 mmol) produced in Example 5 (5a) was dissolved in dimethylformamide (20 mL), 4-{3-[2-(tetrahydropyran-2-yloxy)ethoxy]azetidin-1-yl}phenylamine (2.85 g, 9.76 mmol) produced in Reference Example 1 (1c), and diisopropylethylamine (3.40 mL, 19.5 mmol) were added at room temperature, and the mixture was stirred at 100° C. for 15 hr. The reaction mixture was allowed to cool to room temperature, water was added, and the mixture was extracted twice with ethyl acetate. The organic layer was washed with water and saturated brine, and dried over anhydrous sodium sulfate. The solvent was evaporated under reduced pressure. The obtained residue was purified by silica gel column chromatography (hexane:ethyl acetate, 5:1→3:1→1:1→1:2→1:4→0:1, V/V). The solvent of the object fraction was evaporated under reduced pressure to give the title object compound as a dark red oil (1.70 g, yield 38%).

$^{1}$H-NMR (CDCl$_3$, 400 MHz) δ: 1.50-1.67 (4H, m), 1.70-1.89 (2H, m), 3.49-3.56 (1H, m), 3.60-3.69 (3H, m), 3.79 (2H, dd, J=8.0, 4.8 Hz), 3.85-3.93 (2H, m), 4.12-4.18 (2H, m), 4.50-4.57 (1H, m), 4.62-4.67 (1H, m), 5.50-6.10 (2H, m), 6.48-6.53 (2H, m), 6.99 (1H, dd, J=8.8, 1.7 Hz), 7.08-7.13 (2H, m), 7.40 (1H, d, J=1.7 Hz), 8.12 (1H, d, J=8.8 Hz), 9.41 (1H, s).

(5c) 3-{4-[3-(2-hydroxyethoxy)azetidin-1-yl]phenylamino}-4-nitrobenzamide

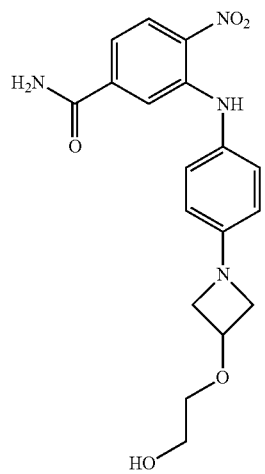 [SMILES: NC(=O)c1ccc([N+](=O)[O-])c(Nc2ccc(N3CC(OCCO)C3)cc2)c1]

Using 4-nitro-3-(4-{3-[2-(tetrahydropyran-2-yloxy)ethoxy]azetidin-1-yl}phenylamino)benzamide (1.70 g, 3.72 mmol) produced in Example 5 (5b) and by a method similar to that in Example 4 (4e), the title object compound was obtained as a dark red powder (630 mg, yield 46%).

$^1$H-NMR (DMSO-d$_6$, 400 MHz) δ: 3.42-3.45 (2H, m), 3.48-3.53 (2H, m), 3.60-3.66 (2H, m), 4.07-4.12 (2H, m), 4.42-4.46 (1H, m), 4.68 (1H, t, J=5.3 Hz), 6.50-6.53 (2H, m), 7.11-7.15 (3H, m), 7.40 (1H, d, J=1.4 Hz), 7.52-7.57 (1H, br), 8.03-8.10 (1H, br), 8.12 (1H, d, J=8.8 Hz), 9.36 (1H, s).

MS (ESI) m/z: 373 (M+H)$^+$.

Example 6

4-acetyl-3-{4-[3-(2-hydroxyethoxy)azetidin-1-yl]phenylamino}benzamide (6a) ethyl 4-acetyl-3-hydroxybenzoate

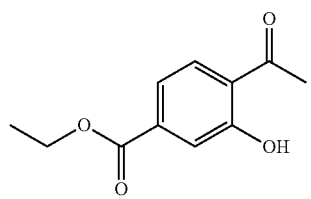

To 3-hydroxybenzoic acid (10.0 g, 72.4 mmol) was added acetic anhydride (20 mL), and the mixture was stirred at 120° C. for 12 hr. The reaction mixture was poured into ice water, and the mixture was extracted twice with ethyl acetate. The organic layers were combined, washed with saturated brine, and dried over anhydrous sodium sulfate. The solvent was evaporated under reduced pressure. The obtained residue was collected by filtration with isopropyl ether-hexane (1:10).

To the obtained powder was added aluminum chloride (24.7 g, 185 mmol), and the mixture was stirred at 180° C. for 3 hr. The mixture was poured into ice, and extracted twice with ethyl acetate. The organic layers were combined, washed successively with 2.0 M hydrochloric acid, saturated brine, and dried over anhydrous sodium sulfate. The solvent was evaporated under reduced pressure. To the obtained residue were added ethanol (30 mL) and concentrated hydrochloric acid (3 mL), and the mixture was heated under reflux for 12 hr. The reaction mixture was concentrated under reduced pressure, water was added, and the mixture was extracted twice with ethyl acetate. The organic layers were combined, washed with saturated brine, and dried over anhydrous sodium sulfate. The solvent was evaporated under reduced pressure. The obtained residue was purified by silica gel column chromatography (hexane:ethyl acetate, 9:1→4:1, V/V), and the solvent of the object fraction was evaporated under reduced pressure to give the title object compound as a pale-yellow powder (916 mg, yield 6.1%).

$^1$H-NMR (CDCl$_3$, 400 MHz) δ: 1.40 (3H, t, J=7.3 Hz), 2.68 (3H, s), 4.38 (2H, q, J=7.3 Hz), 7.54 (1H, dd, J=8.3, 1.7 Hz), 7.63 (1H, d, J=1.7 Hz), 7.79 (1H, d, J=8.3 Hz), 12.15 (1H, s).

(6b) ethyl 4-acetyl-3-trifluoromethanesulfonyloxybenzoate

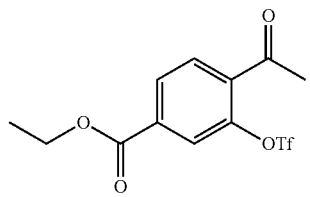 [SMILES: CCOC(=O)c1ccc(C(C)=O)c(OS(=O)(=O)C(F)(F)F)c1]

Ethyl 4-acetyl-3-hydroxybenzoate (900 mg, 4.32 mmol) produced in Example 6 (6a) was dissolved in methylene chloride (10 mL) and, under ice-cooling, pyridine (0.77 mL, 8.6 mmol) and trifluoromethanesulfonic anhydride (0.78 mL, 4.75 mmol) were added, and the mixture was stirred at the same temperature for 1 hr, and stirred further at room temperature for 1 hr. The reaction mixture was washed with water, and dried over anhydrous sodium sulfate. The solvent was evaporated under reduced pressure. The obtained residue was purified by silica gel column chromatography (hexane:ethyl acetate, 9:1→4:1, V/V), and the solvent of the object fraction was evaporated under reduced pressure to give the title object compound as a slightly yellow powder (1.26 g, yield 90%).

$^1$H-NMR (CDCl$_3$, 400 MHz) δ: 1.43 (3H, t, J=7.3 Hz), 2.67 (3H, s), 4.43 (2H, q, J=7.3 Hz), 7.85 (1H, d, J=8.1 Hz), 7.97 (1H, d, J=1.4 Hz), 8.13 (1H, dd, J=8.1, 1.4 Hz).

(6c) ethyl 4-(2-methyl-[1,3]dioxolan-2-yl)-3-trifluoromethanesulfonyloxybenzoate

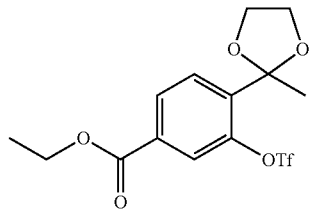 [SMILES: CCOC(=O)c1ccc(C2(C)OCCO2)c(OS(=O)(=O)C(F)(F)F)c1]

Ethyl 4-acetyl-3-trifluoromethanesulfonyloxybenzoate (500 mg, 1.47 mmol) produced in Example 6 (6b) was dissolved in methylene chloride (10 mL) and, under ice-cooling, ethylenedioxybis(trimethylsilane) (0.43 mL, 1.8 mmol) and trimethylsilyl trifluoromethanesulfonate (0.05 mL, 0.3 mmol) were added, and the mixture was stirred at room temperature for 18 hr. The reaction mixture was washed with saturated aqueous sodium hydrogen carbonate, and dried over anhydrous sodium sulfate. The solvent was evaporated under reduced pressure. The obtained residue was purified by silica gel column chromatography (hexane:ethyl acetate, 20:1, V/V), and the solvent of the object fraction was evaporated under reduced pressure to give the title object compound as a pale-yellow powder (490 mg, yield 87%).

$^1$H-NMR (CDCl$_3$, 400 MHz) δ: 1.40 (3H, t, J=7.1 Hz), 1.74 (3H, s), 3.78-3.87 (2H, m), 4.05-4.15 (2H, m), 4.40 (2H, q, J=7.1 Hz), 7.74 (1H, d, J=8.1 Hz), 7.89 (1H, d, J=1.4 Hz), 8.01 (1H, dd, J=8.1, 1.4 Hz).

(6d) ethyl 4-(2-methyl-[1,3]dioxolan-2-yl)-3-(4-{3-[2-(tetrahydropyran-2-yloxy)ethoxy]azetidin-1-yl}phenylamino)benzoate

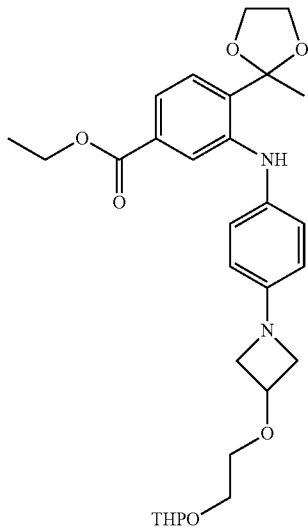

4-{3-[2-(Tetrahydropyran-2-yloxy)ethoxy]azetidin-1-yl}phenylamine (357 mg, 1.22 mmol) produced in Reference Example 1 (1c) was dissolved in 1,4-dioxane (10 mL), ethyl 4-(2-methyl-[1,3]dioxolan-2-yl)-3-trifluoromethanesulfonyloxybenzoate (470 mg, 1.22 mmol) produced in Example 6 (6c), palladium acetate (55 mg, 0.24 mmol), 2,2'-bis(diphenylphosphino)-1,1'-binaphthyl (304 mg, 0.488 mmol), and cesium carbonate (795 mg, 2.44 mmol) were added, and the mixture was stirred under a nitrogen atmosphere at 80° C. for 1 hr. The reaction mixture was diluted with ethyl acetate, washed with water and saturated brine, and dried over anhydrous sodium sulfate. The solvent was evaporated under reduced pressure. The obtained residue was purified by silica gel column chromatography (hexane:ethyl acetate, 9:1→7:3, V/V), and the solvent of the fraction containing the object product was evaporated under reduced pressure to give a pale yellow foam-like powder (158 mg) containing the title object compound.

(6e) 4-(2-methyl-[1,3]dioxolan-2-yl)-3-(4-{3-[2-(tetrahydropyran-2-yloxy)ethoxy]azetidin-1-yl}phenylamino)benzamide

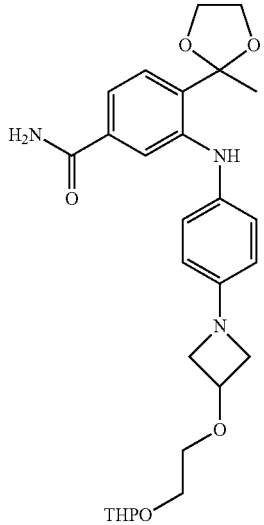

Ethyl 4-(2-methyl-[1,3]dioxolan-2-yl)-3-(4-{3-[2-(tetrahydropyran-2-yloxy)ethoxy]azetidin-1-yl}phenylamino)benzoate (158 mg) produced in Example 6 (6d) was dissolved in tetrahydrofuran (3 mL), methanol (1 mL) and 1.0 M lithium hydroxide water (0.86 mL, 0.86 mmol) were added, and the mixture was stirred at room temperature for 1 hr, and at 40° C. for 4 hr. Water was added to the reaction mixture and the mixture was diluted with toluene, neutralized with 2.0 M hydrochloric acid, and extracted twice with ethyl acetate. The organic layers were combined, washed with saturated brine, and dried over anhydrous sodium sulfate. The solvent was evaporated under reduced pressure.

The obtained residue (70 mg) was dissolved in dimethylformamide (1 mL), 1-ethyl-3-(3-dimethylaminopropyl)carbodiimide hydrochloride (54 mg, 0.28 mmol) and 1-hydroxybenzotriazole (0.38 mg, 0.28 mmol) were added, and the mixture was stirred at room temperature for 10 min. 14.8 M Aqueous ammonia (0.05 mL, 0.7 mmol) was added and the mixture was stirred at the same temperature for 3 hr. 1-Ethyl-3-(3-dimethylaminopropyl)carbodiimide hydrochloride (54 mg, 0.28 mmol), 1-hydroxybenzotriazole (0.38 mg, 0.28 mmol), and 14.8 M aqueous ammonia (0.05 mL, 0.7 mmol) were added, and the mixture was further stirred for 16 hr. The reaction mixture was diluted with ethyl acetate, washed successively with water and saturated brine, and dried over anhydrous sodium sulfate. The solvent was evaporated under reduced pressure. The obtained residue was purified by silica gel column chromatography (hexane:ethyl acetate, 1:1→1:3→0:1, V/V). The solvent of the object fraction was evaporated under reduced pressure to give the title object compound as a pale-yellow powder (52 mg, yield 8.6%).

$^1$H-NMR (CDCl$_3$, 400 MHz) δ: 1.47-1.92 (9H, m), 3.46-3.66 (4H, m), 3.69-3.78 (2H, m), 3.84-3.94 (4H, m), 4.06-4.16 (4H, m), 4.46-4.54 (1H, m), 4.61-4.66 (1H, m), 5.27-5.58 (1H, br), 5.70-6.02 (1H, br), 6.44-6.50 (2H, m), 6.98-7.06 (2H, m), 7.12 (1H, dd, J=8.0, 1.7 Hz), 7.22 (1H, s), 7.36 (1H, d, J=1.7 Hz), 7.46 (1H, d, J=8.0 Hz).

(6f) 4-acetyl-3-{4-[3-(2-hydroxyethoxy)azetidin-1-yl]phenylamino}benzamide

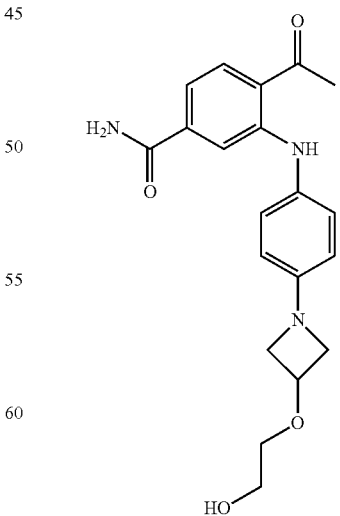

Using 4-(2-methyl-[1,3]dioxolan-2-yl)-3-(4-{3-[2-(tetrahydropyran-2-yloxy)ethoxy]azetidin-1-yl}phenylamino)

benzamide (52 mg, 0.105 mmol) produced in Example 6 (6e) and by a method similar to that in Example 4 (4e), the title object compound was obtained as an orange powder (25 mg, yield 64%).

$^1$H-NMR (CDCl$_3$, 400 MHz) δ: 1.96-2.07 (1H, br), 2.65 (3H, s), 3.57 (2H, t, J=4.4 Hz), 3.72-3.82 (4H, m), 4.11-4.17 (2H, m), 4.45-4.52 (1H, m), 5.45-5.75 (1H, br), 5.75-6.10 (1H, br), 6.45-6.51 (2H, m), 6.97 (1H, dd, J=8.3, 1.4 Hz), 7.05-7.12 (2H, m), 7.30 (1H, d, J=1.4 Hz), 7.82 (1H, d, J=8.3 Hz), 10.33 (1H, s).

MS (ESI) m/z: 370 (M+H)$^+$.

Example 7

(5-acetyl-2-methoxypyridin-4-yl)-{4-[3-(2-hydroxyethoxy)azetidin-1-yl]phenyl}amine (7a) 5-bromo-2-methoxypyridine-N-oxide

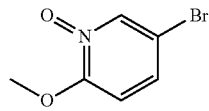

5-Bromo-2-methoxypyridine (84.5 g, 0.450 mol) was dissolved in chloroform (500 ml) and, under ice-cooling, 3-chloroperbenzoic acid (P=77%) (101 g, 0.450 mol) was added and the mixture was stirred at room temperature for 19 hr. The reaction mixture was dried over anhydrous sodium sulfate, and the solvent was evaporated under reduced pressure. The residue was purified by silica gel column chromatography (chloroform:ethyl acetate, 1:1→chloroform:methanol, 10:1, V/V). The solvent of the object fraction was evaporated under reduced pressure to give the title object compound as a white powder (43.9 g, yield 48%).

$^1$H-NMR (CDCl$_3$, 400 MHz) δ: 4.07 (3H, s), 6.78 (1H, d, J=9.0 Hz), 7.38 (1H, d, J=9.0 Hz), 8.38-8.42 (1H, m).

(7b) 5-bromo-2-methoxy-4-nitropyridine

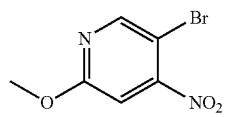

Under ice-cooling, to concentrated sulfuric acid (80 mL) was separately added 5-bromo-2-methoxypyridine-N-oxide (43.9 g, 0.220 mol) produced in Example 7 (7a), and fuming nitric acid (101 mL, 2.20 mol) was added dropwise. The reaction mixture was gradually warmed, and stirred at 80° C. for 3 days. The reaction mixture was poured into ice water, neutralized with potassium carbonate, extracted with chloroform, and dried over anhydrous sodium sulfate. The solvent was evaporated under reduced pressure to give the title object compound as a yellow powder (30.0 g, yield 60%).

$^1$H-NMR (CDCl$_3$, 400 MHz) δ: 3.99 (3H, s), 7.11 (1H, s), 8.45 (1H, s).

(7c) 5-bromo-2-methoxypyridin-4-ylamine

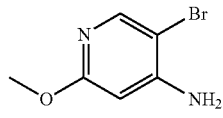

5-Bromo-2-methoxy-4-nitropyridine (80.4 g) produced in Example 7 (7b) was dissolved in acetic acid (250 mL), iron powder (67.4 g, 1.21 mol) was added, and the mixture was stirred at 80° C. for 1 hr. The mixture was allowed to cool, the insoluble material was filtered through celite, and the solvent was evaporated under reduced pressure. To the residue was added water (400 mL), and the mixture was adjusted to pH>8 with potassium carbonate. Ethyl acetate was added, and the mixture was filtered through celite whereby two layers of the filtrate were separated. The organic layer was washed with saturated brine and dried over anhydrous sodium sulfate, and the solvent was evaporated under reduced pressure. The residue was purified by silica gel column chromatography (hexane:ethyl acetate, 5:1→2:1, V/V), and the solvent of the object fraction was evaporated under reduced pressure to give the title object compound as a yellow powder (24.0 g).

(7d) 5-acetyl-2-methoxypyridin-4-ylamine

5-Bromo-2-methoxypyridin-4-ylamine (500 mg, 2.46 mmol) produced in Example 7 (7c) was dissolved in dimethylformamide (7.4 mL), butyl vinyl ether (1.6 mL, 12 mmol), palladium acetate (17 mg, 0.076 mmol), 1,3-bis(diphenylphosphino)propane (67 mg, 0.16 mmol) and 2.0 M potassium carbonate water (3.7 mL, 7.4 mmol) were added. After nitrogen bubbling, the mixture was stirred under a nitrogen atmosphere at 100° C. for 5 hr. The mixture was allowed to cool, 2.0 M hydrochloric acid (12 mL, 24 mmol) was slowly added, and the mixture was stirred at room temperature for 3 hr. The mixture was neutralized with saturated aqueous sodium hydrogen carbonate, and extracted twice with ethyl acetate (20 mL). The organic layers were combined, washed successively with water and saturated brine, and dried over anhydrous sodium sulfate. The solvent was evaporated under reduced pressure. The residue was purified by silica gel column chromatography (hexane:ethyl acetate, 1:1, V/V), and the solvent of the object fraction was evaporated under reduced pressure to give the title object compound as a pale-yellow powder (286 mg, yield 70%).

$^1$H-NMR (CDCl$_3$, 400 MHz) δ: 2.55 (3H, s), 3.93 (3H, s), 5.84 (1H, s), 6.00-7.20 (2H, br), 8.58 (1H, s).

MS(ESI) m/z: 167 (M+H)$^+$.

(7e) (5-acetyl-2-methoxypyridin-4-yl)-(4-{3-[2-(tetrahydropyran-2-yloxy)ethoxy]azetidin-1-yl}phenyl)amine

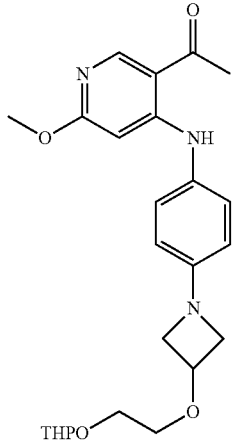

Using 5-acetyl-2-methoxypyridin-4-ylamine (150 mg, 0.903 mmol) produced in Example 7 (7d) and 1-(4-iodophenyl)-3-[2-(tetrahydropyran-2-yloxy)ethoxy]azetidine (436 mg, 1.08 mmol) produced in Reference Example 2 (2b) and by a method similar to that in Example 1 (1e), the title object compound was obtained as a yellow oil (52 mg, yield 13%).

(7f) (5-acetyl-2-methoxypyridin-4-yl)-{4-[3-(2-hydroxyethoxy)azetidin-1-yl]phenyl}amine

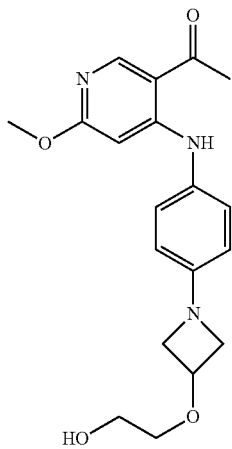 [SMILES: COc1cc(Nc2ccc(N3CC(OCCO)C3)cc2)c(C(C)=O)cn1]

Using (5-acetyl-2-methoxypyridin-4-yl)-(4-{3-[2-(tetrahydropyran-2-yloxy)ethoxy]azetidin-1-yl}phenyl)amine (52 mg, 0.12 mmol) produced in Example 7 (7e) and by a method similar to that in Example 4 (4e), the title object compound was obtained as a yellow powder (24 mg, yield 56%).

$^1$H-NMR (CDCl$_3$, 400 MHz) δ: 1.90-2.00 (1H, m), 2.60 (3H, s), 3.54-3.60 (2H, m), 3.72-3.82 (4H, m), 3.88 (3H, s), 4.10-4.19 (2H, m), 4.45-4.54 (1H, m), 6.02 (1H, s), 6.44-6.50 (2H, m), 7.02-7.08 (2H, m), 8.62 (1H, s), 10.25-10.35 (1H, br).

MS (ESI) m/z: 358 (M+H)$^+$.

Example 8

N-(4-{4-[3-(4-hydroxymethylpiperidin-1-yl)azetidin-1-yl]phenylamino}-6-methoxypyridin-3-yl)acetamide (8a) 1-benzhydrylazetidin-3-yl methanesulfonate

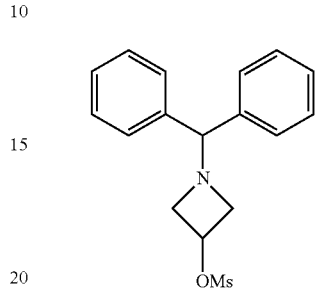

1-Benzhydrylazetidin-3-ol (30.0 g, 125 mmol) was dissolved in methylene chloride (240 mL), triethylamine (26 mL, 0.19 mol) was added and, under ice-cooling, methanesulfonyl chloride (11.6 mL, 150 mmol) was added, and the mixture was stirred for 1.5 hr. Water (100 mL) was added, two layers were separated, and the organic layer was washed successively with water and saturated brine, and dried over anhydrous sodium sulfate. The solvent was evaporated under reduced pressure to give the title object compound as a pale-yellow powder (40.1 g, yield 100%).

$^1$H-NMR (CDCl$_3$, 400 MHz) δ: 2.99 (3H, s), 3.15-3.23 (2H, m), 3.59-3.68 (2H, m), 4.39 (1H, s), 5.10 (1H, quintet, J=5.8 Hz), 7.16-7.22 (2H, m), 7.24-7.30 (4H, m), 7.36-7.41 (4H, m).

(8b) ethyl 1-(1-benzhydrylazetidin-3-yl)piperidine-4-carboxylate

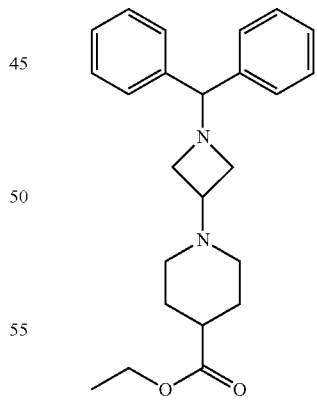

1-Benzhydrylazetidin-3-yl methanesulfonate (5.00 g, 15.8 mmol) produced in Example 8 (8a) was dissolved in dimethylformamide (32 mL), triethylamine (4.4 mL, 32.0 mmol) and ethyl isonipecotate (4.9 mL, 32.0 mmol) were added and the reaction mixture was stirred at 80° C. for 15.5 hr. The reaction mixture was poured into ice water (200 mL), and the mixture was extracted twice with ethyl acetate (150 mL). The organic layers were combined, washed successively with water and saturated brine, and dried over anhydrous sodium sulfate. The solvent was evaporated under reduced pressure. The obtained residue was purified by silica gel column chromatography (hexane:ethyl acetate, 2:1, V/V), and the solvent of the object fraction was evaporated under reduced pressure to give the title object compound as a yellow oil (3.97 g, yield 66%).

$^1$H-NMR (CDCl$_3$, 400 MHz) δ: 1.23 (3H, t, J=7.1 Hz), 1.67-1.90 (6H, m), 2.21-2.30 (1H, m), 2.62-2.70 (2H, m), 2.84-2.96 (3H, m), 3.37-3.42 (2H, m), 4.11 (2H, q, J=7.1 Hz), 4.41 (1H, s), 7.14-7.20 (2H, m), 7.22-7.28 (4H, m), 7.37-7.42 (4H, m).

(8c) ethyl 1-[1-(4-nitrophenyl)azetidin-3-yl]piperidine-4-carboxylate

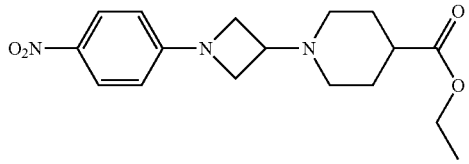 [SMILES: CCOC(=O)C1CCN(C2CN(c3ccc([N+](=O)[O-])cc3)C2)CC1]

10% Palladium hydroxide-carbon (0.4 g) was suspended in methanol (50 mL), ethyl 1-(1-benzhydrylazetidin-3-yl)piperidine-4-carboxylate (3.97 g, 10.5 mmol) produced in Example 8 (8b) was added, and catalytic hydrogenation was performed at room temperature, 0.3 MPa for 4 hr. The insoluble material was filtered off through celite, and the solvent was evaporated under reduced pressure.

The obtained oil (3.88 g) was dissolved in N-methylpyrrolidone (20 mL), p-fluoronitrobenzene (1.58 g, 11.2 mmol) and diisopropylethylamine (2.6 mL, 15 mmol) were added, and the mixture was stirred at 70° C. for 7 hr. The mixture was allowed to cool, water (100 mL) was added, and the mixture was extracted twice with ethyl acetate (100 mL). The organic layers were combined, washed successively with water and saturated brine, and dried over anhydrous sodium sulfate. The solvent was evaporated under reduced pressure. The residue was washed with isopropyl ether (30 mL) and collected by filtration to give the title object compound as a yellow powder (2.48 g, yield 73%).

$^1$H-NMR (CDCl$_3$, 400 MHz) δ: 1.23 (3H, t, J=7.1 Hz), 1.73-1.84 (2H, m), 1.93-2.06 (4H, m), 2.30-2.39 (1H, m), 2.78-2.85 (2H, m), 3.30-3.38 (1H, m), 3.88 (2H, dd, J=8.5, 5.4 Hz), 4.06-4.12 (2H, m), 4.15 (2H, q, J=7.1 Hz), 6.28-6.33 (2H, m), 8.07-8.13 (2H, m).

(8d) 4-(tert-butyldimethylsilanyloxymethyl)-1-[1-(4-nitrophenyl)azetidin-3-yl]piperidine

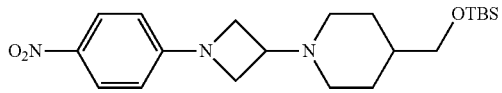

Ethyl 1-[1-(4-nitrophenyl)azetidin-3-yl]piperidine-4-carboxylate (4.0 g, 12 mmol) produced in Example 8 (8c) was dissolved in tetrahydrofuran (18 mL) and, under a nitrogen atmosphere, 2.0 M lithium borohydride/tetrahydrofuran solution (18 mL, 36 mmol) was added dropwise, and the mixture was heated under reflux for 30 min. To the reaction mixture was added saturated aqueous sodium hydrogen carbonate, and the mixture was extracted twice with ethyl acetate. The organic layer was washed with saturated brine and dried over anhydrous sodium sulfate, and the solvent was evaporated under reduced pressure.

The obtained residue was dissolved in methylene chloride (80 mL) and, under ice-cooling, imidazole (1.37 g, 20.1 mmol) and tert-butyldimethylsilyl chloride (2.42 g, 16.1 mmol) were added, and the mixture was stirred at room temperature for 12 hr. Water was added to the reaction mixture, and the mixture was extracted twice with ethyl acetate. The organic layer was washed with saturated brine and dried over anhydrous sodium sulfate, and the solvent was evaporated under reduced pressure. The obtained residue was purified by silica gel column chromatography (hexane:ethyl acetate, 4:1, V/V), and the solvent of the object fraction was evaporated under reduced pressure to give the title object compound as an orange oil (3.61 g, yield 66%).

$^1$H-NMR (CDCl$_3$, 400 MHz) δ: 0.03 (6H, s), 0.89 (9H, s), 1.18-1.33 (2H, m), 1.46-1.59 (1H, m), 1.73-1.82 (2H, m), 1.84-1.95 (2H, m), 2.83-2.94 (2H, m), 3.26-3.38 (1H, m), 3.45 (2H, d, J=6.3 Hz), 3.84-3.92 (2H, m), 4.05-4.12 (2H, m), 6.25-6.33 (2H, m), 8.04-8.13 (2H, m).

(8e) (4-{3-[4-(tert-butyldimethylsilanyloxymethyl)piperidin-1-yl]azetidin-1-yl}phenyl)-(2-methoxy-5-nitropyridin-4-yl)amine

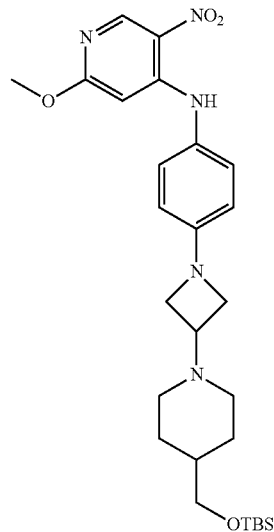 [SMILES: COc1cc(Nc2ccc(N3CC(N4CCC(CO[Si](C)(C)C(C)(C)C)CC4)C3)cc2)c([N+](=O)[O-])cn1]

10% Palladium-carbon (720 mg) was suspended in toluene (1 mL), 4-(tert-butyldimethylsilanyloxymethyl)-1-[1-(4-nitrophenyl)azetidin-3-yl]piperidine (3.61 g, 8.90 mmol) produced in Example 8 (8d) and methanol (72 mL) were added, and catalytic hydrogenation was performed at room temperature, 0.3 MPa for 1 hr. The insoluble material was filtered off through celite and the solvent was evaporated under reduced pressure.

Using the obtained 4-{3-[4-(tert-butyldimethylsilanyloxymethyl)piperidin-1-yl]azetidin-1-yl}phenylamine (2.81 g, 7.48 mmol) and 4-chloro-2-methoxy-5-nitropyridine (1.41 g, 7.48 mmol) produced in Example 4 (4c), and by a method similar to that in Example 4 (4d), the title object compound was obtained as a reddish brown oil (2.86 g, yield 72%).

¹H-NMR (CDCl₃, 400 MHz) δ: 0.04 (6H, s), 0.89 (9H, s), 1.20-1.32 (2H, m), 1.46-1.58 (1H, m), 1.72-1.81 (2H, m), 1.84-1.94 (2H, m), 2.84-2.94 (2H, m), 3.26-3.35 (1H, m), 3.45 (2H, d, J=6.5 Hz), 3.69-3.76 (2H, m), 3.89 (3H, s), 3.97-4.05 (2H, m), 5.99 (1H, s), 6.43-6.52 (2H, m), 7.01-7.10 (2H, m), 9.02 (1H, s), 9.26 (1H, s).

(8f) N-(4-{4-[3-(4-hydroxymethylpiperidin-1-yl) azetidin-1-yl]phenylamino}-6-methoxypyridin-3-yl) acetamide

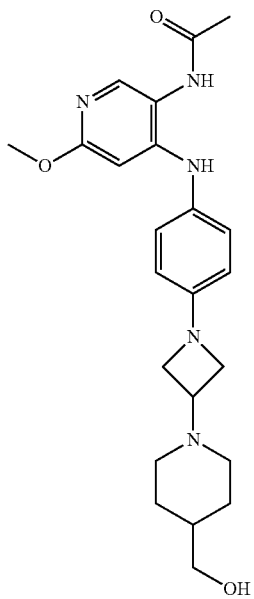 [SMILES: COc1cc(Nc2ccc(N3CC(N4CCC(CO)CC4)C3)cc2)c(NC(C)=O)cn1]

10% Palladium-carbon (570 mg) was suspended in toluene (1 mL), (4-{3-[4-(tert-butyldimethylsilanyloxymethyl) piperidin-1-yl]azetidin-1-yl}phenyl)-(2-methoxy-5-nitropyridin-4-yl)amine (2.86 g, 5.42 mmol) produced in Example 8 (8e) dissolved in methanol (60 mL) was added, and catalytic hydrogenation was performed at room temperature, 0.3 MPa for 30 min. The insoluble material was filtered off, and the solvent was evaporated under reduced pressure to give a residue (2.70 g, yield 100%).

The obtained N⁴-(4-{3-[4-(tert-butyldimethylsilanyloxymethyl)piperidin-1-yl]azetidin-1-yl}phenyl)-6-methoxypyridine-3,4-diamine (750 mg, 1.51 mmol) was dissolved in pyridine (8 mL) and, under ice-cooling, acetic anhydride (0.14 mL, 1.5 mmol) was added, and the mixture was stirred at the same temperature for 1 hr. Water was added to the reaction mixture, and the mixture was extracted twice with ethyl acetate. The organic layer was washed successively with water and saturated brine, and dried over anhydrous sodium sulfate. The solvent was evaporated under reduced pressure. The obtained residue was purified by silica gel column chromatography (hexane:ethyl acetate, 2:1→0:1, V/V), and the solvent of the object fraction was evaporated under reduced pressure.

The obtained N-[4-(4-{3-[4-(tert-butyldimethylsilanyloxymethyl)piperidin-1-yl]azetidin-1-yl}phenylamino)-6-methoxypyridin-3-yl]acetamide (608 mg, 1.13 mmol) was dissolved in tetrahydrofuran (6 mL) and, under ice-cooling, 1.0 M tetrabutylammonium fluoride/tetrahydrofuran solution (1.69 mL, 1.7 mmol) was added, and the mixture was stirred at room temperature for 4 hr. Water was added to the reaction mixture, and the mixture was extracted twice with chloroform. The organic layer was washed with saturated brine, and dried over anhydrous sodium sulfate. The solvent was evaporated under reduced pressure. The obtained residue was purified by silica gel column chromatography (chloroform:methanol, 100:1, V/V). The solvent of the object fraction was evaporated under reduced pressure. The obtained residue was purified by basic silica gel column chromatography (chloroform:methanol, 50:1, V/V). The solvent of the object fraction was evaporated under reduced pressure, and the obtained residue was dissolved in ethyl acetate, washed with water, and dried over anhydrous sodium sulfate. The solvent was evaporated under reduced pressure. The obtained powder was washed with isopropyl ether-hexane (1:1), and collected by filtration to give the title object compound as a pale-red powder (104 mg, yield 21%).

¹H-NMR (CDCl₃, 400 MHz) δ: 1.24-1.37 (2H, m), 1.50-1.70 (2H, m), 1.75-1.84 (2H, m), 1.86-1.96 (2H, m), 1.96 (1H, s), 2.24 (2H, s), 2.87-2.96 (2H, m), 3.26-3.35 (1H, m), 3.51 (2H, d, J=6.3 Hz), 3.64-3.74 (2H, m), 3.82 (2H, s), 3.84 (1H, s), 3.94-4.03 (2H, m), 6.07 (0.35H, s), 6.08 (0.35H, s), 6.12 (0.65H, s), 6.26 (0.65H, s), 6.40-6.47 (2H, m), 6.50 (0.35H, s), 6.96 (0.65H, s), 6.98-7.04 (2H, m), 7.77 (0.65H, s), 7.79 (0.35H, s).

MS (ESI) m/z: 426 (M+H)⁺.

Example 9

N-{6-methoxy-4-[4-(3-morpholin-4-ylazetidin-1-yl) phenylamino]pyridin-3-yl}acetamide (9a) 4-(1-benzhydrylazetidin-3-yl)morpholine

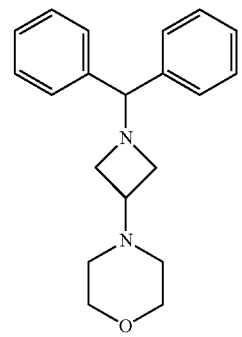 [SMILES: c1ccc(C(c2ccccc2)N2CC(N3CCOCC3)C2)cc1]

Using 1-benzhydrylazetidin-3-ol (5.00 g, 20.9 mmol) and morpholine (3.65 mL, 41.8 mmol), and by a method similar to that in Example 8 (8a) and (8b), the title object compound was obtained as a pale yellow oil (5.51 g, yield 85%).

¹H-NMR (CDCl₃, 400 MHz) 5:2.26-2.33 (4H, m), 2.87-3.02 (3H, m), 3.36-3.43 (2H, m), 3.68-3.73 (4H, m), 4.41 (1H, s), 7.16-7.43 (10H, m).

(9b) 4-[1-(4-nitrophenyl)azetidin-3-yl]morpholine

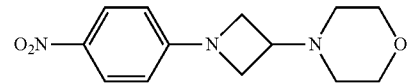

Using 4-(1-benzhydrylazetidin-3-yl)morpholine (5.50 g, 17.8 mmol) produced in Example 9 (9a), and by a method similar to that in Example 8 (8c), the title object compound was obtained as a yellow powder (3.10 g, yield 66%).

¹H-NMR (CDCl₃, 400 MHz) δ: 2.41-2.52 (4H, m), 3.35-3.41 (1H, m), 3.72-3.81 (4H, m), 3.86-3.92 (2H, m), 4.07-4.11 (2H, m), 6.29-6.33 (2H, m), 8.08-8.12 (2H, m).

(9c) (2-methoxy-5-nitropyridin-4-yl)-{4-[3-(morpholin-4-yl)azetidin-1-yl]phenyl}amine

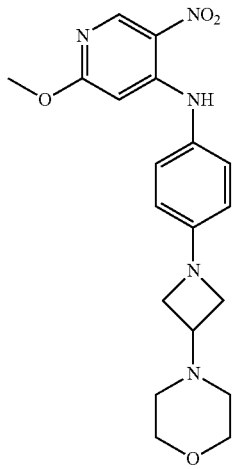 [SMILES: COc1cc(Nc2ccc(N3CC(N4CCOCC4)C3)cc2)c([N+](=O)[O-])cn1]

Using 4-[1-(4-nitrophenyl)azetidin-3-yl]morpholine (1.66 g, 6.30 mmol) produced in Example 9 (9b), and by a method similar to that in Example 8 (8e), the title object compound was obtained as a yellow powder (337 mg).

¹H-NMR (CDCl₃, 400 MHz) δ: 2.40-2.52 (4H, m), 3.30-3.41 (1H, m), 3.70-3.80 (6H, m), 3.90 (3H, s), 3.97-4.05 (2H, m), 6.00 (1H, s), 6.44-6.53 (2H, m), 7.03-7.11 (2H, m), 9.02 (1H, s), 9.26 (1H, s).

(9d) N-(6-methoxy-4-{4-[3-(morpholin-4-yl)azetidin-1-yl]phenylamino}pyridin-3-yl)acetamide

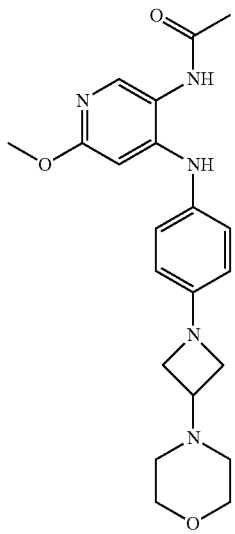 [SMILES: COc1cc(Nc2ccc(N3CC(N4CCOCC4)C3)cc2)c(NC(C)=O)cn1]

Using (2-methoxy-5-nitropyridin-4-yl)-{4-[3-(morpholin-4-yl)azetidin-1-yl]phenyl}amine (0.34 g, 0.87 mmol) produced in Example 9 (9c), and by a method similar to that in Example 8 (8f), the title object compound was obtained as a white powder (241 mg, yield 70%).

¹H-NMR (CDCl₃, 400 MHz) δ: 1.96 (1H, s), 2.24 (2H, s), 2.40-2.51 (4H, m), 3.29-3.39 (1H, m), 3.67-3.78 (6H, m), 3.82 (1.8H, s), 3.85 (1.2H, s), 3.94-4.03 (2H, m), 6.07 (0.4H, s), 6.12 (0.6H, s), 6.29-6.35 (0.6H, m), 6.40-6.50 (2.4H, m), 6.96-7.06 (3H, m), 7.78 (0.6H, s), 7.79 (0.4H, s).

MS (ESI) m/z: 398 (M+H)⁺.

Example 10

N-(4-{4-[4-(2-hydroxyacetyl)piperazin-1-yl]phenylamino}-6-methoxypyridin-3-yl)acetamide (10a) tert-butyl 4-[4-(5-acetylamino-2-methoxypyridin-4-ylamino)phenyl]piperazine-1-carboxylate

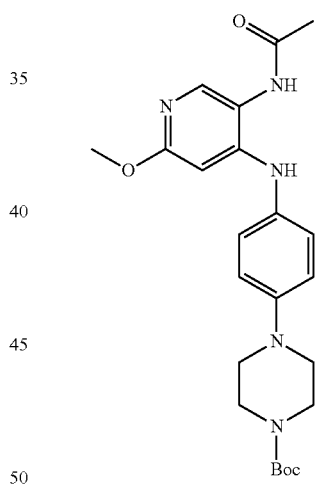

Using tert-butyl 4-(4-aminophenyl)-piperazine-1-carboxylate (1.99 g, 7.19 mmol) and N-(4-iodo-6-methoxypyridin-3-yl)acetamide (2.00 g, 6.85 mmol) produced in Example 1 (1d), and by a method similar to that in Example 1 (1e), the title object compound was obtained as a pale-brown powder (3.05 g, yield 92%).

¹H-NMR (CDCl₃, 400 MHz) δ: 1.49 (9H, s), 1.96 (1H, s), 2.25 (2H, s), 3.05-3.20 (4H, m), 3.52-3.68 (4H, m), 3.83 (2H, s), 3.86 (1H, s), 6.15-6.20 (0.5H, m), 6.26 (0.5H, s), 6.44 (0.7H, s), 6.50-6.53 (0.3H, m), 6.87-6.95 (2H, m), 7.01-7.14 (3H, m), 7.77-7.82 (1H, m).

(10b) N-{6-methoxy-4-[4-(piperazin-1-yl)phenylamino]pyridin-3-yl}acetamide

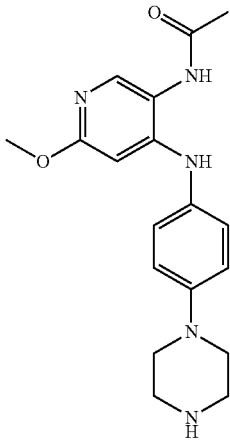 [SMILES: COc1cc(Nc2ccc(N3CCNCC3)cc2)c(NC(C)=O)cn1]

tert-Butyl 4-[4-(5-acetylamino-2-methoxypyridin-4-ylamino)phenyl]piperazine-1-carboxylate (1.43 g, 3.24 mmol) produced in Example 10 (10a) was dissolved in formic acid (5 mL) and, under ice-cooling, hydrogen chloride/isopropanol solution (1.1 mL, 9.7 mmol) was added and the mixture was stirred at the same temperature for 40 min, and at room temperature for 3 hr. Water was added to the reaction mixture, and the mixture was neutralized with saturated aqueous sodium hydrogen carbonate, extracted five times with chloroform, and dried over anhydrous sodium sulfate. The solvent was evaporated under reduced pressure, and the precipitated powder was collected by filtration with isopropyl ether to give the title object compound as a pale-brown powder (330 mg, yield 30%).

$^1$H-NMR (DMSO-$d_5$, 400 MHz) δ: 2.04 (3H, s), 2.80-2.88 (4H, m), 2.97-3.08 (4H, m), 3.71 (3H, s), 5.99 (1H, s), 6.92-6.94 (2H, m), 7.02-7.04 (2H, m), 7.60 (1H, s), 7.64 (1H, s), 9.08 (1H, s).

(10c) N-(4-{4-[4-(2-hydroxyacetyl)piperazin-1-yl]phenylamino}-6-methoxypyridin-3-yl)acetamide

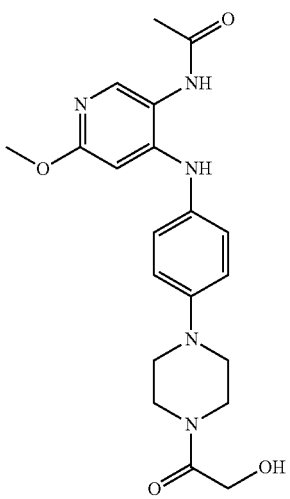 [SMILES: COc1cc(Nc2ccc(N3CCN(C(=O)CO)CC3)cc2)c(NC(C)=O)cn1]

N-{6-Methoxy-4-[4-(piperazin-1-yl)phenylamino]pyridin-3-yl}acetamide (100 mg, 0.293 mmol) produced in Example 10 (10b) was dissolved in methylene chloride (2 mL) and, under ice-cooling, triethylamine (0.053 mL, 0.38 mmol) and 1.0 M acetoxyacetyl chloride/methylene chloride solution (0.29 mL, 0.29 mmol) were added and the mixture was stirred at the same temperature for 1 hr. The reaction mixture was washed with water and saturated brine, and dried over anhydrous sodium sulfate. The solvent was evaporated under reduced pressure to give a pale-brown oil.

The obtained oil was dissolved in methanol (2 mL), 5.0 M aqueous sodium hydroxide (0.29 mL, 1.5 mmol) was added at room temperature and the mixture was stirred at the same temperature for 30 min. The reaction mixture was diluted with chloroform, washed with water and saturated brine, and dried over anhydrous sodium sulfate. The solvent was evaporated under reduced pressure, ethyl acetate was added and the solvent was evaporated under reduced pressure. The precipitated powder was collected by filtration with ethyl acetate to give the title object compound as a white powder (75 mg, yield 64%).

$^1$H-NMR (DMSO-$d_6$, 400 MHz) δ: 2.04 (3H, s), 3.05-3.15 (4H, m), 3.42-3.55 (2H, m), 3.56-3.65 (2H, m), 3.71 (3H, s), 6.02 (1H, s), 6.97-6.99 (2H, m), 7.05-7.08 (2H, m), 7.71 (1H, s), 9.10-9.30 (1H, s).

MS (ESI) m/z: 400 (M+H)$^+$.

Example 11

3-{4-[4-(5-acetylamino-2-methoxypyridin-4-ylamino)phenyl]piperazin-1-yl}-2,2-dimethylpropionic acid

(11a) methyl 2,2-dimethyl-3-oxopropionate

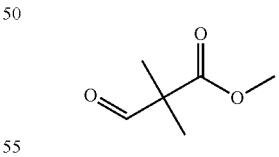

Methyl 3-hydroxy-2,2-dimethylpropionate (10.0 g, 75.7 mmol) was dissolved in methylene chloride (100 mL) and, under ice-cooling, dimethyl sulfoxide (16.1 mL, 227 mmol), triethylamine (15.8 mL, 114 mmol) and sulfur trioxide-pyridine complex (18.1 g, 114 mmol) were added and the mixture was stirred at the same temperature for 1.5 hr. The reaction mixture was washed with 5% citric acid water and water, and dried over anhydrous sodium sulfate. Under reduced pressure (400 mmHg), the solvent was evaporated to give the title object compound as a colorless oil (10.1 g, P=64%, yield 66%).

(11b) methyl 3-{4-[4-(5-acetylamino-2-methoxy-pyridin-4-ylamino)phenyl]piperazin-1-yl}-2,2-dimethylpropionate

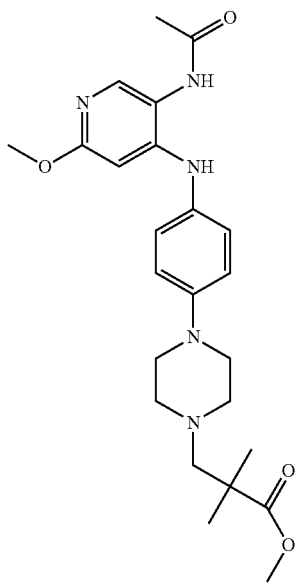 [SMILES: COC(=O)C(C)(C)CN1CCN(c2ccc(Nc3cc(OC)ncc3NC(C)=O)cc2)CC1]

N-[6-Methoxy-4-(4-piperazin-1-ylphenylamino)pyridin-3-yl]acetamide (230 mg, 0.674 mmol) produced in Example 10 (10b) was dissolved in acetonitrile-methanol (1:1) (10 mL), methyl 2,2-dimethyl-3-oxopropionate (1.37 g, 6.74 mmol) produced in Example 11 (11a) was added at room temperature, and the mixture was heated under reflux for 14 hr. Sodium triacetoxyborohydride (714 mg, 3.37 mmol) was added and the mixture was stirred at room temperature for 3 hr. To the reaction mixture was added saturated aqueous sodium hydrogen carbonate, and the mixture was extracted twice with ethyl acetate. The organic layers were combined, washed with saturated brine, and dried over anhydrous sodium sulfate. The solvent was evaporated under reduced pressure, and the obtained residue was purified by silica gel column chromatography (hexane:ethyl acetate, 10%→100%, V/V). The solvent of the object fraction was evaporated under reduced pressure to give the title object compound as a pale yellow oil (93 mg, yield 30%).

$^1$H-NMR (CDCl$_3$, 400 MHz) δ: 1.21 (6H, s), 1.96 (1H, s), 2.25 (2H, s), 2.59 (2H, s), 2.63-2.74 (4H, m), 3.00-3.20 (4H, m), 3.69 (3H, s), 3.83 (2H, s), 3.86 (1H, s), 6.10 (0.3H, s), 6.17 (0.3H, s), 6.46 (0.4H, s), 6.88-6.90 (2H, m), 7.04-7.07 (2H, m), 7.81 (1H, s).

(11c) 3-{4-[4-(5-acetylamino-2-methoxypyridin-4-ylamino)phenyl]piperazin-1-yl}-2,2-dimethylpropionic acid

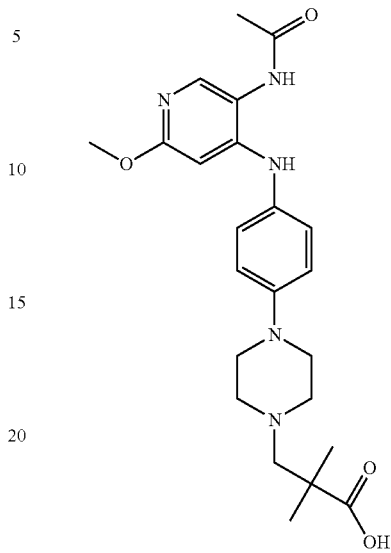

Methyl 3-{4-[4-(5-acetylamino-2-methoxypyridin-4-ylamino)phenyl]piperazin-1-yl}-2,2-dimethylpropionate (93 mg, 0.20 mmol) produced in Example 11 (11b) was dissolved in methanol (2 mL), 5.0 M aqueous sodium hydroxide (0.20 mL, 1.0 mmol) was added and the mixture was stirred at room temperature for 13 hr. The reaction mixture was neutralized with 6 M hydrochloric acid and the solvent was evaporated under reduced pressure. The residue was purified by reversed-phase silica gel column chromatography (water:methanol, 6:4→5:5, V/V). The solvent of the object fraction was evaporated under reduced pressure, and the precipitated powder was washed with isopropyl ether, ethyl acetate and chloroform to give the title object compound as a white powder (35 mg, yield 39%).

$^1$H-NMR (DMSO-d$_5$, 400 MHz) δ: 1.11 (6H, s), 2.03 (3H, s), 2.53-2.58 (2H, br), 2.63-2.74 (4H, m), 3.05-3.15 (4H, m), 3.70 (3H, s), 5.99 (1H, s), 6.92-6.95 (2H, m), 7.02-7.04 (2H, m), 9.14 (1H, s).

MS (ESI) m/z: 442 (M+H)$^+$.

Example 12

1-{4-[4-(4-fluoro-5-methoxy-2-nitrophenylamino)phenyl]piperazin-1-yl}-2-hydroxyethanone

(12a) tert-butyl 4-[4-(4-fluoro-5-methoxy-2-nitrophenylamino)phenyl]piperazine-1-carboxylate

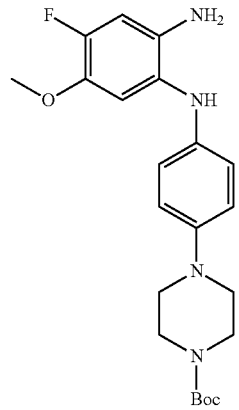 [SMILES: COc1cc(Nc2ccc(N3CCN(C(=O)OC(C)(C)C)CC3)cc2)c(N)cc1F]

Using tert-butyl 4-(4-aminophenyl)piperazine-1-carboxylate (2.83 g, 10.2 mmol) and 1,4-difluoro-2-methoxy-5-nitrobenzene (1.93 g, 10.2 mmol) produced in Example 2 (2a), and by a method similar to that in Example 2 (2b), the title object compound was obtained as a red powder (3.71 g, yield 82%).

¹H-NMR (CDCl₃, 400 MHz) δ: 1.49 (9H, s), 3.12-3.30 (4H, m), 3.57-3.70 (4H, m), 3.74 (3H, s), 6.44 (1H, d, J=8.3 Hz), 6.97-6.99 (2H, m), 7.17-7.19 (2H, m), 7.93 (1H, d, J=11.7 Hz), 9.66 (1H, s).

(12b) (4-fluoro-5-methoxy-2-nitrophenyl)-(4-piperazin-1-ylphenyl)amine

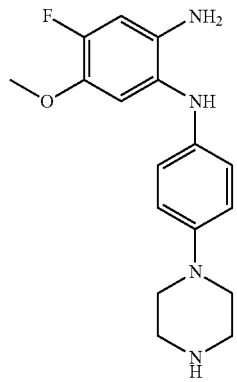 [SMILES: COc1cc(Nc2ccc(N3CCNCC3)cc2)c(N)cc1F]

Using tert-butyl 4-[4-(4-fluoro-5-methoxy-2-nitrophenylamino)phenyl]piperazine-1-carboxylate (600 mg, 1.34 mmol) produced in Example 12 (12a), and by a method similar to that in Example 10 (10b), the title object compound was obtained as a red powder (300 mg, yield 65%).

¹H-NMR (DMSO-d₆, 400 MHz) δ: 2.82-2.88 (4H, m), 3.06-3.14 (4H, m), 3.74 (3H, s), 6.53 (1H, d, J=7.8 Hz), 6.97-7.00 (2H, m), 7.23-7.25 (2H, m), 7.94 (1H, d, J=12.0 Hz), 9.66 (1H, s).

(12c) 1-{4-[4-(4-fluoro-5-methoxy-2-nitrophenylamino)phenyl]piperazin-1-yl}-2-hydroxyethanone

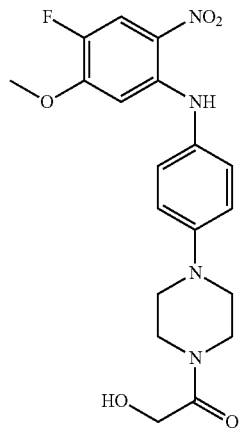 [SMILES: COc1cc(Nc2ccc(N3CCN(C(=O)CO)CC3)cc2)c([N+](=O)[O-])cc1F]

Using (4-fluoro-5-methoxy-2-nitrophenyl)-(4-piperazin-1-ylphenyl)amine (70 mg, 0.20 mmol) produced in Example 12 (12b), and by a method similar to that in Example 10 (10c), the title object compound was obtained as a red powder (80 mg, yield 99%).

¹H-NMR (DMSO-d₅, 400 MHz) δ: 3.12-3.24 (4H, m), 3.46-3.54 (2H, m), 3.59-3.66 (2H, m), 3.74 (3H, s), 4.10-4.14 (2H, m), 4.58-4.68 (1H, br), 6.55 (1H, d, J=7.6 Hz), 7.02-7.04 (2H, m), 7.26-7.28 (2H, m), 7.95 (1H, d, J=12.0 Hz), 9.66 (1H, s).

MS (ESI) m/z: 405 (M+H)⁺.

Example 13

3-{4-[4-(4-fluoro-5-methoxy-2-nitrophenylamino)phenyl]piperazin-1-yl}-2,2-dimethylpropionic acid (13a) methyl 3-{4-[4-(4-fluoro-5-methoxy-2-nitrophenylamino)phenyl]piperazin-1-yl}-2,2-dimethylpropionate

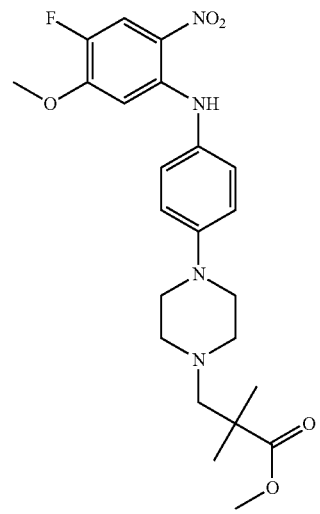 [SMILES: COC(=O)C(C)(C)CN1CCN(c2ccc(Nc3cc(OC)c(F)cc3[N+](=O)[O-])cc2)CC1]

Using (4-fluoro-5-methoxy-2-nitrophenyl)-(4-piperazin-1-ylphenyl)amine (156 mg, 0.450 mmol) produced in Example 12 (12b) and methyl 2,2-dimethyl-3-oxopropionate (174 mg, 0.90 mmol) produced in Example 11 (11a), and by a method similar to that in Example 11 (11b), the title object compound was obtained as a red powder (130 mg, yield 63%).

¹H-NMR (CDCl₃, 400 MHz) δ: 1.20 (6H, s), 2.57 (2H, s), 2.65-2.74 (4H, m), 3.13-3.20 (4H, m), 3.68 (3H, s), 3.73 (3H, s), 6.41 (1H, d, J=7.6 Hz), 6.93-6.95 (2H, m), 7.13-7.16 (2H, m), 7.92 (1H, d, J=11.7 Hz), 9.65 (1H, s).

(13b) 3-{4-[4-(4-fluoro-5-methoxy-2-nitrophenylamino)phenyl]piperazin-1-yl}-2,2-dimethylpropionic acid

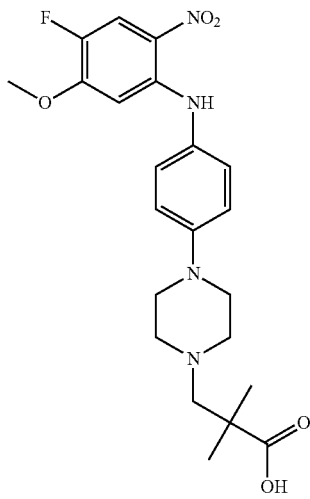 [SMILES: COc1cc(Nc2ccc(N3CCN(CC(C)(C)C(=O)O)CC3)cc2)c([N+](=O)[O-])cc1F]

Using methyl 3-{4-[4-(4-fluoro-5-methoxy-2-nitrophenylamino)phenyl]piperazin-1-yl}-2,2-dimethylpropionate (130 mg, 0.282 mmol) produced in Example 13 (13a), and by a method similar to that in Example 11 (11c), the title object compound was obtained as a pale-red powder (110 mg, yield 88%).

$^1$H-NMR (DMSO-d$_6$, 400 MHz) δ: 1.10 (6H, s), 2.45-2.55 (2H, m), 2.59-2.64 (4H, m), 3.07-3.18 (4H, m), 3.73 (3H, s), 6.52 (1H, d, J=7.6 Hz), 6.97-6.99 (2H, m), 7.22-7.25 (2H, m), 7.94 (1H, d, J=12.0 Hz), 9.66 (1H, s).

MS (ESI) m/z: 447 (M+H)$^+$.

Example 14

N-(6-methoxy-4-{4-[2-(tetrahydrofuran-3-yloxy]phenylamino}pyridin-3-yl)acetamide (14a) 3-[2-(4-nitrophenoxy)ethoxy]tetrahydrofuran

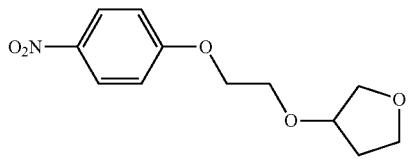 [SMILES: O=[N+]([O-])c1ccc(OCCOC2CCOC2)cc1]

2-(Tetrahydrofuran-3-yloxy)ethanol (1.4 g, 11 mmol) produced in Reference Example 3 (3b) was dissolved in methylene chloride (30 mL) and, under ice-cooling, triethylamine (2.21 mL, 15.9 mmol), methanesulfonyl chloride (1.07 mL, 13.8 mmol) was added, and the mixture was stirred at room temperature for 1 hr was stirred. Water was added to the reaction mixture, and the mixture was extracted twice with ethyl acetate. The organic layer was washed with saturated brine and dried over anhydrous sodium sulfate, and the solvent was evaporated under reduced pressure.

The obtained oil was dissolved in dimethylformamide (45 mL), 4-nitrophenol (1.77 g, 12.7 mmol) and potassium carbonate (2.93 g, 21.2 mmol) were added, and the mixture was stirred at 80° C. for 2 hr. Water was added to the reaction mixture, and the mixture was extracted twice with ethyl acetate. The organic layer was washed successively with water and saturated brine and dried over anhydrous sodium sulfate, and the solvent was evaporated under reduced pressure. The obtained residue was purified by silica gel column chromatography (hexane:ethyl acetate, 1:1→1:1, V/V), and the solvent of the object fraction was evaporated under reduced pressure to give the title object compound as a yellow oil (2.33 g, yield 87%).

$^1$H-NMR (CDCl$_3$, 400 MHz) δ: 1.99-2.07 (2H, m), 3.76-3.96 (6H, m), 4.18-4.26 (3H, m), 6.93-7.04 (2H, m), 8.15-8.25 (2H, m).

(14b) 4-[2-(tetrahydrofuran-3-yloxy)ethoxy]phenylamine

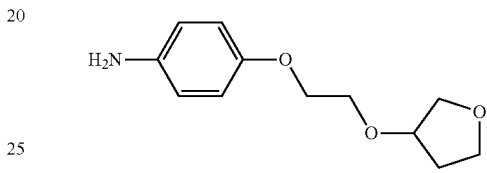

10% Palladium-carbon (470 mg) was suspended in toluene (1 mL), 3-[2-(4-nitrophenoxy)ethoxy]tetrahydrofuran (2.33 g, 9.20 mmol) produced in Example 14 (14a) and methanol (50 mL) were added, and catalytic hydrogenation was performed at room temperature, 0.3 MPa for 2 hr. The insoluble material was filtered off through celite and the solvent was evaporated under reduced pressure to give the title object compound as a brown oil (2.02 g, 98%).

$^1$H-NMR (CDCl$_3$, 400 MHz) δ: 1.95-2.07 (2H, m), 3.38-3.49 (2H, br), 3.69-3.95 (6H, m), 4.03 (2H, t, J=4.8 Hz), 4.19-4.25 (1H, m), 6.60-6.66 (2H, m), 6.70-6.79 (2H, m).

(14c) (2-methoxy-5-nitropyridin-4-yl)-{4-[2-(tetrahydrofuran-3-yloxy)ethoxy]phenyl}amine

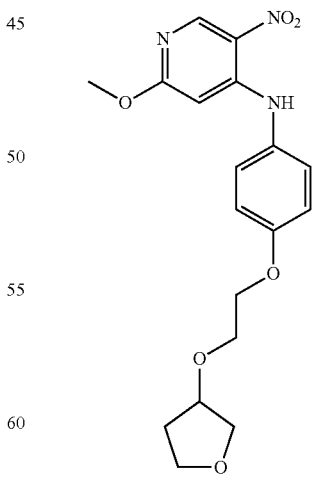

Using 4-[2-(tetrahydrofuran-3-yloxy)ethoxy]phenylamine (2.02 g, 9.05 mmol) produced in Example 14 (14b) and 4-chloro-2-methoxy-5-nitropyridine (1.71 g, 9.05 mmol) produced in Example 4 (4c), and by a method similar to that in Example 4 (4d), the title object compound was obtained as a yellow powder (3.04 g, yield 90%).

$^1$H-NMR (CDCl$_3$, 400 MHz) δ: 2.01-2.09 (2H, m), 3.76-3.98 (6H, m), 3.91 (3H, s), 4.08-4.17 (2H, m), 4.20-4.29 (1H, m), 6.04 (1H, s), 6.92-7.02 (2H, m), 7.12-7.21 (2H, m), 9.04 (1H, s), 9.31 (1H, s).

(14d) N-(6-methoxy-4-{4-[2-(tetrahydrofuran-3-yloxy]phenylamino}pyridin-3-yl)acetamide

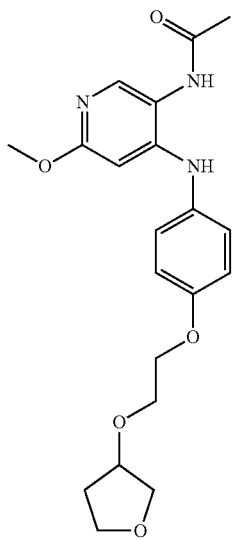 [SMILES: COc1cc(Nc2ccc(OCCOC3CCOC3)cc2)c(NC(C)=O)cn1]

Using (2-methoxy-5-nitropyridin-4-yl)-{4-[2-(tetrahydrofuran-3-yloxy)ethoxy]phenyl}amine (3.04 g, 8.10 mmol) produced in Example 14 (14c), and by a method similar to that in Example 8 (8f), the title object compound was obtained as a pale-purple powder (603 mg).

$^1$H-NMR (CDCl$_3$, 400 MHz) δ: 1.96 (1H, s), 1.97-2.09 (2H, m), 2.25 (2H, s), 3.74-3.96 (6H, m), 3.82 (3H, s), 4.08-4.14 (2H, m), 4.20-4.27 (1H, m), 6.15 (0.3H, s), 6.20 (1H, s), 6.56 (0.3H, s), 6.67 (0.7H, s), 6.85-6.96 (2H, m), 7.05-7.14 (2H, m), 7.35 (0.7H, s), 7.82 (1H, s).

MS (ESI) m/z: 388 (M+H)$^+$.

Example 15

N-(6-methoxy-4-{4-[2-(4-methylpiperazin-1-yl)ethoxy]phenylamino}pyridin-3-yl)acetamide (15a) 2-(4-nitrophenoxy)ethanol

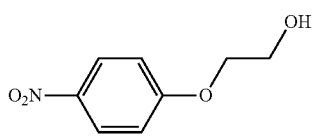

4-Nitrophenol (5.00 g, 35.9 mmol) was dissolved in dimethylformamide (50 mL), 2-bromoethanol (5.39 g, 43.1 mmol) and potassium carbonate (6.45 g, 46.7 mmol) were added, and the mixture was stirred at 90° C. for 18 hr. The insoluble material was filtered off, water (200 mL) was added, and the mixture was extracted twice with ethyl acetate. The organic layer was washed successively with water and saturated brine, and dried over anhydrous sodium sulfate. The solvent was evaporated under reduced pressure. The obtained residue was purified by silica gel column chromatography (chloroform:ethyl acetate, 6:1, V/V), and the solvent of the object fraction was evaporated under reduced pressure to give the title object compound as a white powder (4.41 g, yield 67%).

$^1$H-NMR (CDCl$_3$, 400 MHz) δ: 1.24-1.28 (1H, m), 4.01-4.05 (2H, m), 4.18-4.20 (2H, m), 6.98-7.00 (2H, m), 8.20-8.22 (2H, m).

(15b) 1-methyl-4-[2-(4-nitrophenoxy)ethyl]piperazine

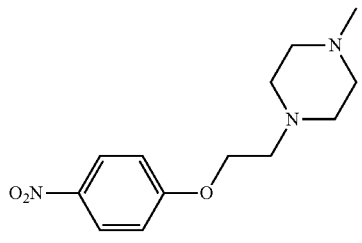 [SMILES: CN1CCN(CCOc2ccc([N+](=O)[O-])cc2)CC1]

Using 2-(4-nitrophenoxy)ethanol (1.00 g, 5.46 mmol) produced in Example 15 (15a) and N-methylpiperazine (1.21 mL, 10.9 mmol), and by a method similar to that in Example 8 (8a) and (8b), the title object compound was obtained as a yellow oil (763 mg, yield 53%).

$^1$H-NMR (CDCl$_3$, 400 MHz) δ: 2.30 (3H, s), 2.47-2.62 (8H, m), 2.84-2.87 (2H, m), 4.18-4.20 (2H, m), 6.95-6.97 (2H, m), 8.90-8.92 (2H, m).

(15c) 4-[2-(4-methylpiperazin-1-yl)ethoxy]phenylamine

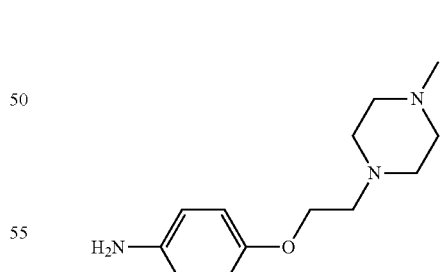

Using 1-methyl-4-[2-(4-nitrophenoxy)ethyl]piperazine (761 mg, 2.87 mmol) produced in Example 15 (15b), and by a method similar to that in Example 14 (14b), the title object compound was obtained as a yellow powder (684 mg, yield 100%).

$^1$H-NMR (DMSO-d$_5$, 400 MHz) δ: 2.29 (3H, s), 2.45-2.58 (8H, m), 2.63-2.66 (2H, m), 3.90-3.93 (2H, m), 6.47-6.49 (2H, m), 6.62-6.64 (2H, m).

(15d) N-(6-methoxy-4-{4-[2-(4-methylpiperazin-1-yl)ethoxy]phenylamino}pyridin-3-yl)acetamide

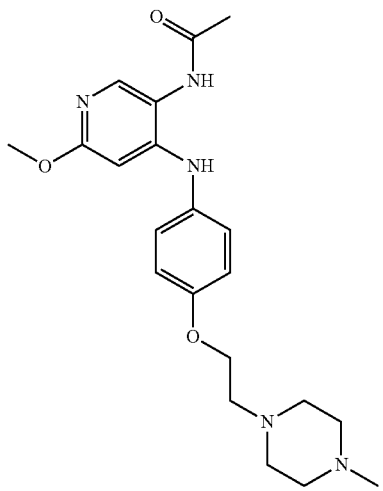

Using 4-[2-(4-methylpiperazin-1-yl)ethoxy]phenylamine (222 mg, 0.942 mmol) produced in Example 15 (15c) and N-(4-iodo-6-methoxypyridin-3-yl)acetamide (250 mg, 0.856 mmol) produced in Example 1 (1d), and by a method similar to that in Example 1 (1e), the title object compound was obtained as a white powder (200 mg, yield 58%).

$^1$H-NMR (DMSO-d$_6$, 400 MHz) δ: 2.04 (3H, s), 2.14 (3H, s), 2.26-2.39 (4H, m), 2.47-2.54 (4H, m), 2.66-2.69 (2H, m), 3.71 (3H, s), 4.04-4.07 (2H, m), 6.00 (1H, s), 6.94-6.97 (2H, m), 6.94-6.97 (2H, m), 7.08-7.10 (1H, s), 7.71 (1H, s), 9.10 (1H, s).

MS (ESI) m/z: 400 (M+H)$^+$.

Example 16

N-(4-{4-[3-(2-sulfamoylaminoethoxy)azetidin-1-yl]phenylamino}-6-methoxypyridin-3-yl)acetamide

(16a) N-(4-{4-[3-(2-tert-butoxycarbonylsulfamoylaminoethoxy)azetidin-1-yl]phenylamino}-6-methoxypyridin-3-yl)acetamide

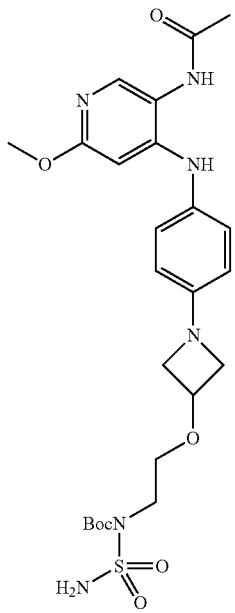 [SMILES: COc1cc(Nc2ccc(N3CC(OCCN(C(=O)OC(C)(C)C)S(N)(=O)=O)C3)cc2)c(NC(C)=O)cn1]

N-(4-{4-[3-(2-Hydroxyethoxy)azetidin-1-yl]phenylamino}-6-methoxypyridin-3-yl)acetamide (850 mg, 2.28 mmol) produced in Example 1 (1f), N-tert-butoxycarbonylsulfamoyl amine (0.67 g, 3.4 mmol), and triphenylphosphine (0.72 g, 2.7 mmol) were suspended in ethyl acetate: tetrahydrofuran (3:1, 15 mL), diethyl azodicarboxylate (0.74 mL, 3.4 mmol) was added, and the mixture was stirred at room temperature for 20 hr. The solvent of the reaction mixture was evaporated under reduced pressure, and the obtained residue was purified by silica gel column chromatography (chloroform:methanol, 100:0→100:4, V/V). The solvent of the object fraction was evaporated under reduced pressure to give the title object compound as a pale-yellow foam-like powder (1.05 g, yield 84%).

$^1$H-NMR (CDCl$_3$, 400 MHz) δ: 1.55 (9H, s), 1.96 (1H, s), 2.24 (2H, s), 3.61 (2H, t, J=5.3 Hz), 3.66-3.74 (2H, m), 3.82 (2H, s), 3.85 (1H, s), 3.98 (2H, t, J=5.3 Hz), 4.00-4.08 (2H, m), 4.38-4.46 (1H, m), 5.44-5.55 (2H, br), 6.10 (0.35H, s), 6.12 (0.35H, s), 6.15 (0.65H, s), 6.34 (0.65H, s), 6.41-6.50 (2H, m), 6.54 (0.65H, s), 6.98-7.07 (2.35H, m), 7.78 (0.65H, s), 7.79 (0.35H, s).

(16b) N-(4-{4-[3-(2-sulfamoylaminoethoxy)azetidin-1-yl]phenylamino}-6-methoxypyridin-3-yl)acetamide

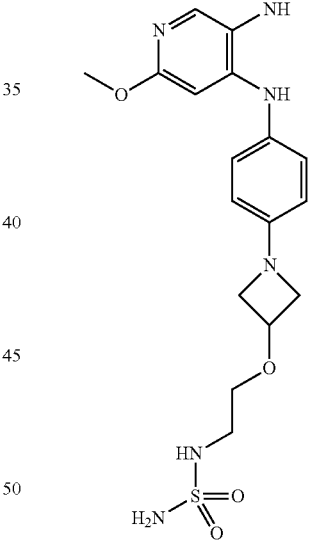

Under ice-cooling, to trifluoroacetic acid (10 mL) was added a suspension of N-(4-{4-[3-(2-tert-butoxycarbonylsulfamoylaminoethoxy)azetidin-1-yl]phenylamino}-6-methoxypyridin-3-yl)acetamide (1.05 g, 1.91 mmol) produced in Example 16 (16a) in methylene chloride (2 mL), and the mixture was stirred at room temperature for 1 hr. The reaction mixture was neutralized with saturated aqueous sodium hydrogen carbonate. The mixture was extracted twice with chloroform.

The organic layer was washed with saturated brine, and dried over anhydrous sodium sulfate. The solvent was evaporated under reduced pressure. The obtained residue was purified by silica gel column chromatography (chloroform:methanol, 98:2→84:16, V/V). The solvent of the object fraction was evaporated under reduced pressure, and the obtained residue was recrystallized from ethanol (70 mL) to give the title object compound as a white powder (215 mg, yield 25%).

$^1$H-NMR (DMSO-d$_6$, 400 MHz) δ: 2.03 (3H, s), 3.04 (2H, q, J=6.1 Hz), 3.49 (2H, t, J=6.1 Hz), 3.57-3.64 (2H, m), 3.69 (3H, s), 4.01-4.10 (2H, m), 4.38-4.46 (1H, m), 5.89 (1H, s), 6.43-6.50 (2H, m), 6.51-6.60 (3H, m), 6.95-7.05 (2H, m), 7.54 (1H, s), 7.67 (1H, s), 9.05 (1H, s).

MS (ESI) m/z: 451 (M+H)$^+$.

Example 17

4-acetyl-3-{4-[2-(tetrahydropyran-4-yloxy)ethoxy]phenylamino}benzamide (17a) 4-[2-(4-nitrophenoxy)ethoxy]tetrahydropyran

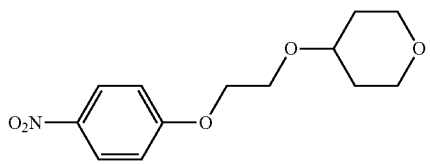 [SMILES: O=[N+]([O-])c1ccc(OCCOC2CCOCC2)cc1]

Using 2-(tetrahydropyran-4-yloxy)ethanol (4.83 g, 33.0 mol) produced in Reference Example 4 (4b), and by a method similar to that in Example 14 (14a), the title object compound was obtained as a pale-yellow oil (6.20 g, yield 70%).

$^1$H-NMR (CDCl$_3$, 400 MHz) δ: 1.57-1.69 (2H, m), 1.88-1.98 (2H, m), 3.40-3.50 (2H, m), 3.54-3.65 (1H, m), 3.83-3.90 (2H, m), 3.91-4.00 (2H, m), 4.20-4.25 (2H, m), 6.95-7.02 (2H, m), 8.16-8.24 (2H, m).

(17b) 4-[2-(tetrahydropyran-4-yloxy)ethoxy]phenylamine

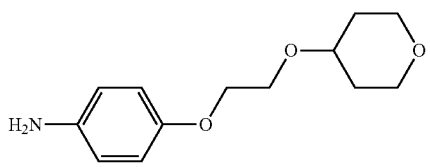

Using 4-[2-(4-nitrophenoxy)ethoxy]tetrahydropyran (6.20 g, 23.2 mmol) produced in Example 17 (17a), and by a method similar to that in Example 14 (14b), the title object compound was obtained as a brown oil (5.20 g, yield 95%).

$^1$H-NMR (CDCl$_3$, 400 MHz) δ: 1.55-1.72 (2H, m), 1.85-1.98 (2H, m), 3.37-3.50 (4H, m), 3.53-3.64 (1H, m), 3.75-3.83 (2H, m), 3.90-3.99 (2H, m), 4.00-4.08 (2H, m), 6.60-6.67 (2H, m), 6.72-6.80 (2H, m).

(17c) ethyl 4-(2-methyl-[1,3]dioxolan-2-yl)-3-{4-[2-(tetrahydropyran-4-yloxy)ethoxy]phenylamino}benzoate

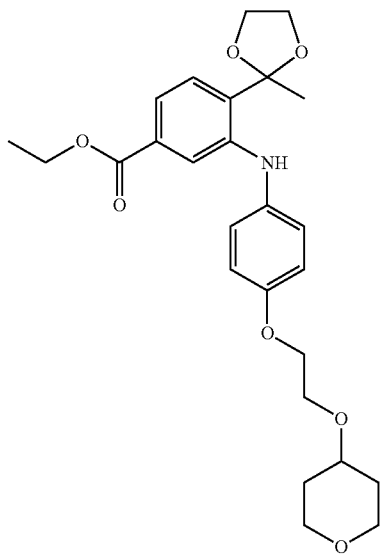 [SMILES: CCOC(=O)c1ccc(C2(C)OCCO2)c(Nc2ccc(OCCOC3CCOCC3)cc2)c1]

Using 4-[2-(tetrahydropyran-4-yloxy)ethoxy]phenylamine (1.24 g, 5.20 mmol) produced in Example 17 (17b) and ethyl 4-(2-methyl-[1,3]dioxolan-2-yl)-3-trifluoromethanesulfonyloxybenzoate (2.0 g, 5.2 mmol) produced in Example 6 (6c), and by a method similar to that in Example 6 (6d), the title object compound was obtained (630 mg, yield 26%).

(17d) 4-(2-methyl-[1,3]dioxolan-2-yl)-3-{4-[2-(tetrahydropyran-4-yloxy)ethoxy]phenylamino}benzoic acid

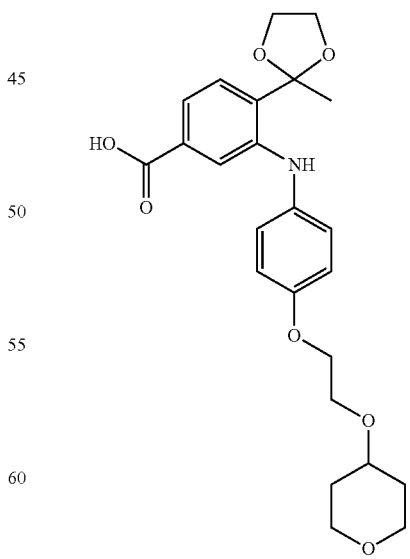

Ethyl 4-(2-methyl-[1,3]dioxolan-2-yl)-3-{4-[2-(tetrahydropyran-4-yloxy)ethoxy]phenylamino}benzoate (630 mg, 1.34 mmol) produced in Example 17 (17c) was dissolved in methanol (6 mL), 5.0 M aqueous sodium hydroxide (0.83 mL, 4.2 mmol) was added and the mixture was stirred at 50° C. for 2 hr. To the reaction mixture was added water (6 mL), methanol was evaporated under reduced pressure, and the residue was washed with toluene. The aqueous layer was neutralized with 6.0 M hydrochloric acid under ice-cooling, extracted three times with chloroform, and dried over anhydrous sodium sulfate. The solvent was evaporated under reduced pressure to give the title object compound as a pale-brown powder (366 mg, yield 62%).

$^1$H-NMR (DMSO-d$_6$, 400 MHz) δ: 1.55-1.70 (2H, m), 1.73 (3H, s), 1.88-1.98 (2H, m), 3.42-3.68 (3H, m), 3.82-4.01 (6H, m), 4.07-4.20 (4H, m), 6.88-6.90 (2H, m), 7.04-7.06 (2H, m), 7.30 (1H, s), 7.45-7.51 (2H, m), 7.76 (1H, s).

(17e) 4-(2-methyl-[1,3]dioxolan-2-yl)-3-{14-[2-(tetrahydropyran-4-yloxy]phenylamino}benzamide

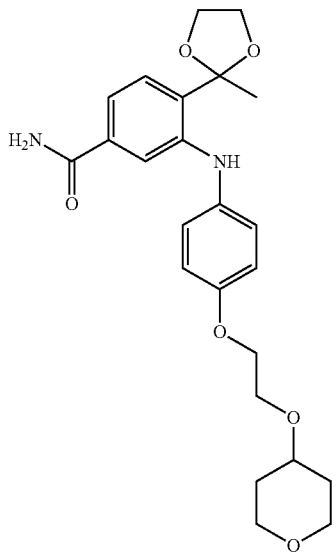 [SMILES: CC1(c2ccc(C(N)=O)cc2Nc2ccc(OCCOC3CCOCC3)cc2)OCCO1]

4-(2-Methyl-[1,3]dioxolan-2-yl)-3-{4-[2-(tetrahydropyran-4-yloxy)ethoxy]phenylamino}benzoic acid (160 mg, 0.361 mmol) produced in Example 17 (17d) was dissolved in dimethylformamide (3 mL), 1-ethyl-3-(3-dimethylaminopropyl)carbodiimide hydrochloride (208 mg, 1.08 mmol), 1-hydroxybenzotriazole (146 mg, 1.08 mmol) and 28% aqueous ammonia (0.15 mL, 2.2 mmol) were added at room temperature, and the mixture was stirred at the same temperature for 14 hr. Water was added to the reaction mixture and the mixture was extracted twice with ethyl acetate. The organic layer was washed successively with water and saturated brine, and dried over anhydrous sodium sulfate. The solvent was evaporated under reduced pressure, the obtained residue was purified by column chromatography (hexane:ethyl acetate, 9:1→0:1, V/V). The solvent of the object fraction was evaporated under reduced pressure to give the title object compound as a pale-brown oil (143 mg, yield 89%).

$^1$H-NMR (DMSO-d$_5$, 400 MHz) δ: 1.55-1.70 (2H, m), 1.73 (3H, s), 1.90-1.98 (2H, m), 3.42-3.49 (2H, m), 3.57-3.66 (1H, m), 3.82-3.88 (4H, m), 3.92-4.00 (2H, m), 4.09-4.20 (4H, m), 5.40-5.60 (1H, br), 5.80-6.05 (1H, br), 6.89-6.91 (2H, m), 7.05-7.07 (2H, m), 7.14 (1H, dd, J=8.1, 1.7 Hz), 7.31 (1H, s), 7.48-7.50 (2H, m).

(17f) 4-acetyl-3-{4-[2-(tetrahydropyran-4-yloxy)ethoxy]phenylamino}benzamide

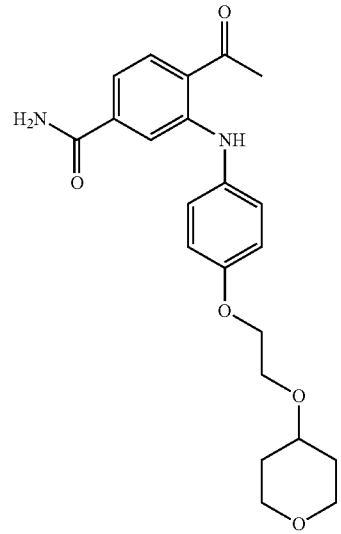 [SMILES: CC(=O)c1ccc(C(N)=O)cc1Nc1ccc(OCCOC2CCOCC2)cc1]

4-(2-Methyl-[1,3]dioxolan-2-yl)-3-{4-[2-(tetrahydropyran-4-yloxy]phenylamino}benzamide (143 mg, 0.316 mmol) produced in Example 17 (17e) was dissolved in tetrahydrofuran (1 mL), 2.0 M hydrochloric acid (1 mL) was added at room temperature and the mixture was stirred at the same temperature for 2 hr. The reaction mixture was neutralized with saturated aqueous sodium hydrogen carbonate, extracted twice with ethyl acetate, and dried over anhydrous sodium sulfate. The solvent was evaporated under reduced pressure, and the obtained powder was collected by filtration with diisopropyl ether to give the title object compound as a yellow powder (95 mg, yield 75%).

$^1$H-NMR (DMSO-d$_5$, 400 MHz) δ: 1.60-1.70 (2H, m), 1.90-1.98 (2H, m), 2.66 (3H, s), 3.42-3.52 (2H, m), 3.57-3.66 (1H, m), 3.82-3.88 (2H, m), 3.92-4.02 (2H, m), 4.10-4.16 (2H, m), 5.40-5.60 (1H, br), 5.80-6.00 (1H, br), 6.93-6.95 (2H, m), 7.00 (1H, dd, J=8.3, 1.7 Hz), 7.15-7.17 (2H, m), 7.36 (1H, d, J=1.7 Hz), 7.84 (1H, d, J=8.3 Hz), 10.39 (1H, s).

MS (ESI) m/z: 399 (M+H)$^+$.

Example 18

4-(1,1-difluoroethyl)-3-{4-[2-(tetrahydropyran-4-yloxy)ethoxy]phenylamino}benzamide (18a) methyl 4-acetyl-3-bromobenzoate

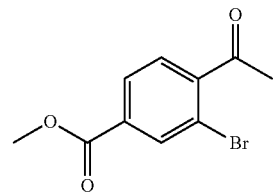

4-acetyl-3-bromobenzoic acid (4.17 g, 17.2 mmol) was dissolved in dimethylformamide (40 mL), methyl iodide (3.20 mL, 51.5 mmol), potassium carbonate (3.57 g, 25.8 mmol) was added, and the mixture was stirred at room temperature for 3 hr was stirred. Water was added to the reaction mixture, and the mixture was extracted twice with ethyl acetate. The organic layer was washed successively with water and saturated brine, and dried over anhydrous sodium sulfate. The solvent was evaporated under reduced pressure, and the obtained residue was purified by silica gel column chromatography (hexane:ethyl acetate, 9:1→7:3, V/V). The solvent of the object fraction was evaporated under reduced pressure to give the title object compound as a pale yellow oil (4.32 g, yield 98%).

$^1$H-NMR (CDCl$_3$, 400 MHz) δ: 2.64 (3H, s), 3.94 (3H, s), 7.47 (1H, d, J=8.0 Hz), 8.01 (1H, dd, J=8.0, 1.4 Hz), 8.27 (1H, d, J=1.4 Hz)

(18b) methyl 3-bromo-4-(1,1-difluoroethyl)benzoate

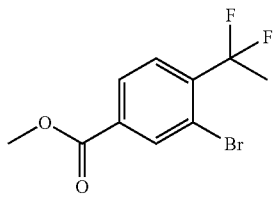

bis(2-Methoxyethyl)aminosulfur trifluoride (2.32 g, 10.5 mmol) was dissolved in chloroform (10 mL), methyl 4-acetyl-3-bromobenzoate (900 mg, 3.50 mmol) produced in Example 18 (18a) was added, and the mixture was stirred at 50° C. for 66 hr. The reaction mixture was washed with saturated aqueous sodium hydrogen carbonate, and dried over anhydrous sodium sulfate. The solvent was evaporated under reduced pressure. The obtained residue was purified by silica gel column chromatography (hexane:ethyl acetate, 20:1→5:1, V/V). The solvent of the object fraction was evaporated under reduced pressure to give the title object compound as a slightly yellow oil (660 mg, yield 68%).

$^1$H-NMR (CDCl$_3$, 400 MHz) δ: 2.06 (3H, t, J=18.3 Hz), 4.43 (3H, s), 7.68 (1H, d, J=8.3 Hz), 8.01 (1H, dd, J=8.3, 0.5 Hz), 8.30 (1H, d, J=0.5 Hz).

(18c) methyl 4-(1,1-difluoroethyl)-3-{4-[2-(tetrahydropyran-4-yloxy)ethoxy]phenylamino}benzoate

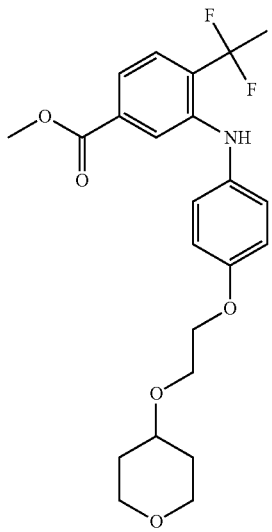 [SMILES: COC(=O)c1ccc(C(C)(F)F)c(Nc2ccc(OCCOC3CCOCC3)cc2)c1]

Using methyl 3-bromo-4-(1,1-difluoroethyl)benzoate (660 mg, 2.36 mmol) produced in Example 18 (18b) and 4-[2-(tetrahydropyran-4-yloxy)ethoxy]phenylamine (616 mg, 2.60 mmol) produced in Example 17 (17b), and by a method similar to that in Example 6 (6d), the title object compound was obtained as a slightly yellow oil (600 mg, yield 58%).

$^1$H-NMR (CDCl$_3$, 400 MHz) δ: 1.59-1.71 (2H, m), 1.90-2.00 (2H, m), 2.03 (3H, t, J=18.6 Hz), 3.42-3.50 (2H, m), 3.57-3.68 (1H, m), 3.80-3.89 (5H, m), 3.92-4.01 (2H, m), 4.10-4.16 (2H, m), 6.10-6.18 (1H, m), 6.90-6.97 (2H, m), 7.04-7.09 (2H, m), 7.46-7.51 (2H, m), 7.67-7.71 (1H, m).

(18d) 4-(1,1-difluoroethyl)-3-{4-[2-(tetrahydropyran-4-yloxy)ethoxy]phenylamino}benzamide

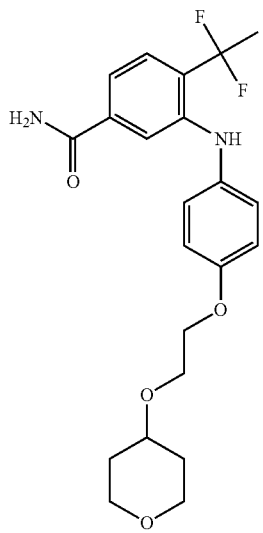 [SMILES: CC(F)(F)c1ccc(C(N)=O)cc1Nc1ccc(OCCOC2CCOCC2)cc1]

Using methyl 4-(1,1-difluoroethyl)-3-{4-[2-(tetrahydropyran-4-yloxy)ethoxy]phenylamino}benzoate (600 mg, 1.38 mmol) produced in Example 18 (18c), and by a method similar to that in Example 6 (6e), the title object compound was obtained as a yellow foam-like powder (266 mg, yield 48%).

$^1$H-NMR (CDCl$_3$, 400 MHz) δ: 1.59-1.70 (2H, m), 1.90-2.00 (2H, m), 2.04 (3H, t, J=18.6 Hz), 3.41-3.52 (2H, m), 3.57-3.66 (1H, m), 3.80-3.88 (2H, m), 3.94-4.01 (2H, m), 4.10-4.16 (2H, m), 5.40-6.05 (1H, m), 6.14-6.22 (1H, m), 6.89-6.96 (2H, m), 7.03-7.10 (2H, m), 7.17-7.22 (1H, m), 7.43-7.48 (2H, m).

MS (ESI) m/z: 421 (M+H)$^+$.

Example 19

4-acetyl-3-{4-[2-(2-hydroxyethoxy)ethoxy]phenylamino}benzamide

(19a) methyl 3-bromo-4-(2-methyl-[1,3]dioxolan-2-yl)benzoate

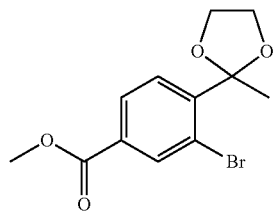

Using methyl 4-acetyl-3-bromobenzoate (4.32 g, 16.8 mmol) produced in Example 18 (18a), and by a method similar to that in Example 6 (6c), the title object compound was obtained as a colorless oil (4.29 g, yield 85%).

$^1$H-NMR (CDCl$_3$, 400 MHz) δ: 1.80 (3H, s), 3.70-3.81 (2H, m), 3.91 (3H, s), 4.04-4.11 (2H, m), 7.73 (1H, d, J=8.0 Hz), 7.92 (1H, dd, J=8.0, 1.4 Hz), 8.25 (1H, d, J=1.4 Hz).

(19b) 2-[2-(2-chloroethoxy)ethoxy]tetrahydropyran

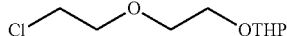

2-(2-Chloroethoxy)ethanol (10.0 g, 80.3 mmol) was dissolved in methylene chloride (50 mL) and, under ice-cooling, pyridinium p-toluenesulfonate (2.0 g, 8.0 mmol) and 3,4-dihydro-2H-pyran (6.8 g, 81 mmol) were added, and the mixture was stirred at room temperature for 14 hr. The solvent of the reaction mixture was evaporated under reduced pressure, to the obtained residue was added diethyl ether, and the organic layer was washed successively with water and saturated brine, and dried over anhydrous sodium sulfate. The solvent was evaporated under reduced pressure to give the title object compound as a colorless oil (16.4 g, yield 98%).

$^1$H-NMR (CDCl$_3$, 400 MHz) δ: 1.47-1.68 (4H, m), 1.69-1.91 (2H, m), 3.47-3.55 (1H, m), 3.58-3.67 (3H, m), 3.68-3.74 (2H, m), 3.75-3.82 (2H, m, THP C6-H, —OCH2CH2OTHP), 3.83-3.93 (2H, m), 4.61-4.68 (1H, m).

(19c) 2-{2-[2-(4-nitrophenoxy)ethoxy]ethoxy}tetrahydropyran

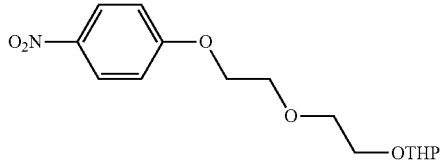

2-[2-(2-Chloroethoxy)ethoxy]tetrahydropyran (2.0 g, 14 mmol) synthesized in Example 19 (19b) and 4-nitrophenol (3.3 g, 16 mmol) were dissolved in dimethylformamide (40 mL), potassium carbonate (2.99 g, 21.6 mmol) was added, and the mixture was stirred at 80° C. for 30 hr. Water was added to the reaction mixture, and the mixture was extracted twice with ethyl acetate. The organic layer was washed successively with water and saturated brine, and dried over anhydrous sodium sulfate. The solvent was evaporated under reduced pressure, and the obtained residue was purified by silica gel column chromatography (hexane:ethyl acetate, 8:1→2:1, V/V). The solvent of the object fraction was evaporated under reduced pressure to give the title object compound as a pale yellow oil (3.54 g, yield 79%).

$^1$H-NMR (CDCl$_3$, 400 MHz) δ: 1.46-1.65 (4H, m), 1.68-1.90 (2H, m), 3.46-3.56 (1H, m), 3.59-3.68 (1H, m), 3.72-3.80 (2H, m), 3.83-3.96 (4H, m), 4.20-4.29 (2H, m), 4.60-4.68 (1H, m), 6.94-7.03 (2H, m), 8.15-8.24 (2H, m).

(19d) 4-{2-[2-(tetrahydropyran-2-yloxy)ethoxy]ethoxy}phenylamine

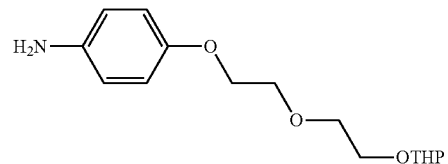

Using 2-{2-[2-(4-nitrophenoxy)ethoxy]ethoxy}tetrahydropyran produced in Example 19 (19c), and by the method used in Example 14 (14b), the title object compound was obtained as a brown oil (3.21 g, yield 100%).

$^1$H-NMR (CDCl$_3$, 400 MHz) δ: 1.45-1.65 (4H, m), 1.67-1.91 (2H, m), 3.36-3.46 (2H, br), 3.47-3.56 (1H, m), 3.59-3.68 (1H, m), 3.70-3.78 (2H, m), 3.80-3.93 (4H, m), 4.01-4.09 (2H, m), 4.60-4.68 (1H, m), 6.58-6.66 (2H, m), 6.72-6.80 (2H, m).

(19e) methyl 4-(2-methyl-[1,3]dioxolan-2-yl)-3-(4-{2-[2-(tetrahydropyran-2-yloxy)ethoxy]ethoxy}phenylamino)benzoate

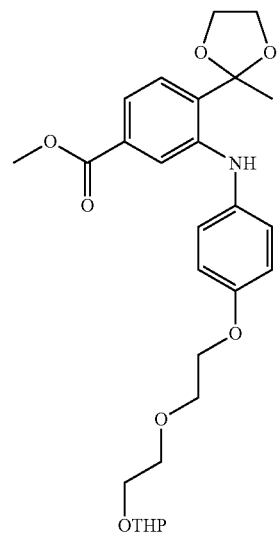

Using 4-{2-[2-(tetrahydropyran-2-yloxy)ethoxy]ethoxy}phenylamine (930 mg, 3.32 mmol) produced in Example 19 (19d) and methyl 3-bromo-4-(2-methyl-[1,3]dioxolan-2-yl)benzoate (1.00 g, 3.32 mmol) produced in Example 19 (19a), and by a method similar to that in Example 6 (6d), the title object compound was obtained as a brown oil (1.45 g, yield 87%).

¹H-NMR (CDCl₃, 400 MHz) δ: 1.47-1.63 (4H, m), 1.69-1.78 (1H, m), 1.72 (3H, s), 1.79-1.90 (1H, m), 3.46-3.56 (1H, m), 3.61-3.70 (1H, m), 3.74-3.80 (2H, m), 3.82-3.95 (6H, m), 3.83 (3H, s), 4.07-4.17 (4H, m), 4.62-4.68 (1H, m), 6.86-6.94 (2H, m), 7.01-7.08 (2H, m), 7.27 (1H, s), 7.41 (1H, dd, J=8.0, 1.4 Hz), 7.48 (1H, d, J=8.0 Hz), 7.71 (1H, d, J=1.4 Hz).

(19f) 4-(2-methyl-[1,3]dioxolan-2-yl)-3-(4-{2-[2-(tetrahydropyran-2-yloxy)ethoxy]ethoxy}phenylamino)benzamide

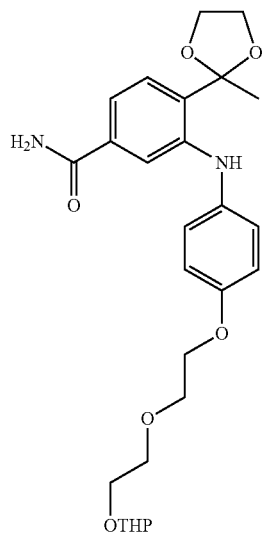

Using methyl 4-(2-methyl-[1,3]dioxolan-2-yl)-3-(4-{2-[2-(tetrahydropyran-2-yloxy)ethoxy]ethoxy}phenylamino)benzoate (1.45 g, 2.89 mmol) produced in Example 19 (19e), and by a method similar to that in Example 6 (6e), the title object compound was obtained as a brown oil (1.41 g, yield 100%).

¹H-NMR (CDCl₃, 400 MHz) δ: 1.47-1.68 (4H, m), 1.69-1.89 (2H, m), 1.72 (3H, s), 3.47-3.56 (1H, m), 3.61-3.70 (1H, m), 3.74-3.80 (2H, m), 3.84-3.95 (6H, m), 4.08-4.17 (4H, m), 4.62-4.68 (1H, m), 5.42-5.66 (1H, br), 5.84-6.06 (1H, br), 6.86-6.93 (2H, m), 7.01-7.09 (2H, m), 7.15 (1H, dd, J=8.0, 1.7 Hz), 7.29 (1H, s), 7.46 (1H, d, J=1.7 Hz), 7.48 (1H, d, J=8.0 Hz).

(19 g) 4-acetyl-3-{4-[2-(2-hydroxyethoxy)ethoxy]phenylamino}benzamide

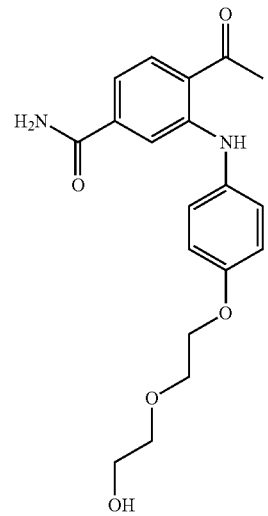 [SMILES: CC(=O)c1ccc(C(N)=O)cc1Nc1ccc(OCCOCCO)cc1]

Using 4-(2-methyl-[1,3]dioxolan-2-yl)-3-(4-{2-[2-(tetrahydropyran-2-yloxy)ethoxy]ethoxy}phenylamino)benzamide (1.41 g, 2.90 mmol) produced in Example 19 (19f), and by a method similar to that in Example 17 (17f), the title object compound was obtained as a yellow powder (680 mg, yield 66%).

¹H-NMR (CDCl₃, 400 MHz) δ: 2.06-2.30 (1H, br), 2.66 (3H, s), 3.64-3.71 (2H, m), 3.72-3.78 (2H, m), 3.85-3.94 (2H, m), 4.16-4.24 (2H, m), 5.60-5.80 (1H, br), 6.04-6.28 (1H, br), 6.92-7.00 (2H, m), 7.03 (1H, dd, J=8.3, 1.4 Hz), 7.12-7.21 (2H, m), 7.33 (1H, d, J=1.4 Hz), 7.84 (1H, d, J=8.3 Hz), 10.37 (1H, s).

MS (ESI) m/z: 357 (M−H)⁻.

Example 20

4-acetyl-3-{4-[2-(1,1-dioxohexahydro-1λ⁶-thiopyran-4-yloxy)ethoxy]phenylamino}benzamide (20a) 1,4-dioxa-8-thiaspiro[4.5]decane

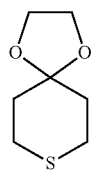

Tetrahydrothiopyran-4-one (5.20 g, 44.8 mmol) was dissolved in toluene (100 mL), ethylene glycol (2.63 mL, 47.0 mmol) and p-toluenesulfonic acid (260 mg, 1.34 mmol) were added, and the mixture was heated under reflux for 3 hr while evaporating water by Dean-Stark trap. The reaction mixture was allowed to cool, washed successively with saturated aqueous sodium hydrogen carbonate, water and saturated brine, and dried over anhydrous sodium sulfate. The solvent was evaporated under reduced pressure to give the title object compound as a brown oil (6.91 g, yield 96%).

¹H-NMR (CDCl₃, 400 MHz) δ: 1.87-1.95 (4H, m), 2.71-2.78 (4H, m), 3.94 (4H, s).

(20b) 2-(tetrahydropyran-4-yloxy)ethanol

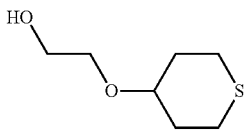

1,4-Dioxa-8-thiaspiro[4.5]decane (3.90 g, 24.3 mmol) produced in Example 20 (20a) was dissolved in tetrahydrofuran (15 mL), 0.9 M borane.tetrahydrofuran complex/tetrahydrofuran solution (32.4 mL, 29 mmol) and trimethylsilyl trifluoromethanesulfonate (0.22 mL, 1.2 mmol) were added at −78° C., and the mixture was stirred at room temperature for 15 hr.

Water was added to the reaction mixture, and the mixture was extracted twice with ethyl acetate. The organic layer was washed successively with water and saturated brine, and dried over anhydrous sodium sulfate. The solvent was evaporated under reduced pressure, and the obtained residue was purified by silica gel column chromatography (chloroform:methanol, 98:2→92:8, V/V). The solvent of the object fraction was evaporated under reduced pressure to give the title object compound as a yellow oil (3.54 g, yield 90%).

¹H-NMR (CDCl₃, 400 MHz) δ: 1.76-1.88 (2H, m), 2.08-2.19 (2H, m), 2.48-2.58 (2H, m), 2.75-2.86 (2H, m), 3.32-3.42 (1H, m), 3.53-3.60 (2H, m), 3.68-3.77 (2H, m).

(20c) 4-[2-(4-nitrophenoxy)ethoxy]tetrahydrothiopyran

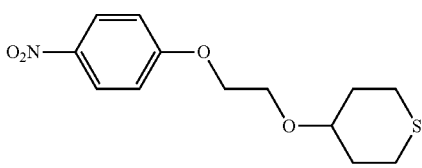 [SMILES: O=[N+]([O-])c1ccc(OCCOC2CCSCC2)cc1]

2-(Tetrahydropyran-4-yloxy)ethanol (2.20 g, 13.6 mmol) produced in Example 20 (20b) was dissolved in methylene chloride (20 mL) and, under ice-cooling, 4-nitrophenol (1.89 g, 13.6 mmol), triphenylphosphine (4.99 g, 19.0 mmol) and diisopropyl azodicarboxylate (3.94 mL, 20.4 mmol) were added, and the mixture was stirred at room temperature for 18 hr. The solvent of the reaction mixture was evaporated under reduced pressure, and the obtained residue was purified by silica gel column chromatography (hexane:ethyl acetate, 9:1→7:3, V/V). The solvent of the object fraction was evaporated under reduced pressure to give the title object compound as a yellow oil (2.10 g, yield 54%).

¹H-NMR (CDCl₃, 400 MHz) δ: 1.77-1.92 (2H, m), 2.09-2.20 (2H, m), 2.46-2.58 (2H, m), 2.76-2.89 (2H, m), 3.38-3.48 (1H, m), 3.80-3.88 (2H, m), 4.18-4.25 (2H, m), 6.94-7.02 (2H, m), 8.16-8.24 (2H, m).

(20d) 4-[2-(4-nitrophenoxy)ethoxy]tetrahydrothiopyran-1,1-dioxide

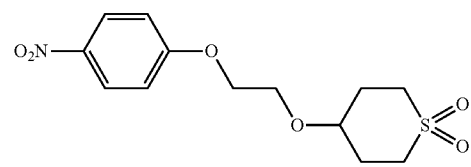 [SMILES: O=[N+]([O-])c1ccc(OCCOC2CCS(=O)(=O)CC2)cc1]

4-[2-(4-Nitrophenoxy)ethoxy]tetrahydrothiopyran (2.10 g, 7.41 mmol) produced in Example 20 (20c) was dissolved in methylene chloride (20 mL) and, under ice-cooling, 3-chloroperbenzoic acid (5.11 g, 22 mmol) was added, and the mixture was stirred at room temperature for 1 hr. The reaction mixture was washed successively with saturated aqueous sodium hydrogen carbonate and saturated brine, and dried over anhydrous sodium sulfate. The solvent was evaporated under reduced pressure, and the obtained residue was purified by silica gel column chromatography (hexane:ethyl acetate, 7:3→4:6, V/V). The solvent of the object fraction was evaporated under reduced pressure to give the title object compound as a yellow oil (2.25 g, yield 96%).

¹H-NMR (CDCl₃, 400 MHz) δ: 2.18-2.30 (2H, m), 2.31-2.42 (2H, m), 2.83-2.95 (2H, m), 3.25-3.38 (2H, m), 3.74-3.81 (1H, m), 3.83-3.91 (2H, m), 4.19-4.26 (2H, m), 6.93-7.02 (2H, m), 8.17-8.26 (2H, m).

(20e) 4-[2-(1,1-dioxohexahydro-1λ⁶-thiopyran-4-yloxy)ethoxy]phenylamine

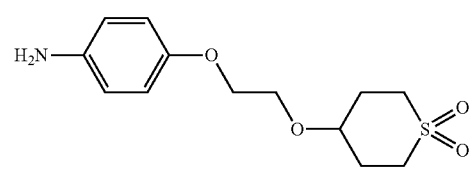

Using 4-[2-(4-nitrophenoxy)ethoxy]tetrahydrothiopyran-1,1-dioxide (2.20 g, 6.98 mmol) produced in Example 20 (20d), and by a method similar to that in Example 14 (14b), the title object compound was obtained as a pale-brown powder (1.73 g, yield 87%).

¹H-NMR (CDCl₃, 400 MHz) δ: 2.13-2.26 (2H, m), 2.28-2.39 (2H, m), 2.79-2.89 (2H, m), 3.26-3.38 (2H, m), 3.71-3.80 (3H, m), 4.01-4.08 (2H, m), 6.60-6.66 (2H, m), 6.70-6.77 (2H, m).

(20f) methyl 3-{4-[2-(1,1-dioxohexahydro-1λ⁶-thiopyran-4-yloxy)ethoxy]phenylamino}-4-(2-methyl-[1,3]dioxolan-2-yl)benzoate

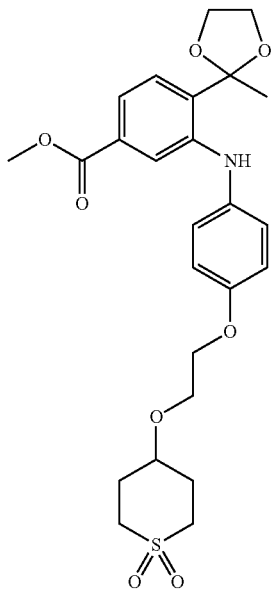 [SMILES: COC(=O)c1ccc(C2(C)OCCO2)c(Nc2ccc(OCCOC3CCS(=O)(=O)CC3)cc2)c1]

Using 4-[2-(1,1-dioxohexahydro-1λ⁶-thiopyran-4-yloxy)ethoxy]phenylamine (600 mg, 2.10 mmol) produced in Example 20 (20e) and methyl 3-bromo-4-(2-methyl-[1,3]dioxolan-2-yl)benzoate (630 mg, 2.10 mmol) produced in Example 19 (19a), and by a method similar to that in Example 6 (6d), the title object compound was obtained as a yellow foam-like powder (440 mg, yield 41%).

$^1$H-NMR (CDCl$_3$, 400 MHz) δ (ppm): 1.72 (3H, s), 2.17-2.30 (2H, m), 2.31-2.43 (2H, m), 2.82-2.94 (2H, m), 3.30-3.43 (2H, m), 3.75-3.80 (1H, m), 3.80-3.91 (4H, m), 3.84 (3H, s), 4.07-4.17 (4H, m), 6.84-6.92 (2H, m), 7.03-7.11 (2H, m), 7.29 (1H, s), 7.42 (1H, dd, J=8.0, 1.4 Hz), 7.49 (1H, d, J=8.0 Hz), 7.73 (1H, d, J=1.4 Hz).

(20 g) 3-{4-[2-(1,1-dioxohexahydro-1λ⁶-thiopyran-4-yloxy)ethoxy]phenylamino}-4-(2-methyl-[1,3]dioxolan-2-yl)benzamide

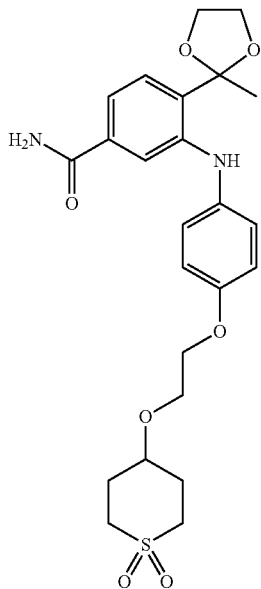 [SMILES: CC1(c2ccc(C(N)=O)cc2Nc2ccc(OCCOC3CCS(=O)(=O)CC3)cc2)OCCO1]

Using methyl 3-{4-[2-(1,1-dioxohexahydro-1λ⁶-thiopyran-4-yloxy)ethoxy]phenylamino}-4-(2-methyl-[1,3]dioxolan-2-yl)benzoate (0.44 g, 0.87 mmol) produced in Example 20 (20f), and by a method similar to that in Example 6 (6e), the title object compound was obtained as a yellow foam-like powder (360 mg, yield 84%).

$^1$H-NMR (CDCl$_3$, 400 MHz) δ: 1.72 (3H, s), 2.15-2.27 (2H, m), 2.30-2.42 (2H, m), 2.80-2.92 (2H, m), 3.24-3.40 (2H, m), 3.73-3.79 (1H, m), 3.79-3.95 (4H, m), 4.07-4.20 (4H, m), 5.35-5.60 ($^1$H, br), 5.90-6.15 (1H, br), 6.85-6.91 (2H, m), 7.04-7.10 (2H, m), 7.16 (1H, dd, J=7.8, 1.6 Hz), 7.30 (1H, s), 7.49 (1H, d, J=7.8 Hz), 7.51 (1H, d, J=1.6 Hz).

(20h) 4-acetyl-3-{4-[2-(1,1-dioxohexahydro-1λ⁶-thiopyran-4-yloxy)ethoxy]phenylamino}benzamide

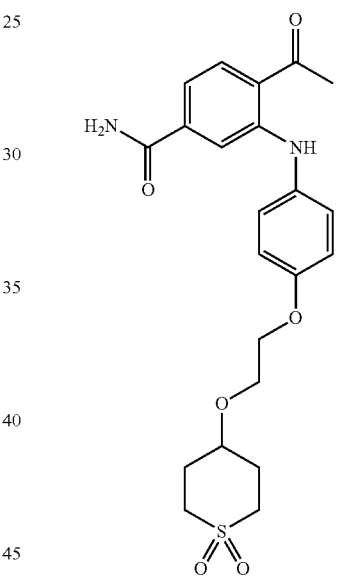

Using 3-{4-[2-(1,1-dioxohexahydro-1λ⁶-thiopyran-4-yloxy)ethoxy]phenylamino}-4-(2-methyl-[1,3]dioxolan-2-yl)benzamide (0.36 g, 0.73 mmol) produced in Example 20 (20g), and by the method used in Example 17 (17f), the title object compound was obtained as a yellow powder (279 mg, yield 85%).

$^1$H-NMR (CDCl$_3$, 400 MHz) δ: 2.15-2.27 (2H, m), 2.31-2.41 (2H, m), 2.66 (3H, s), 2.80-2.90 (2H, m), 3.24-3.37 (2H, m), 3.72-3.79 (1H, m), 3.80-3.86 (2H, m), 4.14-4.20 (2H, m), 5.55-5.75 (1H, br), 6.05-6.20 (1H, br), 6.89-6.95 (2H, m), 7.02 (1H, dd, J=8.3, 1.7 Hz), 7.14-7.20 (2H, m), 7.40 (1H, d, J=1.7 Hz), 7.84 (1H, d, J=8.3 Hz), 10.40 (1H, s).

MS (ESI) m/z: 447 (M+H)$^+$.

Example 21

4-acetyl-3-{4-[2-(2-oxotetrahydrofuran-3-yloxy)ethoxy]phenylamino}benzamide

(21a) 3-[2-(tetrahydropyran-2-yloxy)ethoxy]dihydrofuran-2-one

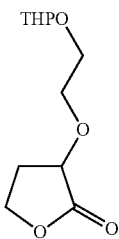

3-Hydroxydihydrofuran-2-one (5.00 g, 49.0 mmol) was dissolved in dimethylformamide (100 mL) and, under ice-cooling, sodium hydride (P=60%) (1.96 g, 49 mmol) was separately added, and the mixture was stirred at room temperature for 15 min. 2-(2-Bromoethoxy)tetrahydropyran (8.59 g, 57.9 mmol) was added and the mixture was stirred at 100° C. for 15 hr. The mixture was allowed to cool, water was added to the reaction mixture, and the mixture was extracted with ethyl acetate. The organic layer was washed successively with water and saturated brine, and dried over anhydrous sodium sulfate. The solvent was evaporated under reduced pressure. The obtained residue was purified by silica gel column chromatography (hexane:ethyl acetate 1:1, V/V). The solvent of the object fraction was evaporated under reduced pressure to give the title object compound as a slightly yellow oil (2.88 g, yield 26%).

$^1$H-NMR (CDCl$_3$, 400 MHz) δ: 1.48-1.88 (6H, m), 2.25-2.36 (1H, m), 2.48-2.57 (1H, m), 3.46-3.54 (1H, m), 3.60-3.68 (1H, m), 3.78-3.94 (3H, m), 4.02-4.11 (1H, m), 4.18-4.27 (2H, m), 4.37-4.45 (1H, m), 4.60-4.66 (1H, m).

(21b) 3-(2-hydroxyethoxy)dihydrofuran-2-one

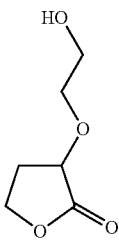

Using 3-[2-(tetrahydropyran-2-yloxy)ethoxy]dihydrofuran-2-one (2.86 g, 12.4 mmol) produced in Example 21 (21a), and by the method used in Example 4 (4e), the title object compound was obtained as a colorless oil (1.23 g, yield 68%).

$^1$H-NMR (CDCl$_3$, 400 MHz) δ: 2.25-2.40 (1H, m), 2.53-2.64 (1H, m), 3.70-3.85 (3H, m), 3.89-4.00 (1H, m), 4.02-4.11 (1H, m), 4.19-4.30 (1H, m), 4.39-4.50 (1H, m).

(21c) 2-(2-oxotetrahydrofuran-3-yloxy)ethyl methanesulfonate

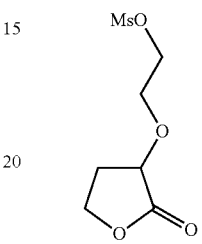

Using 3-(2-hydroxyethoxy)dihydrofuran-2-one (585 mg, 4.00 mmol) produced in Example 21 (21b), and by a method similar to that in Example 8 (8a), the title object compound was obtained as a yellow oil (940 mg, yield 100%).

$^1$H-NMR (CDCl$_3$, 400 MHz) δ: 2.25-2.36 (1H, m), 2.53-2.64 (1H, m), 3.07 (3H, s), 3.87-3.96 (1H, m), 4.17-4.30 (3H, m), 4.37-4.47 (3H, m).

(21d) 4-(tert-butyldimethylsilanyloxy)phenylamine

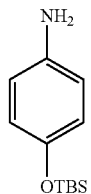

4-Aminophenol (5.00 g, 45.8 mmol) was dissolved in dimethylformamide (50 mL), tert-butyldimethylchlorosilane (7.60 g, 50.4 mmol) and imidazole (4.70 g, 69.0 mmol) were added and the mixture was stirred at room temperature for 3 hr. To the reaction mixture was added ethyl acetate, and the mixture was washed successively with water and saturated brine, and dried over anhydrous sodium sulfate. The solvent was evaporated under reduced pressure. The obtained residue was purified by silica gel column chromatography (hexane:ethyl acetate, 10:1→7:1, V/V). The solvent of the object fraction was evaporated under reduced pressure to give the title object compound as a dark brown oil (3.67 g, yield 36%).

$^1$H-NMR (CDCl$_3$, 400 MHz) δ: 0.15 (6H, s), 0.96 (9H, s), 3.10-3.70 (2H, br), 6.54-6.60 (2H, m), 6.62-6.68 (2H, m).

(21e) methyl 3-[4-(tert-butyldimethylsilanyloxy)phenylamino]-4-(2-methyl-[1,3]dioxolan-2-yl)benzoate

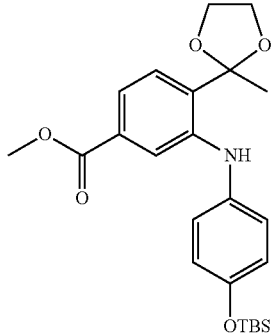 [SMILES: COC(=O)c1ccc(C2(C)OCCO2)c(Nc2ccc(O[Si](C)(C)C(C)(C)C)cc2)c1]

Using 4-(tert-butyldimethylsilanyloxy)phenylamine (1.48 g, 6.62 mmol) produced in Example 21 (21d) and methyl 3-bromo-4-(2-methyl-[1,3]dioxolan-2-yl)benzoate (2.00 g, 6.64 mmol) produced in Example 19 (19a), and by a method similar to that in Example 6 (6d), the title object compound was obtained as a reddish orange oil (2.30 g, yield 78%).

$^1$H-NMR (CDCl$_3$, 400 MHz) δ: 0.21 (6H, s), 1.00 (9H, s), 1.72 (3H, s), 3.83 (3H, s), 3.84-3.89 (2H, m), 4.07-4.12 (2H, m), 6.76-6.83 (2H, m), 6.96-7.02 (2H, m), 7.23-7.30 (1H, br), 7.41 (1H, dd, J=8.0, 1.5 Hz), 7.48 (1H, d, J=8.0 Hz), 7.73 (1H, d, J=1.5 Hz).

(21f) 3-(4-hydroxyphenylamino)-4-(2-methyl-[1,3]dioxolan-2-yl)benzamide

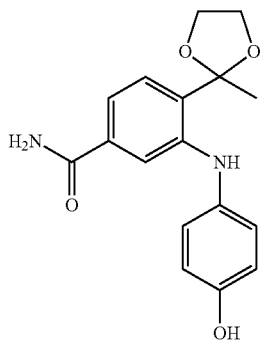 [SMILES: CC1(c2ccc(C(N)=O)cc2Nc2ccc(O)cc2)OCCO1]

Using methyl 3-[4-(tert-butyldimethylsilanyloxy)phenylamino]-4-(2-methyl-[1,3]dioxolan-2-yl)benzoate (2.30 g, 5.18 mmol) produced in Example 21 (21e), and by a method similar to that in Example 6 (6e), the title object compound was obtained as a yellow powder (1.05 g, yield 80%).

$^1$H-NMR (DMSO-d$_6$, 400 MHz) δ: 1.62 (3H, s), 3.75-3.84 (2H, m), 4.00-4.11 (2H, m), 6.71-6.78 (2H, m), 6.92-6.98 (2H, m), 7.16-7.23 (3H, m), 7.33 (1H, d, J=8.0 Hz), 7.38 (1H, d, J=1.7 Hz), 7.72-7.80 (1H, br), 9.15 (1H, s).

(21g) 4-acetyl-3-(4-hydroxyphenylamino)benzamide

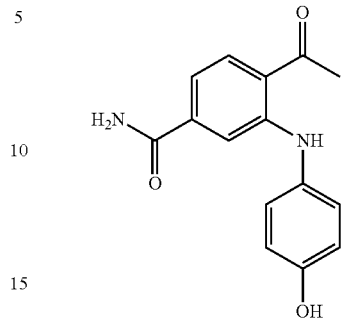

Using 3-(4-hydroxyphenylamino)-4-(2-methyl-[1,3]dioxolan-2-yl)benzamide (500 mg, 1.59 mmol) produced in Example 21 (21f), and by the method used in Example 17 (17f), the title object compound was obtained as a yellowish orange powder (480 mg, yield 100%).

$^1$H-NMR (DMSO-d$_5$, 400 MHz) δ: 2.63 (3H, s), 6.77-6.83 (2H, m), 7.03-7.13 (3H, m), 7.33-7.35 (1H, m), 7.42 (1H, s), 7.92-7.98 (2H, m), 9.41 (1H, s), 10.19 (1H, s).

(21h) 4-acetyl-3-{4-[2-(2-oxotetrahydrofuran-3-yloxy)ethoxy]phenylamino}benzamide

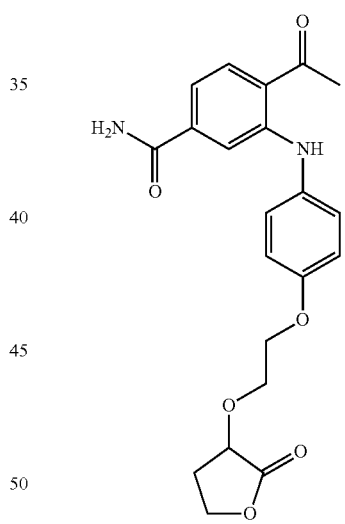

Using 4-acetyl-3-(4-hydroxyphenylamino)benzamide (280 mg, 1.04 mmol) produced in Example 21 (21 g) and 2-(2-oxotetrahydrofuran-3-yloxy)ethyl methanesulfonate (280 mg, 1.24 mmol) produced in Example 21 (21c), and by the method used in Example 19 (19c), the title object compound was obtained as an orange powder (102 mg, yield 25%).

$^1$H-NMR (CDCl$_3$, 400 MHz) δ: 2.30-2.40 (1H, m), 2.53-2.62 (1H, m), 2.66 (3H, s), 3.98-4.06 (1H, m), 4.10-4.33 (5H, m), 4.40-4.46 (1H, m), 5.45-5.70 (1H, br), 5.80-6.10 (1H, br), 6.91-6.97 (2H, m), 7.01 (1H, dd, J=8.0, 1.7 Hz), 7.13-7.19 (2H, m), 7.36 (1H, d, J=1.7 Hz), 7.84 (1H, d, J=8.0 Hz), 10.38 (1H, s).

MS (ESI) m/z: 397 (M−H)$^-$.

Example 22

4-{2-[4-(2-acetyl-5-carbamoylphenylamino)phenoxy]ethoxy}butyric acid

(22a) 4-acetyl-3-hydroxybenzonitrile

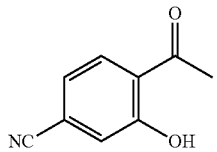

1-(4-Bromo-2-hydroxyphenyl)ethanone (5.00 g, 23.3 mmol) was dissolved in dimethylformamide (30 mL), copper cyanide (I) (6.25 g, 69.8 mmol) was added, and the mixture was heated under reflux for 3 hr. The reaction mixture was allowed to cool, a solution of iron chloride (III) (6.8 g) in 6.0 M hydrochloric acid (60 mL) was added, and the mixture was stirred at 70° C. for 30 min. The insoluble material in the reaction mixture was filtered off, and the filtrate was extracted twice with chloroform. The organic layers were combined, washed successively with 1.0 M hydrochloric acid and water, and dried over anhydrous sodium sulfate. The solvent was evaporated under reduced pressure, and the obtained residue was purified by silica gel column chromatography (chloroform:ethyl acetate, 9:1→1:1, V/V). The solvent of the object fraction was evaporated under reduced pressure to give the title object compound as a yellow powder (1.72 g, yield 46%).

$^1$H-NMR (CDCl$_3$, 400 MHz) δ: 2.68 (3H, s), 7.17 (1H, dd, J=8.0, 1.4 Hz), 7.28 (1H, d, J=1.4 Hz), 7.83 (1H, d, J=8.0 Hz), 12.26 (1H, s).

(22b) 2-acetyl-5-cyanophenyl trifluoromethanesulfonate

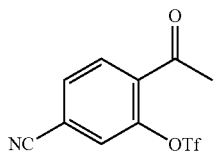 [SMILES: CC(=O)c1ccc(C#N)cc1OS(=O)(=O)C(F)(F)F]

Using 4-acetyl-3-hydroxybenzonitrile (1.72 g, 10.7 mmol) produced in Example 22 (22a), and by a method similar to that in Example 6 (6b), the title object compound was obtained as a yellow powder (2.93 g, yield 93%).

$^1$H-NMR (CDCl$_3$, 400 MHz) δ: 2.67 (3H, s), 7.64 (1H, d, J=1.2 Hz), 7.79 (1H, dd, J=8.0, 1.2 Hz), 7.89 (1H, d, J=8.0 Hz).

(22c) 5-cyano-2-(2-methyl-[1,3]dioxolan-2-yl)phenyl trifluoromethanesulfonate

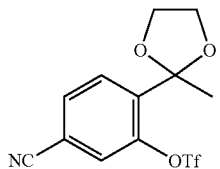 [SMILES: CC1(c2ccc(C#N)cc2OS(=O)(=O)C(F)(F)F)OCCO1]

Using 2-acetyl-5-cyanophenyl trifluoromethanesulfonate (2.93 g, 9.99 mmol) produced in Example 22 (22b), and by a method similar to that in Example 6 (6c), the title object compound was obtained as a white powder (2.58 g, yield 77%).

$^1$H-NMR (CDCl$_3$, 400 MHz) δ: 1.72 (3H, s), 3.77-3.88 (2H, m), 4.06-4.17 (2H, m), 7.53 (1H, d, J=1.4 Hz), 7.66 (1H, dd, J=8.0, 1.4 Hz), 7.81 (1H, d, J=8.0 Hz).

(22d) 2-[2-(4-nitrophenoxy) ethoxy]ethanol

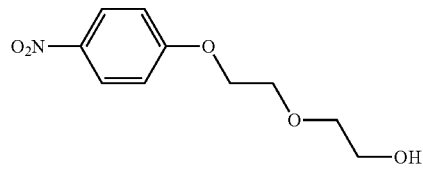

Using 4-nitrophenol (10.0 g, 71.9 mmol) and 2-(2-chloroethoxy)ethanol (9.87 mL, 93.5 mmol), and by a method similar to that in Example 19 (19c), the title object compound was obtained as a white powder (9.79 g, yield 60%).

$^1$H-NMR (CDCl$_3$, 400 MHz) δ: 1.81-2.15 (1H, br), 3.67-3.71 (2H, m), 3.75-3.80 (2H, m), 3.89-3.94 (2H, m), 4.12-4.27 (2H, m), 6.96-7.01 (2H, m), 8.11-8.22 (2H, m).

(22e) diethyl 2-{2-[2-(4-nitrophenoxy)ethoxy]ethyl}malonate

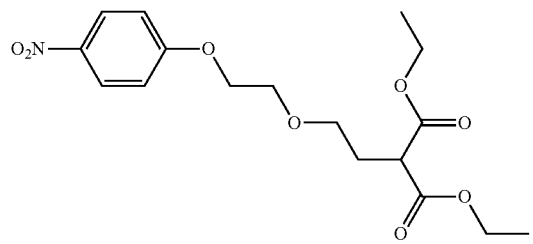 [SMILES: CCOC(=O)C(CCOCCOc1ccc([N+](=O)[O-])cc1)C(=O)OCC]

2-[2-(4-Nitrophenoxy)ethoxy]ethanol (9.79 g, 43.1 mmol) produced in Example 22 (22d) was dissolved in methylene chloride (100 mL), triethylamine (8.41 mL, 60.3 mmol) was added and, under ice-cooling, methanesulfonyl chloride (4.00 mL, 51.7 mmol) was added, and the mixture was stirred at the same temperature for 30 min. Water was added to the reaction mixture, and the mixture was extracted twice with chloroform. The organic layer was washed successively with saturated aqueous sodium hydrogen carbonate and saturated brine, and dried over anhydrous sodium sulfate. The solvent was evaporated under reduced pressure.

Diethyl malonate (9.77 mL, 64.7 mmol) was dissolved in dimethylformamide (120 mL) and, under ice-cooling, sodium hydride (P=60%) (2.59 g, 64.7 mmol) was added, and the mixture was stirred at the same temperature for 30 min. A solution (30 mL) of the residue obtained earlier in dimethylformamide was added, and the mixture was stirred at 80° C. for 18 hr. Water was added to the reaction mixture, and the mixture was extracted twice with ethyl acetate. The organic layer was washed successively with water and saturated brine, and dried over anhydrous sodium sulfate. The solvent was evaporated under reduced pressure. The obtained residue was purified by silica gel column chromatography (hexane:ethyl acetate, 9:1→8:2, V/V), and the solvent of the object fraction was evaporated under reduced pressure to give the title object compound as a yellow oil (7.06 g, yield 44%).

$^1$H-NMR (CDCl$_3$, 400 MHz) δ: 1.25 (6H, t, J=7.1 Hz), 2.17-2.26 (2H, m), 3.54 (1H, t, J=7.5 Hz), 3.58-3.63 (2H, m), 3.78-3.84 (2H, m), 4.10-4.24 (6H, m), 6.95-7.00 (2H, m), 8.17-8.21 (2H, m).

(22f) ethyl 4-[2-(4-nitrophenoxy)ethoxy]butyrate

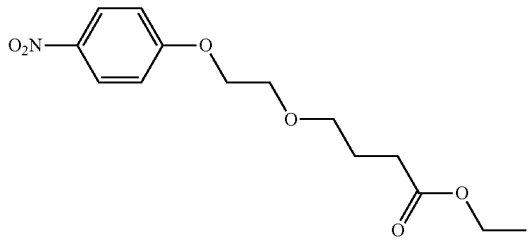 [SMILES: CCOC(=O)CCCOCCOc1ccc([N+](=O)[O-])cc1]

Diethyl 2-{2-[2-(4-nitrophenoxy)ethoxy]ethyl}malonate (7.06 g, 19.1 mmol) produced in Example 22 (22e) was dissolved in dimethylsulfoxide (35 mL), water (0.69 mL, 38 mmol) and sodium chloride (2.23 g, 38.2 mmol) were added, and the mixture was heated under reflux for 5 hr. Water was added to the reaction mixture, and the mixture was extracted twice with ethyl acetate. The organic layer was washed successively with water and saturated brine, and dried over anhydrous sodium sulfate. The solvent was evaporated under reduced pressure.

The obtained residue was purified by silica gel column chromatography (hexane:ethyl acetate, 85:15→55:45, V/V), and the solvent of the object fraction was evaporated under reduced pressure to give the title object compound as a yellow oil (4.40 g, yield 77%).

$^1$H-NMR (CDCl$_3$, 400 MHz) δ: 1.25 (3H, t, J=7.1 Hz), 1.89-1.97 (2H, m), 2.40 (2H, t, J=7.3 Hz), 3.55-3.61 (2H, m), 3.79-3.84 (2H, m), 4.12 (2H, q, J=7.1 Hz), 4.17-4.23 (2H, m), 6.95-7.02 (2H, m), 8.17-8.23 (2H, m).

(22g) ethyl 4-[2-(4-aminophenoxy)ethoxy]butyrate

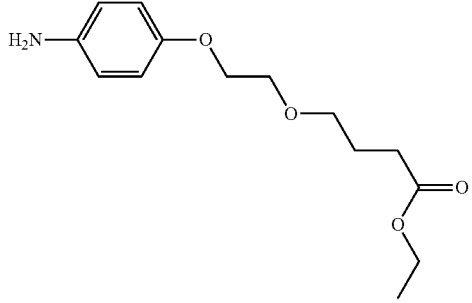 [SMILES: CCOC(=O)CCCOCCOc1ccc(N)cc1]

Using ethyl 4-[2-(4-nitrophenoxy)ethoxy]butyrate (4.40 g, 14.8 mmol) produced in Example 22 (22f), and by the method used in Example 14 (14b), the title object compound was obtained as a reddish brown oil (3.94 g, yield 99%).

$^1$H-NMR (CDCl$_3$, 400 MHz) δ: 1.25 (3H, t, J=7.1 Hz), 1.89-1.97 (2H, m), 2.41 (2H, t, J=7.3 Hz), 3.35-3.48 (2H, br), 3.54-3.59 (2H, m), 3.71-3.77 (2H, m), 4.00-4.06 (2H, m), 4.12 (2H, q, J=7.1 Hz), 6.60-6.67 (2H, m), 6.72-6.78 (2H, m).

(22h) ethyl 4-(2-{4-[5-cyano-2-(2-methyl-[1,3]dioxolan-2-yl)phenylamino]phenoxy}ethoxy)butyrate

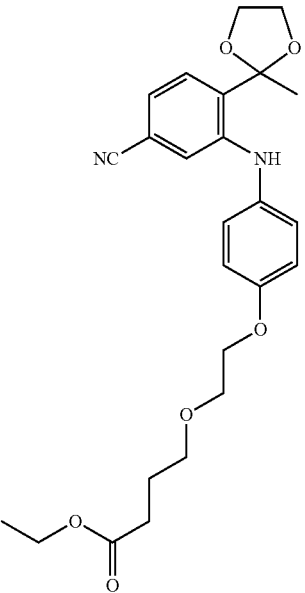 [SMILES: CCOC(=O)CCCOCCOc1ccc(Nc2cc(C#N)ccc2C2(C)OCCO2)cc1]

Using ethyl 4-[2-(4-aminophenoxy)ethoxy]butyrate (1.75 g, 6.52 mmol) produced in Example 22 (22g) and 5-cyano-2-(2-methyl-[1,3]dioxolan-2-yl)phenyl trifluoromethanesulfonate (2.00 g, 5.93 mmol) in Example 22 (22c), and by a method similar to that in Example 6 (6d), the title object compound was obtained as a yellow oil (1.06 g, yield 39%).

$^1$H-NMR (CDCl$_3$, 400 MHz) δ: 1.25 (3H, t, J=7.1 Hz), 1.72 (3H, s), 1.90-2.00 (2H, m), 2.42 (2H, t, J=7.3 Hz), 3.59 (2H, t, J=6.1 Hz), 3.77-3.82 (2H, m), 3.82-3.88 (2H, m), 4.08-4.17 (6H, m), 6.90-6.95 (2H, m), 6.99 (1H, dd, J=7.8, 1.4 Hz), 7.01-7.07 (2H, m), 7.18 (1H, d, J=1.4 Hz), 7.35 (1H, s), 7.48 (1H, d, J=7.8 Hz).

(22i) ethyl 4-(2-{4-[5-carbamoyl-2-(2-methyl-[1,3]dioxolan-2-yl)phenylamino]phenoxy}ethoxy)butyrate

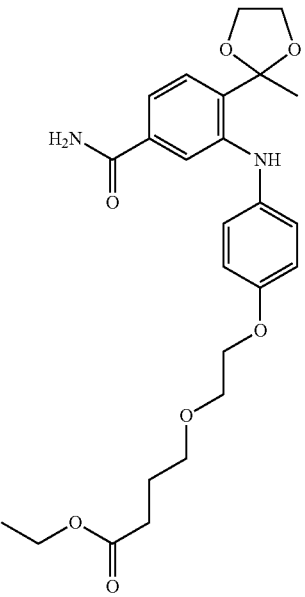 [SMILES: CCOC(=O)CCCOCCOc1ccc(Nc2cc(C(N)=O)ccc2C2(C)OCCO2)cc1]

Ethyl 4-(2-{4-[5-cyano-2-(2-methyl-[1,3]dioxolan-2-yl)phenylamino]phenoxy}ethoxy)butyrate (1.06 g, 2.33 mmol) produced in Example 22 (22h) was dissolved in dimethylsulfoxide (10 mL), 30% hydrogen peroxide water (0.75 mL, 7.0 mmol) and potassium carbonate (0.39 g, 2.8 mmol) were added, and the mixture was stirred at room temperature for 22 hr. To the reaction mixture was added 10% citric acid water and the mixture was extracted twice with ethyl acetate. The organic layers were combined, washed successively with water and saturated brine, and dried over anhydrous sodium sulfate. The solvent was evaporated under reduced pressure, and the obtained residue was purified by silica gel column chromatography (hexane:ethyl acetate, 1:1→0:1, V/V). The solvent of the object fraction was evaporated under reduced pressure to give the title object compound as a pale yellow oil (640 mg, yield 58%).

$^1$H-NMR (CDCl$_3$, 400 MHz) δ: 1.25 (3H, t, J=7.1 Hz), 1.73 (3H, s), 1.89-1.99 (2H, m), 2.41 (2H, t, J=7.3 Hz), 3.58 (2H, t, J=6.1 Hz), 3.74-3.81 (2H, m), 3.83-3.90 (2H, m), 4.07-4.16 (6H, m), 5.40-5.60 (1H, br), 5.80-6.00 (1H, br), 6.86-6.93 (2H, m), 7.01-7.08 (2H, m), 7.15 (1H, dd, J=8.0, 1.7 Hz), 7.29 (1H, s), 7.46 (1H, d, J=1.7 Hz), 7.48 (1H, d, J=8.0 Hz).

(22j) ethyl 4-{2-[4-(2-acetyl-5-carbamoylphenylamino)phenoxy]ethoxy}butyrate

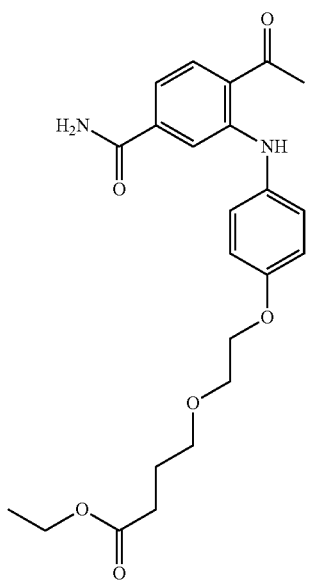 [SMILES: CCOC(=O)CCCOCCOc1ccc(Nc2cc(C(N)=O)ccc2C(C)=O)cc1]

Using ethyl 4-(2-{4-[5-carbamoyl-2-(2-methyl-[1,3]dioxolan-2-yl)phenylamino]phenoxy}ethoxy)butyrate (640 mg, 1.35 mmol) produced in Example 22 (22i), and by the method used in Example 17 (17f), the title object compound was obtained as an orange powder (470 mg, yield 81%).

$^1$H-NMR (CDCl$_3$, 400 MHz) δ: 1.24 (3H, t, J=7.1 Hz), 1.90-1.99 (2H, m), 2.41 (2H, t, J=7.3 Hz), 2.66 (3H, s), 3.58 (2H, t, J=6.1 Hz), 3.76-3.84 (2H, m), 4.08-4.17 (4H, m), 5.45-5.65 (1H, br), 5.85-6.05 (1H, br), 6.90-6.98 (2H, m), 7.01 (1H, dd, J=8.6, 1.7 Hz), 7.12-7.20 (2H, m), 7.35 (1H, d, J=1.7 Hz), 7.84 (1H, d, J=8.6 Hz), 10.38 (1H, s).

(22k) 4-{2-[4-(2-acetyl-5-carbamoylphenylamino)phenoxy]ethoxy}butyric acid

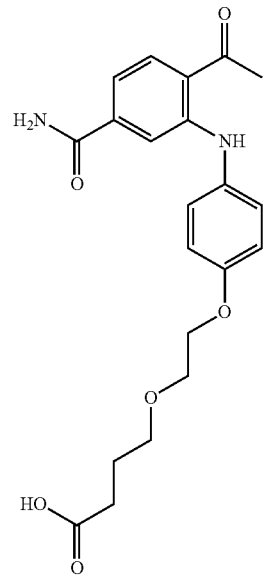 [SMILES: CC(=O)c1ccc(C(N)=O)cc1Nc1ccc(OCCOCCCC(=O)O)cc1]

Ethyl 4-{2-[4-(2-acetyl-5-carbamoylphenylamino)phenoxy]ethoxy}butyrate (470 mg, 1.10 mmol) produced in Example 22 (22j) was dissolved in tetrahydrofuran (10 mL), methanol (3.3 mL) and 1.0 M aqueous lithium hydroxide (3.3 mL, 3.3 mmol) were added, and the mixture was stirred at room temperature for 1 hr. The reaction mixture was washed twice with diethyl ether, acidified with 10% citric acid water, and extracted with ethyl acetate. The organic layer was washed with saturated brine, and dried over anhydrous sodium sulfate. The solvent was evaporated under reduced pressure to give the title object compound as an orange powder (400 mg). The obtained powder was recrystallized from ethanol (15 mL) to give the title object compound as an orange powder (222 mg, yield 50%).

$^1$H-NMR (CDCl$_3$, 400 MHz) δ: 1.87-2.00 (2H, m), 2.46 (2H, t, J=7.1 Hz), 2.65 (3H, s), 3.60 (2H, t, J=6.1 Hz), 3.76-3.87 (2H, m), 4.10-4.20 (2H, m), 6.06-6.22 (1H, br), 6.40-6.56 (1H, br), 6.92-7.02 (3H, m), 7.10-7.18 (2H, m), 7.31-7.37 (1H, m), 7.82 (1H, d, J=8.0 Hz), 10.35 (1H, s).

MS (ESI) m/z: 399 (M−H)$^-$.

Example 23

4-acetyl-2-{4-[2-(tetrahydropyran-4-yloxy)ethoxy]phenylamino}benzonitrile (23a) 1-(4-amino-3-bromophenyl)ethanone

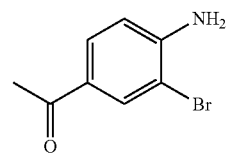

1-(4-Aminophenyl)ethanone (10.0 g, 74.0 mmol) was dissolved in acetonitrile (50 mL) and, under ice-cooling, a solution (30 mL) of N-bromosuccinimide (13.8 g, 77.7 mmol) in acetonitrile was added dropwise, and the mixture was stirred at room temperature for 20 hr. The solvent of the reaction mixture was evaporated under reduced pressure, and the obtained residue was dissolved in ethyl acetate. The organic layer was washed successively with saturated aqueous sodium hydrogen carbonate and saturated brine, and dried over anhydrous sodium sulfate. The solvent was evaporated under reduced pressure to give the title object compound as a yellow powder (15.8 g, yield 100%).

$^1$H-NMR (CDCl$_3$, 400 MHz) δ: 2.49 (3H, s), 4.52-4.70 (2H, br), 6.73 (1H, d, J=8.5 Hz), 7.73 (1H, dd, J=8.5, 1.9 Hz), 8.05 (1H, d, J=1.9 Hz).

(23b) 4-acetyl-2-bromobenzonitrile

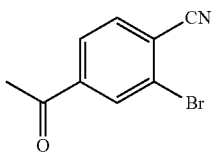

1-(4-Amino-3-bromophenyl)ethanone (15.8 g, 73.8 mmol) produced in Example 23 (23a) was dissolved in acetic acid (265 mL) and, under ice-cooling, concentrated sulfuric acid (12.5 mL) was added, and the mixture was stirred at the same temperature for 10 min. Then, an aqueous solution (50 mL) of sodium nitrite (5.09 g, 73.8 mmol) was added dropwise, and the mixture was further stirred for 30 min. An aqueous solution (100 mL) of copper (I) cyanide (6.61 g, 73.8 mmol) and potassium cyanide (14.4 g, 221 mmol) was added dropwise, and the mixture was stirred at room temperature for 2 hr. The reaction mixture was poured into water (600 mL), the insoluble material was filtered off, and the organic layer of the filtrate was dried over anhydrous sodium sulfate. The solvent was evaporated under reduced pressure. The obtained residue was purified by silica gel column chromatography (hexane:ethyl acetate, 6:1→2:1, V/V), and the solvent of the object fraction was evaporated under reduced pressure to give the title object compound as a yellow powder (2.84 g, yield 17%).

$^1$H-NMR (CDCl$_3$, 400 MHz) δ: 2.63 (3H, s), 7.77 (1H, d, J=8.0 Hz), 7.95 (1H, dd, J=8.0, 1.7 Hz), 8.22 (1H, d, J=1.7 Hz).

(23c) 2-bromo-4-(2-methyl-[1,3]dioxolan-2-yl)benzonitrile

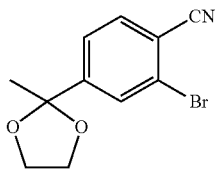

Using 4-acetyl-2-bromobenzonitrile (1.40 g, 6.25 mmol) produced in Example 22 (22b), and by the method used in Example 6 (6c), the title object compound was obtained as a pale-reddish brown powder (1.36 g, yield 81%).

$^1$H-NMR (CDCl$_3$, 400 MHz) δ: 1.62 (3H, s), 3.70-3.82 (2H, m), 4.01-4.12 (2H, m), 7.53 (1H, dd, J=7.8, 1.4 Hz), 7.63 (1H, d, J=7.8 Hz), 7.81 (1H, d, J=1.4 Hz).

(23d) 4-(2-methyl-[1,3]dioxolan-2-yl)-2-{4-[2-(tetrahydropyran-4-yloxy)ethoxy]phenylamino}benzonitrile

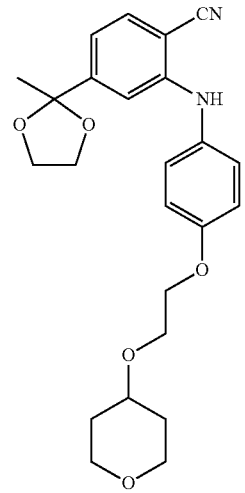 [SMILES: CC1(c2ccc(C#N)c(Nc3ccc(OCCOC4CCOCC4)cc3)c2)OCCO1]

Using 2-bromo-4-(2-methyl-[1,3]dioxolan-2-yl)benzonitrile (1.36 g, 5.37 mmol) produced in Example 23 (23c) and 4-[2-(tetrahydropyran-4-yloxy)ethoxy]phenylamine (1.29 g, 5.91 mmol) produced in Example 17 (17b), and by a method similar to that in Example 6 (6d), the title object compound was obtained as a brown oil (846 mg, yield 39%).

$^1$H-NMR (CDCl$_3$, 400 MHz) δ: 1.55 (3H, s), 1.60-1.71 (2H, m), 1.91-2.00 (2H, m), 3.41-3.51 (2H, m), 3.57-3.67 (1H, m), 3.68-3.73 (2H, m), 3.80-3.88 (2H, m), 3.94-4.02 (4H, m), 3.80-3.88 (2H, m), 6.20 (1H, s), 6.88 (1H, dd, J=8.0, 1.4 Hz), 6.91-6.98 (2H, m), 7.05 (1H, d, J=1.4 Hz), 7.09-7.15 (2H, m), 7.63 (1H, d, J=8.0 Hz).

(23e) 4-acetyl-2-{4-[2-(tetrahydropyran-4-yloxy)ethoxy]phenylamino}benzonitrile

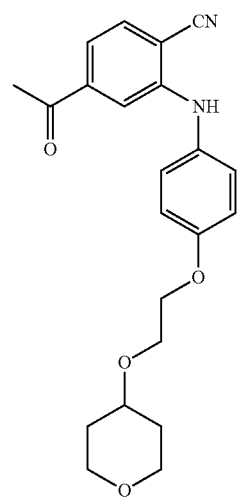 [SMILES: CC(=O)c1ccc(C#N)c(Nc2ccc(OCCOC3CCOCC3)cc2)c1]

Using 4-(2-methyl-[1,3]dioxolan-2-yl)-2-{4-[2-(tetrahydropyran-4-yloxy)ethoxy]phenylamino}benzonitrile (50 mg, 0.12 mmol) produced in Example 23 (23d), and by the method used in Example 17 (17f), the title object compound was obtained as a yellow oil (49 mg, yield 100%).

$^1$H-NMR (CDCl$_3$, 400 MHz) δ: 1.61-1.73 (2H, m), 1.91-2.02 (2H, m), 2.49 (3H, s), 3.41-3.53 (2H, m), 3.58-3.67 (1H, m), 3.83-3.91 (2H, m), 3.93-4.03 (2H, m), 4.11-4.22 (2H, m), 6.30 (1H, s), 6.92-7.02 (2H, m), 7.10-7.20 (2H, m), 7.24-7.29 (1H, m), 7.40-7.44 (1H, m), 7.55 (1H, d, J=8.0 Hz).

MS (ESI) m/z: 379 (M−H)$^−$.

Example 24

4-acetyl-3-[4-(2-morpholin-4-ylethyl)phenylamino]benzamide (24a) 4-[2-(4-nitrophenyl)ethyl]morpholine

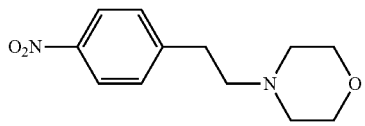 [SMILES: O=[N+]([O-])c1ccc(CCN2CCOCC2)cc1]

1-(2-Bromoethyl)-4-nitrobenzene (4.60 g, 20.0 mmol) was dissolved in dimethylformamide (20 mL), morpholine (3.48 mL, 40.0 mmol) was added, and the mixture was stirred at 80° C. for 18 hr. The reaction mixture was diluted with ethyl acetate, washed with water and saturated brine, and dried over anhydrous sodium sulfate. The solvent was evaporated under reduced pressure. The obtained residue was purified by basic silica gel column chromatography (hexane:ethyl acetate 4:41→2:1, V/V). The solvent of the object fraction was evaporated under reduced pressure to give the title object compound as a yellow oil (5.75 g, yield 100%).

$^1$H-NMR (CDCl$_3$, 400 MHz) δ: 2.48-2.55 (4H, m), 2.60-2.67 (2H, m), 2.87-2.94 (2H, m), 3.70-3.75 (4H, m), 7.34-7.40 (2H, m), 8.12-8.18 (2H, m).

(24b) 4-(2-morpholin-4-ylethyl)phenylamine

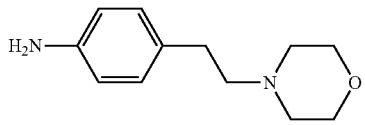

Using 4-[2-(4-nitrophenyl)ethyl]morpholine (5.75 g, 20.0 mmol) produced in Example 24 (24a), and by the method used in Example 14 (14b), the title object compound was obtained as a pale-yellow powder (1.50 g, yield 36%).

$^1$H-NMR (DMSO-d$_6$, 400 MHz) δ: 2.87-3.50 (10H, m), 3.70-4.05 (4H, br), 6.69-6.75 (2H, m), 6.98-7.04 (2H, m).

(24c) 4-(2-methyl-[1,3]dioxolan-2-yl)-3-[4-(2-morpholin-4-ylethyl)phenylamino]benzonitrile

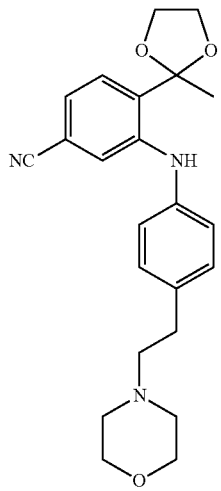 [SMILES: CC1(c2ccc(C#N)cc2Nc2ccc(CCN3CCOCC3)cc2)OCCO1]

Using 5-cyano-2-(2-methyl-[1,3]dioxolan-2-yl)phenyl trifluoromethanesulfonate (700 mg, 2.08 mmol) produced in Example 22 (22c) and 4-(2-morpholin-4-ylethyl)phenylamine (470 mg, 2.28 mmol) produced in Example 24 (24b), and by a method similar to that in Example 6 (6d), the title object compound was obtained as a yellow powder (670 mg, yield 82%).

$^1$H-NMR (CDCl$_3$, 400 MHz) δ: 1.70 (3H, s), 2.52-2.68 (6H, m), 2.76-2.88 (2H, m), 3.73-3.83 (4H, m), 3.84-3.92 (2H, m), 4.09-4.16 (2H, m), 7.00-7.09 (3H, m), 7.15-7.24 (2H, m), 7.41 (1H, d, J=1.5 Hz), 7.47 (1H, s), 7.51 (1H, d, J=7.8 Hz).

(24d) 4-(2-methyl-[1,3]dioxolan-2-yl)-3-[4-(2-morpholin-4-ylethyl)phenylamino]benzamide

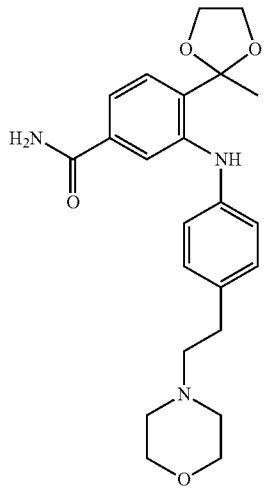 [SMILES: CC1(c2ccc(C(N)=O)cc2Nc2ccc(CCN3CCOCC3)cc2)OCCO1]

Using 4-(2-methyl-[1,3]dioxolan-2-yl)-3-[4-(2-morpholin-4-ylethyl)phenylamino]benzonitrile (670 mg, 1.70 mmol) produced in Example 24 (24c), and by the method used in Example 22 (22i), the title object compound was obtained as a pale-yellow powder (630 mg, yield 90%).

¹H-NMR (CDCl₃, 400 MHz) δ: 1.71 (3H, s), 2.50-2.64 (6H, m), 2.74-2.81 (2H, m), 3.73-3.80 (4H, m), 3.82-3.92 (2H, m), 4.05-4.16 (2H, m), 5.40-6.10 (2H, br), 7.02-7.07 (2H, m), 7.10-7.16 (2H, m), 7.17-7.22 (1H, m), 7.42 (1H, s), 7.49-7.54 (1H, m), 7.69-7.72 (1H, m).

(24e) 4-acetyl-3-[4-(2-morpholin-4-ylethyl)phenylamino]benzamide

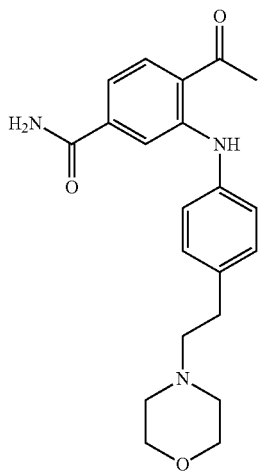 [SMILES: CC(=O)c1ccc(C(N)=O)cc1Nc1ccc(CCN2CCOCC2)cc1]

Using 4-(2-methyl-[1,3]dioxolan-2-yl)-3-[4-(2-morpholin-4-ylethyl)phenylamino]benzamide (630 mg, 1.53 mmol) produced in Example 24 (24d), and by a method similar to that in Example 17 (17f), the title object compound was obtained as a yellow powder (412 mg, yield 73%).

¹H-NMR (CDCl₃, 400 MHz) δ: 2.52-2.68 (9H, m), 2.78-2.88 (2H, m), 3.75-3.82 (4H, m), 5.70-6.20 (2H, br), 7.02 (1H, d, J=1.7, 8.3 Hz), 7.16-7.24 (4H, m), 7.58 (1H, d, J=1.7 Hz), 7.85 (1H, d, J=8.3 Hz), 10.49 (1H, s).

MS (ESI) m/z: 368 (M+H)⁺.

Example 25

(E)-4-acetyl-3-[4-(3-morpholin-4-ylpropenyl)phenylamino]benzamide (25a) (E)-4-[3-(4-nitrophenyl)allyl]morpholine

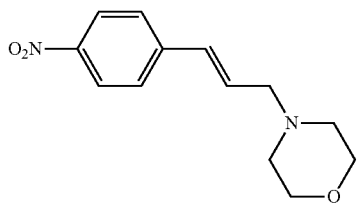 [SMILES: O=[N+]([O-])c1ccc(/C=C/CN2CCOCC2)cc1]

3-(4-Nitrophenyl)prop-2-en-1-ol (1.50 g, 8.37 mmol) was dissolved in methylene chloride (15 mL), pyridine (5.1 mL, 63 mmol) was added and, under ice-cooling, thionyl chloride (0.92 mL, 13 mmol) was added dropwise, and the mixture was stirred at room temperature for 30 min. The reaction mixture was washed successively with water, 1.0 M hydrochloric acid and saturated brine, and dried over anhydrous sodium sulfate. The solvent was evaporated under reduced pressure. To the obtained residue was added morpholine (10 mL, 0.12 mol), and the mixture was stirred at room temperature for 30 min. The reaction mixture was diluted with diethyl ether, washed successively with water and saturated brine, and dried over anhydrous sodium sulfate. The solvent was evaporated under reduced pressure. The obtained residue was purified by silica gel column chromatography (hexane:ethyl acetate, 2:1→0:1, V/V). The solvent of the object fraction was evaporated under reduced pressure to give the title object compound as a brown powder (870 mg, yield 42%).

¹H-NMR (CDCl₃, 400 MHz) δ: 2.48-2.55 (4H, m), 3.20 (2H, dd, J=6.6, 1.3 Hz), 3.71-3.78 (4H, m), 6.45 (1H, dt, J=15.8, 6.6 Hz), 6.58-6.65 (1H, m), 7.46-7.52 (2H, m), 8.14-8.20 (2H, m).

(25b) (E)-4-(3-morpholin-4-ylpropenyl)phenylamine

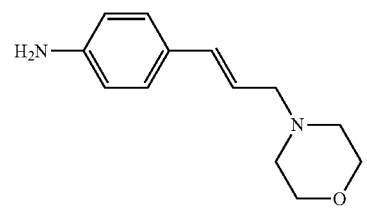

(E)-4-[3-(4-Nitrophenyl)allyl]morpholine (770 mg, 3.10 mmol) produced in Example 25 (25a) was dissolved in ethanol (40 mL), tin (II) chloride dihydrate (3.50 g, 15.5 mmol) was added, and the mixture was stirred under a nitrogen atmosphere at 80° C. for 1 hr. The mixture was allowed to cool, ethyl acetate was added, and the mixture was neutralized with saturated aqueous sodium hydrogen carbonate, and two layers were separated. The organic layer was washed with saturated brine, and dried over anhydrous sodium sulfate. The solvent was evaporated under reduced pressure. The obtained residue was purified by silica gel column chromatography (ethyl acetate). The solvent of the object fraction was evaporated under reduced pressure to give the title object compound as a yellow oil (467 mg, yield 69%).

¹H-NMR (CDCl₃, 400 MHz) δ: 2.44-2.53 (4H, m), 3.11 (2H, dd, J=6.8, 1.2 Hz), 3.60-3.76 (6H, m), 6.04 (1H, dt, J=15.9, 6.8 Hz), 6.37-6.45 (1H, m), 6.59-6.65 (2H, m), 7.15-7.21 (2H, m).

(25c) methyl (E)-4-(2-methyl-[1,3]dioxolan-2-yl)-3-[4-(3-morpholin-4-ylpropenyl)phenylamino]benzoate

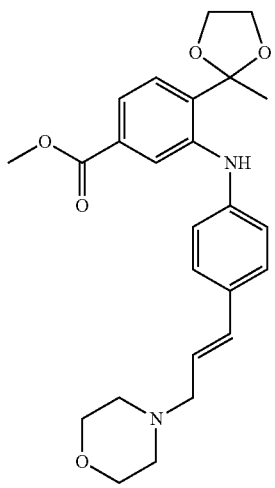

Using (E)-4-(3-morpholin-4-ylpropenyl)phenylamine (460 mg, 2.11 mmol) produced in Example 25 (25b) and methyl 3-bromo-4-(2-methyl-[1,3]dioxolan-2-yl)benzoate (630 mg, 2.09 mmol) produced in Example 19 (19a), and by the method used in Example 6 (6d), the title object compound was obtained as a yellow oil (366 mg, yield 40%).

$^1$H-NMR (CDCl$_3$, 400 MHz) δ: 1.68 (3H, s), 2.45-2.55 (4H, m), 3.15 (2H, d, J=6.8 Hz), 3.72-3.77 (4H, m), 3.84-3.89 (2H, m), 3.86 (3H, s), 4.07-4.12 (2H, m), 6.13 (1H, dt, J=15.8, 6.8 Hz), 6.52 (1H, d, J=15.8 Hz), 7.01-7.07 (2H, m), 7.28-7.34 (2H, m), 7.46-7.55 (3H, m), 7.98 (1H, s).

(25d) (E)-4-(2-methyl-[1,3]dioxolan-2-yl)-3-[4-(3-morpholin-4-ylpropenyl)phenylamino]benzamide

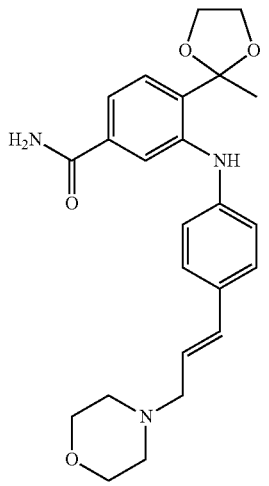 [SMILES: CC1(c2ccc(C(N)=O)cc2Nc2ccc(/C=C/CN3CCOCC3)cc2)OCCO1]

Using methyl (E)-4-(2-methyl-[1,3]dioxolan-2-yl)-3-[4-(3-morpholin-4-ylpropenyl)phenylamino]benzoate (361 mg, 0.823 mmol) produced in Example 25 (25c), and by the method used in Example 6 (6e), the title object compound was obtained as a yellow oil (230 mg, yield 66%).

$^1$H-NMR (CDCl$_3$, 400 MHz) δ: 1.69 (3H, s), 2.46-2.55 (4H, m), 3.14 (2H, d, J=6.8 Hz), 3.72-3.77 (4H, m), 3.83-3.89 (2H, m), 4.07-4.13 (2H, m), 5.40-5.70 (1H, br), 5.75-6.10 (1H, br), 6.13 (1H, dt, J=15.9, 6.8 Hz), 6.48 (1H, d, J=15.9 Hz), 7.02-7.07 (2H, m), 7.24 (1H, dd, J=8.0, 1.7 Hz), 7.27-7.33 (2H, m), 7.53 (1H, d, J=8.0 Hz), 7.76 (1H, d, J=1.7 Hz), 8.01 (1H, s).

(25e) (E)-4-acetyl-3-[4-(3-morpholin-4-ylpropenyl)phenylamino]benzamide

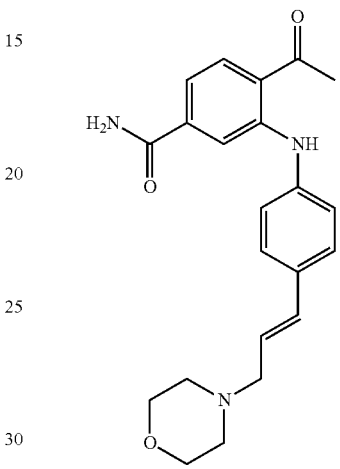

Using 4-(2-methyl-[1,3]dioxolan-2-yl)-3-[4-(3-morpholin-4-ylpropenyl)phenylamino]benzamide (230 mg, 0.543 mmol) produced in Example 25 (25d), and by a method similar to that in Example 17 (17f), the title object compound was obtained as a yellowish orange powder (99 mg, yield 48%).

$^1$H-NMR (DMSO-d$_6$, 400 MHz) δ: 2.34-2.43 (4H, m), 2.65 (3H, s), 3.08 (2H, d, J=6.4 Hz), 3.54-3.62 (4H, m), 6.22 (1H, dt, J=15.8, 6.4 Hz), 6.52 (1H, d, J=15.8 Hz), 7.18-7.27 (3H, m), 7.42-7.53 (3H, m), 7.69 (1H, d, J=1.2 Hz), 8.00 (1H, d, J=8.3 Hz), 8.02-8.09 (1H, br), 10.35 (1H, s).

MS (ESI) m/z: 378 (M−H)$^−$.

Example 26

4-hydroxymethyl-3-{4-[2-(tetrahydropyran-4-yloxy)ethoxy]phenylamino}benzamide (26a) methyl 4-cyano-2-fluorobenzoate

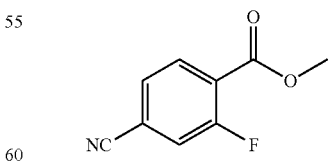

To 4-cyano-2-fluorobenzoic acid (1.00 g, 6.06 mmol) were added toluene (10 mL) and methanol (10 mL), and 2.0 M trimethylsilyldiazomethane/diethyl ether solution (about 5 mL) was added dropwise. The reaction mixture was evaporated under reduced pressure to give the title object compound as a slightly yellow powder (1.11 g, yield 100%).

¹H-NMR (CDCl₃, 400 MHz) δ: 3.97 (3H, s), 7.44-7.48 (1H, m), 7.50-7.55 (1H, m), 8.02-8.08 (1H, m).

(26b) methyl 4-cyano-2-{4-[2-(tetrahydropyran-4-yloxy)ethoxy]phenylamino}benzoate

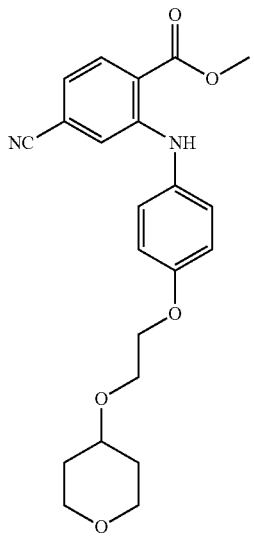 [SMILES: COC(=O)c1ccc(C#N)cc1Nc1ccc(OCCOC2CCOCC2)cc1]

Using 4-[2-(tetrahydropyran-4-yloxy)ethoxy]phenylamine (728 mg, 3.07 mmol) produced in Example 17 (17b) and methyl 4-cyano-2-fluorobenzoate (500 mg, 2.79 mmol) produced in Example 26 (26a), and by the method used in Example 5 (5b), the title object compound was obtained as a slightly yellow powder (175 mg, yield 16%).

¹H-NMR (CDCl₃, 400 MHz) δ: 1.59-1.72 (2H, m), 1.90-2.00 (2H, m), 3.44-3.52 (2H, m), 3.58-3.68 (1H, m), 3.80-3.89 (2H, m), 3.92-4.01 (5H, m), 4.12-4.18 (2H, m), 6.85 (1H, dd, J=8.3, 1.5 Hz), 6.84-7.00 (2H, m), 7.10-7.17 (3H, m), 7.98 (1H, d, J=8.3 Hz), 9.35 (1H, s).

(26c) methyl 2-{4-[2-(tetrahydropyran-4-yloxy)ethoxy]phenylamino}terephthalate

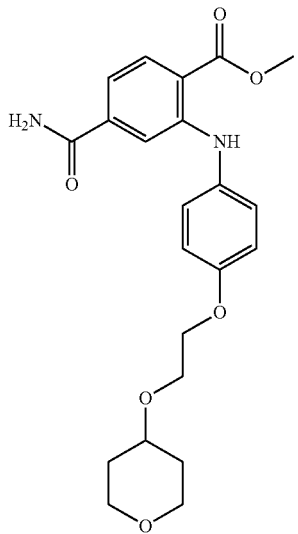 [SMILES: COC(=O)c1ccc(C(N)=O)cc1Nc1ccc(OCCOC2CCOCC2)cc1]

Using methyl 4-cyano-2-{4-[2-(tetrahydropyran-4-yloxy)ethoxy]phenylamino}benzoate (175 mg, 0.441 mmol) produced in Example 26 (26b), and by the method used in Example 22 (22i), the title object compound was obtained as a pale-yellow powder (190 mg, yield 100%).

¹H-NMR (CDCl₃, 400 MHz) δ: 1.56-1.72 (2H, m), 1.90-2.00 (2H, m), 3.42-3.50 (2H, m), 3.57-3.66 (1H, m), 3.83-3.89 (2H, m), 3.92-4.01 (5H, m), 4.12-4.17 (2H, m), 5.45-5.75 (1H, br), 5.85-6.10 (1H, br), 6.91-6.97 (2H, m), 6.98 (1H, dd, J=8.0, 1.7 Hz), 7.13-7.19 (2H, m), 7.36 (1H, d, J=1.7 Hz), 7.99 (1H, d, J=8.3 Hz), 9.33 (1H, s).

(26d) 4-hydroxymethyl-3-{4-[2-(tetrahydropyran-4-yloxy)ethoxy]phenylamino}benzamide

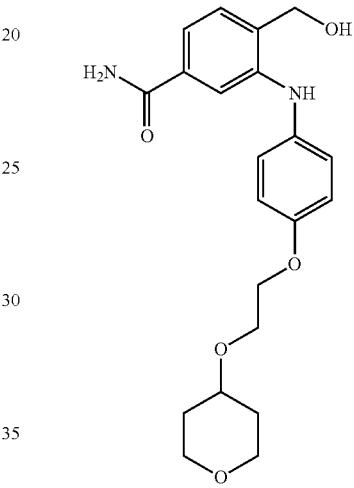

Methyl 2-{4-[2-(tetrahydropyran-4-yloxy)ethoxy]phenylamino}terephthalate (190 mg, 0.441 mmol) produced in Example 26 (26c) was dissolved in tetrahydrofuran (3 mL), lithium aluminum hydride (17 mg, 0.44 mmol) was added, and the mixture was stirred at room temperature for 0.5 hr. To the reaction mixture were added diethyl ether (3 mL), one drop of water, and one drop of 15% aqueous sodium hydroxide, and the mixture was stirred for 10 min. Water (3 drops) was added, and the mixture was stirred for 0.5 hr. The precipitate was filtered off, and the solvent in the filtrate was evaporated under reduced pressure and the obtained residue was purified by silica gel column chromatography (chloroform:methanol, 100:0→97:3, V/V). The solvent of the object fraction was evaporated under reduced pressure, and the obtained residue was powderized with ethyl acetate and evaporated under reduced pressure. The obtained residue collected by filtration with diethyl ether to give the title object compound as a pale-yellow powder (70 mg, yield 41%).

¹H-NMR (CDCl₃, 400 MHz) δ: 1.58-1.72 (2H, m), 1.90-1.98 (2H, m), 2.30-2.40 (1H, br), 3.41-3.50 (2H, m), 3.55-3.65 (1H, m), 3.80-3.86 (2H, m), 3.91-3.99 (2H, m), 4.05-4.12 (2H, m), 4.73 (2H, d, J=2.9 Hz), 5.50-6.20 (2H, br), 6.77 (1H, s), 6.84-6.90 (2H, m), 7.00-7.06 (2H, m), 7.12 (1H, dd, J=7.8, 1.4 Hz), 7.16 (1H, d, J=7.8 Hz), 7.47 (1H, d, J=1.4 Hz).

MS (ESI) m/z: 387 (M+H)⁺.

Example 27

N-(4-{4-[3-(2-hydroxyethoxy)azetidin-1-yl]phenoxy}-6-methoxypyridin-3-yl)acetamide (27a) 2-methoxy-5-nitro-4-(4-{3-[2-(tetrahydropyran-2-yloxy)ethoxy]azetidin-1-yl}phenoxy)pyridine

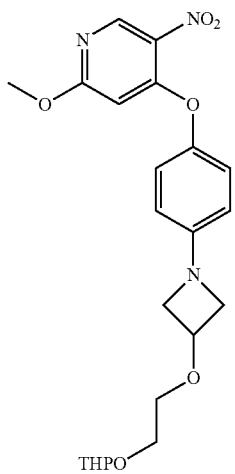

4-{3-[2-(Tetrahydropyran-2-yloxy)ethoxy]azetidin-1-yl}phenol (210 mg, 0.716 mmol) produced in Reference Example 5 (5b) was dissolved in dimethylformamide (2 mL) and, under ice-cooling, sodium hydride (P=60%) (35 mg, 0.86 mmol) was added and the mixture was stirred at the same temperature for 30 min. 4-Chloro-2-methoxy-5-nitropyridine (134 mg, 0.716 mmol) produced in Example 4 (4c) was added and the mixture was stirred at room temperature for 1 hr. To the reaction mixture was added saturated aqueous sodium hydrogen carbonate, and the mixture was extracted twice with ethyl acetate, washed successively with water and saturated brine, and dried over anhydrous sodium sulfate. The solvent was evaporated under reduced pressure, and the obtained residue was purified by silica gel column chromatography (hexane:ethyl acetate, 4:1→2:1, V/V). The solvent of the object fraction was evaporated under reduced pressure to give the title object compound as a brown oil (220 mg, yield 69%).

$^1$H-NMR (CDCl$_3$, 400 MHz) δ: 1.50-1.90 (6H, m), 3.47-3.56 (1H, m), 3.59-3.68 (3H, m), 3.72-3.80 (2H, m), 3.85-3.92 (2H, m), 3.93 (3H, s), 4.08-4.20 (2H, m), 4.47-4.58 (1H, m), 4.60-4.70 (1H, m), 6.00 (1H, s), 6.46-6.49 (2H, m), 6.95-6.97 (2H, m), 8.85 (1H, s).

(27b) N-(6-methoxy-4-(4-{3-[2-(tetrahydropyran-2-yloxy)ethoxy]azetidin-1-yl}phenoxy)pyridin-3-yl)acetamide

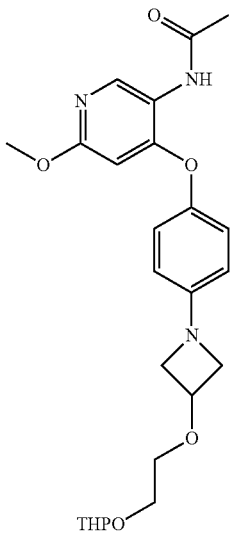

Using 2-methoxy-5-nitro-4-(4-{3-[2-(tetrahydropyran-2-yloxy)ethoxy]azetidin-1-yl}phenoxy)pyridine (210 mg, 0.470 mmol) produced in Example 27 (27a), and by the method used in Example 8 (8f), the title object compound was obtained as a brown oil (200 mg, yield 93%).

$^1$H-NMR (CDCl$_3$, 400 MHz) δ: 1.50-1.90 (6H, m), 2.23 (3H, s), 3.47-3.57 (1H, m), 3.58-3.68 (4H, m), 3.70-3.80 (2H, m), 3.84 (3H, s), 3.85-3.94 (2H, m), 4.08-4.18 (2H, m), 4.46-4.58 (1H, m), 4.60-4.70 (1H, m), 5.92 (1H, s), 6.46-6.48 (2H, m), 6.92-6.94 (2H, m), 7.40-7.48 (1H, br), 8.98 (1H, s).

(27c) N-(4-{4-[3-(2-hydroxyethoxy)azetidin-1-yl]phenoxy}-6-methoxypyridin-3-yl)acetamide

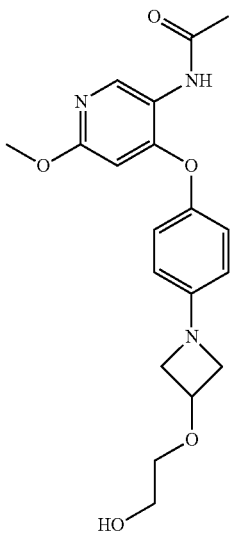 [SMILES: COc1cc(Oc2ccc(N3CC(OCCO)C3)cc2)c(NC(C)=O)cn1]

Using N-(6-methoxy-4-(4-{3-[2-(tetrahydropyran-2-yloxy)ethoxy]azetidin-1-yl}phenoxy)pyridin-3-yl)acetamide (200 mg, 0.437 mmol) produced in Example 27 (27b), and by the method used in Example 4 (4e), the title object compound was obtained as a pale-brown powder (115 mg, yield 71%).

¹H-NMR (DMSO-d₆, 400 MHz) δ: 2.06 (3H, s), 3.38-3.43 (2H, m), 3.49-3.56 (2H, m), 3.59-3.66 (2H, m), 3.74 (3H, s), 4.03-4.13 (2H, m), 4.39-4.48 (1H, m), 5.78 (1H, s), 6.49-6.51 (2H, m), 6.97-6.99 (2H, m), 8.36 (1H, s), 9.44 (1H, br).

MS (ESI) m/z: 374 (M+H)⁺.

Example 28

4-acetyl-3-{4-[3-(2-hydroxyethoxy)azetidin-1-yl]phenoxy}benzamide (28a) 4-cyano-2-fluoro-N-methoxy-N-methylbenzamide

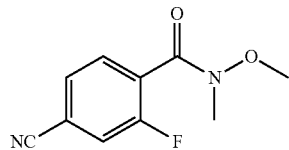

4-Cyano-2-fluorobenzoic acid (4.00 g, 24.2 mmol) was dissolved in methylene chloride (25 mL), oxalyl chloride (4.16 mL, 48.4 mmol), and dimethylformamide (0.08 mL, 1.0 mmol) were added, and the mixture was stirred at room temperature for 1 hr. The solvent of the reaction mixture was evaporated under reduced pressure, and the residue was azeotropically distilled three times with toluene (25 mL). A solution (10 mL) of the obtained residue in methylene chloride was added to a solution of N,O-dimethylhydroxylamine hydrochloride (3.30 g, 33.9 mmol) and potassium carbonate (13.4 g, 96.8 mmol) in methylene chloride-water (1:1) (50 mL), and the mixture was further stirred at the same temperature for 1 hr. The reaction mixture was washed successively with water and saturated brine, and dried over anhydrous sodium sulfate. The solvent was evaporated under reduced pressure to give the title object compound as a yellow oil (5.67 g, yield 100%).

¹H-NMR (CDCl₃, 400 MHz) δ: 3.38 (3H, s), 3.52 (3H, s), 7.39-7.46 (1H, m), 7.48-7.60 (2H, m).

(28b) 4-acetyl-3-fluorobenzonitrile

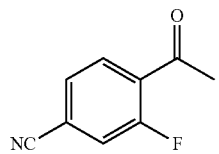

4-Cyano-2-fluoro-N-methoxy-N-methylbenzamide (5.67 g, 27.2 mmol) produced in Example 28 (28a) was dissolved in tetrahydrofuran (50 mL) and, under ice-cooling, 1.0 M methyl magnesium bromide/tetrahydrofuran solution (68 mL, 68 mmol) was added, and the mixture was stirred at room temperature for 2 hr. To the reaction mixture was added 10% citric acid water, and the mixture was extracted with ethyl acetate. The organic layer was washed with saturated brine, and dried over anhydrous sodium sulfate. The solvent was evaporated under reduced pressure, and the obtained residue was purified by silica gel column chromatography (hexane:ethyl acetate, 9:1→7:3, V/V). The solvent of the object fraction was evaporated under reduced pressure to give the title object compound as a pale-yellow powder (2.85 g, yield 64%).

¹H-NMR (CDCl₃, 400 MHz) δ: 2.68 (3H, d, J=4.8 Hz), 7.47 (1H, dd, J=10.2, 1.4 Hz), 7.53 (1H, dd, J=8.0, 1.4 Hz), 7.93-8.01 (1H, m).

(28c) 4-acetyl-3-(4-{3-[2-(tetrahydropyran-2-yloxy)ethoxy]azetidin-1-yl}phenoxy)benzonitrile

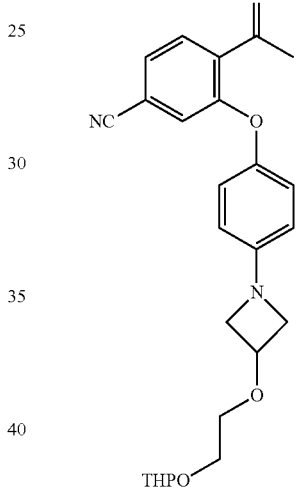

4-{3-[2-(Tetrahydropyran-2-yloxy)ethoxy]azetidin-1-yl}phenol (490 mg, 1.67 mmol) produced in Reference 5 (5b), and 4-acetyl-3-fluorobenzonitrile (273 mg, 1.67 mmol) produced in Example 28 (28b) were dissolved in dimethylformamide (10 mL), potassium carbonate (463 mg, 3.35 mmol) was added, and the mixture was stirred at 100° C. for 11 hr. To the reaction mixture was added ethyl acetate, and the mixture was washed successively with water and saturated brine, and dried over anhydrous sodium sulfate. The solvent was evaporated under reduced pressure. The obtained residue was purified by silica gel column chromatography (hexane:ethyl acetate, 3:1, V/V), and the solvent of the object fraction was evaporated under reduced pressure to give the title object compound as a reddish brown powder (236 mg, yield 32%).

¹H-NMR (CDCl₃, 400 MHz) δ: 1.47-1.66 (4H, m), 1.69-1.89 (2H, m), 2.72 (3H, s), 3.46-3.56 (1H, m), 3.59-3.68 (1H, m), 3.66 (2H, t, J=6.8 Hz), 3.75-3.81 (2H, m), 3.85-3.93 (2H, m), 4.15 (2H, t, J=6.8 Hz), 4.49-4.56 (1H, m), 4.61-4.66 (1H, m), 6.47-6.53 (2H, m), 6.90-6.96 (2H, m), 7.00 (1H, d, J=1.2 Hz), 7.31 (1H, dd, J=8.1, 1.2 Hz), 7.82 (1H, d, J=8.1 Hz).

(28d) 4-acetyl-3-(4-{3-[2-(tetrahydropyran-2-yloxy)ethoxy]azetidin-1-yl}phenoxy)benzamide

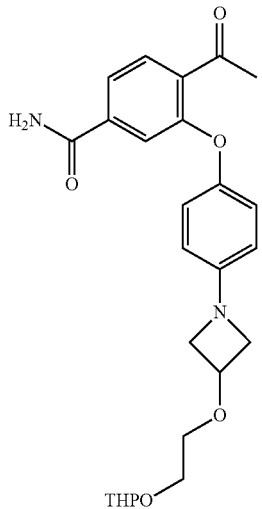

Using 4-acetyl-3-(4-{3-[2-(tetrahydropyran-2-yloxy)ethoxy]azetidin-1-yl}phenoxy)benzonitrile (230 mg, 0.526 mmol) produced in Example 28 (28c), and by the method used in Example 22 (22i), the title object compound was obtained as a yellow oil (215 mg, yield 90%).

$^1$H-NMR (CDCl$_3$, 400 MHz) δ: 1.48-1.68 (4H, m), 1.69-1.91 (2H, m), 2.70 (3H, s), 3.47-3.55 (1H, m), 3.58-3.69 (3H, m), 3.73-3.79 (2H, m), 3.84-3.92 (2H, m), 4.13 (2H, t, J=6.8 Hz), 4.47-4.55 (1H, m), 4.61-4.66 (1H, m), 6.45-6.51 (2H, m), 6.90-6.96 (2H, m), 7.23 (1H, d, J=1.7 Hz), 7.41 (1H, dd, J=8.0, 1.7 Hz), 7.82 (1H, d, J=8.0 Hz).

(28e) 4-acetyl-3-{4-[3-(2-hydroxyethoxy)azetidin-1-yl]phenoxy}benzamide

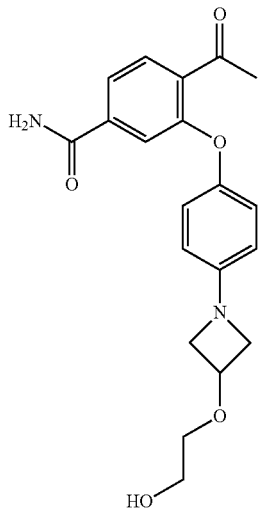 [SMILES: CC(=O)c1ccc(C(N)=O)cc1Oc1ccc(N2CC(OCCO)C2)cc1]

Using 4-acetyl-3-(4-{3-[2-(tetrahydropyran-2-yloxy)ethoxy]azetidin-1-yl}phenoxy)benzamide (210 mg, 0.462 mmol) produced in Example 28 (28d), and by the method used in Example 17 (17f), the title object compound was obtained as a yellow gum (121 mg, yield 71%).

$^1$H-NMR (CDCl$_3$, 400 MHz) δ: 2.06-2.17 (1H, br), 2.70 (3H, s), 3.54-3.61 (2H, m), 3.70-3.83 (4H, m), 4.13 (2H, t, J=6.9 Hz), 4.44-4.52 (1H, m), 5.60-6.30 (2H, br), 6.45-6.52 (2H, m), 6.90-6.97 (2H, m), 7.23-7.27 (1H, m), 7.37-7.43 (1H, m), 7.82 (1H, d, J=8.1 Hz).

MS (ESI) m/z: 371 (M+H)$^+$.

Example 29

4-acetyl-2-{4-[3-(2-hydroxyethoxy)azetidin-1-yl]phenoxy}benzamide

(29a) 4-bromo-3-fluoro-N-methoxy-N-methylbenzamide

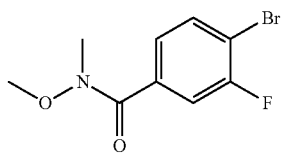

Using 4-bromo-3-fluorobenzoic acid (3.00 g, 13.7 mmol), and by a method similar to that in Example 28 (28a), the title object compound was obtained as a crude product (3.59 g, yield 100%).

$^1$H-NMR (CDCl$_3$, 400 MHz) δ: 3.36 (3H, s), 3.54 (3H, s), 7.40 (1H, dd, J=8.2, 1.9 Hz), 7.49 (1H, dd, J=9.0, 1.9 Hz), 7.59 (1H, dd, J=8.2, 6.8 Hz).

(29b) 1-(4-bromo-3-fluorophenyl)ethanone

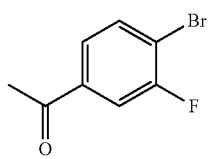

Using 4-bromo-3-fluoro-N-methoxy-N-methylbenzamide (3.59 g, 13.7 mmol) produced in Example 29 (29a), and by the method used in Example 28 (28b), the title object compound was obtained as a yellow oil (2.49 g, yield 84%).

$^1$H-NMR (CDCl$_3$, 400 MHz) δ: 2.59 (3H, s), 7.60 (1H, dd, J=8.2, 1.9 Hz), 7.64-7.73 (2H, m).

(29c) 4-acetyl-2-fluorobenzonitrile

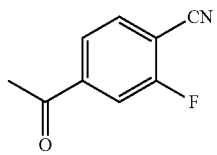

1-(4-Bromo-3-fluorophenyl)ethanone (2.49 g, 11.5 mmol) produced in Example 29 (29b) was dissolved in dimethylformamide (55 mL), zinc cyanide (2.71 g, 23.0 mmol) was added. After nitrogen gas bubbling for 1 min, tetrakistriphenylphosphine palladium (2.66 g, 2.30 mmol) was added, and the mixture was stirred under a nitrogen atmosphere at 80° C. for 1 hr. Water was added to the reaction mixture, and the mixture was extracted with ethyl acetate. The organic layer was washed successively with water and saturated brine, and dried over anhydrous sodium sulfate. The solvent was evaporated under reduced pressure, and the obtained residue was purified by silica gel column chromatography (hexane:ethyl acetate, 9:1→6:4, V/V). The solvent of the object fraction was evaporated under reduced pressure to give the title object compound as a pale-yellow powder (1.59 g, yield 85%).

$^1$H-NMR (CDCl$_3$, 400 MHz) δ: 2.64 (3H, s), 7.73-7.80 (2H, m), 7.82 (1H, dd, J=7.8, 1.4 Hz).

(29d) 4-acetyl-2-(4-{3-[2-(tetrahydropyran-2-yloxy)ethoxy]azetidin-1-yl}phenoxy)benzonitrile

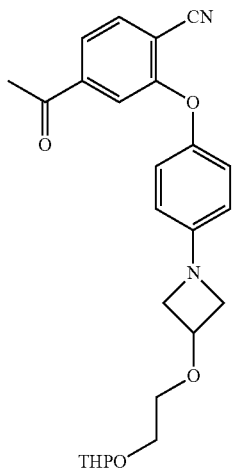

Using 4-{3-[2-(tetrahydropyran-2-yloxy)ethoxy]azetidin-1-yl}phenol (1.00 g, 3.41 mmol) produced in Reference Example 5 (5b) and 4-acetyl-2-fluorobenzonitrile (560 mg, 3.43 mmol) produced in Example 29 (29c), and by the method used in Example 28 (28c), the title object compound was obtained as a yellow oil (460 mg, yield 31%).

$^1$H-NMR (CDCl$_3$, 400 MHz) δ: 1.47-1.67 (4H, m), 1.71-1.91 (2H, m), 2.50 (3H, s), 3.46-3.56 (1H, m), 3.59-3.68 (1H, m), 3.66 (2H, t, J=7.1 Hz), 3.75-3.81 (2H, m), 3.85-3.93 (2H, m), 4.14 (2H, t, J=7.1 Hz), 4.49-4.56 (1H, m), 4.61-4.66 (1H, m), 6.46-6.52 (2H, m), 6.93-6.99 (2H, m), 7.28 (1H, d, J=1.9 Hz), 7.58 (1H, dd, J=8.1, 1.9 Hz), 7.71 (1H, d, J=8.1 Hz).

(29e) 4-acetyl-2-(4-{3-[2-(tetrahydropyran-2-yloxy)ethoxy]azetidin-1-yl}phenoxy)benzamide

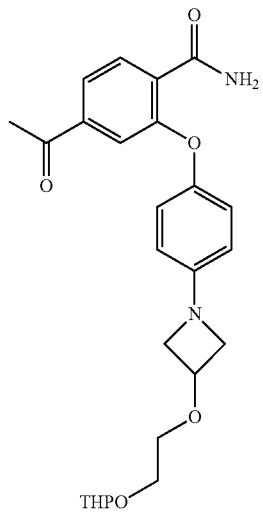

Using 4-acetyl-2-(4-{3-[2-(tetrahydropyran-2-yloxy)ethoxy]azetidin-1-yl}phenoxy)benzonitrile (1.42 g, 3.25 mmol) produced in Example 29 (29d), and by the method used in Example 22 (22i), the title object compound was obtained as a yellow oil (1.18 g, yield 80%).

$^1$H-NMR (CDCl$_3$, 400 MHz) δ: 1.48-1.68 (4H, m), 1.69-1.90 (2H, m), 2.51 (3H, s), 3.47-3.55 (1H, m), 3.58-3.69 (3H, m), 3.74-3.81 (2H, m), 3.85-3.93 (2H, m), 4.14 (2H, t, J=7.1 Hz), 4.49-4.56 (1H, m), 4.61-4.66 (1H, m), 6.01-6.12 (1H, br), 6.45-6.51 (2H, m), 6.93-6.98 (2H, m), 7.31 (1H, d, J=1.4 Hz), 7.37 (1H, dd, J=8.0, 1.4 Hz), 7.75-7.86 (1H, br), 8.33 (1H, d, J=8.0 Hz).

(29f) 4-acetyl-2-{4-[3-(2-hydroxyethoxy)azetidin-1-yl]phenoxy}benzamide

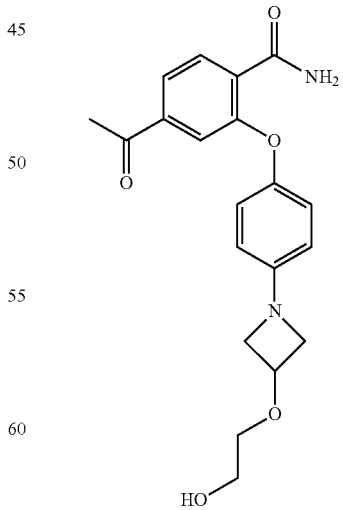

Using 4-acetyl-2-(4-{3-[2-(tetrahydropyran-2-yloxy)ethoxy]azetidin-1-yl}phenoxy)benzamide (1.18 g, 2.60 mmol) produced in Example 29 (29e), and by the method used in Example 17 (17f), the title object compound was obtained as white crystals (301 mg, yield 31%).

¹H-NMR (CDCl₃, 400 MHz) δ: 1.93 (1H, t, J=6.1 Hz), 2.52 (3H, s), 3.56-3.61 (2H, m), 3.75-3.83 (4H, m), 4.15 (2H, t, J=7.1 Hz), 4.44-4.55 (1H, m), 5.76-5.89 (1H, br), 6.46-6.53 (2H, m), 6.93-6.99 (2H, m), 7.31 (1H, J=1.5 Hz), 7.64 (1H, J=8.0, 1.5 Hz), 7.73-7.86 (1H, br), 8.34 (1H, d, J=8.0 Hz).

MS (ESI) m/z: 371 (M+H)⁺.

Example 30

4-acetyl-3-{4-[4-(2-hydroxyethoxy)piperidin-1-yl]phenoxy}benzamide (30a) tert-butyl 4-tert-butoxycarbonylmethoxypiperidine-1-carboxylate

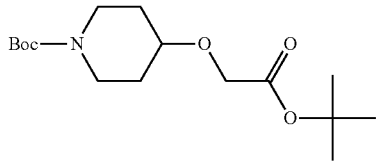 [SMILES: CC(C)(C)OC(=O)COC1CCN(C(=O)OC(C)(C)C)CC1]

tert-Butyl 4-hydroxypiperidine-1-carboxylate (5.00 g, 24.8 mmol) and tert-butyl bromoacetate (8.72 g, 44.7 mmol) were dissolved in toluene (100 mL), pulverized sodium hydroxide (1.20 g, 30.0 mmol) and tetrabutylammonium hydrogen sulfate (2.53 g, 7.45 mmol) were added, and the mixture was heated under reflux for 6 hr. The mixture was allowed to cool, the reaction mixture was diluted with ethyl acetate, washed successively with water and saturated brine, and dried over anhydrous sodium sulfate. The solvent was evaporated under reduced pressure. The obtained residue was purified by silica gel column chromatography (hexane:ethyl acetate, 10:1, V/V). The solvent of the object fraction was evaporated under reduced pressure to give the title object compound as a pale-yellow powder (4.44 g, yield 57%).

¹H-NMR (CDCl₃, 400 MHz) δ: 1.50 (9H, s), 1.52 (9H, s), 1.56-1.65 (2H, m), 1.84-1.94 (2H, m), 3.08-3.17 (2H, m), 3.54-3.64 (1H, m), 3.76-3.86 (2H, m), 4.04 (2H, s).

(30b) tert-butyl 4-(2-hydroxyethoxy)piperidine-1-carboxylate

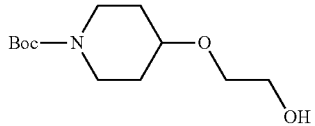 [SMILES: CC(C)(C)OC(=O)N1CCC(OCCO)CC1]

tert-Butyl 4-tert-butoxycarbonylmethoxypiperidine-1-carboxylate (4.44 g, 14.1 mmol) produced in Example 30 (30a) was dissolved in tetrahydrofuran (70 mL) and, under ice-cooling, lithium aluminum hydride (642 mg, 16.9 mmol) was added, and the mixture was stirred for 2.5 hr. Water (0.64 mL), 15% aqueous sodium hydroxide (0.64 mL) and water (1.9 mL) were sequentially added, and the mixture was stirred for 1 hr. The insoluble material was filtered off, and the solvent of the filtrate was evaporated under reduced pressure to give the title object compound as a yellow oil (3.12 g, yield 90%).

¹H-NMR (CDCl₃, 400 MHz) δ: 1.46-1.62 (11H, m), 1.84-1.94 (2H, m), 2.02 (1H, t, J=6.1 Hz), 3.08-3.17 (2H, m), 3.50-3.58 (1H, m), 3.60-3.65 (2H, m), 3.74-3.85 (4H, m).

(30c) 4-[2-(tert-butyldimethylsilanyloxy)ethoxy]piperidine

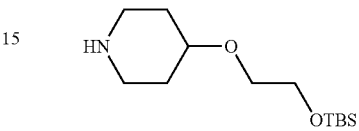

To tert-butyl 4-(2-hydroxyethoxy)piperidine-1-carboxylate (3.01 g, 12.3 mmol) produced in Example 30 (30b) was added trifluoroacetic acid (12 mL) under ice-cooling, and the mixture was stirred for 1 hr. The solvent was evaporated under reduced pressure.

The residue was dissolved in tetrahydrofuran (14 mL) and, under ice-cooling, triethylamine (14 mL, 98 mmol) and tert-butyldimethylchlorosilane (3.71 g, 24.6 mmol) were added, and the mixture was stirred at room temperature for 50 min. The solvent was evaporated under reduced pressure, saturated aqueous sodium hydrogen carbonate (20 mL) was added, and the mixture was extracted twice with ethyl acetate (50 mL). The organic layers were combined, washed successively with saturated aqueous sodium hydrogen carbonate and saturated brine, and dried over anhydrous sodium sulfate. The solvent was evaporated under reduced pressure. The obtained residue was purified by silica gel column chromatography (ethyl acetate→chloroform:methanol, 5:1, V/V). The solvent of the object fraction was evaporated under reduced pressure to give the title object compound as a brown oil (3.46 g, 100%).

¹H-NMR (CDCl₃, 400 MHz) δ: 0.07 (6H, s), 0.90 (9H, s), 1.46-1.56 (2H, m), 1.88-1.98 (2H, m), 2.20-2.45 (1H, br), 2.64-2.72 (2H, m), 3.12 (2H, dt, J=13.2, 4.6 Hz), 3.41-3.48 (1H, m), 3.53 (2H, t, J=5.6 Hz), 3.75 (2H, t, J=5.6 Hz).

(30d) 1-(4-benzyloxyphenyl)-4-[2-(tert-butyldimethylsilanyloxy)ethoxy]piperidine

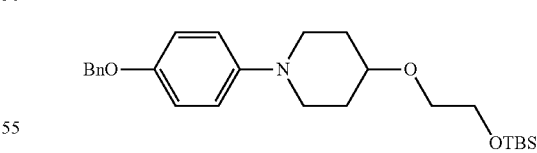

To 4-[2-(tert-butyldimethylsilanyloxy)ethoxy]piperidine (3.46 g, 12.3 mmol) produced in Example 30 (30c) were added 4-benzyloxyiodobenzene (3.47 g, 11.2 mmol), palladium(II) acetate (126 mg, 0.56 mmol), (2-biphenyl)dicyclohexylphosphine (393 mg, 1.12 mmol), sodium tert-butoxide (1.61 g, 16.8 mmol) and 1,4-dioxane (35 mL), and the mixture was stirred under a nitrogen atmosphere at 80° C. for 10 hr. The mixture was allowed to cool, ethyl acetate was added to the reaction mixture, and the mixture was washed successively with water and saturated brine, and dried over anhydrous sodium sulfate. The solvent was evaporated under reduced pressure. The obtained residue was purified by silica gel column chromatography (hexane:ethyl acetate, 10:1, V/V). The solvent of the object fraction was evaporated under reduced pressure to give the title object compound as a pale orange oil (560 mg, yield 25%).

$^1$H-NMR (CDCl$_3$, 400 MHz) δ: 0.07 (6H, s), 0.90 (9H, s), 1.68-1.80 (2H, m), 1.95-2.06 (2H, m), 2.76-2.85 (2H, m), 3.33-3.41 (2H, m), 3.43-3.51 (1H, m), 3.55 (2H, t, J=5.6 Hz), 3.76 (2H, t, J=5.6 Hz), 5.01 (2H, s), 6.87-6.91 (4H, m), 7.27-7.45 (5H, m).

(30e) 4-{4-[2-(tert-butyldimethylsilanyloxy)ethoxy]piperidin-1-yl}phenol

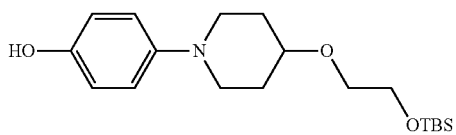 [SMILES: CC(C)(C)[Si](C)(C)OCCOC1CCN(c2ccc(O)cc2)CC1]

Using 1-(4-benzyloxyphenyl)-4-[2-(tert-butyldimethylsilanyloxy)ethoxy]piperidine (500 mg, 1.13 mmol) produced in Example 30 (30d), and by a method similar to that in Example 14 (14b), the title object compound was obtained as a colorless oil (440 mg, yield 100%).

(30f) 4-acetyl-3-{4-[4-(2-hydroxyethoxy)piperidin-1-yl]phenoxy}benzonitrile

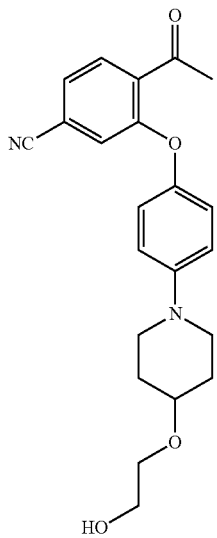 [SMILES: CC(=O)c1ccc(C#N)cc1Oc1ccc(N2CCC(OCCO)CC2)cc1]

Using 4-{4-[2-(tert-dimethylsilanyloxy)ethoxy]piperidin-1-yl}phenol (440 mg, 1.13 mmol) produced in Example 30 (30e) and 4-acetyl-3-fluorobenzonitrile (306 mg, 1.88 mmol) produced in Example 28 (28b), and by a method similar to that in Example 28 (28c), the title object compound was obtained as a reddish brown powder (216 mg, yield 46%).

$^1$H-NMR (CDCl$_3$, 400 MHz) δ: 1.73-1.83 (2H, m), 1.97-2.10 (3H, m), 2.71 (3H, s), 2.94-3.03 (2H, m), 3.47-3.58 (3H, m), 3.60-3.65 (2H, m), 3.73-3.78 (2H, m), 6.94-7.01 (4H, m), 7.03 (1H, d, J=1.5 Hz), 7.32 (1H, dd, J=7.8, 1.5 Hz), 7.83 (1H, d, J=7.8 Hz).

(30g) 4-acetyl-3-{4-[4-(2-hydroxyethoxy)piperidin-1-yl]phenoxy}benzamide

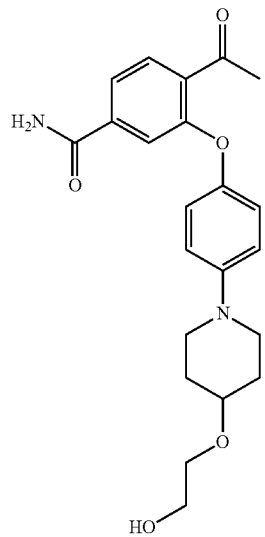 [SMILES: CC(=O)c1ccc(C(N)=O)cc1Oc1ccc(N2CCC(OCCO)CC2)cc1]

Using 4-acetyl-3-{4-[4-(2-hydroxyethoxy)piperidin-1-yl]phenoxy}benzonitrile (210 mg, 0.552 mmol) produced in Example 30 (30f), and by a method similar to that in Example 22 (22i), the title object compound was obtained as a yellow powder (158 mg, yield 72%).

$^1$H-NMR (CDCl$_3$, 400 MHz) δ: 1.70-1.84 (2H, m), 1.97-2.03 (2H, m), 2.88-3.02 (2H, m), 2.69 (3H, s), 2.88-3.00 (2H, m), 3.43-3.57 (3H, m), 3.62 (2H, t, J=4.4 Hz), 3.73-3.79 (2H, m), 6.92-7.00 (4H, m), 7.30 (1H, d, J=1.2 Hz), 7.42 (1H, dd, J=8.0, 1.2 Hz), 7.83 (1H, d, J=8.0 Hz).

MS (ESI) m/z: 399 (M+H)$^+$.

Example 31

4-(1,1-difluoroethyl)-3-{4-[4-(2-hydroxyethoxy)piperidin-1-yl]phenoxy}benzamide (31a) 4-(1,1-difluoroethyl)-3-fluorobenzonitrile

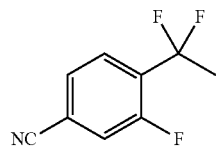

Using 4-acetyl-3-fluorobenzonitrile (500 mg, 29.7 mmol) produced in Example 28 (28b), and by the method used in Example 18 (18b), the title object compound was obtained as a white powder (525 mg, yield 93%).

$^1$H-NMR (CDCl$_3$, 400 MHz) δ: 2.01 (3H, t, J=18.6 Hz), 7.41-7.47 (1H, m), 7.50-7.55 (1H, m), 7.65-7.71 (1H, m).

(31b) 1-benzyloxy-4-iodobenzene

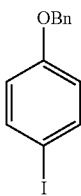

4-Iodophenol (5.00 g, 22.7 mmol) was dissolved in dimethylformamide (50 mL), pulverized sodium hydroxide (1.20 g, 30.0 mmol) and potassium carbonate (4.71 g, 34.1 mmol) and benzyl bromide (2.70 mL, 22.7 mmol) were added, and the mixture was stirred at room temperature for 2 hr. The reaction mixture was diluted with ethyl acetate and washed successively with water and saturated brine, and dried over anhydrous sodium sulfate. The solvent was evaporated under reduced pressure. The obtained residue was purified by silica gel column chromatography (hexane:ethyl acetate 20:1, V/V). The solvent of the object fraction was evaporated under reduced pressure to give the title object compound as a pale-yellow powder (6.43 g, yield 91%).

$^1$H-NMR (CDCl$_3$, 400 MHz) δ: 5.03 (2H, s), 6.72-6.77 (2H, m), 7.50-7.55 (5H, m), 7.51-7.58 (2H, m).

(31c) 1-(4-benzyloxyphenyl)piperidin-4-ol

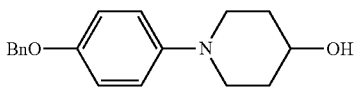

1-Benzyloxy-4-iodobenzene (3.46 g, 11.2 mmol) produced in Example 31 (31b) and piperidin-4-ol (1.35 g, 13.37 mmol) were dissolved in 1,4-dioxane (35 mL), (2-biphenyl)dicyclohexylphosphine (333 mg, 0.950 mmol), sodium tert-butoxide (1.61 g, 16.8 mmol) and palladium acetate (105 mg, 0.472 mmol) were added, and the mixture was stirred under a nitrogen atmosphere at 80° C. for 2 hr. The mixture was allowed to cool, and the reaction mixture was diluted with ethyl acetate and washed successively with water and saturated brine, and dried over anhydrous sodium sulfate. The solvent was evaporated under reduced pressure. The obtained residue was purified by silica gel column chromatography (hexane:ethyl acetate, 1:1, V/V). The solvent of the object fraction was evaporated under reduced pressure to give the title object compound as a yellow powder (1.23 g, yield 39%).

$^1$H-NMR (CDCl$_3$, 400 MHz) δ: 1.40-1.50 (1H, br), 1.66-1.77 (2H, m), 1.97-2.06 (2H, m), 2.77-2.86 (2H, m), 3.36-3.45 (2H, m), 3.76-3.86 (1H, m), 5.01 (2H, s), 6.88-6.91 (4H, m), 7.28-7.44 (5H, m).

(31d) 1-(4-benzyloxyphenyl)-4-[2-(tetrahydropyran-2-yloxy)ethoxy]piperidine

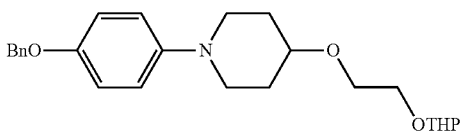

1-(4-Benzyloxyphenyl)piperidin-4-ol (713 mg, 2.52 mmol) produced in Example 31 (31c) was dissolved in dimethylformamide (15 mL) and, under ice-cooling, sodium hydride (P=60%) (150 mg, 3.8 mmol) was added and the mixture was stirred at room temperature for 30 min. 2-(2-Bromoethoxy)tetrahydropyran (790 mg, 3.78 mmol) was added, and the mixture was stirred at room temperature for 17 hr. To the reaction mixture was added ethyl acetate, and the mixture was washed successively with water and saturated brine, and dried over anhydrous sodium sulfate. The solvent was evaporated under reduced pressure. The obtained residue was purified by silica gel column chromatography (hexane:ethyl acetate, 2:1, V/V). The solvent of the object fraction was evaporated under reduced pressure to give the title object compound as a yellowish brown powder (264 mg, 25%).

$^1$H-NMR (CDCl$_3$, 400 MHz) δ: 1.47-1.65 (4H, m), 1.68-1.90 (4H, m), 1.97-2.06 (2H, m), 2.76-2.86 (2H, m), 3.37-3.43 (2H, m), 3.45-3.55 (2H, m), 3.65-3.71 (2H, m), 3.83-3.93 (2H, m), 4.61-4.67 (1H, m), 5.01 (2H, s), 6.87-6.90 (4H, m), 7.28-7.44 (5H, m).

(31e) 4-{4-[2-(tetrahydropyran-2-yloxy)ethoxy]piperidin-1-yl}phenol

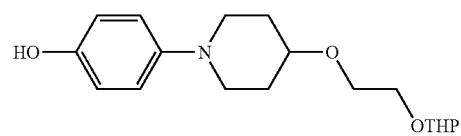

Using 1-(4-benzyloxyphenyl)-4-[2-(tetrahydropyran-2-yloxy)ethoxy]piperidine (264 mg, 0.642 mmol) produced in Example 31 (31d), and by the method used in Example 14 (14b), the title object compound was obtained as a colorless oil (212 mg, yield 100%).

(31f) 4-(1,1-difluoroethyl)-3-(4-{4-[2-(tetrahydropyran-2-yloxy)ethoxy]piperidin-1-yl}phenoxy)benzonitrile

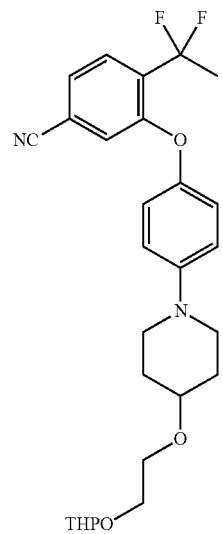

Using 4-{4-[2-(tetrahydropyran-2-yloxy)ethoxy]piperidin-1-yl}phenol (212 mg, 0.642 mmol) produced in Example 31 (31e) and 4-(1,1-difluoroethyl)-3-fluorobenzonitrile (120 mg, 0.642 mmol) produced in Example 31 (31a), and by the method used in Example 28 (28c), the title object compound was obtained as a yellow oil (76 mg, yield 24%).

¹H-NMR (CDCl₃, 400 MHz) δ: 1.47-1.65 (4H, m), 1.68-1.90 (2H, m), 1.97-2.10 (2H, m), 2.09 (3H, t, J=18.8 Hz), 2.90-3.00 (2H, m), 3.47-3.72 (6H, m), 3.83-3.94 (2H, m), 4.61-4.67 (4H, m), 5.01 (2H, s), 6.90-6.99 (4H, m), 6.99-7.03 (1H, m), 7.33 (1H, dd, J=8.0, 1.8 Hz), 7.67 (1H, d, J=8.0 Hz).

(31g) 4-(1,1-difluoroethyl)-3-{4-[4-(2-hydroxyethoxy)piperidin-1-yl]phenoxy}benzamide

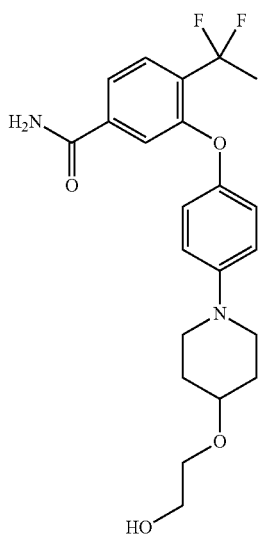 [SMILES: CC(F)(F)c1ccc(C(N)=O)cc1Oc1ccc(N2CCC(OCCO)CC2)cc1]

Using 4-(1,1-difluoroethyl)-3-(4-{4-[2-(tetrahydropyran-2-yloxy)ethoxy]piperidin-1-yl}phenoxy)benzonitrile (70 mg, 0.14 mmol) produced in Example 31 (31f), and by a method similar to that in Example 22 (22i) and Example 4 (4e), the title object compound was obtained as a white powder (33 mg, yield 55%).

¹H-NMR (CDCl₃, 400 MHz) δ: 1.70-1.82 (2H, m), 1.99-2.07 (3H, m), 2.69 (3H, t, J=18.8 Hz), 2.88-2.98 (2H, m), 3.42-3.56 (3H, m), 3.62 (2H, t, J=4.4 Hz), 3.73-3.79 (2H, m), 6.91-6.94 (4H, m), 7.24-7.28 (1H, br), 7.41-7.47 (1H, m), 7.66 (1H, d, J=8.0 Hz).

MS (ESI) m/z: 421 (M+H)⁺.

Example 32

4-acetyl-3-{4-[2-(tetrahydropyran-4-yloxy)ethoxy]phenoxy}benzamide (32a) 4-[2-(4-benzyloxyphenoxy)ethoxy]tetrahydropyran

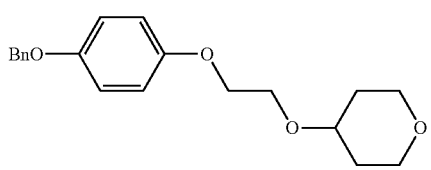 [SMILES: c1ccc(COc2ccc(OCCOC3CCOCC3)cc2)cc1]

Using 4-benzyloxyphenol (2.0 g, 10 mmol) and 2-(tetrahydropyran-4-yloxy)ethanol (1.46 g, 9.99 mmol) produced in Reference Example 4 (4b), and by the method used in Example 20 (20c), the title object compound was obtained as a pale yellow oil (2.86 g, yield 87%).

¹H-NMR (CDCl₃, 400 MHz) δ: 1.57-1.68 (2H, m), 1.88-1.97 (2H, m), 3.41-3.49 (2H, m), 3.54-3.63 (1H, m), 3.80 (2H, t, J=5.1 Hz), 3.91-3.99 (2H, m), 4.07 (2H, t, J=5.1 Hz), 5.00 (2H, s), 6.82-6.92 (4H, m), 7.28-7.43 (5H, m).

(32b) 4-[2-(tetrahydropyran-4-yloxy)ethoxy]phenol

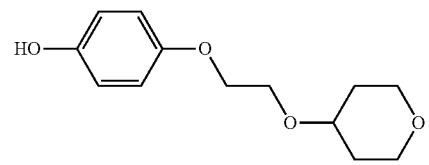

Using 4-[2-(4-benzyloxyphenoxy)ethoxy]tetrahydropyran (1.8 g, 5.5 mmol) produced in Example 32 (32a), and by the method used in Example 14 (14b), the title object compound was obtained as a pale-brown oil (1.11 g, yield 85%).

¹H-NMR (CDCl₃, 400 MHz) δ: 1.59-1.68 (2H, m), 1.89-1.97 (2H, m), 3.40-3.48 (2H, m), 3.55-3.64 (1H, m), 3.80 (2H, t, J=5.1 Hz), 3.92-3.99 (2H, m), 4.06 (2H, t, J=5.1 Hz), 4.68-4.73 (1H, br), 6.70-6.82 (4H, m).

(32c) methyl 4-bromo-3-fluorobenzoate

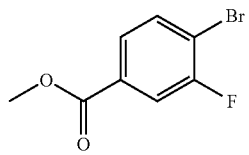

4-Bromo-3-fluorobenzoic acid (5.0 g, 23 mmol) was suspended in dimethylformamide (20 mL), potassium carbonate (6.30 g, 45.6 mmol) and methyl iodide (1.71 mL, 27.4 mmol) were added, and the mixture was stirred at room temperature for 2.5 hr. Ethyl acetate was added and the mixture was washed with water and saturated brine, and dried over anhydrous sodium sulfate. The solvent was evaporated under reduced pressure to give the title object compound as a pale-yellow powder (5.7 g, yield 100%).

¹H-NMR (CDCl₃, 400 MH) δ: 3.93 (3H, s), 7.60-7.80 (3H, m).

(32d) methyl 4-acetyl-3-fluorobenzoate

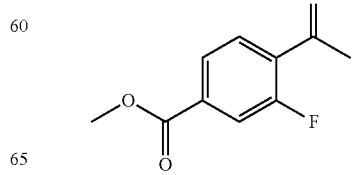

Cobalt (II) bromide (976 mg, 4.46 mmol) and zinc (4.96 g, 75.8 mmol) were suspended in acetonitrile (40 mL) and, under a nitrogen atmosphere, allyl chloride (1.10 mL, 13.4 mmol) and trifluoroacetic acid (0.205 mL, 2.68 mmol) were added, and the mixture was stirred for 10 min. A solution (60 mL) of methyl 4-bromo-3-fluorobenzoate (10.4 g, 44.6 mmol) produced in Example 32 (32c) and acetic anhydride (4.64 mL, 49.1 mmol) in acetonitrile was added, and the mixture was stirred at room temperature for 18 hr. To the reaction mixture was added 1.0 M hydrochloric acid (2.7 mL), and the mixture was extracted with ethyl acetate, washed with saturated aqueous sodium hydrogen carbonate and saturated brine, and dried over anhydrous sodium sulfate. The solvent was evaporated under reduced pressure, and the obtained residue was purified by silica gel column chromatography (hexane:ethyl acetate 10:1, V/V). The solvent of the object fraction was evaporated under reduced pressure to give the title object compound as a pale-yellow powder (1.78 g, yield 20%).

$^1$H-NMR (CDCl$_3$, 400 MH) δ: 2.68 (3H, d, J=4.6 Hz), 3.96 (3H, s), 7.77-7.95 (3H, m).

(32e) methyl 4-acetyl-3-{4-[2-(tetrahydropyran-4-yloxy)ethoxy]phenoxy}benzoate

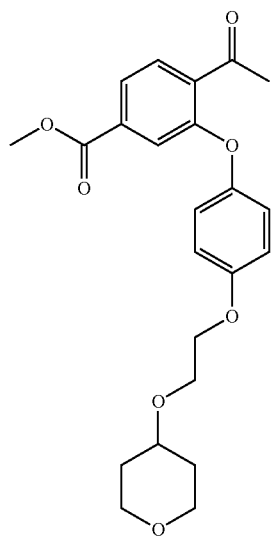 [SMILES: COC(=O)c1ccc(C(C)=O)c(Oc2ccc(OCCOC3CCOCC3)cc2)c1]

Using methyl 4-acetyl-3-fluorobenzoate (494 mg, 2.51 mmol) produced in Example 32 (32d) and 4-[2-(tetrahydropyran-4-yloxy)ethoxy]phenol (600 mg, 2.51 mmol) produced in Example 32 (32b), and by a method similar to that in Example 28 (28c), the title object compound was obtained as a pale-brown oil (326 mg, yield 35%).

$^1$H-NMR (CDCl$_3$, 400 MHz) δ: 1.60-1.70 (2H, m), 1.90-2.00 (2H, m), 2.69 (3H, s), 3.41-3.50 (2H, m), 3.57-3.65 (1H, m), 3.83-3.87 (5H, m), 3.93-4.00 (2H, m), 4.11-4.18 (2H, m), 6.93-7.00 (4H, m), 7.45 (1H, d, J=1.5 Hz), 7.73 (1H, dd, J=8.4, 1.5 Hz), 7.81 (1H, d, J=8.4 Hz).

(32f) 4-acetyl-3-{4-[2-(tetrahydropyran-4-yloxy)ethoxy]phenoxy}benzamide

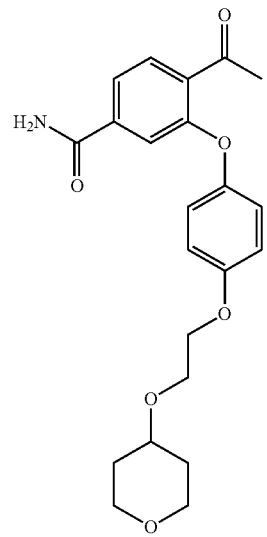 [SMILES: CC(=O)c1ccc(C(N)=O)cc1Oc1ccc(OCCOC2CCOCC2)cc1]

Using methyl 4-acetyl-3-{4-[2-(tetrahydropyran-4-yloxy)ethoxy]phenoxy}benzoate (360 mg, 0.869 mmol) produced in Example 32 (32e), and by a method similar to that in Example 6 (6e), the title object compound was obtained as a white powder (257 mg, yield 74%).

$^1$H-NMR (CDCl$_3$, 400 MHz) δ: 1.61-1.70 (2H, m), 1.90-2.00 (2H, m), 2.70 (3H, s), 3.42-3.51 (2H, m), 3.57-3.67 (1H, m), 3.82-3.88 (2H, m), 3.92-3.89 (2H, m), 4.11-4.18 (2H, m), 5.50-5.80 (1H, br), 5.90-6.13 (1H, br), 6.93-7.02 (4H, m), 7.27-7.30 (1H, m), 7.41-7.46 (1H, m), 7.82-7.86 (1H, m).

MS (ESI) m/z: 400 (M+H)$^+$.

Example 33

4-acetyl-3-{4-[2-(2-isopropoxyethoxy)ethoxy]phenoxy}benzamide

(33a) 2-[2-(2-chloroethoxy)ethoxy]propane

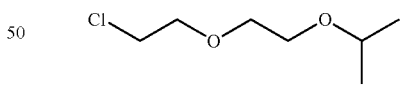

2-(2-Chloroethoxy)ethanol (68.5 g, 0.550 mol) was dissolved in methylene chloride (600 mL) and, under ice-cooling, triethylamine (115 mL, 0.825 mol) and methanesulfonyl chloride (46.8 mL, 0.605 mol) were added dropwise, and the mixture was stirred at the same temperature for 1 hr. The reaction mixture was washed successively with water and saturated brine, and dried over anhydrous sodium sulfate, and the solvent was evaporated under reduced pressure to give an oil.

Under a nitrogen atmosphere, to anhydrous isopropanol (132 g, 2.20 mol) was separately added sodium (12.6 g, 0.550 mol), and the mixture was heated under reflux for 3 hr. The oil obtained earlier was added dropwise, and the mixture was heated under reflux for 15 hr. The mixture was allowed to cool, 10% citric acid water was added and the mixture was extracted twice with ethyl acetate. The organic layer was washed successively with water and saturated brine, and dried over anhydrous sodium sulfate. The solvent was evaporated under reduced pressure. The obtained residue was distilled (20 mmHg) and a fraction of 62° C. to 73° C. was purified by silica gel column chromatography (hexane:ethyl acetate 10:1, V/V). The solvent of the object fraction was evaporated under reduced pressure to give the title object compound as a colorless oil (20.9 g, yield 23%).

$^1$H-NMR (DMSO-d$_5$, 400 MHz) δ: 1.17 (6H, d, J=6.1 Hz), 3.57-3.67 (7H, m), 3.75-3.80 (2H, m).

(33b) 4-benzyloxy-[2-(3-isopropoxyethoxy)ethoxy] benzene

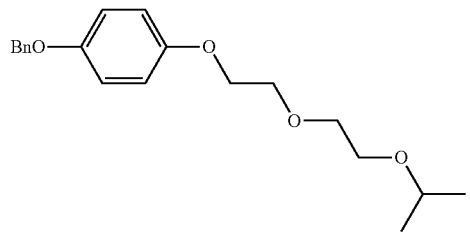 [SMILES: CC(C)OCCOCCOc1ccc(OCc2ccccc2)cc1]

4-Benzyloxyphenol (3.85 g, 19.2 mol) was dissolved in dimethylformamide (80 mL), 2-[2-(2-chloroethoxy)ethoxy]propane (2.74 g, 16.4 mmol) produced in Example 33 (33a) and potassium carbonate (4.53 g, 32.8 mmol) were added, and the mixture was stirred at 80° C. for 12 hr. Water was added to the reaction mixture and the mixture was extracted twice with ethyl acetate. The organic layer was washed successively with water and saturated brine, and dried over anhydrous sodium sulfate. The solvent was evaporated under reduced pressure. The obtained residue was purified by silica gel column chromatography (hexane:ethyl acetate 8:1, V/V). The solvent of the object fraction was evaporated under reduced pressure to give the title object compound as a colorless oil (1.95 g, yield 36%).

$^1$H-NMR (CDCl$_3$, 400 MHz) δ: 1.16 (6H, d, J=6.1 Hz), 3.56-3.63 (3H, m), 3.66-3.71 (2H, m), 3.80-3.86 (2H, m), 4.05-4.10 (2H, m), 5.00 (2H, s), 6.81-6.92 (4H, m), 7.27-7.45 (5H, m).

(33c) 4-[2-(2-isopropoxyethoxy)ethoxy]phenol

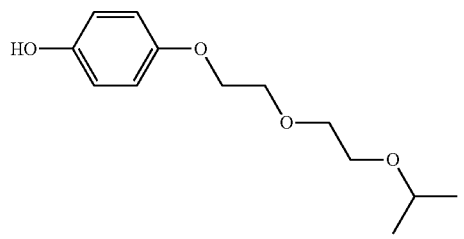 [SMILES: CC(C)OCCOCCOc1ccc(O)cc1]

Using 4-benzyloxy-[2-(3-isopropoxyethoxy)ethoxy]benzene (1.95 g, 5.90 mmol) produced in Example 33 (33b), and by the method used in Example 14 (14b), the title object compound was obtained as a brown oil (1.36 g, yield 96%).

$^1$H-NMR (CDCl$_3$, 400 MHz) δ: 1.17 (6H, d, J=6.1 Hz), 3.59-3.65 (3H, m), 3.67-3.72 (2H, m), 3.79-3.85 (2H, m), 4.00-4.06 (2H, m), 6.70-6.80 (4H, m).

(33d) 4-acetyl-3-{4-[2-(2-isopropoxyethoxy)ethoxy]phenoxy}benzonitrile

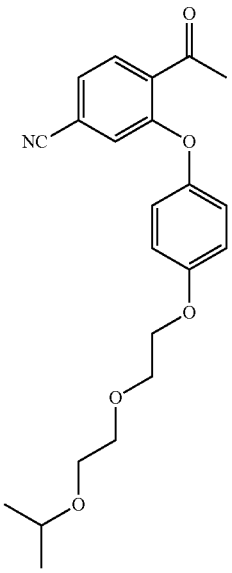 [SMILES: CC(=O)c1ccc(C#N)cc1Oc1ccc(OCCOCCOC(C)C)cc1]

Using 4-[2-(2-isopropoxyethoxy)ethoxy]phenol (1.36 g, 5.66 mol) produced in Example 33 (33c) and 4-acetyl-3-fluorobenzonitrile (1.02 g, 6.23 mmol) produced in Example 28 (28b), and by a method similar to that in Example 28 (28c), the title object compound was obtained as an orange oil (1.83 g, yield 84%).

$^1$H-NMR (CDCl$_3$, 400 MHz) δ: 1.17 (6H, d, J=6.1 Hz), 2.70 (3H, s), 3.58-3.66 (3H, m), 3.69-3.75 (2H, m), 3.86-3.93 (2H, m), 4.13-4.19 (2H, m), 6.98 (4H, m), 7.01 (1H, s), 7.34 (1H, dd, J=7.8, 1.2 Hz), 7.83 (1H, d, J=7.8 Hz).

(33e) 4-acetyl-3-{4-[2-(2-isopropoxyethoxy)ethoxy]phenoxy}benzamide

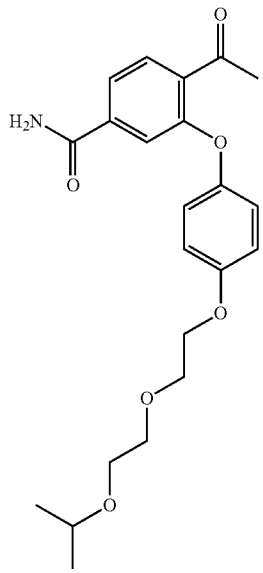

Using 4-acetyl-3-{4-[2-(2-isopropoxyethoxy)ethoxy]phenoxy}benzonitrile (1.83 g, 4.77 mmol) produced in Example 33 (33d), and by a method similar to that in Example 22 (22i), the title object compound was obtained as a white powder (1.53 g, yield 80%).

$^1$H-NMR (DMSO-d$_6$, 400 MHz) δ: 1.06 (6H, d, J=6.1 Hz), 2.58 (3H, s), 3.45-3.60 (5H, m), 3.70-3.78 (2H, m), 4.05-4.13 (2H, m), 6.96-7.10 (4H, m), 7.28 (1H, d, J=1.5 Hz), 7.45-7.55 (1H, br), 7.62 (1H, dd, J=8.0, 1.5 Hz), 7.71 (1H, d, J=8.0 Hz), 8.00-8.10 (1H, br).

MS (ESI) m/z: 400 (M–H)$^-$.

Example 34

4-acetyl-3-{4-[3-(tetrahydropyran-4-yloxy)propenyl]phenoxy}benzamide (35a) 4-iodophenyl acetate

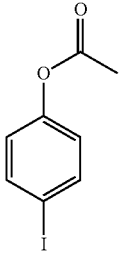

4-Iodophenol (3.00 g, 13.6 mmol) was dissolved in pyridine (15 mL) and, under ice-cooling, acetic anhydride (1.42 mL, 15.0 mmol) was added, and the mixture was stirred at room temperature for 30 min. To the reaction mixture was added ethyl acetate, and the mixture was washed successively with water, 10% citric acid water and saturated brine, and dried over anhydrous sodium sulfate. The solvent was evaporated under reduced pressure. The obtained residue was purified by silica gel column chromatography (hexane:ethyl acetate, 5:1, V/V), and the solvent of the object fraction was evaporated under reduced pressure to give the title object compound as a colorless oil (3.56 g, yield 100%).

$^1$H-NMR (CDCl$_3$, 400 MHz) δ: 2.29 (3H, s), 6.83-6.88 (2H, m), 7.65-7.70 (2H, m).

(34b) 4-allyloxytetrahydropyran

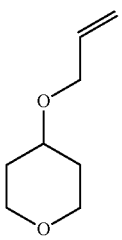

Tetrahydropyran-4-ol (2.00 g, 19.6 mmol) was dissolved in dimethylformamide (40 mL), sodium hydride (P=60%) (940 mg, 23.5 mmol) was separately added at room temperature, and the mixture was stirred at the same temperature for 30 min. Allyl bromide (1.66 mL, 19.6 mmol) was added and the mixture was stirred at room temperature for 3 hr. To the reaction mixture was added ethyl acetate, and the mixture was washed successively with water and saturated brine, and dried over anhydrous sodium sulfate. The solvent was evaporated under reduced pressure. The obtained residue was purified by silica gel column chromatography (hexane:ethyl acetate, 5:1, V/V), and the solvent of the object fraction was evaporated under reduced pressure to give the title object compound as a colorless oil (1.26 g, yield 45%).

$^1$H-NMR (CDCl$_3$, 400 MHz) δ: 1.56-1.66 (2H, m), 1.85-1.95 (2H, m), 3.39-3.48 (2H, m), 3.49-3.57 (1H, m), 3.91-3.99 (2H, m), 4.00-4.06 (2H, m), 5.14-5.21 (1H, m), 5.25-5.33 (1H, m), 5.87-5.99 (1H, m).

(34c) 4-[3-(tetrahydropyran-4-yloxy)propenyl]phenyl acetate

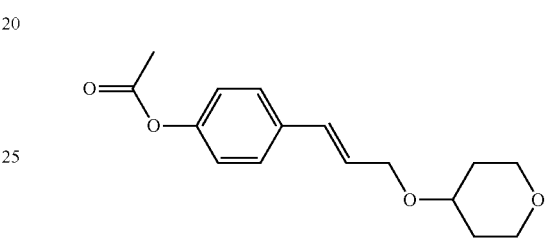

4-Iodophenyl acetate (1.92 g, 7.33 mmol) produced in Example 34 (34a) and 4-allyloxytetrahydropyran (1.04 g, 7.31 mmol) produced in Example 34 (34b) were dissolved in dimethylformamide (30 mL), palladium acetate (247 mg, 1.10 mmol), triphenylphosphine (577 mg, 2.20 mmol) and silver acetate (3.67 g, 22.0 mmol) were added, and the mixture was stirred under a nitrogen atmosphere at 70° C. for 23 hr. The mixture was allowed to cool, and the reaction mixture was diluted with ethyl acetate, and filtered through celite. The filtrate was washed successively with water and saturated brine, and dried over anhydrous sodium sulfate. The solvent was evaporated under reduced pressure, and the obtained residue was purified by silica gel column chromatography (hexane:ethyl acetate, 5:1, V/V). The solvent of the object fraction was evaporated under reduced pressure to give the title object compound as a white powder (0.46 g, yield 23%).

$^1$H-NMR (CDCl$_3$, 400 MHz) δ: 1.58-1.68 (2H, m), 1.88-1.98 (2H, m), 2.29 (3H, s), 3.40-3.49 (2H, m), 3.54-3.63 (1H, m), 3.92-4.00 (2H, m), 4.16-4.21 (2H, m), 6.25 (1H, dt, J=15.9, 5.8 Hz), 6.59 (1H, d, J=15.9 Hz), 7.01-7.07 (2H, m), 7.35-7.42 (2H, m).

(34d) 4-[3-(tetrahydropyran-4-yloxy)propenyl]phenol

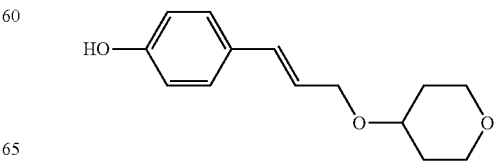

4-[3-(Tetrahydropyran-4-yloxy)propenyl]phenyl acetate (0.46 g, 1.7 mmol) produced in Example 34 (34c) was dissolved in methanol (15 mL), 1.0 M aqueous lithium hydroxide (5.0 mL, 5.0 mmol) was added, and the mixture was stirred at room temperature for 30 min. Methanol was evaporated under reduced pressure, the residue was acidified with 6.0 M hydrochloric acid, and extracted with ethyl acetate. The organic layer was washed successively with water and saturated brine, and dried over anhydrous sodium sulfate. The solvent was evaporated under reduced pressure. The obtained residue was purified by silica gel column chromatography (hexane:ethyl acetate, 5:1, V/V), and the solvent of the object fraction was evaporated under reduced pressure to give the title object compound as a white powder (0.29 g, yield 74%).

$^1$H-NMR (CDCl$_3$, 400 MHz) δ: 1.60-1.70 (2H, m), 1.90-1.98 (2H, m), 3.42-3.51 (2H, m), 3.57-3.65 (1H, m), 3.95-4.02 (2H, m), 4.15-4.19 (2H, m), 6.14 (1H, dt, J=15.6, 6.3 Hz), 6.53 (1H, d, J=15.6 Hz), 6.74-6.79 (2H, m), 7.23-7.28 (2H, m).

(34e) 4-acetyl-3-{4-[3-(tetrahydropyran-4-yloxy)propenyl]phenoxy}benzonitrile

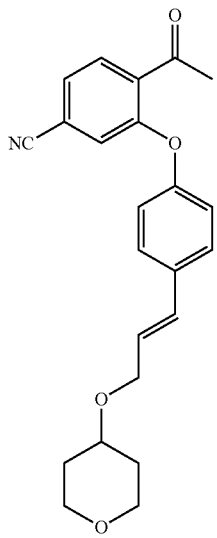 [SMILES: CC(=O)c1ccc(C#N)cc1Oc1ccc(/C=C/COC2CCOCC2)cc1]

Using 4-[3-(tetrahydropyran-4-yloxy)propenyl]phenol (0.29 g, 1.1 mmol) produced in Example 34 (34d) and 4-acetyl-3-fluorobenzonitrile (206 mg, 1.05 mmol) produced in Example 28 (28b), and by the method used in Example 28 (28c), the title object compound was obtained as a yellow oil (396 mg, yield 100%).

$^1$H-NMR (CDCl$_3$, 400 MHz) δ: 1.60-1.71 (2H, m), 1.90-1.99 (2H, m), 2.68 (3H, s), 3.42-3.50 (2H, m), 3.56-3.65 (1H, m), 3.94-4.02 (2H, m), 4.19-4.24 (2H, m), 6.29 (1H, dt, J=15.9, 5.8 Hz), 6.63 (1H, d, J=15.9 Hz), 6.97-7.03 (2H, m), 7.11 (1H, d, J=1.4 Hz), 7.41 (1H, dd, J=8.0, 1.4 Hz), 7.43-7.48 (2H, m), 7.86 (1H, d, J=8.0 Hz).

(34f) 4-acetyl-3-{4-[3-(tetrahydropyran-4-yloxy)propenyl]phenoxy}benzamide

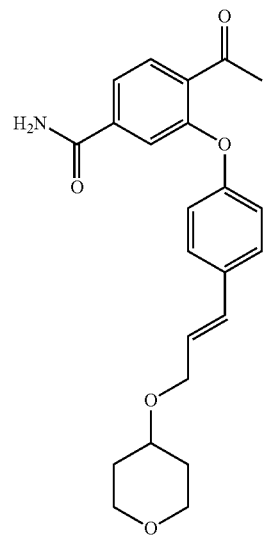 [SMILES: CC(=O)c1ccc(C(N)=O)cc1Oc1ccc(/C=C/COC2CCOCC2)cc1]

Using 4-acetyl-3-{4-[3-(tetrahydropyran-4-yloxy)propenyl]phenoxy}benzonitrile (390 mg, 1.03 mmol) produced in Example 34 (34e), and by the method used in Example 22 (22i), the title object compound was obtained as a white powder (300 mg, yield 73%).

$^1$H-NMR (CDCl$_3$, 400 MHz) δ: 1.62-1.71 (2H, m), 1.90-1.99 (2H, m), 2.66 (3H, s), 3.42-3.51 (2H, m), 3.56-3.65 (1H, m), 3.94-4.02 (2H, m), 4.18-4.23 (2H, m), 5.60-6.20 (2H, br), 6.25 (1H, dt, J=16.1, 5.8 Hz), 6.63 (1H, d, J=16.1 Hz), 6.95-7.01 (2H, m), 7.38 (1H, d, J=1.5 Hz), 7.38-7.43 (2H, m), 7.49 (1H, dd, J=8.0, 1.5 Hz), 7.87 (1H, d, J=8.0 Hz).

MS (ESI) m/z: 394 (M−H)$^−$.

Example 35

4-difluoromethyl-3-{4-[2-(tetrahydropyran-4-yloxy)ethoxy]phenoxy}benzamide

(35a) 3-fluoro-4-formylbenzonitrile

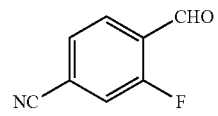 [SMILES: N#Cc1ccc(C=O)c(F)c1]

4-Bromo-2-fluorobenzaldehyde (3.00 g, 14.8 mmol) was dissolved in dimethylformamide (12 mL), copper cyanide (1.45 g, 16.2 mmol) was added, and the mixture was stirred under a nitrogen atmosphere at 150° C. for 18 hr. The mixture was allowed to cool, to the reaction mixture were added a solution (12 mL) of iron chloride (III) (2.64 g) in 2.0 M hydrochloric acid and water (30 mL), and the mixture was stirred at room temperature for 1 hr. The precipitate was collected by filtration, dissolved in ethyl acetate/tetrahydrofuran (2:1) (60 mL), washed with saturated brine, and dried over anhydrous sodium sulfate. The solvent was evaporated under reduced pressure to give the title object compound as a brown powder (1.54 g, yield 70%).

$^1$H-NMR (CDCl$_3$, 400 MHz) δ: 7.53 (1H, dd, J=9.5, 1.0 Hz), 7.57-7.61 (1H, m), 8.00 (1H, dd, J=8.1, 6.8 Hz), 10.40 (1H, s).

(35b) 4-difluoromethyl-3-fluorobenzonitrile

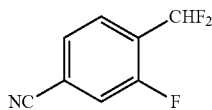 [SMILES: N#Cc1ccc(C(F)F)c(F)c1]

3-Fluoro-4-formylbenzonitrile (1.53 g, 10.3 mmol) produced in Example 35 (35a) was dissolved in methylene chloride (20 mL) and, under ice-cooling, a solution (6 mL) of N,N-diethylsulfur trifluoride (1.82 g, 11.3 mmol) in methylene chloride was added dropwise, and the mixture was stirred at room temperature for 21 hr. To the reaction mixture was added saturated aqueous sodium hydrogen carbonate to adjust the pH to 8-9 and, after partitioning, the organic layer was dried over anhydrous sodium sulfate. The solvent was evaporated under reduced pressure. The obtained residue was purified by silica gel column chromatography (hexane:ethyl acetate, 1:0→7:3, V/V), and the solvent of the object fraction was evaporated under reduced pressure to give the title object compound as a pale-yellow powder (1.40 g, yield 80%).

$^1$H-NMR (CDCl$_3$, 400 MHz) δ: 6.91 (1H, t, J=54.4 Hz), 7.46 (1H, dd, J=9.3, 1.2 Hz), 7.58 (1H, d, J=8.0 Hz), 7.72-7.77 (1H, m).

(35c) 4-difluoromethyl-3-{4-[2-(tetrahydropyran-4-yloxy)ethoxy]phenoxy}benzonitrile

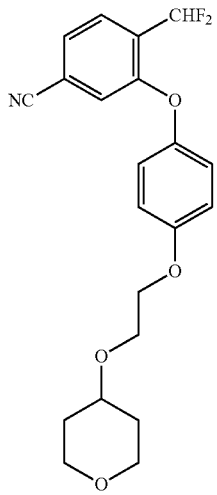 [SMILES: N#Cc1ccc(C(F)F)c(Oc2ccc(OCCOC3CCOCC3)cc2)c1]

Using 4-[2-(tetrahydropyran-4-yloxy)ethoxy]phenol (835 mg, 3.51 mmol) produced in Example 32 (32b) and 4-difluoromethyl-3-fluorobenzonitrile (600 mg, 3.51 mmol) produced in Example 35 (35b), and by the method used in Example 28 (28c), the title object compound was obtained as a white powder (1.2 g, yield 88%).

$^1$H-NMR (CDCl$_3$, 400 MHz) δ: 1.58-2.04 (2H, m), 1.92-1.99 (2H, m), 3.42-3.49 (2H, m), 3.57-3.64 (1H, m), 3.83-3.87 (2H, m), 3.93-4.00 (2H, m), 4.10-4.17 (2H, m), 6.92-7.22 (6H, m), 7.38-7.42 (1H, m), 7.72-7.76 (1H, m).

(35d) 4-difluoromethyl-3-{4-[2-(tetrahydropyran-4-yloxy)ethoxy]phenoxy}benzamide

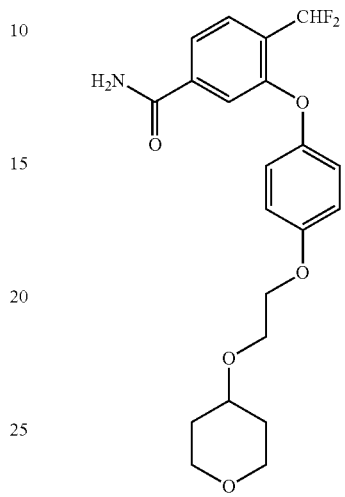

Using 4-difluoromethyl-3-{4-[2-(tetrahydropyran-4-yloxy)ethoxy]phenoxy}benzonitrile (1.18 g, 3.28 mmol) produced in Example 35 (35c), and by the method used in Example 22 (22i), the title object compound was obtained as a white powder (1.06 g, yield 86%).

$^1$H-NMR (DMSO-d$_6$, 400 MHz) δ: 1.34-1.45 (2H, m), 1.81-1.90 (2H, m), 2.99-3.36 (2H, m), 3.52-3.60 (1H, m), 3.72-3.84 (4H, m), 4.07-4.13 (2H, m), 6.98-7.07 (4H, m), 7.11-7.41 (2H, m), 7.48-7.56 (1H, br), 7.64-7.72 (2H, m), 8.03-8.12 (1H, br).

MS (ESI) m/z m 408 (M+H)$^+$.

Example 36

1-(3-{4-[2-(tetrahydropyran-4-yloxy)ethoxy]phenoxy}-4-trifluoromethylphenyl)ethanone (36a) 3-fluoro-N-methoxy-N-methyl-4-trifluoromethylbenzamide

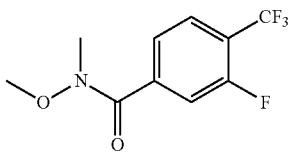 [SMILES: CON(C)C(=O)c1ccc(C(F)(F)F)c(F)c1]

Using 3-fluoro-4-trifluoromethylbenzoic acid (3.00 g, 14.4 mmol), and by a method similar to that in Example 28 (28a), the title object compound was obtained as a colorless oil (3.51 g, 97%).

$^1$H-NMR (CDCl$_3$, 400 MHz) δ: 3.38 (3H, s), 3.55 (3H, s), 7.50-7.59 (2H, m), 7.63-7.68 (1H, m).

(36b) 1-(3-fluoro-4-trifluoromethylphenyl)ethanone

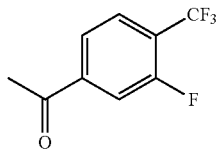

Using 3-fluoro-N-methoxy-N-methyl-4-trifluoromethyl-benzamide (3.50 g, 13.9 mmol) produced in Example 36 (36a), and by a method similar to that in Example 28 (28b), the title object compound was obtained as a colorless oil (3.05 g, 100%).

$^1$H-NMR (CDCl$_3$, 400 MHz) δ: 2.64 (3H, s), 7.70-7.78 (2H, m), 7.79-7.83 (1H, m).

(36c) 1-(3-{4-[2-(tetrahydropyran-4-yloxy)ethoxy]phenoxy}-4-trifluoromethylphenyl)ethanone

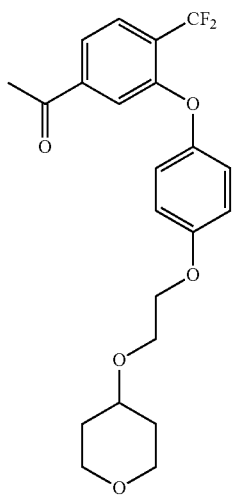

Using 1-(3-fluoro-4-trifluoromethylphenyl)ethanone (606 mg, 2.94 mmol) produced in Example 36 (36b) and 4-[2-(tetrahydropyran-4-yloxy)ethoxy]phenol (500 mg, 2.10 mmol) produced in Example 32 (32b), and by the method used in Example 28 (28c), the title object compound was obtained as a pale yellow oil (162 mg, yield 18%).

$^1$H-NMR (DMSO-d$_6$, 400 MHz) δ: 1.36-1.47 (2H, m), 1.83-1.90 (2H, m), 2.55 (3H, s), 3.29-3.37 (2H, m), 3.52-3.60 (1H, m), 3.75-3.84 (4H, m), 4.09-4.13 (2H, m), 7.01-7.09 (4H, m), 7.27 (1H, s), 7.83 (1H, d, J=8.3 Hz), 7.93 (1H, d, J=8.3 Hz).

MS (ESI) m/z: 425 (M+H)$^+$.

Example 37

4-acetyl-2-{4-[2-(tetrahydropyran-4-yloxy)ethoxy]phenoxy}benzonitrile

(37a) 4-bromo-3-fluoro-N-methoxy-N-methylbenzamide

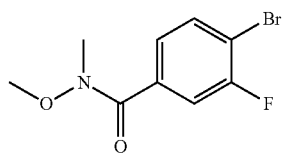

Using 4-bromo-3-fluorobenzoic acid (3.00 g, 13.7 mmol), and by the method used in Example 28 (28a), the title object compound was obtained as a pale-brown oil (3.59 g, yield 100%).

$^1$H-NMR (CDCl$_3$, 400 MHz) δ: 3.36 (3H, s), 3.54 (3H, s), 7.40 (1H, dd, J=8.2, 1.9 Hz), 7.49 (1H, dd, J=9.0, 1.9 Hz), 7.59 (1H, dd, J=8.2, 6.8 Hz).

(37b) 1-(4-bromo-3-fluorophenyl)ethanone

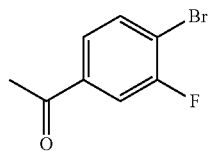

Using 4-bromo-3-fluoro-N-methoxy-N-methylbenzamide (3.59 g, 13.7 mmol) produced in Example 37 (37a), and by a method similar to that in Example 28 (28b), the title object compound was obtained as a yellow oil (2.49 g, yield 84%).

$^1$H-NMR (CDCl$_3$, 400 MHz) δ: 2.59 (3H, s), 7.60 (1H, dd, J=8.2, 1.9 Hz), 7.64-7.73 (2H, m).

(37c) 4-acetyl-2-fluorobenzonitrile

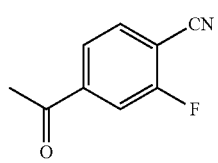

Using 1-(4-bromo-3-fluorophenyl)ethanone (2.49 g, 11.5 mmol) produced in Example 37 (37b), and by the method used in Example 29 (29c), the title object compound was obtained as a pale-yellow powder (1.59 g, yield 85%).

$^1$H-NMR (CDCl$_3$, 400 MHz) δ: 2.64 (3H, s), 7.73-7.80 (2H, m), 7.82 (1H, dd, J=7.8, 1.4 Hz).

(37d) 4-acetyl-2-{4-[2-(tetrahydropyran-4-yloxy)ethoxy]phenoxy}benzonitrile

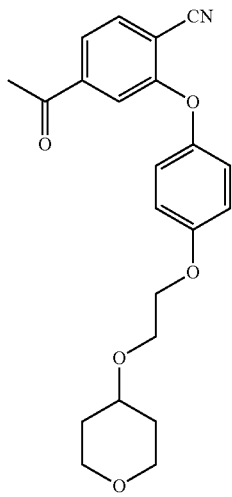 [SMILES: CC(=O)c1ccc(C#N)c(Oc2ccc(OCCOC3CCOCC3)cc2)c1]

Using 4-acetyl-2-fluorobenzonitrile (548 mg, 3.36 mmol) produced in Example 37 (37c) and 4-[2-(tetrahydropyran-4-yloxy)ethoxy]phenol (800 mg, 3.36 mmol) produced in Example 32 (32b), and by the method used in Example 28 (28c), the title object compound was obtained as a pale yellow oil (710 mg, yield 55%).

$^1$H-NMR (DMSO-$d_6$, 400 MHz) δ: 1.36-1.47 (2H, m), 1.82-1.91 (2H, m), 2.54 (3H, s), 3.28-3.38 (2H, m), 3.52-3.61 (1H, m), 3.74-3.84 (4H, m), 4.09-4.16 (2H, m), 7.02-7.09 (2H, m), 7.12-7.20 (3H, m), 7.77-7.83 (1H, m), 8.06 (1H, d, J=8.0 Hz).

MS (ESI) m/z: 382 (M+H)$^+$.

Example 38

4-(1-hydroxyethyl)-3-{4-[2-(tetrahydropyran-4-yloxy)ethoxy]phenoxy}benzamide

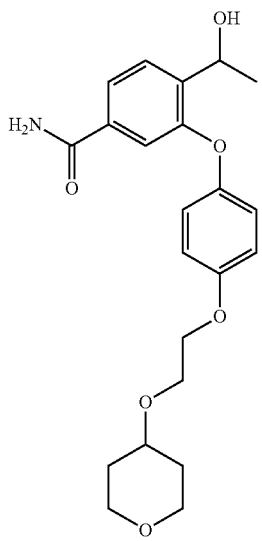

4-Acetyl-3-{4-[2-(tetrahydropyran-4-yloxy)ethoxy]phenoxy}benzamide (50 mg, 0.13 mmol) produced in Example 32 (32f) was dissolved in methanol (1 mL), sodium borohydride (6 mg, 0.2 mmol) was added, and the mixture was stirred at room temperature for 30 min. Water was added to the reaction mixture and the mixture was extracted twice with ethyl acetate. The organic layers were combined, washed with saturated brine, and dried over anhydrous sodium sulfate. The solvent was evaporated under reduced pressure. The obtained residue was purified by silica gel column chromatography (chloroform:methanol, 100:0→94:6, V/V), and the solvent of the object fraction was evaporated under reduced pressure. The obtained residue was powderized with tert-butyl methyl ether and collected by filtration. The obtained powder was dissolved with heating in ethyl acetate:tert-butyl methyl ether (3:1) (4 mL). The solution was stirred at room temperature for 30 min, and the precipitate was collected by filtration to give the title object compound as a white powder (30 mg, yield 60%).

$^1$H-NMR (DMSO-$d_6$, 400 MHz) δ: 1.32 (3H, d, J=6.4 Hz), 1.35-1.46 (2H, m), 1.81-1.90 (2H, m), 3.31-3.37 (2H, m), 3.51-3.60 (1H, m), 3.72-3.85 (4H, m), 4.03-4.11 (2H, m), 5.01-5.10 (1H, m), 5.25 (1H, d, J=4.4 Hz), 6.90-7.01 (4H, m), 7.16-7.21 (1H, m), 7.27-7.35 (1H, br), 7.57-7.64 (2H, m), 7.87-7.94 (1H, br).

MS (ESI) m/z: 402 (M+H)$^+$.

Example 39

4-(1-fluoroethyl)-3-{4-[2-(tetrahydropyran-4-yloxy)ethoxy]phenoxy}benzamide

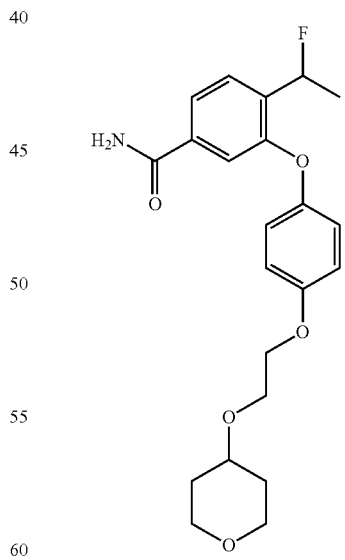

4-(1-hydroxyethyl)-3-{4-[2-(tetrahydropyran-4-yloxy)ethoxy]phenoxy}benzamide (900 mg, 2.25 mmol) produced in Example 38 was dissolved in chloroform (1 mL) and, under ice-cooling, N,N-diethylaminosulfur trifluoride (0.89 mL, 6.75 mmol) was added, and the mixture was stirred at

143 the same temperature for 30 min. The reaction mixture was washed with saturated aqueous sodium hydrogen carbonate, and dried over anhydrous sodium sulfate. The solvent was evaporated under reduced pressure, and the residue was purified by silica gel column chromatography (hexane:ethyl acetate, 1:3→0:1, V/V). The solvent of the object fraction was evaporated under reduced pressure to give the title object compound (610 mg, yield 67%).

The obtained powder (610 mg) was dissolved with heating in tert-butyl methyl ether (3 mL) and ethyl acetate (1 mL), and the mixture was stirred for 30 min while allowing to cool to room temperature. The precipitate was collected by filtration to give the title object compound as a white powder (378 mg, yield 62%).

$^1$H-NMR (DMSO-$d_6$, 400 MHz) δ: 1.34-1.46 (2H, m), 1.62 (3H, dd, J=24, 6.3 Hz), 1.82-1.91 (2H, m), 3.30-3.37 (2H, m), 3.52-3.60 (1H, m), 3.75 (2H, t, J=4.4 Hz), 3.77-3.84 (2H, m), 4.08 (2H, t, J=4.4 Hz), 5.92-6.11 (1H, m), 6.98-7.02 (4H, m), 7.19-7.23 (1H, m), 7.36-7.45 (1H, br), 7.52-7.57 (1H, m), 7.62-7.68 (1H, m), 7.94-8.02 (1H, br).

MS (ESI) m/z: 404 (M+H)$^+$.

Example 40

4-acetyl-3-[4-(2-isopropoxyethoxymethyl)phenoxy]benzamide (40a) 4-(2-isopropoxyethoxymethyl)phenol

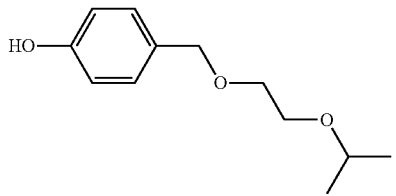

To 4-hydroxymethylphenol (1.63 g, 13.1 mmol) were added 2-isopropoxyethanol (6.84 g, 65.6 mmol), ytterbium (III) trifluoromethanesulfonate n-hydrate (163 mg), and the mixture was stirred at 80° C. for 1.5 hr. The mixture was allowed to cool, water was added and the mixture was extracted twice with ethyl acetate. The organic layer was washed with saturated brine, and dried over anhydrous sodium sulfate. The solvent was evaporated under reduced pressure, and the obtained residue was purified by silica gel column chromatography (hexane:ethyl acetate, 9:1→1:1, V/V). The solvent of the object fraction was evaporated under reduced pressure to give the title object compound as a colorless oil (2.65 g, P=70%, yield 67%).

$^1$H-NMR (CDCl$_3$, 400 MHz) δ: 1.15-1.21 (6H, m), 3.58-3.68 (5H, m), 4.47 (2H, s), 5.48-5.55 (1H, br), 6.75-6.77 (2H, m), 7.17-7.19 (2H, m).

144

(40b) methyl 4-acetyl-3-[4-(2-isopropoxyethoxymethyl)phenoxy]benzoate

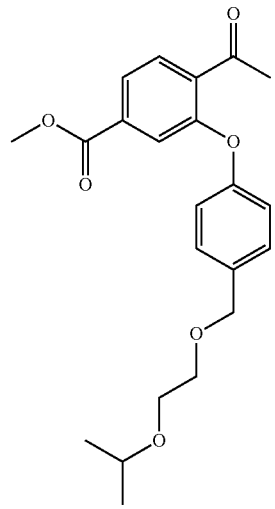 [SMILES: COC(=O)c1ccc(C(C)=O)c(Oc2ccc(COCCOC(C)C)cc2)c1]

Using 4-(2-isopropoxyethoxymethyl)phenol (P=70%) (1.16 g, 3.85 mmol) produced in Example 40 (40a) and methyl 4-acetyl-3-fluorobenzoate (630 mg, 3.21 mmol) produced in Example 32 (32d), and by a method similar to that in Example 28 (28c), the title object compound was obtained as a colorless oil (810 mg, yield 65%).

$^1$H-NMR (CDCl$_3$, 400 MHz) δ: 1.18 (6H, d, J=6.1 Hz), 2.66 (3H, s), 3.56-3.75 (5H, m), 3.87 (3H, s), 4.58 (2H, s), 6.99-7.01 (2H, m), 7.36-7.39 (2H, m), 7.56 (1H, d, J=8.5 Hz), 7.78-7.89 (2H, m).

(40c) 4-acetyl-3-[4-(2-isopropoxyethoxymethyl)phenoxy]benzamide

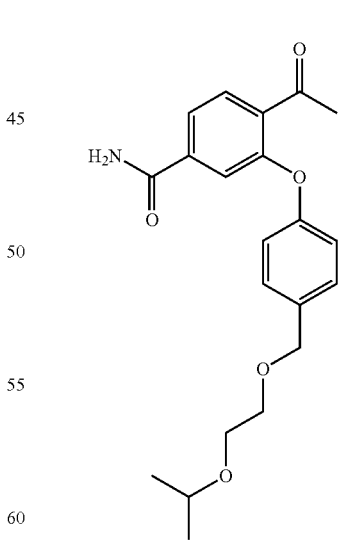

Using methyl 4-acetyl-3-[4-(2-isopropoxyethoxymethyl)phenoxy]benzoate (810 mg, 2.10 mmol) produced in Example 40 (40b), and by a method similar to that in Example 6 (6e), the title object compound was obtained as a white powder (370 mg, yield 51%).

¹H-NMR (CDCl₃, 400 MHz) δ: 1.18 (6H, d, J=6.1 Hz), 2.67 (3H, s), 3.60-3.72 (5H, m), 4.57 (2H, s), 5.45-6.25 (2H, br), 6.99-7.01 (2H, m), 7.37-7.39 (3H, m), 7.50 (1H, d, J=8.0 Hz), 7.87 (1H, d, J=8.0 Hz).

MS (ESI) m/z: 370 (M−H).

Example 41

4-acetyl-3-[4-(tetrahydropyran-4-yloxymethyl)phenoxy]benzamide (41a) 4-(4-bromobenzyloxy)tetrahydropyran

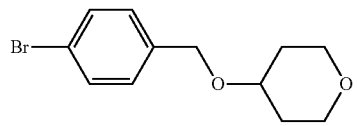

Tetrahydropyran-4-ol (2.04 g, 20.0 mmol) was dissolved in dimethylformamide (10 mL) and, under ice-cooling, sodium hydride (P=60%) (960 mg, 24.0 mmol) was added, and the mixture was stirred at room temperature for 0.5 hr. A solution (10 mL) of 1-bromo-4-bromomethylbenzene (7.50 g, 30.0 mmol) in dimethylformamide was slowly added dropwise, and the mixture was stirred at the same temperature for 2 hr. Water was added to the reaction mixture, and the mixture was extracted twice with ethyl acetate. The organic layers were combined, washed with saturated brine, and dried over anhydrous sodium sulfate. The solvent was evaporated under reduced pressure, and the obtained residue was purified by silica gel column chromatography (hexane:ethyl acetate, 100:1→1:1, V/V). The solvent of the object fraction was evaporated under reduced pressure to give the title object compound as a colorless oil (3.95 g, yield 73%).

¹H-NMR (CDCl₃, 400 MHz) δ: 1.59-1.72 (2H, m), 1.89-1.99 (2H, m), 3.40-3.50 (2H, m), 3.53-3.63 (1H, m), 3.92-4.01 (2H, m), 4.51 (2H, s), 7.20-7.26 (2H, m), 7.44-7.50 (2H, m).

(41b) 4-[4-(4,4,5,5-tetramethyl-[1,3,2]dioxaborolan-2-yl)benzyloxy]tetrahydropyran

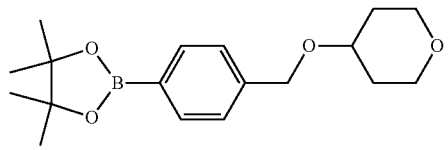 [SMILES: CC1(C)OB(c2ccc(COC3CCOCC3)cc2)OC1(C)C]

4-(4-Bromobenzyloxy)tetrahydropyran (3.95 g, 14.6 mmol) produced in Example 41 (41a) was dissolved in 1,4-dioxane (50 mL), bis(pinacolato)diboron (4.07 g, 16.0 mmol), bis(triphenylphosphine)palladium(II) dichloride (512 mg, 0.730 mmol), and potassium acetate (5.02 g, 51.1 mmol) were added, and the mixture was stirred under a nitrogen atmosphere at 100° C. for 1.5 hr. The reaction mixture was allowed to cool, ethyl acetate was added, and the mixture was washed with water and saturated brine, and dried over anhydrous sodium sulfate. The solvent was evaporated under reduced pressure, and the obtained residue was purified by silica gel column chromatography (hexane: ethyl acetate, 9:1→1:1, V/V). The solvent of the object fraction was evaporated under reduced pressure to give the title object compound as a colorless oil (3.90 g, yield 84%).

(41c) 4-acetyl-3-[4-(tetrahydropyran-4-yloxymethyl)phenoxy]benzonitrile

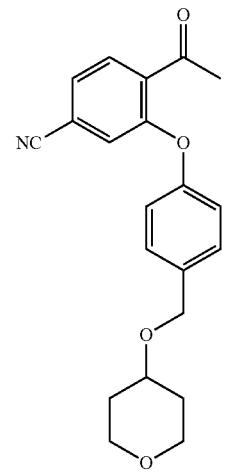

4-[4-(4,4,5,5-Tetramethyl-[1,3,2]dioxaborolan-2-yl)benzyloxy]tetrahydropyran (400 mg, 1.26 mmol) produced in Example 41 (41b) was dissolved in tetrahydrofuran (5 mL), 5.0 M aqueous sodium hydroxide (0.75 mL, 3.8 mmol), and 9.79 M hydrogen peroxide water (0.39 mL, 3.8 mmol) were added, and the mixture was stirred at room temperature for 0.5 hr. The reaction mixture was neutralized with 6.0 M hydrochloric acid, and the mixture was extracted twice with ethyl acetate, washed with saturated brine, and dried over anhydrous sodium sulfate. The solvent was evaporated under reduced pressure.

The obtained residue was dissolved in dimethylformamide (5 mL), 4-acetyl-3-fluorobenzonitrile (206 mg, 1.26 mmol) produced in Example 28 (28b) and potassium carbonate (348 mg, 2.52 mmol) were added, and the mixture was stirred at 100° C. for 2 hr. The reaction mixture was allowed to cool, ethyl acetate was added, and the mixture was washed with water and saturated brine, and dried over anhydrous sodium sulfate. The solvent was evaporated under reduced pressure, and purified by silica gel column chromatography (hexane:ethyl acetate, 4:1→1:1, V/V). The solvent of the object fraction was evaporated under reduced pressure to give the title object compound as a slightly yellow powder (315 mg, yield 71%).

¹H-NMR (CDCl₃, 400 MH) δ: 1.62-1.75 (2H, m), 1.93-2.02 (2H, m), 2.69 (3H, s), 3.42-3.52 (2H, m), 3.59-3.69 (1H, m), 3.94-4.04 (2H, m), 4.58 (2H, s), 7.01-7.06 (2H, m), 7.10 (1H, d, J=1.2 Hz), 7.39 (1H, dd, J=1.2, 8.0 Hz), 7.40-7.46 (2H, m), 7.86 (1H, d, J=8.0 Hz).

147

(41d) 4-acetyl-3-[4-(tetrahydropyran-4-yloxymethyl)phenoxy]benzamide

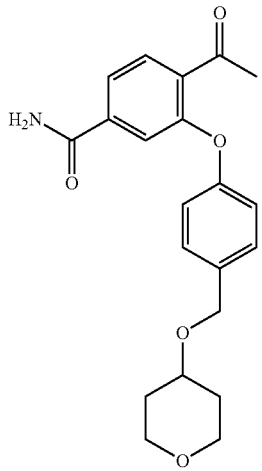 [SMILES: CC(=O)c1ccc(C(N)=O)cc1Oc1ccc(COC2CCOCC2)cc1]

Using 4-acetyl-3-[4-(tetrahydropyran-4-yloxymethyl)phenoxy]benzonitrile (315 mg, 0.896 mmol) produced in Example 41 (41c), and by the method used in Example 22 (22i), the title object compound was obtained as a white powder (292 mg, yield 88%).

$^1$H-NMR (DMSO-$d_6$, 400 MHz) δ: 1.42-1.55 (2H, m), 1.85-1.95 (2H, m), 2.57 (3H, s), 3.30-3.38 (2H, m), 3.54-3.64 (1H, m), 3.77-3.87 (2H, m), 4.52 (2H, s), 7.03-7.09 (2H, m), 7.35-7.42 (3H, m), 7.55 (1H, s), 7.67-7.74 (1H, m), 7.77 (1H, d, J=8.0 Hz), 8.10 (1H, s).

MS (ESI) m/z: 392 (M+Na)$^+$.

Example 42

4-fluoromethyl-3-[4-(tetrahydropyran-4-yloxymethyl)phenoxy]benzamide (42a) methyl 4-cyano-2-fluorobenzoate

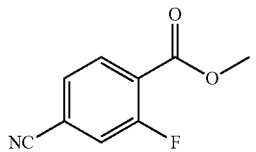

4-Cyano-2-fluorobenzoic acid (5.15 g, 31.2 mol) was dissolved in dimethylformamide (50 mL), potassium carbonate (6.47 g, 46.8 mmol) and methyl iodide (3.88 mL, 62.4 mmol) were added, and the mixture was stirred at room temperature for 18 hr. Water was added to the reaction mixture, and the mixture was extracted twice with ethyl acetate. The organic layer was washed successively with water and saturated brine, and dried over anhydrous sodium sulfate, and the solvent was evaporated under reduced pressure to give the title object compound as a white powder (1.70 g, yield 30%).

$^1$H-NMR (CHCl$_3$, 400 MHz) δ: 3.97 (3H, s), 7.48 (1H, dd, J=9.8, 1.5 Hz), 7.52 (1H, dd, J=8.1, 1.5 Hz), 8.05 (1H, dd, J=8.1, 7.3 Hz).

148

(42b) methyl 4-cyano-2-[4-(tetrahydropyran-4-yloxymethyl)phenoxy]benzoate

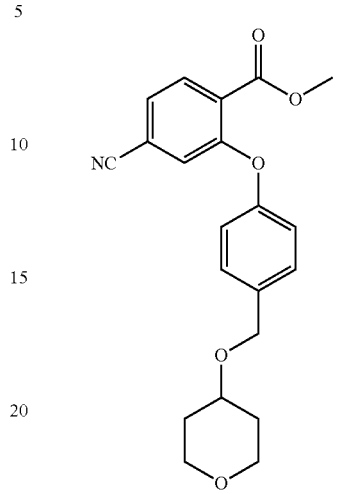

Using 4-[4-(4,4,5,5-tetramethyl-[1,3,2]dioxaborolan-2-yl)benzyloxy]tetrahydropyran (3.13 g, 9.85 mmol) produced in Example 41 (41b) and methyl 4-cyano-2-fluorobenzoate (1.68 g, 9.38 mmol) produced in Example 42 (42a), and by the method used in Example 41 (41c), the title object compound was obtained as a white powder (2.57 g, yield 75%).

$^1$H-NMR (CHCl$_3$, 400 MHz) δ: 1.62-1.78 (2H, m), 1.90-2.03 (2H, m), 3.42-3.56 (2H, m), 3.58-3.68 (1H, m), 3.89 (3H, s), 3.92-4.05 (2H, m), 4.57 (2H, s), 6.98-7.00 (2H, m), 7.13 (1H, s), 7.38-7.41 (3H, m), 7.94 (1H, d, J=8.1 Hz).

(42c) 4-hydroxymethyl-3-[4-(tetrahydropyran-4-yloxymethyl)phenoxy]benzonitrile

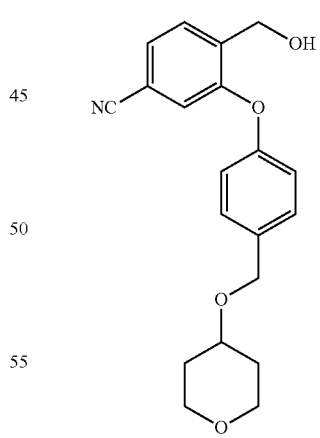

Methyl 4-cyano-2-[4-(tetrahydropyran-4-yloxymethyl)phenoxy]benzoate (180 mg, 0.490 mmol) produced in Example 42 (42b) was dissolved in tetrahydrofuran (2 mL), 3.0 M lithium borohydride/tetrahydrofuran solution (0.24 mL, 0.72 mmol) was added under a nitrogen atmosphere and ice-cooling, and the mixture was stirred at room temperature for 30 min, and heated under reflux for 1 hr. The mixture was allowed to cool, water was added and the mixture was extracted twice with ethyl acetate. The organic layer was washed successively with water and saturated brine, and dried over anhydrous sodium sulfate. The solvent was evaporated under reduced pressure. The obtained residue was purified by silica gel column chromatography (hexane: ethyl acetate, 9:1→1:4, V/V). The solvent of the object fraction was evaporated under reduced pressure to give the title object compound as a white powder (140 mg, yield 84%).

$^1$H-NMR (CHCl$_3$, 400 MHz) δ: 1.63-1.76 (2H, m), 1.90-2.03 (2H, m), 2.20-2.40 (1H, br), 3.42-3.52 (2H, m), 3.59-3.68 (1H, m), 3.92-4.03 (2H, m), 4.56 (2H, s), 4.84 (2H, d, J=4.4 Hz), 6.97-7.00 (3H, m), 7.37-7.39 (3H, m), 7.61 (1H, d, J=7.8 Hz).

(42d) 4-fluoromethyl-3-[4-(tetrahydropyran-4-yloxymethyl)phenoxy]benzonitrile

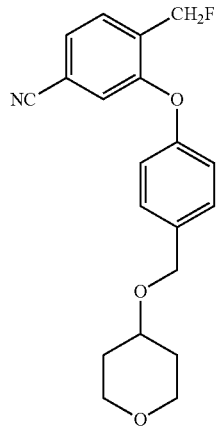

Using 4-hydroxymethyl-3-[4-(tetrahydropyran-4-yloxymethyl)phenoxy]benzonitrile (140 mg, 0.413 mmol) produced in Example 42 (42c), and by a method similar to that in Example 39, the title object compound was obtained as a white powder (60 mg, yield 43%).

$^1$H-NMR (CHCl$_3$, 400 MHz) δ: 1.61-1.75 (2H, m), 1.91-2.03 (2H, m), 3.43-3.53 (2H, m), 3.58-3.68 (1H, m), 3.92-4.05 (2H, m), 4.57 (2H, s), 5.59 (2H, d, J=47 Hz), 6.98-7.01 (3H, m), 7.39-7.42 (3H, m), 7.60 (1H, d, J=7.8 Hz).

(42e) 4-fluoromethyl-3-[4-(tetrahydropyran-4-yloxymethyl)phenoxy]benzamide

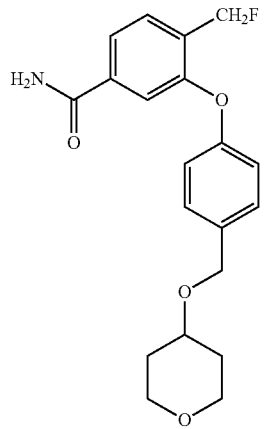

Using 4-fluoromethyl-3-[4-(tetrahydropyran-4-yloxymethyl)phenoxy]benzonitrile (1.17 g, 3.43 mmol) produced in Example 42 (42d), and by the method used in Example 22 (22i), the title object compound was obtained as a white powder (720 mg, yield 72%).

$^1$H-NMR (DMSO-d$_5$, 400 MHz) δ: 1.39-1.50 (2H, m), 1.82-1.93 (2H, m), 3.29-3.35 (2H, m), 3.52-3.62 (1H, m), 3.75-3.85 (2H, m), 4.50 (2H, s), 5.51 (2H, d, J=47 Hz), 6.98-7.00 (2H, m), 7.33-7.38 (3H, m), 7.40-7.46 (1H, br), 7.59 (1H, d, J=8.0 Hz), 7.68 (1H, d, J=8.0 Hz), 8.00-8.05 (1H, br).

MS (ESI) m/z: 358 (M−H)$^-$.

Example 43

(R)-4-(1-hydroxyethyl)-3-{4-[2-(tetrahydropyran-4-yloxy)ethoxy]phenoxy}benzamide

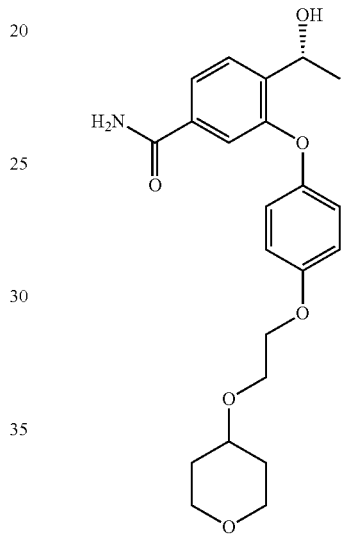

(S)-5,5-Diphenyl-2-methyl-3,4-propano-1,3,2-oxazaborolidine/tetrahydrofuran solution (833 mg, 3.00 mmol) was dissolved in anhydrous tetrahydrofuran (30 mL), dimethylsulfide-borane (0.238 mL, 2.50 mmol) was added and, under ice-cooling, a solution (30 mL) of 4-acetyl-3-{4-[2-(tetrahydropyran-4-yloxy)ethoxy]phenoxy}benzamide (1.00 g, 2.50 mmol) produced in Example 32 (32f) in anhydrous tetrahydrofuran was added dropwise over 20 min, and then, the mixture was stirred at the same temperature for 40 min. To the reaction mixture was added methanol (1 mL) and the mixture was concentrated under reduced pressure. The obtained residue was purified by silica gel column chromatography (chloroform:methanol, 10:0→9:1, V/V), and the solvent of the object fraction was evaporated under reduced pressure. The obtained residue was dissolved with heating in ethyl acetate-tert-butyl methyl ether (1:1) (20 mL), and the mixture was stirred while allowing to cool. The precipitate was collected by filtration to give the title object compound as a white powder (1.0 g, yield 100%).

$^1$H-NMR (DMSO-d$_6$, 400 MHz) δ: 1.32 (3H, d, J=6.4 Hz), 1.35-1.46 (2H, m), 1.81-1.90 (2H, m), 3.31-3.37 (2H, m), 3.51-3.60 (1H, m), 3.72-3.85 (4H, m), 4.03-4.11 (2H, m), 5.01-5.10 (1H, m), 5.25 (1H, d, J=4.4 Hz), 6.90-7.01 (4H, m), 7.16-7.21 (1H, m), 7.27-7.35 (1H, br), 7.57-7.64 (2H, m), 7.87-7.94 (1H, br).

MS (ESI) m/z: 402 (M+H)$^+$.

Examples 44-99 shown in the following Tables were produced by methods similar to those in Examples 1-43.

TABLE 1-1
| Example No. | structure | data |
|---|---|---|
| Example 44 | 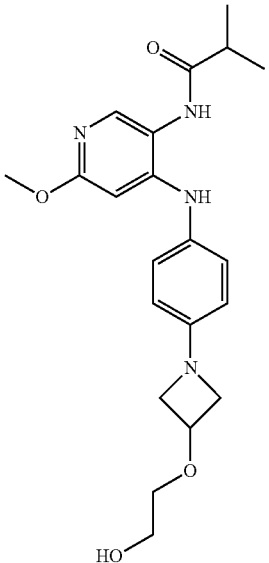 [SMILES: COc1cc(Nc2ccc(N3CC(OCCO)C3)cc2)c(NC(=O)C(C)C)cn1] | $^1$H-NMR (CDCl$_3$) δ: 1.30 (6H, d), 2.57-2.68 (1H, m), 3.55-3.60 (2H, m), 3.70-3.85 (7H, m), 4.08-4.18 (2H, m), 4.42-4.55 (1H, m), 6.05-6.18 (1H, m), 6.35-6.50 (3H, m), 6.97-7.10 (3H, m), 7.75-7.82 (1H, m). MS (ESI) m/z: 401 (M + H)$^+$. |
| Example 45 | 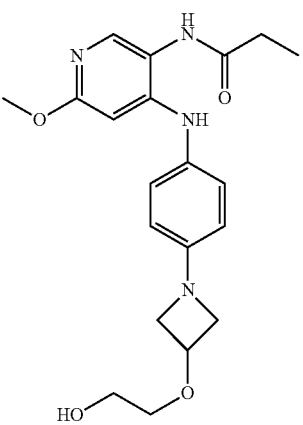 [SMILES: CCC(=O)Nc1cnc(OC)cc1Nc1ccc(N2CC(OCCO)C2)cc1] | $^1$H-NMR (DMSO-d$_6$) δ: 1.08 (3H, t, J = 7.6 Hz), 2.36 (2H, q, J = 7.6 Hz), 3.41-3.44 (2H, m), 3.49-3.53 (2H, m), 3.57-3.60 (2H, m), 3.70 (3H, s), 4.04-4.07 (2H, m), 4.40-4.45 (1H, m), 4.65-4.68 (1H, m), 5.90 (1H, s), 6.47 (2H, d, J = 8.5 Hz), 7.00 (2H, d, J = 8.5 Hz), 7.51 (1H, s), 7.69 (1H, s), 8.97 (1H, s). MS (ESI) m/z: 387 (M + H)$^+$. |
| Example 46 | 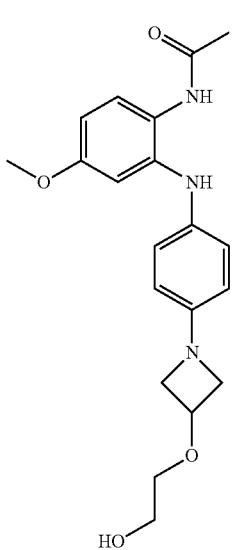 | $^1$H-NMR (DMSO-d$_6$) δ: 2.01 (3H, s), 3.39-3.46 (2H, m), 3.47-3.58 (4H, m), 3.61 (3H, s), 3.95-4.06 (2H, m), 4.36-4.46 (1H, m), 4.62-4.70 (1H, br), 6.28 (1H, d), 6.36-6.48 (3H, m), 6.85-7.00 (3H, m), 7.10 (1H, d, J = 8.4 Hz), 9.11 (1H, s). MS (ESI) m/z: 372 (M + H)$^+$. |

TABLE 1-1-continued

| Example No. | structure | data |
|---|---|---|
| Example 47 | (structure) | $^1$H-NMR (CDCl$_3$) δ: 1.63-1.87 (1H, br), 3.55-3.62 (2H, m), 3.73-3.83 (4H, m), 4.11-4.20 (2H, m), 4.45-4.54 (1H, m), 5.53-5.70 (1H, br), 5.86-5.97 (1H, br), 6.01 (1H, s), 6.45-6.54 (2H, m), 7.03-7.14 (3H, m), 7.24-7.31 (1H, m), 7.53 (1H, d, J = 8.2 Hz). MS (ESI) m/z: 396 (M + H)$^+$. |

TABLE 1-2

| Example No. | structure | data |
|---|---|---|
| Example 48 | (structure) | $^1$H-NMR (DMSO-d$_6$) δ: 2.71 (3H, J = 4.6 Hz), 3.41-3.47 (2H, m), 3.48-3.56 (2H, m), 3.60-3.68 (2H, m), 4.06-4.15 (2H, m), 4.41-4.50 (1H, m), 4.63-4.70 (1H, m), 6.48-6.56 (2H, m), 7.07 (1H, dd, J = 8.8, 1.2 Hz), 7.10-7.18 (2H, m), 7.37 (1H, d, J = 1.2 Hz), 8.13 (1H, d, J = 8.8 Hz), 8.48-8.58 (1H, m), 9.37 (1H, s). MS (ESI) m/z: 387 (M + H)$^+$. |
| Example 49 | (structure) | $^1$H-NMR (CDCl$_3$) δ: 1.21 (3H, t, J = 7.4 Hz), 1.60-1.70 (2H, m), 1.90-2.02 (2H, m), 2.65 (3H, s), 3.38-3.50 (4H, m), 3.56-3.68 (1H, m), 3.80-3.87 (2H, m), 3.94-3.99 (2H, m), 4.10-4.17 (2H, m), 5.90-6.00 (1H, br), 6.92-6.95 (3H, m), 7.15-7.17 (2H, m), 7.34 (1H, s), 7.82 (1H, d, J = 8.3 Hz), 10.40 (1H, s). MS (ESI) m/z: 427 (M + H)$^+$. |

TABLE 1-2-continued

| Example No. | structure | data |
|---|---|---|
| Example 50 | (structure) | $^1$H-NMR (CDCl$_3$) δ: 1.60-1.71 (2H, m), 1.90-2.00 (2H, m), 3.41-3.52 (2H, m), 3.57-3.67 (1H, m), 3.81-3.89 (2H, m), 3.92-4.00 (2H, m), 4.13-4.20 (2H, m), 5.55-5.78 (1H, br), 5.87-6.08 (1H, br), 6.95-7.03 (3H, m), 7.15-7.22 (2H, m), 7.45 (1H, d, J = 2.0 Hz), 8.25 (1H, d, J = 9.0 Hz), 9.41 (1H, s). MS (ESI) m/z: 402 (M + H)$^+$. |
| Example 51 | (structure) | $^1$H-NMR (CDCl$_3$) δ: 2.00-2.10 (1H, br), 2.66 (3H, s), 3.94-4.04 (2H, m), 4.07-4.15 (2H, m), 5.44-5.66 (1H, br), 5.84-6.02 (1H, br), 6.91-6.98 (2H, m), 6.99 (1H, dd, J = 8.3, 1.2 Hz), 7.13-7.22 (2H, m), 7.38 (1H, d, J = 1.4 Hz), 7.85 (1H, d, J = 8.3 Hz), 10.39 (1H, s). MS (ESI) m/z: 315 (M + H)$^+$. |

TABLE 1-3

| Example No. | structure | data |
|---|---|---|
| Example 52 | (structure) | $^1$H-NMR (CDCl$_3$) δ: 2.67 (3H, s), 3.65-4.05 (9H, m), 5.40-5.65 (1H, br), 5.80-6.05 (1H, br), 6.92-6.94 (2H, m), 7.00 (1H, dd, J = 8.5, 1.9 Hz), 7.15-7.17 (2H, m), 7.36 (1H, d, J = 1.9 Hz), 7.85 (1H, d, J = 8.5 Hz), 10.39 (1H, s). MS (ESI) m/z: 371 (M + H)$^+$. |

TABLE 1-3-continued

| Example No. | structure | data |
|---|---|---|
| Example 53 | (structure) | ¹H-NMR (CDCl₃) δ: 1.98-2.08 (2H, m), 2.66 (3H, s), 3.75-3.95 (6H, m), 4.13 (2H, t, J = 4.9 Hz), 4.21-4.27 (1H, m), 5.50-6.20 (2H, br), 6.89-6.96 (2H, m), 7.00 (1H, dd, J = 8.0, 1.7 Hz), 7.12-7.18 (2H, m), 7.36 (1H, d, J = 1.7 Hz), 7.84 (1H, d, J = 8.0 Hz), 10.38 (1H, s). MS (ESI) m/z: 383 (M − H)⁻. |
| Example 54 | (structure) | ¹H-NMR (DMSO-d₆) δ: 1.60-1.79 (4H, m), 1.92-2.01 (2H, m), 2.19 (3H, s), 2.40-2.49 (1H, m), 2.74-2.86 (2H, m), 2.64 (3H, s), 2.83-2.91 (2H, m), 7.17-7.22 (3H, m), 7.23-7.28 (2H, m), 7.45-7.52 (1H, br), 7.63 (1H, s), 7.97-8.06 (2H, m), 10.36 (1H, s). MS (ESI) m/z: 352 (M + H)⁺. |
| Example 55 | (structure) | ¹H-NMR (DMSO-d₆) δ: 1.59-1.79 (4H, m), 2.03-2.13 (2H, m), 2.40-2.54 (3H, m), 2.64 (3H, s), 2.95-3.03 (2H, m), 3.49-3.55 (2H, m), 4.36-4.45 (1H, br), 7.17-7.22 (3H, m), 7.24-7.29 (2H, m), 7.46-7.52 (1H, br), 7.63 (1H, s), 7.97-8.07 (2H, m), 10.35 (1H, s). MS (ESI) m/z: 382 (M + H)⁺. |

TABLE 1-4

| Example No. | structure | data |
|---|---|---|
| Example 56 | 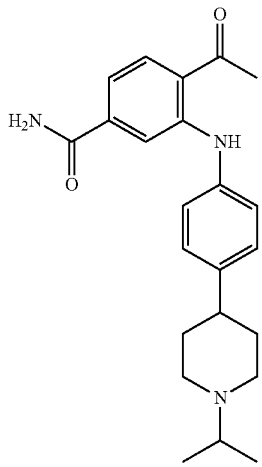 [SMILES: CC(=O)c1ccc(C(N)=O)cc1Nc1ccc(C2CCN(C(C)C)CC2)cc1] | ¹H-NMR (DMSO-d₆) δ: 0.99 (6H, d, J = 6.6 Hz), 1.54-1.66 (4H, m), 1.73-1.82 (4H, m), 2.17-2.26 (2H, m), 2.41-2.50 (1H, m), 2.64 (3H, s), 2.71 (1H, septet, J = 6.6 Hz), 2.84-2.92 (2H, m), 7.16-7.21 (3H, m), 7.23-7.28 (2H, m), 7.44-7.51 (1H, br), 7.63 (1H, s), 7.96-8.07 (2H, m), 10.35 (1H, s). MS (ESI) m/z: 380 (M + H)⁺. |
| Example 57 | 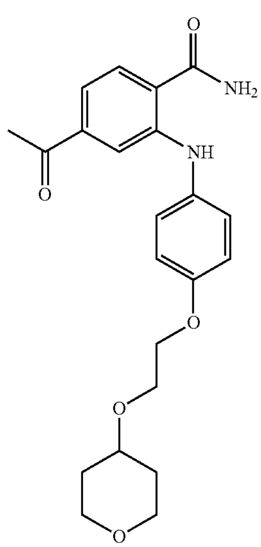 [SMILES: CC(=O)c1ccc(C(N)=O)c(Nc2ccc(OCCOC3CCOCC3)cc2)c1] | ¹H-NMR (CDCl₃) δ : 1.61-1.72 (2H, m), 1.91-2.00 (2H, m), 2.48 (3H, s), 3.40-3.52 (2H, m), 3.57-3.67 (1H, m), 3.82-3.90 (2H, m), 3.93-4.02 (2H, m), 4.10-4.20 (2H, m), 5.40-6.30 (2H, br), 6.90-6.98 (2H, m), 7.12-7.17 (2H, m), 7.19 (1H, dd, J = 8.0, 1.4 Hz), 7.50 (1H, d, J = 8.0 Hz), 7.57 (1H, d, J = 1.4 Hz), 9.39 (1H, s). MS (ESI) m/z: 399 (M + H)⁺. |

TABLE 1-4-continued

| Example No. | structure | data |
|---|---|---|
| Example 58 | 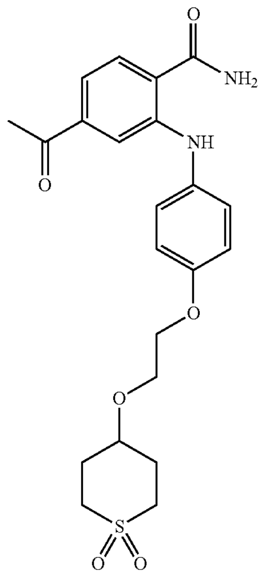 [SMILES: CC(=O)c1ccc(C(N)=O)c(Nc2ccc(OCCOC3CCS(=O)(=O)CC3)cc2)c1] | ¹H-NMR (CDCl₃) δ: 2.17-2.29 (2H, m), 2.32-2.42 (2H, m), 2.49 (3H, s), 2.82-2.93 (2H, m), 3.30-3.43 (2H, m), 3.76-3.81 (1H, m), 3.81-3.87 (2H, m), 4.10-4.18 (2H, m), 5.50-6.10 (2H, br), 6.88-6.94 (2H, m), 7.12-7.18 (2H, m), 7.19 (1H, dd, J = 8.0, 1.4 Hz), 7.50 (1H, d, J = 8.0 Hz), 7.59 (1H, d, J = 1.4 Hz), 9.40 (1H, s). MS (ESI) m/z: 447 (M + H)⁺. |
| Example 59 | 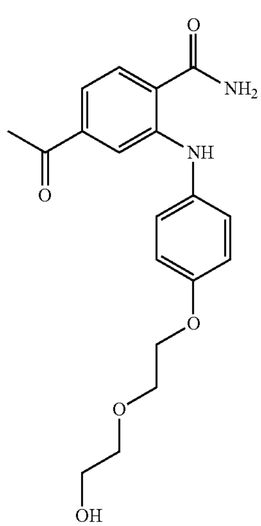 [SMILES: CC(=O)c1ccc(C(N)=O)c(Nc2ccc(OCCOCCO)cc2)c1] | ¹H-NMR (CDCl₃) δ: 2.16-2.30 (1H, br), 2.48 (3H, s), 3.66-3.73 (2H, m), 3.75-3.82 (2H, m), 3.86-3.93 (2H, m), 4.12-4.20 (2H, m), 5.50-6.20 (2H, br), 6.90-6.97 (2H, m), 7.12-7.18 (2H, m), 7.19 (1H, dd, J = 8.3, 1.4 Hz), 7.49 (1H, d, = 8.3 Hz), 7.57 (1H, d, J = 1.4 Hz), 9.39 (1H, s). MS (ESI) m/z: 359 (M + H)⁺. |

TABLE 1-5
| Example No. | structure | data |
|---|---|---|
| Example 60 | 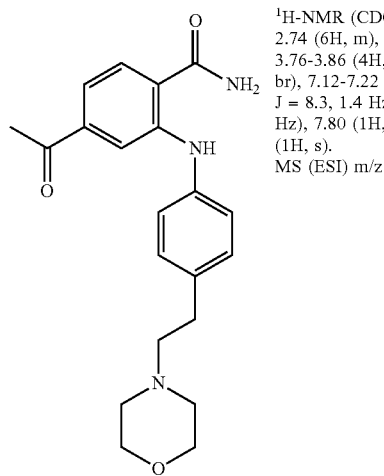 | ¹H-NMR (CDCl₃) δ: 2.51 (3H, s), 2.52-2.74 (6H, m), 2.78-2.91 (2H, m), 3.76-3.86 (4H, m), 5.40-6.30 (2H, br), 7.12-7.22 (4H, m), 7.24 (1H, dd, J = 8.3, 1.4 Hz), 7.52 (1H, d, J = 8.3 Hz), 7.80 (1H, d, J = 1.4 Hz), 9.48 (1H, s).<br>MS (ESI) m/z: 368 (M + H)⁺. |
| Example 61 | 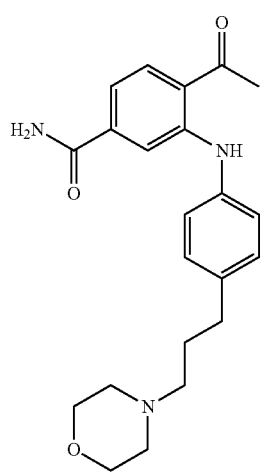 [SMILES: CC(=O)c1ccc(C(N)=O)cc1Nc1ccc(CCCN2CCOCC2)cc1] | ¹H-NMR (CDCl₃) δ: 1.77-1.88 (2H, m), 2.33-2.42 (2H, m), 2.42-2.50 (4H, m), 2.62-2.68 (2H, m), 2.67 (3H, s), 3.72 (4H, t, J = 4.6 Hz), 5.40-5.70 (1H, br), 5.80-6.10 (1H, br), 7.02 (1H, dd, J = 8.3, 1.7 Hz), 7.12-7.21 (4H, m), 7.57 (1H, d, J = 1.7 Hz), 7.86 (1H, d, J = 8.3 Hz), 10.50 (1H, s).<br>MS (ESI) m/z: 382 (M + H)⁺. |

TABLE 1-5-continued
| Example No. | structure | data |
|---|---|---|
| Example 62 | 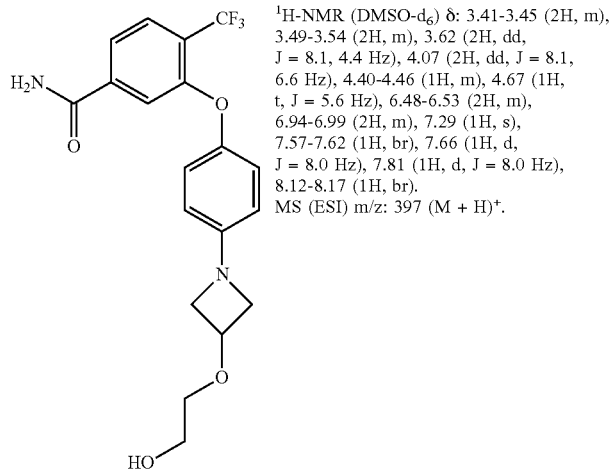 | ¹H-NMR (DMSO-d₆) δ: 3.41-3.45 (2H, m), 3.49-3.54 (2H, m), 3.62 (2H, dd, J = 8.1, 4.4 Hz), 4.07 (2H, dd, J = 8.1, 6.6 Hz), 4.40-4.46 (1H, m), 4.67 (1H, t, J = 5.6 Hz), 6.48-6.53 (2H, m), 6.94-6.99 (2H, m), 7.29 (1H, s), 7.57-7.62 (1H, br), 7.66 (1H, d, J = 8.0 Hz), 7.81 (1H, d, J = 8.0 Hz), 8.12-8.17 (1H, br).<br>MS (ESI) m/z: 397 (M + H)⁺. |
| Example 63 | 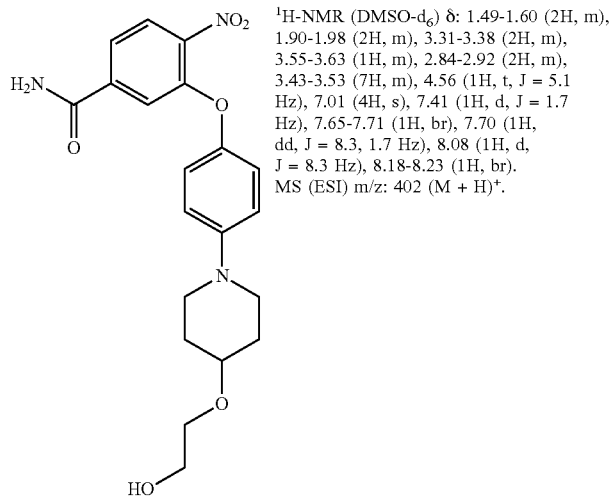 | ¹H-NMR (DMSO-d₆) δ: 1.49-1.60 (2H, m), 1.90-1.98 (2H, m), 3.31-3.38 (2H, m), 3.55-3.63 (1H, m), 2.84-2.92 (2H, m), 3.43-3.53 (7H, m), 4.56 (1H, t, J = 5.1 Hz), 7.01 (4H, s), 7.41 (1H, d, J = 1.7 Hz), 7.65-7.71 (1H, br), 7.70 (1H, dd, J = 8.3, 1.7 Hz), 8.08 (1H, d, J = 8.3 Hz), 8.18-8.23 (1H, br).<br>MS (ESI) m/z: 402 (M + H)⁺. |

TABLE 1-6
| Example No. | structure | data |
|---|---|---|
| Example 64 | 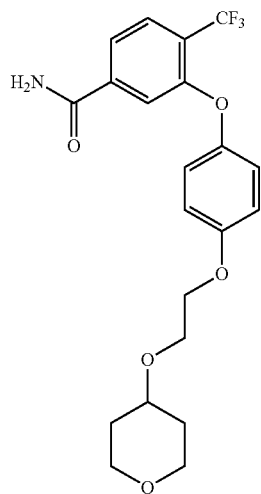 [SMILES: NC(=O)c1ccc(C(F)(F)F)c(Oc2ccc(OCCOC3CCOCC3)cc2)c1] | ¹H-NMR (DMSO-d₆) δ: 1.35-1.46 (2H, m), 1.82-1.90 (2H, m), 3.29-3.37 (2H, m), 3.52-3.60 (1H, m), 3.74-3.84 (4H, m), 4.08-4.12 (2H, m), 7.00-7.07 (4H, m), 7.33 (1H, s), 7.58-7.64 (1H, br), 7.70 (1H, d, J = 8.0 Hz), 7.84 (1H, d, J = 8.0 Hz), 8.13-8.19 (1H, br). MS (ESI) m/z: 426 (M + H)⁺. |
| Example 65 | 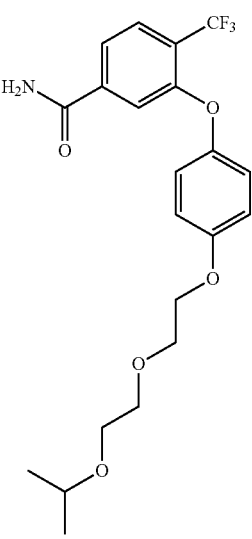 [SMILES: CC(C)OCCOCCOc1ccc(Oc2cc(C(N)=O)ccc2C(F)(F)F)cc1] | ¹H-NMR (DMSO-d₆) δ: 1.06 (6H, d, J = 6.1 Hz), 3.47-3.57 (5H, m), 3.72-3.75 (2H, m), 4.08-4.10 (2H, m), 6.99-7.05 (4H, m), 7.33 (1H, s), 7.55-7.64 (1H, br), 7.69 (1H, d, J = 8.0 Hz), 7.83 (1H, d, J = 8.0 Hz), 8.13-8.20 (1H, br). MS (ESI) m/z: 426 (M − H)⁻. |

TABLE 1-6-continued
| Example No. | structure | data |
|---|---|---|
| Example 66 | 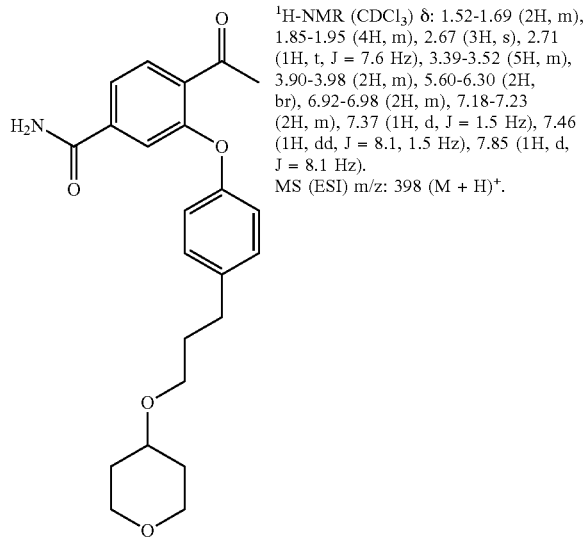 | $^1$H-NMR (CDCl$_3$) δ: 1.52-1.69 (2H, m), 1.85-1.95 (4H, m), 2.67 (3H, s), 2.71 (1H, t, J = 7.6 Hz), 3.39-3.52 (5H, m), 3.90-3.98 (2H, m), 5.60-6.30 (2H, br), 6.92-6.98 (2H, m), 7.18-7.23 (2H, m), 7.37 (1H, d, J = 1.5 Hz), 7.46 (1H, dd, J = 8.1, 1.5 Hz), 7.85 (1H, d, J = 8.1 Hz). MS (ESI) m/z: 398 (M + H)$^+$. |
| Example 67 | 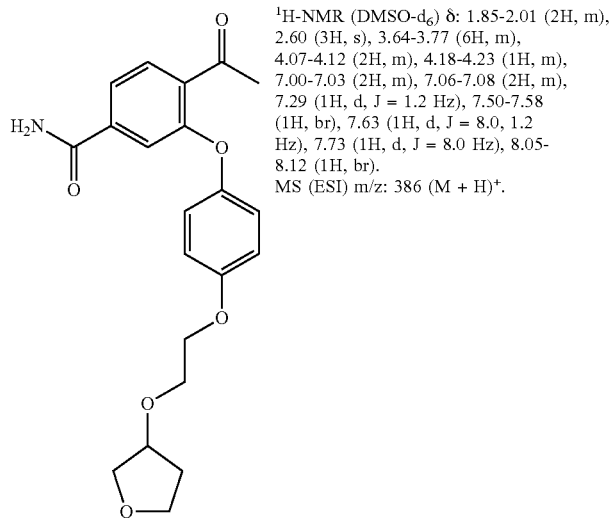 | $^1$H-NMR (DMSO-d$_6$) δ: 1.85-2.01 (2H, m), 2.60 (3H, s), 3.64-3.77 (6H, m), 4.07-4.12 (2H, m), 4.18-4.23 (1H, m), 7.00-7.03 (2H, m), 7.06-7.08 (2H, m), 7.29 (1H, d, J = 1.2 Hz), 7.50-7.58 (1H, br), 7.63 (1H, d, J = 8.0, 1.2 Hz), 7.73 (1H, d, J = 8.0 Hz), 8.05-8.12 (1H, br). MS (ESI) m/z: 386 (M + H)$^+$. |

TABLE 1-7
| Example No. | structure | data |
|---|---|---|
| Example 68 | 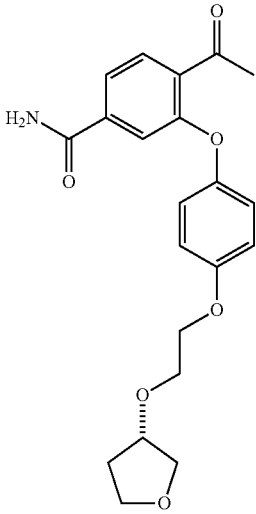 | ¹H-NMR (DMSO-d₆) δ: 1.85-2.01 (2H, m), 2.60 (3H, s), 3.63-3.77 (6H, m), 4.06-4.12 (2H, m), 4.17-4.24 (1H, m), 7.00-7.04 (2H, m), 7.05-7.09 (2H, m), 7.27-7.31 (1H, m), 7.50-7.57 (1H, br), 7.61-7.66 (1H, m), 7.71-7.75 (1H, m), 8.05-8.12 (1H, br). MS (ESI) m/z: 386 (M + H)⁺. |
| Example 69 | 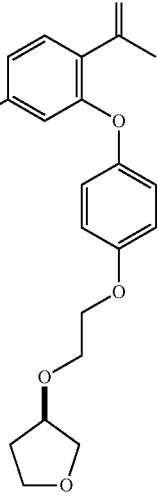 | ¹H-NMR (DMSO-d₆) δ: 1.85-2.01 (2H, m), 2.60 (3H, s), 3.63-3.77 (6H, m), 4.06-4.12 (2H, m), 4.17-4.24 (1H, m), 6.99-7.04 (2H, m), 7.05-7.09 (2H, m), 7.29 (1H, d, J = 1.0 Hz), 7.50-7.57 (1H, br), 7.63 (1H, dd, J = 8.1, 1.0 Hz), 7.72 (1H, d, J = 8.1 Hz), 8.04-8.12 (1H, br). MS (ESI) m/z: 386 (M + H)⁺. |

TABLE 1-7-continued
| Example No. | structure | data |
|---|---|---|
| Example 70 | 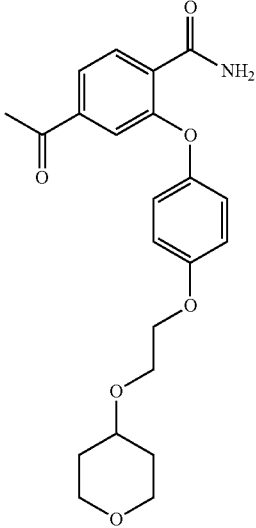 | ¹H-NMR (CDCl₃) δ: 1.36-1.47 (2H, m), 1.82-1.91 (2H, m), 2.51 (3H, s), 3.30-3.37 (2H, m), 3.52-3.61 (1H, m), 3.74-3.84 (4H, m), 4.07-4.12 (2H, m), 6.98-7.09 (4H, m), 7.18 (1H, d, J = 1.5 Hz), 7.67-7.73 (1H, br), 7.73 (1H, dd, J = 8.0, 1.5 Hz), 7.75-7.82 (1H, br), 7.78 (1H, d, J = 8.0 Hz). MS (ESI) m/z: 400 (M + H)⁺. |
| Example 71 | 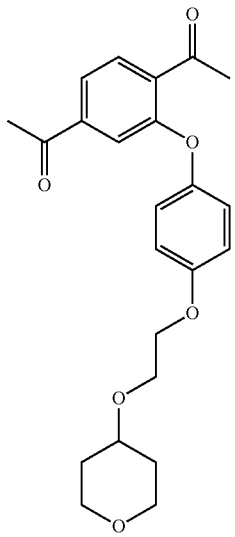 | ¹H-NMR (DMSO-d₆) δ: 1.36-1.46 (2H, m), 1.83-1.90 (2H, m), 2.53 (3H, s), 3.30-3.38 (2H, m), 3.53-3.60 (1H, m), 3.71 (3H, s), 3.74-3.83 (4H, m), 4.06-4.11 (2H, m), 6.24 (1H, d, J = 2.2 Hz), 6.77 (1H, dd, J = 9.0, 2.2 Hz), 6.98-7.07 (4H, m), 7.77 (1H, d, J = 9.0 Hz). MS (ESI) m/z: 387 (M + H)⁺. |

TABLE 1-8

| Example No. | structure | data |
|---|---|---|
| Example 72 | 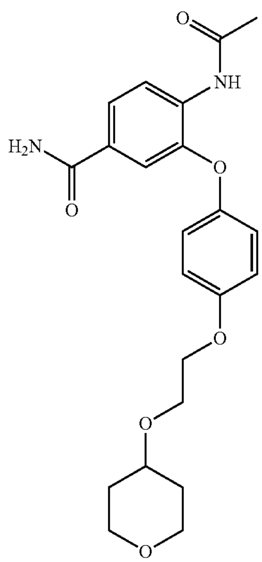 [SMILES: CC(=O)Nc1ccc(C(N)=O)cc1Oc1ccc(OCCOC2CCOCC2)cc1] | ¹H-NMR (DMSO-d₆) δ: 1.35-1.46 (2H, m), 1.81-1.92 (2H, m), 2.11 (3H, s), 3.29-3.37 (2H, m), 3.51-3.61 (1H, m), 3.72-3.85 (4H, m), 4.09 (2H, t, J = 4.6 Hz), 6.97-7.04 (4H, m), 7.21-7.31 (1H, br), 7.23 (1H, d, J = 1.2 Hz), 7.56 (1H, dd, J = 8.8, 1.2 Hz), 7.84-7.93 (1H, br), 8.15 (1H, d, J = 8.8 Hz), 9.62-9.69 (1H, br). MS (ESI) m/z: 415 (M + H)⁺. |
| Example 73 | 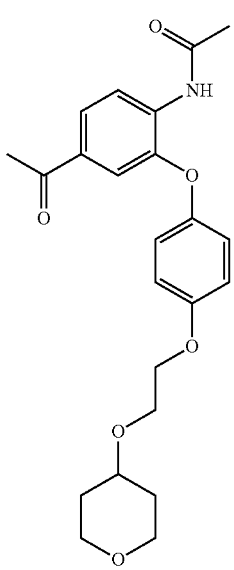 [SMILES: CC(=O)Nc1ccc(C(C)=O)cc1Oc1ccc(OCCOC2CCOCC2)cc1] | ¹H-NMR (DMSO-d₆) δ: 1.35-1.46 (2H, m), 1.83-1.92 (2H, m), 2.15 (3H, s), 2.45 (3H, s), 3.30-3.38 (2H, m), 3.52-3.62 (1H, m), 3.74-3.85 (4H, m), 3.80 (2H, dt, J = 11.5, 4.4 Hz), 4.09 (2H, t, J = 4.7 Hz), 6.98-7.08 (4H, m), 7.17 (1H, d, J = J = 1.7 Hz), 7.70 (1H, dd, J = 8.5, 1.7 Hz), 8.30 (1H, d, J = 8.5 Hz), 9.76 (1H, s). MS (ESI) m/z: 414 (M + H)⁺. |

TABLE 1-8-continued
| Example No. | structure | data |
|---|---|---|
| Example 74 | 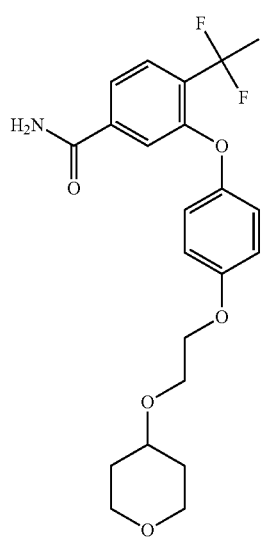 [SMILES: CC(F)(F)c1ccc(C(N)=O)cc1Oc1ccc(OCCOC2CCOCC2)cc1] | $^1$H-NMR (DMSO-$d_6$) δ: 1.34-1.47 (2H, m), 1.82-1.90 (2H, m), 2.06 (3H, t, J = 19.0 Hz), 3.30-3.37 (2H, m), 3.52-3.61 (1H, m), 3.76 (2H, t, J = 4.4 Hz), 3.77-3.84 (2H, m), 4.09 (2H, t, J = 4.4 Hz), 6.98-7.03 (4H, m), 7.27-7.31 (1H, m), 7.45-7.53 (1H, br), 7.61-7.68 (2H, m), 8.02-8.11 (1H, br). MS (ESI) m/z: 422 (M + H)$^+$. |
| Example 75 | 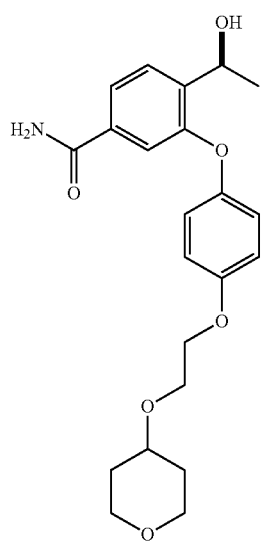 [SMILES: C[C@H](O)c1ccc(C(N)=O)cc1Oc1ccc(OCCOC2CCOCC2)cc1] | $^1$H-NMR (DMSO-$d_6$) δ: 1.32 (3H, d, J = 6.4 Hz), 1.35-1.46 (2H, m), 1.81-1.90 (2H, m), 3.31-3.37 (2H, m), 3.51-3.60 (1H, m), 3.72-3.85 (4H, m), 4.03-4.11 (2H, m), 5.01-5.10 (1H, m), 5.25 (1H, d, J = 4.4 Hz), 6.90-7.01 (4H, m), 7.16-7.21 (1H, m), 7.27-7.35 (1H, br), 7.57-7.64 (2H, m), 7.87-7.94 (1H, br). MS (ESI) m/z: 402 (M + H)$^+$. |

TABLE 1-9
| Example No. | structure | data |
|---|---|---|
| Example 76 | 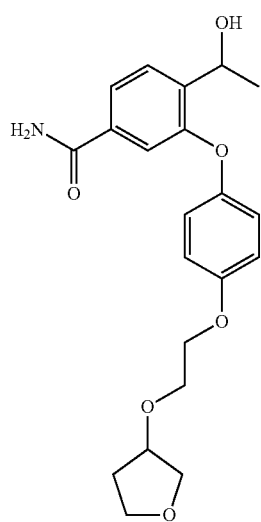 | ¹H-NMR (DMSO-d₆) δ: 1.32 (3H, d, J = 6.4 Hz), 1.85-2.00 (2H, m), 3.60-3.75 (6H, m), 4.05-4.10 (2H, m), 4.15-4.25 (1H, m), 5.01-5.10 (1H, m), 5.23 (1H, d, J = 3.9 Hz), 6.91-6.97 (1H, m), 7.18 (1H, s), 7.25-7.35 (1H, br), 7.57-7.63 (2H, m), 7.85-7.95 (1H, br).<br>MS (ESI) m/z: 388 (M + H)⁺. |
| Example 77 | 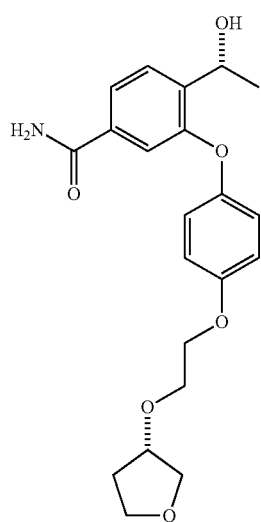 | ¹H-NMR (DMSO-d₆) δ: 1.32 (3H, d, J = 6.3 Hz), 1.99-2.07 (2H, m), 3.61-3.75 (6H, m), 4.05 (2H, t, J = 4.6 Hz), 4.15-4.21 (1H, m), 5.00-5.09 (1H, m), 5.23 (1H, d, J = 4.2 Hz), 6.88-6.99 (4H, m), 7.18 (1H, s), 7.25-7.34 (1H, br), 7.56-7.64 (2H, m), 7.83-7.93 (1H, br).<br>MS (ESI) m/z: 388 (M + H)⁺. |

TABLE 1-9-continued
| Example No. | structure | data |
|---|---|---|
| Example 78 | 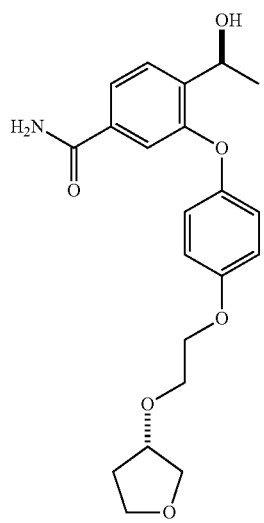 | $^1$H-NMR (DMSO-$d_6$) δ: 1.32 (3, d, J = 6.3 Hz), 1.84-2.00 (2H, m), 3.61-3.75 (6H, m), 4.04 (2H, t, J = 4.6 Hz), 4.15-4.21 (1H, m), 5.00-5.09 (1H, m), 5.23 (1H, d, J = 4.2 Hz), 6.88-6.99 (4H, m), 7.18 (1H, s), 7.25-7.34 (1H, br), 7.56-7.64 (2H, m), 7.83-7.93 (1H, br). MS (ESI) m/z: 388 (M + H)$^+$. |
| Example 79 | 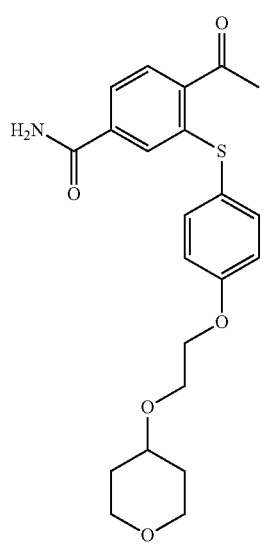 [SMILES: CC(=O)c1ccc(C(N)=O)cc1Sc1ccc(OCCOC2CCOCC2)cc1] | $^1$H-NMR (DMSO-$d_6$) δ: 1.36-1.48 (2H, m), 1.83-1.93 (2H, m), 2.64 (3H, s), 3.30-3.38 (2H, m), 3.52-3.63 (1H, m), 3.76-3.85 (4H, m), 4.12-4.20 (2H, m), 7.03-7.10 (2H, m), 7.31 (1H, d, J = 1.4 Hz), 7.39-7.47 (3H, m), 7.64 (1H, dd, J = 8.0, 1.4 Hz), 7.99 (1H, s), 8.03 (1H, d, J = 8.0 Hz). MS (ESI) m/z: 416 (M + H)$^+$. |

TABLE 1-10

| Example No. | structure | data |
|---|---|---|
| Example 80 | (structure) | ¹H-NMR (CDCl₃) δ: 1.18 (6H, d, J = 6.1 Hz), 2.53 (3H, s), 3.58-3.69 (5H, m), 4.59 (2H, s), 5.85-5.95 (1H, br), 7.00-7.08 (2H, m), 7.37-7.44 (3H, m), 7.55-7.65 (1H, br), 7.71 (1H, dd, J = 8.2, 1.4 Hz), 8.35 (1H, d, J = 8.2 Hz). MS (ESI) m/z: 394 (M + Na)⁺. |
| Example 81 | (structure) | ¹H-NMR (DMSO-d₆) δ: 1.41-1.52 (2H, m), 1.86-1.93 (2H, m), 3.31-3.38 (2H, m), 3.55-3.63 (1H, m), 3.82 (2H, dt, J = 11.7, 4.2 Hz), 4.53 (2H, s), 7.07-7.12 (2H, m), 7.38-7.43 (2H, m), 7.53 (1H, d, J = 1.7 Hz), 7.69-7.75 (1H, br), 7.79 (1H, dd, J = 8.6, 1.7 Hz), 8.14 (1H, d, J = 8.6 Hz), 8.21-8.26 (1H, br). MS (ESI) m/z: 395 (M + Na)⁺. |
| Example 82 | (structure) | ¹H-NMR (DMSO-d₆) δ: 1.41-1.52 (2H, m), 1.86-1.94 (2H, m), 3.32-3.39 (2H, m), 3.56-3.63 (1H, m), 3.82 (2H, dt, J = 11.7, 4.4 Hz), 4.53 (2H, s), 7.04-7.08 (2H, m), 7.38-7.43 (2H, m), 7.44 (1H, s), 7.59-7.65 (1H, br), 7.77 (1H, d, J = 8.0 Hz), 7.88 (1H, d, J = 8.0 Hz), 8.14-8.20 (1H, br). MS (ESI) m/z: 394 (M − H)⁻. |

TABLE 1-10-continued
| Example No. | structure | data |
|---|---|---|
| Example 83 | 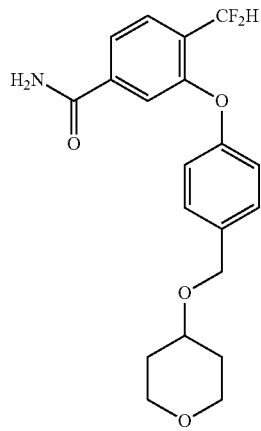 [SMILES: NC(=O)c1ccc(C(F)F)c(Oc2ccc(COC3CCOCC3)cc2)c1] | $^1$H-NMR (DMSO-$d_6$) δ: 1.41-1.52 (2H, m), 1.86-1.94 (2H, m), 3.32-3.38 (2H, m), 3.55-3.63 (1H, m), 3.82 (2H, dt, J = 11.7, 4.4 Hz), 4.53 (2H, s), 7.03-7.08 (2H, m), 7.24 (1H, t, J = 54.4 Hz), 7.35 (1H, s), 7.37-7.42 (2H, m), 7.50-7.56 (1H, br), 7.74 (2H, s), 8.06-8.13 (1H, br). MS (ESI) m/z: 376 (M − H)$^-$. |
| Example 84 | 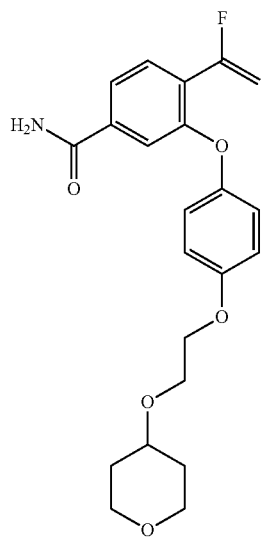 | $^1$H-NMR (DMSO-$d_6$) δ: 1.35-1.45 (2H, m), 1.80-1.90 (2H, m), 3.26-3.35 (2H, m), 3.48-3.58 (1H, m), 3.72-3.84 (4H, m), 4.02-4.12 (2H, m), 5.20 (1H, dd, J = 20.7, 2.9 Hz), 5.46 (1H, dd, J = 53.4, 2.9 Hz), 6.99 (4H, s), 7.30 (1H, s), 7.42-7.51 (1H, br), 7.60-7.69 (2H, m), 8.00-8.09 (1H, br). MS (ESI) m/z: 402 (M + H)$^+$. |

TABLE 1-11
| Example No. | structure | data |
|---|---|---|
| Example 85 | 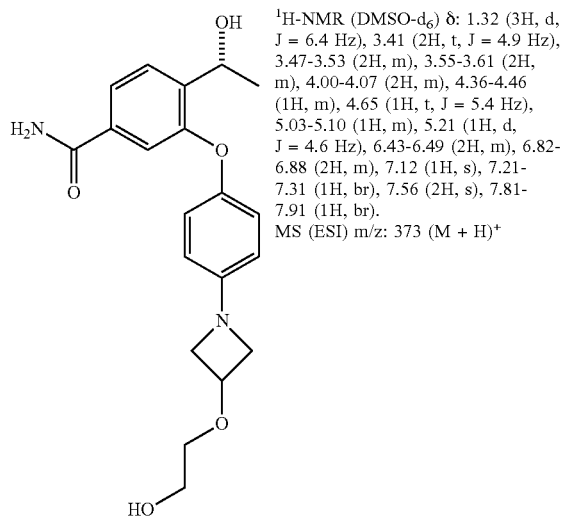 | ¹H-NMR (DMSO-d₆) δ: 1.32 (3H, d, J = 6.4 Hz), 3.41 (2H, t, J = 4.9 Hz), 3.47-3.53 (2H, m), 3.55-3.61 (2H, m), 4.00-4.07 (2H, m), 4.36-4.46 (1H, m), 4.65 (1H, t, J = 5.4 Hz), 5.03-5.10 (1H, m), 5.21 (1H, d, J = 4.6 Hz), 6.43-6.49 (2H, m), 6.82-6.88 (2H, m), 7.12 (1H, s), 7.21-7.31 (1H, br), 7.56 (2H, s), 7.81-7.91 (1H, br). MS (ESI) m/z: 373 (M + H)⁺ |
| Example 86 | 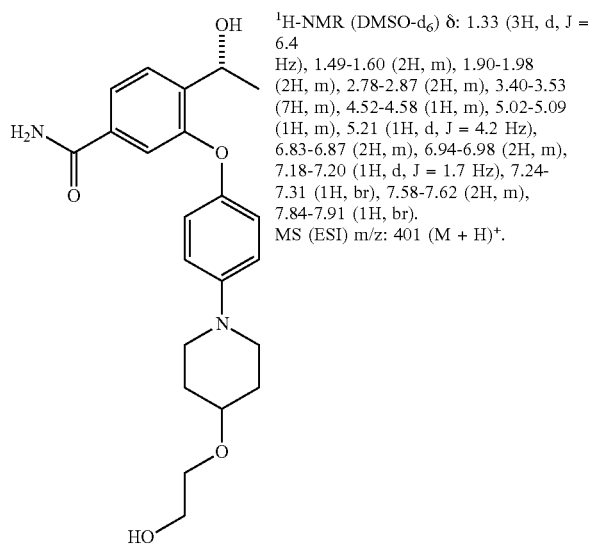 | ¹H-NMR (DMSO-d₆) δ: 1.33 (3H, d, J = 6.4 Hz), 1.49-1.60 (2H, m), 1.90-1.98 (2H, m), 2.78-2.87 (2H, m), 3.40-3.53 (7H, m), 4.52-4.58 (1H, m), 5.02-5.09 (1H, m), 5.21 (1H, d, J = 4.2 Hz), 6.83-6.87 (2H, m), 6.94-6.98 (2H, m), 7.18-7.20 (1H, d, J = 1.7 Hz), 7.24-7.31 (1H, br), 7.58-7.62 (2H, m), 7.84-7.91 (1H, br). MS (ESI) m/z: 401 (M + H)⁺. |
| Example 87 | 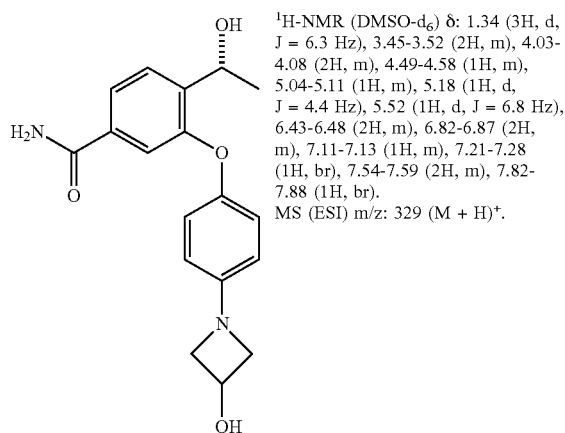 | ¹H-NMR (DMSO-d₆) δ: 1.34 (3H, d, J = 6.3 Hz), 3.45-3.52 (2H, m), 4.03-4.08 (2H, m), 4.49-4.58 (1H, m), 5.04-5.11 (1H, m), 5.18 (1H, d, J = 4.4 Hz), 5.52 (1H, d, J = 6.8 Hz), 6.43-6.48 (2H, m), 6.82-6.87 (2H, m), 7.11-7.13 (1H, m), 7.21-7.28 (1H, br), 7.54-7.59 (2H, m), 7.82-7.88 (1H, br). MS (ESI) m/z: 329 (M + H)⁺. |

TABLE 1-12

| Example No. | structure | data |
|---|---|---|
| Example 88 | 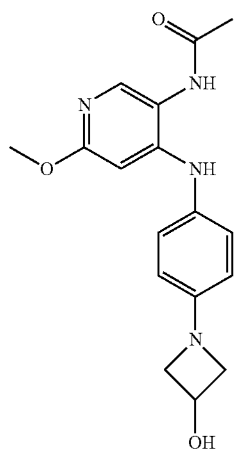 [SMILES: COc1cc(Nc2ccc(N3CC(O)C3)cc2)c(NC(C)=O)cn1] | ¹H-NMR (DMSO-d₆) δ: 2.04 (3H, s), 3.46-3.55 (2H, m), 3.70 (3H, s), 4.02-4.12 (2H, m), 4.50-4.61 (1H, m), 5.54-5.62 (1H, m), 5.89 (1H, s), 6.41-6.52 (2H, m), 6.94-7.05 (2H, m), 7.54 (1H, s), 7.67 (1H, s), 9.01-9.12 (1H, br). MS (ESI) m/z: 329 (M + H)⁺ |
| Example 89 | 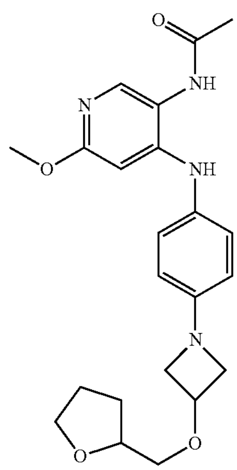 [SMILES: COc1cc(Nc2ccc(N3CC(OCC4CCCO4)C3)cc2)c(NC(C)=O)cn1] | ¹H-NMR (CDCl₃) δ: 1.55-1.70 (1H, m), 1.85-2.02 (3H, m), 3.43 (1H, dd, J = 10.1, 6.3 Hz), 3.50 (1H, dd, J = 10.1, 3.6 Hz), 3.74-3.82 (3H, m), 3.87-3.93 (1H, m), 3.90 (3H, s), 4.01-4.18 (3H, m), 4.47-4.455 (1H, m), 6.01 (1H, s), 6.44-6.52 (2H, m), 7.02-7.11 (2H, m), 9.02 (1H, s), 9.26 (1H, s). MS (ESI) m/z: 413 (M + H)⁺ |
| Example 90 | 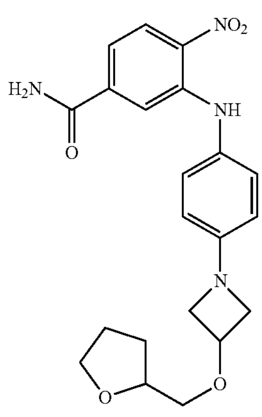 [SMILES: NC(=O)c1ccc([N+](=O)[O-])c(Nc2ccc(N3CC(OCC4CCCO4)C3)cc2)c1] | ¹H-NMR (CDCl₃) δ: 1.57-2.05 (4H, m), 3.40-3.54 (2H, m), 3.74-3.83 (3H, m), 3.86-3.94 (1H, m), 4.02-4.11 (1H, m), 4.12-4.20 (2H, m), 4.46-4.56 (1H, m), 5.57-5.77 (1H, br), 5.88-6.07 (1H, br), 6.46-6.54 (2H, m), 6.99 (1H, dd, J = 8.7, 1.9 Hz), 7.06-7.13 (2H, m), 7.38 (1H, d, J = J = 1.9 Hz), 8.23 (1H, d, J = 8.7 Hz), 9.40 (1H, s). MS (ESI) m/z: 413 ((M + H)⁺ |

TABLE 1-12-continued

| Example No. | structure | data |
|---|---|---|
| Example 91 | 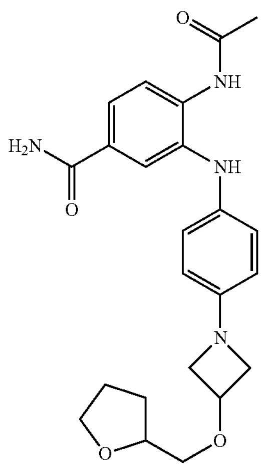 [SMILES: CC(=O)Nc1ccc(C(N)=O)cc1Nc1ccc(N2CC(OCC3CCCO3)C2)cc1] | ¹H-NMR (DMSO-d₆) δ: 1.48-1.96 (4H, m), 2.07 (3H, s), 3.29-3.42 (2H, m), 3.49-3.57 (2H, m), 3.59-3.67 (1H, m), 3.70-3.78 (1H, m), 3.89-3.97 (1H, m), 3.99-4.05 (2H, m), 4.37-4.45 (1H, m), 6.40-6.48 (2H, m), 6.86-6.94 (2H, m), 6.98 (1H, s), 7.15 (1H, s), 7.23 (1H, d, J = 8.3 Hz), 7.44 (1H, s), 7.48 (1H, d, J = 8.3 Hz), 7.76 (1H, s), 9.31 (1H, s). MS (ESI) m/z: 425 (M + H)⁺ |
| Example 92 | 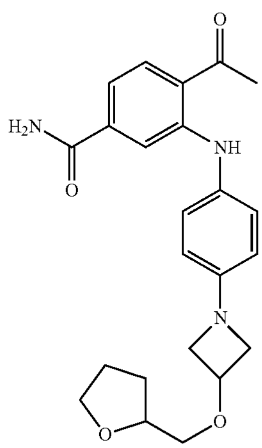 [SMILES: CC(=O)c1ccc(C(N)=O)cc1Nc1ccc(N2CC(OCC3CCCO3)C2)cc1] | ¹H NMR (CDCl₃) δ: 1.57-2.04 (4H, m), 2.65 (3H, s), 3.43 (1H, dd, J = 10.0, 6.6 Hz), 3.49 (1H, dd, J = 10.0, 3.8 Hz), 3.68-3.83 (3H, m), 3.85-3.94 (1H, m), 4.01-4.18 (3H, m), 4.45-4.55 (1H, m), 5.47-5.70 (1H, br), 5.83-6.05 (1H, br), 6.43-6.53 (2H, m), 6.99 (1H, dd, J = 8.2, 1.4 Hz), 7.04-7.12 (2H, m), 7.27 (1H, d, J = 1.4 Hz), 7.82 (1H, d, J = 8.2 Hz), 10.3 (1H, s). MS (ESI) m/z: 410 (M + H)⁺ |

TABLE 1-13

| Example No. | structure | data |
|---|---|---|
| Example 93 | 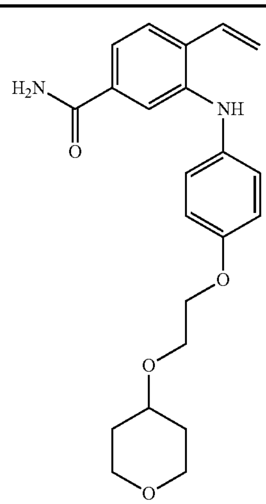 | ¹H-NMR (DMSO-d₆) δ: 1.36-1.48 (2H, m), 1.82-1.92 (2H, m), 3.28-3.34 (2H, m), 3.52-3.58 (1H, m), 3.71-3.84 (4H, m), 4.03-4.08 (2H, m), 5.40 (1H, d, J = 11.2 Hz), 6.00 (1H, d, J = 17.8 Hz), 6.90-7.02 (5H, m), 6.90-7.02 (1H, d, J = 1.7 Hz), 7.36-7.42 (1H, br), 7.62 (1H, dd, J = 8.3, 1.7 Hz), 7.74 (1H, d, J = 8.3 Hz), 7.94-8.01 (1H, br). MS (ESI) m/z: 384 (M + H)⁺ |

TABLE 1-13-continued
| Example No. | structure | data |
|---|---|---|
| Example 94 | 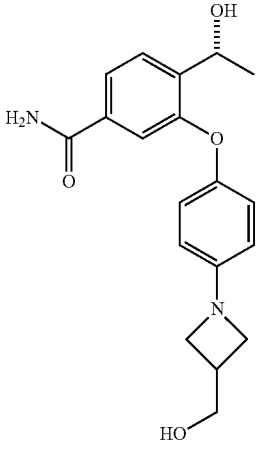 [SMILES: C[C@@H](O)c1ccc(C(N)=O)cc1Oc1ccc(N2CC(CO)C2)cc1] | $^1$H-NMR (DMSO-$d_6$) δ: 1.34 (3H, d, J = 6.4 Hz), 2.70-2.83 (1H, m), 3.48-3.56 (2H, m), 3.57-3.63 (2H, m), 3.81 (2H, t, J = 5.1 Hz), 4.73 (2H, t, J = 5.1 Hz), 5.04-5.11 (1H, m), 5.21 (1H, d, J = 4.4 Hz), 6.40-6.46 (2H, m), 6.83-6.87 (2H, m), 7.11-7.14 (1H, m), 7.24-7.31 (1H, br), 7.54-7.59 (2H, m), 7.84-7.91 (1H, br). MS (ESI) m/z: 343 (M + H)$^+$ |
| Example 95 | 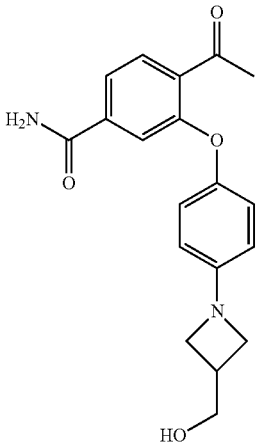 [SMILES: CC(=O)c1ccc(C(N)=O)cc1Oc1ccc(N2CC(CO)C2)cc1] | $^1$H-NMR (CDCl$_3$) δ: 1.65-1.78 (1H, br), 2.71 (3H, s), 2.89-2.97 (1H, m), 3.87-4.00 (4H, m), 5.55-5.75 (1H, br), 5.92-6.11 (1H, br), 6.44-6.50 (2H, m), 6.90-6.97 (2H, m), 7.25 (1H, d, J = J = 1.7 Hz), 7.39 (1H, dd, J = 8.0, 1.7 Hz), 7.82 (1H, d, J = 8.0 Hz). MS (ESI) m/z: 341 (M + H)$^+$ |
| Example 96 | 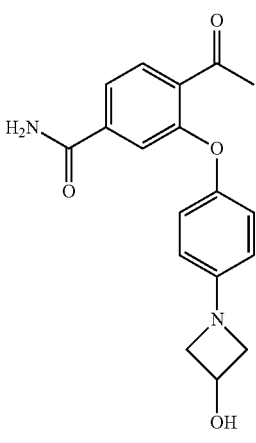 [SMILES: CC(=O)c1ccc(C(N)=O)cc1Oc1ccc(N2CC(O)C2)cc1] | $^1$H-NMR (DMSO-$d_6$) δ: 2.60 (3H, s), 3.50 (2H, dd, J = 7.4, 5.0 Hz), 4.04-4.09 (2H, m), 4.50-4.60 (1H, m), 5.57 (1H, d, J = 6.6 Hz), 6.46-6.51 (2H, m), 6.95-7.00 (2H, m), 7.23-7.25 (1H, m), 7.45-7.52 (1H, br), 7.56-7.60 (1H, m), 7.69 (1H, d, J = 7.8 Hz), 8.01-8.08 (1H, br). MS (ESI) m/z: 327 (M + H)$^+$ |

TABLE 1-14

| Example No. | structure | data |
|---|---|---|
| Example 97 | (structure) | ¹H-NMR (DMSO-d₆) δ: 2.29 (2H, quintet, J = 7.3 Hz), 2.60 (3H, s), 3.80 (4H, t, J = 7.3 Hz), 6.44-6.49 (2H, m), 6.95-7.00 (2H, m), 7.24 (1H, d, J = 1.2 Hz), 7.45-7.55 (1H, br), 7.57 (1H, dd, J = 8.1, 1.2 Hz), 7.69 (1H, d, J = 8.1 Hz), 8.00-8.10 (1H, br). MS (ESI) m/z: 311 (M + H)⁺ |
| Example 98 | (structure) | ¹H-NMR (DMSO-d₆) δ: 2.60 (3H, s), 6.79-6.87 (2H, m), 6.94-7.00 (2H, m), 7.27 (1H, d, J = 1.4 Hz), 7.45-7.56 (1H, br), 7.61 (1H, dd, J = 1.4, 8.1 Hz), 7.70 (1H, d, J = 8.1 Hz), 8.02-8.11 (1H, br), 9.45 (1H, s). MS (ESI) m/z: 272 [M + H]⁺ |
| Example 99 | (structure) | ¹H-NMR (DMSO-d₆) δ: 2.58 (3H, s), 4.50 (2H, d, J = 5.6 Hz), 5.20 (1H, t, J = 5.6 Hz), 7.03-7.08 (2H, m), 7.35-7.42 (2H, m), 7.50-7.60 (1H, br), 7.69 (1H, dd, J = 8.2, 1.6 Hz), 7.76 (1H, d, J = 8.2 Hz), 8.06-8.15 (1H, br). MS (ESI) m/z: 308 (M + Na)⁺ |

Formulation Example 1

A powder can be obtained by mixing the compound of the present invention (5 g), lactose (895 g) and cornstarch (100 g) in a blender.

Formulation Example 2

The compound of the present invention (5 g), lactose (865 g) and low-substituted hydroxypropyl cellulose (100 g) are mixed, 10% aqueous hydroxypropylcellulose solution (300 g) is added and the mixture is kneaded. This is granulated by an extrusion granulator and dried to give granules.

Formulation Example 3

The compound of the present invention (5 g), lactose (90 g), cornstarch (34 g), crystalline cellulose (20 g) and magnesium stearate (1 g) are mixed in a blender, and the mixture is punched by a tablet machine to give tablets.

Experimental Examples

Experimental Example 1

Osteoblast differentiation test

Mouse bone marrow-derived mesenchymal cell line ST2 cells (source of supply: RIKEN) were seeded in α-MEM medium containing 10% fetal bovine serum (source of supply: GIBCO BRL Cat. No. 12000-022) in a 96 well plate at a cell density of $4\times10^3$ cells/0.1 mL/well, and cultured for 24 hr under the conditions of 37° C., 5% $CO_2$. Then, each test compound was added at a final concentration of 0.001-10 μM, and the final concentration 0.1% (v/v) of DMSO was added to the control. After 4 days of culture, alkaline phosphatase (ALP) activity was measured by the following method.

The medium in the cultured 96 well plate was removed, the cells were washed with PBS buffer (KCl 0.2 g/L, $KH_2PO_4$ 0.2 g/L, $Na_2HPO_4.12H_2O$ 2.9 g/L, NaCl 8 g/L) (100 μL/well), cell lysate (10 mM $MgCl_2$, 2% (v/v) Triton X-100) (50 μL/well) was added, and the mixture was stirred at room temperature for 3 min. A substrate solution (50 mM diethanolamine (Wako Pure Chemical Industries, Ltd. Cat. No. 099-03112), 20 mM p-nitrophenylphosphite (Nacalai Tesque Cat. No. 25019-81)) (50 μL/well) was added, and the mixture was left standing at room temperature for 9 min. 1N NaOH 50 μL/well was added to discontinue the reaction, and the absorbance at 405 nm was measured by a microplate reader (Dainippon Pharmaceutical Co., Ltd.)

An increase rate (%) in the absorbance by the test compound was calculated based on the absorbance of the control as 100%, and the differentiation degree of the osteoblast was evaluated.

In this test, the compounds of Examples 1, 2, 5, 6, 8, 9, 13, 16, 17, 18, 20, 28, 29, 30, 32, 33, 34, 35, 38, 39, 40, 41, 43, 45, 47, 48, 50, 53, 57, 58, 62, 63, 64, 65, 66, 67, 68, 69, 70, 74, 77, 82, 83, 85, 88, 89, 90, 91, 92, 94, 95, 96, 97 showed an alkaline phosphatase activity of not less than 200% at 0.1 μg/mL.

Experimental Example 2

Influence on Bone Density 12-week-old female F344 rats (SLC) underwent ovariectomy or sham surgery under anesthesia. The test compound was suspended in 0.5% methylcellulose solution (Wako Pure Chemical Industries, Ltd. Cat. No. 133-14255) and orally administered once per day, 6 or 7 days per week, from two days after the surgery. A 0.5% methylcellulose solution was orally administered to a control group. At 8 weeks from the administration, they were euthanized by drawing the whole blood from the abdominal artery under anesthesia, and the left and right femurs were excised.

The soft tissues were removed from the excised femurs, and the bone density was measured by DXA device DCS-600R (Aloka Co., Ltd.). The bone density was evaluated for the whole femur as well as the whole divided into three equal portions of proximal end, diaphysis and distal end portion.

In this test, the compounds of Examples 1, 32, 38, 43, 67, 77 significantly increased the bone density at not more than 10 mg/kg.

INDUSTRIAL APPLICABILITY

The compound of the present invention has low toxicity, shows good pharmacokinetics, has an action to promote bone formation, and is useful for the prophylaxis or treatment of metabolic bone diseases (osteoporosis, fibrous osteitis (hyperparathyroidism), osteomalacia, Paget's disease that influences the systemic bone metabolism parameter etc.) associated with a decrease in the bone formation ability as compared to the bone resorption capacity. In addition, the pharmaceutical composition of the present invention containing the compound as an active ingredient is also expected to be applicable as a bone formation promoter to the acceleration of healing of bone diseases in the orthopedics field such as bone fracture, bone defect, osteoarthritis and the like, and the treatment of periodontal diseases, stabilization of artificial tooth root and the like in the dental field.

This application is based on patent application No. 2013-178712 filed in Japan, the contents of which are encompassed in full herein.

The invention claimed is:

1. A compound of formula (I) or a pharmacologically acceptable salt thereof:

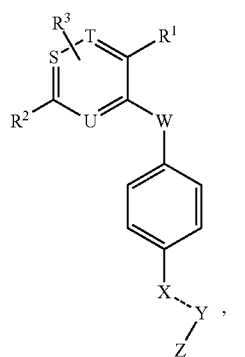

(I)

wherein:
R$^1$ is cyano group, C1-6 alkylcarbonyl group, C1-6 alkylcarbonylamino group, halogeno C1-6 alkyl group, C2-6 alkenyl group, halogeno C2-6 alkenyl group, carbamoyl group, or hydroxy C1-6 alkyl group;
R$^2$ is C1-6 alkoxy group, carbamoyl group, C1-6 alkylaminocarbonyl group, or C1-6 alkylcarbonyl group;
R$^3$ is hydrogen atom or halogen atom;
S, T and U are each =CH— or =C— when R$^3$ is halogen atom;
W is —NH— or —O—;
X is saturated heterocycle-, —CH$_2$—(CH$_2$)$_n$—, —O—(CH$_2$)$_n$—, —(CH$_2$)$_n$—O—, or —CH=CH—(CH$_2$)$_n$—;
n is an integer of 1 to 4;
Y is single bond, —O—, or —CO—;
Z is hydrogen atom, saturated heterocyclic group optionally substituted by any group selected from substituent group α, or C1-6 alkyl group optionally substituted by any group selected from substituent group α; and
substituent group α is saturated heterocyclic group, hydroxy C1-6 alkyl group, aminosulfonylamino group, carboxy group, hydroxy group, C1-6 alkoxy group, or C1-6 alkyl group.

2. The compound according to claim 1, wherein
R$^1$ is cyano group, acetyl group, acetylamino group, trifluoromethyl group, 1,1-difluoroethyl group, 1-fluoroethyl group, difluoromethyl group, carbamoyl group, or 1-hydroxyethyl group, or a pharmacologically acceptable salt thereof.

3. The compound according to claim 1, wherein
R$^2$ is methoxy group, carbamoyl group, methylaminocarbonyl group, or acetyl group, or a pharmacologically acceptable salt thereof.

4. The compound according to claim 1, wherein
X is -saturated heterocycle or —O—(CH$_2$)$_n$—, and n is 2, or a pharmacologically acceptable salt thereof.

5. The compound according to claim 1, wherein
Y is a single bond or —O—, or a pharmacologically acceptable salt thereof.

6. The compound according to claim 1, wherein
Z is C1-6 alkyl group substituted by a hydroxy group, tetrahydrofuranyl group, tetrahydropyranyl group, piperazinyl group, or morpholinyl group, or a pharmacologically acceptable salt thereof.

7. A compound selected from the group consisting of:

(4) 4-acetyl-3-{4-[2-(1,1-dioxohexahydro-1λ$^6$-thiopyran-4-yloxy)ethoxy]phenylamino}benzamide

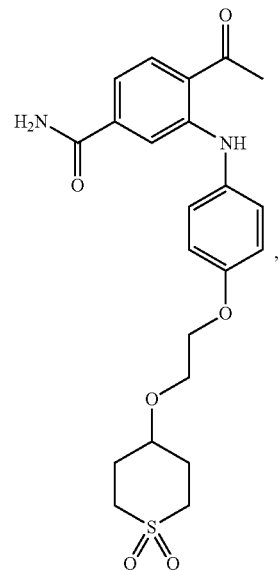 [SMILES: CC(=O)c1ccc(C(N)=O)cc1Nc1ccc(OCCOC2CCS(=O)(=O)CC2)cc1]

(5) 4-acetyl-3-{4-[4-(2-hydroxyethoxy)piperidin-1-yl]phenoxy}benzamide

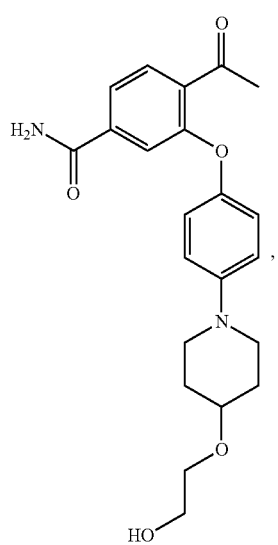 [SMILES: CC(=O)c1ccc(C(N)=O)cc1Oc1ccc(N2CCC(OCCO)CC2)cc1]
(6) 4-acetyl-3-{4-[2-(tetrahydropyran-4-yloxy)ethoxy]phenoxy}benzamide
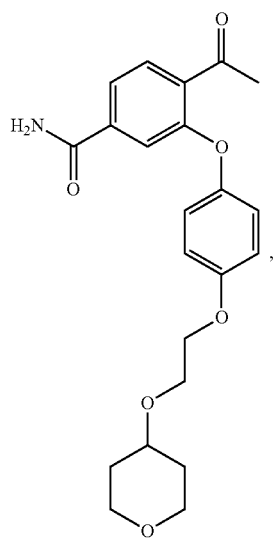 [SMILES: CC(=O)c1ccc(C(N)=O)cc1Oc1ccc(OCCOC2CCOCC2)cc1]
(7) 4-acetyl-3-{4-[2-(2-isopropoxyethoxy)ethoxy]phenoxy}benzamide
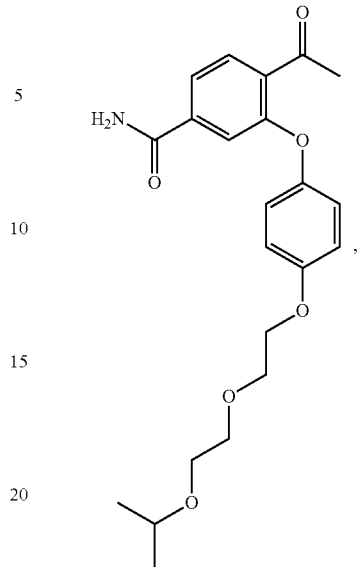
(8) 4-difluoromethyl-3-{4-[2-(tetrahydropyran-4-yloxy)ethoxy]phenoxy}benzamide
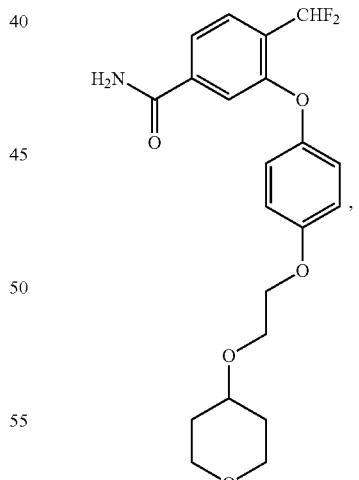
(9) 4-(1-hydroxyethyl)-3-{4-[2-(tetrahydropyran-4-yloxy)ethoxy]phenoxy}benzamide

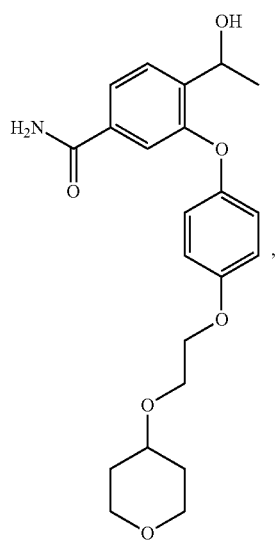 [SMILES: C[C@@H](O)c1ccc(C(N)=O)cc1Oc1ccc(OCCOC2CCOCC2)cc1]
(10) (R)-4-(1-hydroxyethyl)-3-{4-[2-(tetrahydropyran-4-yloxy)ethoxy]phenoxy}benzamide
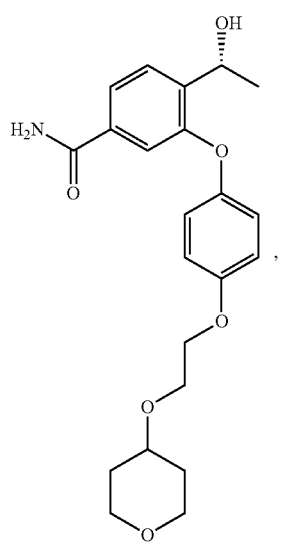
(12) 4-acetyl-2-{4-[2-(1,1-dioxohexahydro-1λ$^6$-thiopyran-4-yloxy)ethoxy]phenylamino}benzamide
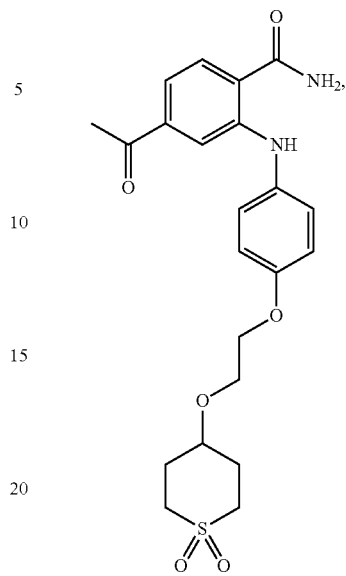
(13) 3-{4-[3-(2-hydroxyethoxy)azetidin-1-yl]phenoxy}-4-trifluoromethylbenzamide
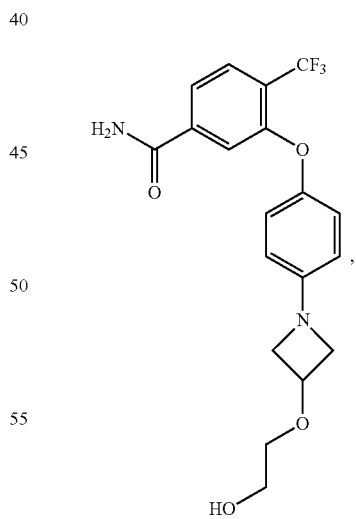
(14) 4-acetyl-3-{4-[2-(tetrahydrofuran-3-yloxy)ethoxy]phenoxy}benzamide

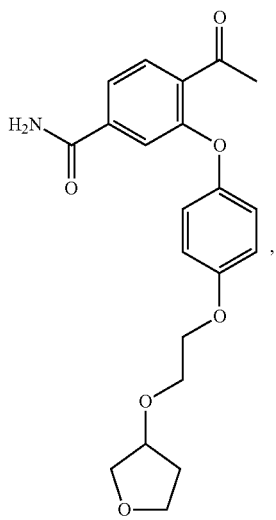

(15) (S)-4-acetyl-3-{4-[2-(tetrahydrofuran-3-yloxy)ethoxy]phenoxy}benzamide

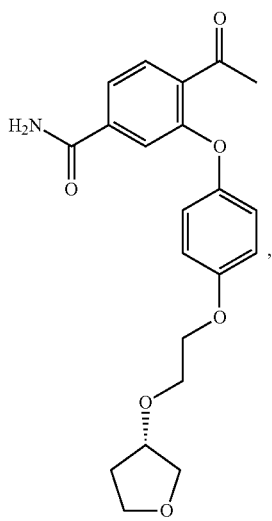 [SMILES: CC(=O)c1ccc(C(N)=O)cc1Oc1ccc(OCCOC2CCOC2)cc1]

(16) (R)-4-acetyl-3-{4-[2-(tetrahydrofuran-3-yloxy)ethoxy]phenoxy}benzamide

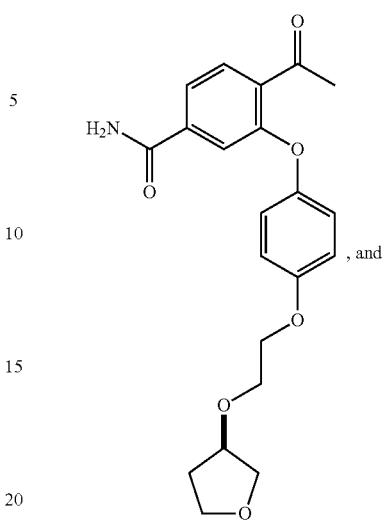

(17) 4-[(R)-1-hydroxyethyl]-3-(4-{2-[(S)-tetrahydrofuran-3-yloxy]ethoxy}phenoxy)benzamide

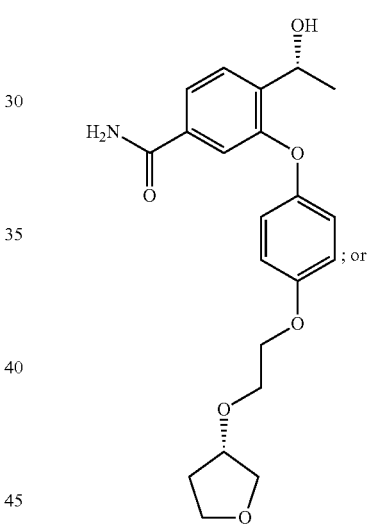

a pharmacologically acceptable salt thereof.

8. A pharmaceutical composition comprising the compound according to claim 1, 2, 3, 4, 5, 6, or 7, or a pharmacologically acceptable salt thereof, as an active ingredient, and a pharmacologically acceptable additive.

9. The pharmaceutical composition according to claim 8, which is used for promoting bone formation.

10. The pharmaceutical composition according to claim 8, which is used for treating osteoporosis.

11. A method of promoting bone formation, comprising administering an effective amount of the pharmaceutical composition according to claim 8 to a mammal.

12. A method of treating osteoporosis, comprising administering an effective amount of the pharmaceutical composition according to claim 8 to a mammal.

13. A compound of formula (Ia) or a pharmacologically acceptable salt thereof:

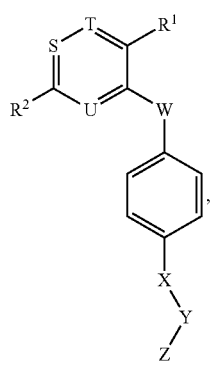

(Ia)

wherein:

R¹ is cyano group, acetyl group, acetylamino group, nitro group, trifluoromethyl group, 1,1-difluoroethyl group, 1-fluoroethyl group, difluoromethyl group, carbamoyl group or 1-hydroxyethyl group;

R² is methoxy group, carbamoyl group, methylaminocarbonyl group or acetyl group;

S, T and U are each =CH—;

W is —NH—, —O—, or —S—;

X is -saturated heterocycle- or —O—$(CH_2)_n$—;

n is 2;

Y is a single bond or —O—; and

Z is C1-6 alkyl group substituted by a hydroxy group, tetrahydrofuranyl group, tetrahydropyranyl group, piperazinyl group or morpholinyl group, or a pharmacologically acceptable salt thereof.

14. A pharmaceutical composition comprising the compound according claim 13, or a pharmacologically acceptable salt thereof, as an active ingredient, and a pharmacologically acceptable additive.

15. The pharmaceutical composition according to claim 14, which is used for promoting bone formation.

16. The pharmaceutical composition according to claim 14, which is used for treating osteoporosis.

17. A method of promoting bone formation, comprising administering an effective amount of the pharmaceutical composition according to claim 14 to a mammal.

18. A method of treating osteoporosis, comprising administering an effective amount of the pharmaceutical composition according to claim 14 to a mammal.

19. A compound selected from the group consisting of:

(2) 3-{4-[3-(2-hydroxyethoxy)azetidin-1-yl] phenylamino}-4-nitrobenzamide

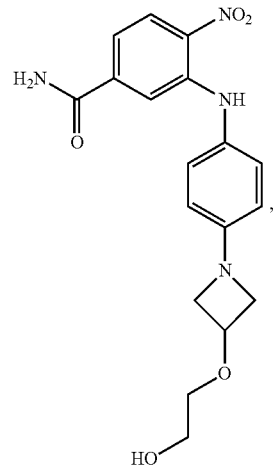 [SMILES: NC(=O)c1ccc([N+](=O)[O-])c(Nc2ccc(N3CC(OCCO)C3)cc2)c1]

(3) 3-{4-[4-(4-fluoro-5-methoxy-2-nitrophenylamino) phenyl]piperazin-1-yl}-2,2-dimethylpropionic acid

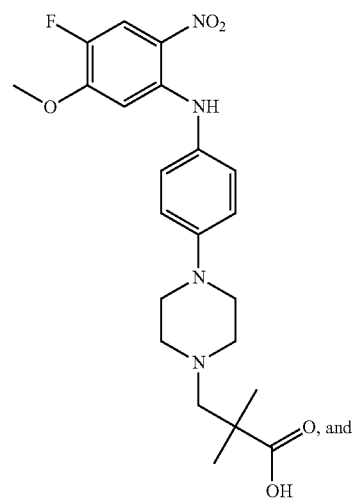

(11) 4-nitro-3-{4-[2-(tetrahydropyran-4-yloxy)ethoxy] phenylamino}benzamide

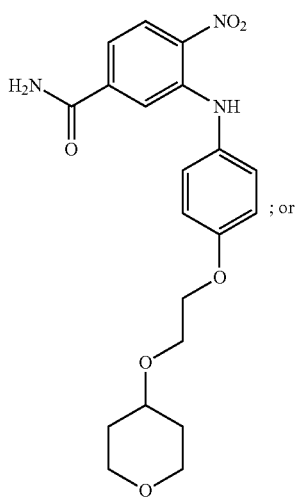 [SMILES: NC(=O)c1ccc([N+](=O)[O-])c(Nc2ccc(OCCOC3CCOCC3)cc2)c1]

; or a pharmacologically acceptable salt thereof.

20. A pharmaceutical composition comprising the compound according claim 19, or a pharmacologically acceptable salt thereof, as an active ingredient, and a pharmacologically acceptable additive.

21. The pharmaceutical composition according to claim 20, which is used for promoting bone formation.

22. The pharmaceutical composition according to claim 20, which is used for treating osteoporosis.

23. A method of promoting bone formation, comprising administering an effective amount of the pharmaceutical composition according to claim 20 to a mammal.

24. A method of treating osteoporosis, comprising administering an effective amount of the pharmaceutical composition according to claim 20 to a mammal.

\* \* \* \* \*